(12) United States Patent
Lerchen et al.

(10) Patent No.: US 11,660,351 B2
(45) Date of Patent: May 30, 2023

(54) ANTIBODY DRUG CONJUGATES (ADCS) HAVING ENZYMATICALLY CLEAVABLE GROUPS

(71) Applicants: Bayer Pharma Aktiengesellschaft, Berlin (DE); Bayer Aktiengesellschaft, Leverkusen (DE)

(72) Inventors: Hans-Georg Lerchen, Leverkusen (DE); Anne-Sophie Rebstock, Champagne au Mont d'Or (FR); Beatrix Stelte-Ludwig, Wülfrath (DE); Dennis Kirchhoff, Berlin (DE); Lisa Dietz, Wuppertal (DE); Christoph Mahlert, Wuppertal (DE); Simone Greven, Dormagen (DE); Stephan Märsch, Cologne (DE); Sandra Berndt, Hohen Neuendorf (DE); Anette Sommer, Berlin (DE); Stefanie Hammer, Berlin (DE)

(73) Assignees: BAYER AKTIENGESELLSCHAFT, Leverkusen (DE); BAYER PHARMA AKTIENGESELLSCHAFT, Berlin (DE)

( * ) Notice: Subject to any disclaimer, the term of this patent is extended or adjusted under 35 U.S.C. 154(b) by 449 days.

(21) Appl. No.: 16/472,749

(22) PCT Filed: Dec. 14, 2017

(86) PCT No.: PCT/EP2017/082789
§ 371 (c)(1),
(2) Date: Jun. 21, 2019

(87) PCT Pub. No.: WO2018/114578
PCT Pub. Date: Jun. 28, 2018

(65) Prior Publication Data
US 2019/0328897 A1    Oct. 31, 2019

(30) Foreign Application Priority Data

Dec. 21, 2016  (EP) .................................. 16205868

(51) Int. Cl.
| | | |
|---|---|---|
| *A61K 39/00* | (2006.01) |
| *A61K 47/68* | (2017.01) |
| *A61K 47/65* | (2017.01) |
| *A61P 35/00* | (2006.01) |
| *C07K 16/28* | (2006.01) |
| *C07K 16/32* | (2006.01) |

(52) U.S. Cl.
CPC .......... *A61K 47/6803* (2017.08); *A61K 47/65* (2017.08); *A61K 47/6849* (2017.08); *A61K 47/6855* (2017.08); *A61P 35/00* (2018.01); *C07K 16/2827* (2013.01); *C07K 16/2863* (2013.01); *C07K 16/2866* (2013.01); *C07K 16/2878* (2013.01); *C07K 16/32* (2013.01); *A61K 2039/505* (2013.01); *C07K 2317/24* (2013.01)

(58) Field of Classification Search
CPC ................ A61K 47/6803; A61K 47/65; A61K 47/6849; A61K 47/6855; A61K 2039/505; A61K 47/6889; A61K 47/6851; A61P 35/00; A61P 43/00

See application file for complete search history.

(56) References Cited

U.S. PATENT DOCUMENTS

| | | |
|---|---|---|
| 4,399,216 A | 8/1983 | Axel |
| 4,474,893 A | 10/1984 | Reading |
| 4,510,245 A | 4/1985 | Cousens |
| 4,634,665 A | 1/1987 | Axel |
| 4,714,681 A | 12/1987 | Reading |
| 4,816,397 A | 3/1989 | Boss |
| 4,816,567 A | 3/1989 | Cabilly |
| 4,925,648 A | 5/1990 | Hansen |
| 4,968,615 A | 11/1990 | Koszinowski |
| 5,168,062 A | 12/1992 | Stinski |
| 5,179,017 A | 1/1993 | Axel |
| 5,270,163 A | 12/1993 | Gold |
| 5,573,920 A | 11/1996 | Randle |
| 5,601,819 A | 2/1997 | Wong |
| 6,177,078 B1 | 1/2001 | Lopez |
| 7,318,924 B2 | 1/2008 | Mckenzie |
| 7,465,449 B2 | 12/2008 | Violette |

(Continued)

FOREIGN PATENT DOCUMENTS

| | | |
|---|---|---|
| CA | 2990411 A1 | 12/2016 |
| CA | 3018630 A1 | 9/2017 |

(Continued)

OTHER PUBLICATIONS

Strome et al., The Oncologist, 2007; 12:1084-95 (Year: 2007).*
Brand et al., Anticancer Res. 2006; 26:463-70 (Year: 2006).*
Johnson et al, Cancer Treatment Reviews vol. 2 p. 1-31 (1975). (Year: 1975).*
Co-pending U.S. Appl. No. 17/166,713, inventors Lerchen; Hans-Georg et al., filed on Mar. 3, 2021.
Co-pending U.S. Appl. No. 17/253,086, inventors Johannes; Sarah Anna Liesa et al., filed on Dec. 16, 2020.

(Continued)

*Primary Examiner* — Sheela J. Huff
(74) *Attorney, Agent, or Firm* — Wilson Sonsini Goodrich & Rosati

(57) ABSTRACT

The invention relates to novel binder-drug conjugates (ADCs) having improved properties, to active metabolites of these ADCs and to processes for their preparation. The present invention furthermore relates to the use of these conjugates for the treatment and/or prevention of diseases and to the use of these conjugates for preparing medicaments for treatment and/or prevention of diseases, in particular hyperproliferative and/or angiogenic disorders such as, for example, cancer diseases.

50 Claims, 23 Drawing Sheets

Specification includes a Sequence Listing.

(56) References Cited

U.S. PATENT DOCUMENTS

| | | | |
|---|---|---|---|
| 7,598,350 B2 | 10/2009 | Liu | |
| 7,628,986 B2 | 12/2009 | Weber | |
| 7,662,581 B1 | 2/2010 | Bussiere | |
| 10,022,453 B2 | 7/2018 | Lerchen | |
| 10,485,880 B2 | 11/2019 | Lerchen et al. | |
| 10,744,205 B2 | 8/2020 | Lerchen et al. | |
| 10,973,923 B2 | 4/2021 | Lerchen et al. | |
| 11,123,439 B2 * | 9/2021 | Lerchen | A61K 31/4439 |
| 2006/0009472 A1 | 1/2006 | Wang et al. | |
| 2007/0037853 A1 | 2/2007 | Barsanti et al. | |
| 2007/0264253 A1 | 11/2007 | Liu | |
| 2008/0021079 A1 | 1/2008 | Zhou et al. | |
| 2008/0193445 A1 | 8/2008 | Goetsch | |
| 2008/0207589 A1 | 8/2008 | Boyce et al. | |
| 2009/0175796 A1 | 7/2009 | Raitano | |
| 2009/0258016 A1 | 10/2009 | Wang et al. | |
| 2010/0028947 A1 | 2/2010 | Goletz | |
| 2010/0143245 A1 | 6/2010 | Cheung | |
| 2011/0003791 A1 | 1/2011 | Boyce et al. | |
| 2012/0189623 A1 | 7/2012 | Boyce et al. | |
| 2013/0017196 A1 | 1/2013 | Wang et al. | |
| 2013/0066055 A1 | 3/2013 | Lerchen | |
| 2014/0322247 A1 | 10/2014 | Barsanti | |
| 2015/0352224 A1 | 12/2015 | Naito | |
| 2016/0346402 A1 | 12/2016 | Lerchen | |
| 2018/0015176 A1 | 1/2018 | Lerchen | |
| 2018/0169256 A1 | 6/2018 | Lerchen et al. | |
| 2018/0185510 A1 | 7/2018 | Lerchen | |
| 2018/0318437 A1 | 11/2018 | Lerchen | |
| 2018/0318438 A1 | 11/2018 | Lerchen | |
| 2019/0077752 A1 | 3/2019 | Lerchen et al. | |
| 2019/0262463 A1 | 8/2019 | Lerchen et al. | |
| 2019/0330357 A1 | 10/2019 | Lerchen et al. | |
| 2019/0351066 A1 | 11/2019 | Lerchen et al. | |
| 2019/0365916 A1 | 12/2019 | Lerchen et al. | |
| 2020/0138970 A1 | 5/2020 | Lerchen et al. | |
| 2021/0230284 A1 | 7/2021 | Lerchen et al. | |
| 2021/0386864 A1 | 12/2021 | Lerchen et al. | |

FOREIGN PATENT DOCUMENTS

| | | |
|---|---|---|
| EP | 0586002 A2 | 3/1994 |
| EP | 0712863 A1 | 5/1996 |
| EP | 0719859 A1 | 7/1996 |
| EP | 1900750 A1 | 3/2008 |
| EP | 1911766 A1 | 4/2008 |
| EP | 2311879 A2 | 4/2011 |
| EP | 1773884 B1 | 3/2012 |
| EP | 2426148 A1 | 3/2012 |
| EP | 1735348 B1 | 6/2012 |
| EP | 2073842 B1 | 12/2014 |
| EP | 2195023 B1 | 3/2018 |
| JP | 2006502219 A | 1/2006 |
| JP | 2010522723 A | 7/2010 |
| JP | 2011506402 A | 3/2011 |
| JP | 2012515749 A | 7/2012 |
| JP | 2017507905 A | 3/2017 |
| WO | WO199100360 A1 | 1/1991 |
| WO | WO199105871 A1 | 5/1991 |
| WO | WO199205793 A1 | 4/1992 |
| WO | WO199208802 A1 | 5/1992 |
| WO | WO199215683 A1 | 9/1992 |
| WO | WO199317715 A1 | 9/1993 |
| WO | WO199708320 A1 | 3/1997 |
| WO | WO199735616 A1 | 10/1997 |
| WO | WO199947554 A1 | 9/1999 |
| WO | WO2001009192 A1 | 2/2001 |
| WO | WO2001062931 A2 | 8/2001 |
| WO | WO2001088138 A1 | 11/2001 |
| WO | WO2002012501 A2 | 2/2002 |
| WO | WO2002077033 A1 | 10/2002 |
| WO | WO2002088170 A2 | 11/2002 |
| WO | WO2002092771 A2 | 11/2002 |
| WO | WO2002100348 A2 | 12/2002 |
| WO | WO2003034903 A2 | 5/2003 |
| WO | WO2003040979 A1 | 5/2003 |
| WO | WO2003049527 A2 | 6/2003 |
| WO | WO2003060064 A2 | 7/2003 |
| WO | WO2003083041 A2 | 10/2003 |
| WO | WO2003106495 A2 | 12/2003 |
| WO | WO2004056847 A3 | 6/2005 |
| WO | WO2005009369 A3 | 6/2005 |
| WO | WO2005051922 A1 | 6/2005 |
| WO | WO2004091375 A3 | 7/2005 |
| WO | WO2004100873 A3 | 8/2005 |
| WO | WO2005010151 A3 | 9/2005 |
| WO | WO2005056606 A3 | 9/2005 |
| WO | WO2005090407 A8 | 12/2005 |
| WO | WO2005081854 A3 | 1/2006 |
| WO | WO2006002236 A1 | 1/2006 |
| WO | WO2006066896 A2 | 6/2006 |
| WO | WO2006060737 A3 | 9/2006 |
| WO | WO2006100036 A1 | 9/2006 |
| WO | WO2006044825 A3 | 10/2006 |
| WO | WO2005081711 A2 | 11/2006 |
| WO | WO2007021794 A3 | 2/2007 |
| WO | WO2006089232 A3 | 3/2007 |
| WO | WO2006074418 A3 | 4/2007 |
| WO | WO2007024536 A3 | 7/2007 |
| WO | WO2007002222 A3 | 8/2007 |
| WO | WO2007038637 A3 | 10/2007 |
| WO | WO2006062779 A3 | 1/2008 |
| WO | WO2007064759 A3 | 1/2008 |
| WO | WO2008004834 A1 | 1/2008 |
| WO | WO2008028686 A3 | 6/2008 |
| WO | WO2008031056 A3 | 10/2008 |
| WO | WO2008070593 A3 | 10/2008 |
| WO | WO2008086122 A3 | 10/2008 |
| WO | WO2008127735 A1 | 10/2008 |
| WO | WO2008140603 A2 | 11/2008 |
| WO | WO2008092117 A3 | 12/2008 |
| WO | WO-2009000786 A2 | 12/2008 |
| WO | WO2007070538 A2 | 1/2009 |
| WO | WO2009023265 A1 | 2/2009 |
| WO | WO2009026274 A1 | 2/2009 |
| WO | WO2009033094 A3 | 4/2009 |
| WO | WO2009068204 A1 | 6/2009 |
| WO | WO2009070844 A1 | 6/2009 |
| WO | WO2009020933 A9 | 7/2009 |
| WO | WO2009080829 A1 | 7/2009 |
| WO | WO2009080830 A1 | 7/2009 |
| WO | WO2008047242 A8 | 8/2009 |
| WO | WO2008036688 A3 | 9/2009 |
| WO | WO2009123894 A3 | 1/2010 |
| WO | WO2010022736 A3 | 4/2010 |
| WO | WO2009140177 A2 | 8/2010 |
| WO | WO2010112413 A1 | 10/2010 |
| WO | WO2010115554 A1 | 10/2010 |
| WO | WO-2011009400 A1 | 1/2011 |
| WO | WO2011044368 A1 | 4/2011 |
| WO | WO2012021934 A1 | 2/2012 |
| WO | WO2012143499 A3 | 12/2012 |
| WO | WO2012171020 A1 | 12/2012 |
| WO | WO2013076186 A1 | 5/2013 |
| WO | WO2013087579 A1 | 6/2013 |
| WO | WO2013173820 A2 | 11/2013 |
| WO | WO2014061277 A1 | 4/2014 |
| WO | WO2014093640 A1 | 6/2014 |
| WO | WO2014151030 A1 | 9/2014 |
| WO | WO2014160160 A2 | 10/2014 |
| WO | WO2014131739 A2 | 12/2014 |
| WO | WO2014198817 A1 | 12/2014 |
| WO | WO2015054659 A1 | 4/2015 |
| WO | WO2015089449 A2 | 6/2015 |
| WO | WO2015096982 A1 | 7/2015 |
| WO | WO2015138615 A3 | 12/2015 |
| WO | WO2015189143 A1 | 12/2015 |
| WO | WO2016020791 A1 | 2/2016 |
| WO | WO2016028573 A1 | 2/2016 |
| WO | WO2016096610 A1 | 6/2016 |
| WO | WO2016201065 A1 | 12/2016 |
| WO | WO2016207089 A1 | 12/2016 |
| WO | WO2016207094 A1 | 12/2016 |
| WO | WO2016207098 A1 | 12/2016 |

(56) References Cited

FOREIGN PATENT DOCUMENTS

| WO | WO2016207103 A1 | 12/2016 |
|---|---|---|
| WO | WO2016207104 A1 | 12/2016 |
| WO | WO2016207090 A3 | 2/2017 |
| WO | WO2017162663 A1 | 9/2017 |
| WO | WO2017216028 A1 | 12/2017 |
| WO | WO2018114578 A1 | 6/2018 |
| WO | WO2018114798 A1 | 6/2018 |
| WO | WO2018114804 A1 | 6/2018 |
| WO | WO-2019243159 A1 | 12/2019 |

OTHER PUBLICATIONS

Co-pending U.S. Appl. No. 17/374,756, inventors Lerchen; Hans-Georg et al., filed on Jul. 13, 2021.
U.S. Appl. No. 15/105,486 Office Action dated Jun. 8, 2017.
International Preliminary Report on Patentability dated Jul. 4, 2019, for PCT Application No. PCT/EP2017/082789, filed on Dec. 14, 2017, 11 pages.
International Preliminary Report on Patentability dated Jul. 4, 2019, for PCT Application No. PCT/EP2017/082789, filed on Dec. 14, 2017, 11 pages. German Language.
International Preliminary Report on Patentability dated Jul. 4, 2019, for PCT Application No. PCT/EP2017/083313, filed on Dec. 14, 2017, 10 pages.
International Preliminary Report on Patentability dated Jul. 4, 2019, for PCT Application No. PCT/EP2017/083313, filed on Dec. 14, 2017, 10 pages. German Language.
U.S. Appl. No. 15/105,486, filed Jun. 16, 2016, for Hans-Georg Lerchen et al. (U.S. Patent Application is not submitted herewith pursuant to the waiver of 37 C.F.R § 1.98(a)(2)(iii) issued by the Office on Sep. 21, 2004.).
U.S. Appl. No. 15/536,112, filed Jun. 14, 2017, for Hans-Georg Lerchen et al. (U.S. Patent Application is not submitted herewith pursuant to the waiver of 37 C.F.R § 1.98(a)(2)(iii) issued by the Office on Sep. 21, 2004.).
U.S. Appl. No. 15/739,134, filed Dec. 21, 2017, for Hans-Georg Lerchen et al. (U.S. Patent Application is not submitted herewith pursuant to the waiver of 37 C.F.R § 1.98(a)(2)(iii) issued by the Office on Sep. 21, 2004.).
U.S. Appl. No. 16/310,285, filed Dec. 14, 2018, for Hans-Georg Lerchen et al. (U.S. Patent Application is not submitted herewith pursuant to the waiver of 37 C.F.R § 1.98(a)(2)(iii) issued by the Office on Sep. 21, 2004.).
U.S. Appl. No. 16/472,682, filed Jun. 21, 2019, for Hans-Georg Lerchen et al. (U.S. Patent Application is not submitted herewith pursuant to the waiver of 37 C.F.R § 1.98(a)(2)(iii) issued by the Office on Sep. 21, 2004.).
Ausubel, F.M., ed. (1988). "Current Protocols in Molecular Biology," John Wiley & Sons, Inc.
Bajjuri, K. et al. (2011). "The Legumain Protease-Activated Auristatin Prodrugs Suppress Tumor Growth and Metastasis without Toxicity," Chem Med Chem 6(1):54-59.
Bebbington C.R. et al. (1992). "High-Level Expression of a Recombinant Antibody from Myeloma Cells using a Glutamine Synthetase Gene as an Arnpiifiable Selectable Marker," Bio Technology 10(2):169-175.
Berger, S.L. (1987), "Isolation of Cytoplamic RNA: Ribonucleoside-Vanadyl Complexes," Methods in Enzymology 152:227-234.
Borrebaeck C. A. K., ed. (1995), "Antibody Engineering (Breakthroughs in Molecular Biology)," Oxford University Press.
Brown S. et al. (2006). "TWEAK binding to the Fn14 cysteine-rich domain depends on charged residues located in both the A1 and D2 modules," Biochem J. 397(2):297-304.
Chen J.M. et al. (1997). "Cloning, Isolation, and Characterization of Mammalian Legumain, an Asparaginyl Endopeptidase," J. Biol. Chem. 272(12):8090-8098.
Chothia, C. et al. (1987), "Canonical Structures for the Hypervariable Regions of Immunoglobulins," J. Mol. Biol, 196:901-917.
Clackson, T. et al. (Aug. 15, 1991). "Making antibody fragments using phage display libraries," Nature 352:624-628.
Culp P.A. et al. (2010), "Antibodies to TWEAK Receptor Inhibit Human Tumor Growth through Dual Mechanisms," Clin Cancer Res, 16(2):497-508.
Delfourne E. et al. (2003), "Synthesis and in Vitro Antitumor Activity of Phenanthrolin-7-one Derivatives, Analogus of the Marine Pyridoacridine Alkaloids Ascididemin and Meridine: Structure-Activity Relationship," J. Med. Chem. 46(16):3536-3545.
Donohue P.J. et al. (2003). "TWEAK is an Endothelial Cell Growth and Chemotactic Factor that also Potentiates FGF-2 and VEGF-A Mitogenic Activity," Arterioscler Thromb Vasc Biol, 23(4):594-600.
Doronina, S.O. et al. (Jul. 2003). "Development of Potent Monoclonal Antibody Auristatin Conjugates for Cancer Therapy," Nat. Biotechnol. 21(7):778-784.
Dubowchik G.M. et al. (1998), "Cathepsin B-Sensitive Dipeptide Prodrugs. 1. A Model Study of Structural Requirements for Efficient Release of Doxorubicin," Bioorg Med Chem Lett 8(23):3341-3346.
Dubowchik G.M. et al. (2002), "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity," Chem. 13(4):855-869.
Ducry, L. et al. (2010), "Antibody—Drug Conjugates: Linking Cytotoxic Payloads to Monoclonal Antibodies," Bioconjugate Chem. 21(1): 5-13.
Durocher Y. et al. (2002). "High-level and high-throughput recombinant protein production by transient, transfection of suspension-growing human 293-EBNA1 cells," Nucleic Acids Research, 30(2):1-9.
Fan L. et al. (2012). "Improving the Efficiency of CHO Cell Line Generation Using Glutamine Synthetase Gene Knockout Cells," Biotechnol Bioeng.109(4):1007-1015.
Gerbauer, M. et al. (2009). "Engineered protein scaffolds as next-generation antibody therapeutics," Curr. Opinion in Chem. Biol. 13:245-255.
Harlow et al. eds. (1988), "Using Antibodies: A Laboratory Manual," Cold Spring Harbor Laboratory Press, pp. iv-ix, (Table of Contents Only).
Harlow, E. et al. (1998). "Using Antibodies: A Laboratory Manual," Cold Spring Harbor Laboratory Press.
Hoet, R.M. et al. (2005), "Generation of high-affinity human antibodies by combining donor-derived and synthetic complementarity-determining-region diversity," Nat Biotechnol, 23(3):344-348.
Hoogenboom H.R. et al. (2005), "Selecting and screening recombinant antibody libraries," Nat Biotechnol. 23(9):1105-1116.
International Preliminary Report on Patentability dated Dec. 27, 2018, for PCT Application No. PCT/EP2017/063951, filed on Jun. 8, 2017, 11 pages.
International Preliminary Report on Patentability dated Jul. 7, 2016, for PCT Application No. PCT/EP2014/077144 filed on Dec. 10, 2014, 12 pages.
International Search Report and Written Opinion dated Apr. 23, 2018, for PCT Application No. PCT/EP2017/083313, filed on Dec. 18, 2017, 17 pages.
International Search Report and Written Opinion dated Apr. 29, 2015, for PCT Application No. PCT/EP2014/077144 filed on Dec. 10, 2014, 12 pages.
International Search Report and Written Opinion dated Mar. 24, 2016, for PCT Application No. PCT/EP2015/079273 filed on Dec. 10, 2015, 14 pages.
International Search Report and Written Opinion dated Sep. 12, 2017, for PCT Application No. PCT/EP2017/063951, filed on Jun. 8, 2017, 16 pages.
International Search Report and Written Opinion dated Sep. 19, 2016, for PCT Application No. PCT/EP2016/064133, filed on Jun. 20, 2016, 14 pages.
Ishii S.I. (1994). "Legumain: Asparaginyl Endopeptidase," Meth Enzymol. 244:604-615.
Junutula J.R. et al. (2008), "Site-specific conjugation of cytotoxic drug to an antibody improves the therapeutic index," Nat Biotechnol. 26(8):925-932.

(56) References Cited

OTHER PUBLICATIONS

Kabat, E.V. et al. (1991). Sequences of Proteins Immunological Interest, 5th Ed. Public Health Service, National Institutes of Health Bethesda, MD, pp. iii-xix.
Kaufman R.J. et al. (1982). "Amplification and Expression of Sequences Cotransfected with a Modular Dihydrofolate Reductase Complementary DNA Gene," J. Mol. Biol. 159:601-621.
Keefe A.D. et al. (2010). "Aptamers as Therapeutics," Nat. Rev. Drug Discov. 9:537-550.
Kohler, G. et al. (Aug. 7, 1975) "Continuous Cultures Of Fused Cells Secreting Antibody Of Predefined Specificity," Nature 256:495-497.
Kontermann R. et al. eds. (2001) "Antibody Engineering," Springer Laboratory Manual, Springer Verlag, pp. vii-xii (Table of Contents Only).
Kostelny, S.A. et al. (Mar. 1, 1992), "Formation of a Bispecific Antibody by The Use of Leucine Zippers," J. Immunol. 148(5):1547-1553.
Kuo, S-R. et al. (2009). "Antibody Internalization after Cell Surface Antigen Binding is Critical for Immunotoxin Development," Bioconjugate Chem. 20(10): 1975-1982.
Lambert, J. (2005), "Drug-conjugated monoclonal antibodies for the treatment of cancer," Current Opinion in Pharmacology 5:543-549.
Lang K. et al. (2014), "Cellular Incorporation of Unnatural Amino Acids and Bioorthogonal Labeling of Proteins," Chem. Rev. 114(9):4764-4806.
Lerchen H.-G. et al. (2017). "Abstract 3234: Development of potent and selective antibody-drug conjugates with pyrrole-based KSP inhibitors as novel payload class," Cancer Research, AACR, 77(13):1-3.
Li B. et al. (2016). "Design, synthesis and evaluation of anti-CD123 antibody drug conjugates," Bioorg Med Chem 24(22):5855-5860.
Lonberg et al. "Human Antibodies From Transgenic Mice," Intern. Rev. Immunol. 13:65-93, (1995).
Mayer, T.U. et al. (1999), "Small Molecule Inhibitor of Mitotic Spindle Bipolarity Identified in a Phenotype-Based Screen," Science 286:971-974.
Michaelson J.S. et al. (2011), "Development of an Fn14 agonistic antibody as an anti-tumor agent," mAbs. 3(4):362-375.
Nakayama M. et al. (2003). "Characterization of murine TWEAK and its receptor (Fn14) by monoclonal antibodies," Biochem Biophys Res Com 306:819-825.
Nuttall S.D. et al. (2008). "Display scaffolds: protein engineering for novel therapeutics," Curr. Opinion in Pharmacol. 8:609-615.
Olsson L. et al. (1983), "[1] Human-Human Monoclonal Antibody-Producing Hybridomas: Technical Aspects," Meth Enzymol. 92:3-16.
Paul W.E. (1998). "Fundamental Immunology," Lippincott-Raven Publishers: Philadelphia, 9 pages (Table of Contents Only).
Pellegrini M. et al. (2013), "Structures of the extracellular domains of human and Xenopus Fn14: implications in the evolution of TWEAK and Fn14 interactions," FEBS 280:1818-1829.
Peterson J.J. et al. (1998), "Cathepsin Substrates as Cleavable Peptide Linkers in Bioconjugates, Selected from a Fluorescence Quench Combinatorial Library," Bioconjug Chem 9(5):618-626.
Polson A.G. et al. (2007), "Antibody-drug conjugates targeted to CD79 for the treatment of non-Hodgkin lymphoma," Blood 110(2):616-623.
Polson A.G. et al. (2009), "Antibody-Drug Conjugates for the Treatment of Non-Hodgkin's Lymphoma: Target and Linker-Drug Selection," Cancer Res. 69(6):2358-2364.
Queen, C. et al. (Dec. 1989), "A Humanized Antibody That Binds to the Interleukin 2 Receptor," Proc. Natl Acad. Sci. USA 86:10029-10033.
Rashidian M. et al. (2013), "Enzymatic Labeling of Proteins: Techniques and Approaches," Bioconjugate Chem. 24(8):1277-1294.
Sambrook, J. et al. (1989). Molecular Cloning: A Laboratory Manual, 2nd ed., Cold Spring Harbor Laboratory, Cold Spring Harbor, NY, Table of Contents, v-xxxii, 29 pages.
Schinkel A.H. et al. (1995), "Absence of the mdr1a P-Glycoprotein in Mice Affects Tissue Distribution and Pharmacokinetics of Dexamethasone, Digoxin, and Cyclosporin A," J. Clin. Invest. 96:1698-1705.
Schwab D. et al. (2003), "Comparison of in Vitro P-Glycoprotein Screening Assays: Recommendations for Their Use in Drug Discovery," J. Med. Chem. 46:1716-1725.
Seki M. et al. (2000), "Practical Synthesis of (R)-4-Mercaptopyrrolidine-2-thione from L-Aspartic Acid. Preparation of a Novel Orally Active 1-β-Methycarbapenem, TA-949," J.Org.Chem. 65(2):517-522.
Senter, P.D. (2009), "Potent antibody drug conjugates for cancer therapy," Current Opinion in Chemical Biology 13:235-244.
Soderlind, E. et al. (2000). "Recombining germline-derived CDR sequences for creating diverse single-framework antibody libraries," Nature Biotechnology 18:852-856.
Sommer A. et al. (2017). "Abstract 46: Preclinical activity of novel antibody-drug conjugates with pyrrole-based kinesin spindle protein inhibitors targeting different tumor antigens," Cancer Research, AACR 77(13):1-3.
Stern L. et al. (2009). "A Novel Antitumor Prodrug Platform Designed to be Cleaved by the Endoprotease Legumain," Bioconjugate Chem. 20(3):500-510.
Sun, Q. et al. (1996). "Monoclonal Antibody 7G3 Recognizes the N-Terminal Domain of the Human Interleukin-3 (IL-3) Receptor α-Chain and Functions as a Specific IL-3 Receptor Antagonist," Blood 87(1): 83-92.
Tao, W. et al. (2005), "Induction of apoptosis by an inhibitor of the mitotic kinesin KSP requires both activation of the spindle assembly checkpoint and mitotic slippage," Cancer Cell 8(1): 49-59.
Tom R. et al. (2007), "Transient expression in HEK293-EBNA1 cells," in Expression Systems: Methods Express, Dyson, M.R. et al. eds., Scion Publishing Ltd.: Oxfordshire, pp. 204-223.
Troutman M.D. et al. (2003), "Novel Experimental Parameters to Quantify the Modulation of Absorptive and Secretory Transport of Compounds by P-Glycoprotein in Cell Culture Models of Intestinal Epithelium," Pharm. Res. 20(8):1210-1224.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Urlaub G. et al. (1980). "Isolation of Chinese hamster cell mutants deficient in dihydrofolate reductase activity," Proc. Natl. Acad. Sci. USA 77(7):4216-4220.
Urlaub G. et al. (1983). "Deletion of the Diploid Dihydrofolate Reductase Locus from Cultured Mammalian Cells," Cell 33(2):405-412.
Wang Y. et al. (2014). "Protease-Activatable Hybrid Nanoprobe for Tumor Imaging," Adv. Fund. Mater. 24(34):5443-5453.
Wiley S.R. et al. (2001). "A Novel TNF Receptor Family Member Binds TWEAK and is implicated in Angiogenesis," Immunity 15:837-846.
Wu W. et al. (2006). "Targeting Cell-Impermeable Prodrug Activation to Tumor Microenvironment Eradicates Multiple Drug-Resistant Neoplasms," Cancer Res. 66(2):970-980.
Wu, A. et al. (2005). "Arming antibodies: prospects and challenges for immunoconjugates," Nature Biotechnology 23(9): 1137-1146.
Zhou H. et al. (2011). "Development and Characterization of a Potent Immunoconjugate Targeting the Fn14 Receptor on Solid Tumor Cells," Mol Cancer Therapeutics 10(7):276-1288.
Zhou H. et al. (2012). "The TWEAK Receptor Fn14 is a Novel Therapeutic Target in Melanoma: Immunotoxins Targeting Fn14 Receptor for Malignant Melanoma Treatment," J. Invest Dermatol. 133(4):1052-1062.
Lerchen et al. Tailored Linker Chemistries for the Efficient and Selective Activation of ADCs with KSPi Payloads. Bioconjug Chem. 31(8):1893-1898 (2020).
Co-pending U.S. Appl. No. 17/733,760, inventors Lerchen; Hans-Georg et al., filed on Apr. 29, 2022.

(56) References Cited

OTHER PUBLICATIONS

Co-pending U.S. Appl. No. 17/812,095, inventors Lerchen; Hans-Georg et al., filed on Jul. 12, 2022.
U.S. Appl. No. 17/464,565 Office Action dated Apr. 20, 2022.

* cited by examiner

FIG. 1A

```
>TPP-981 VH (PRT)
QVQLKQSGPGLVQPSQSLSITCTVSGFSLTNYGVHWVRQSPGKGLEWLGVIWSGGNTDYNTPFTSRLSINKDNSKSQVFF
                            |---|                   |----HCDR2-----|
                            HCDR1

KMNSLQSNDTAIYYCARALTYYDYEFAYWGQGTLVTVSA
              |--HCDR3--|

>TPP-981 VL (PRT)
DILLTQSPVILSVSPGERVSFSCRASQSIGTNIHWYQQRTNGSPRLLIKYASESISGIPSRFSGSGSGTDFTLSINSVES
                     |--LCDR1--|                 |-----|
                                                   LCDR2

EDIADYYCQQNNNWPTTFGAGTKLELK
        |-LCDR3-|

>TPP-981 Heavy Chain (PRT)
QVQLKQSGPGLVQPSQSLSITCTVSGFSLTNYGVHWVRQSPGKGLEWLGVIWSGGNTDYNTPFTSRLSINKDNSKSQVFF
|-----------------------------------------------------------VH--------------------
                            |---|                   |----HCDR2-----|
                            HCDR1

KMNSLQSNDTAIYYCARALTYYDYEFAYWGQGTLVTVSAASTKGPSVFPLAPSSKSTSGGTAALGCLVKDYFPEPVTVSW
-----------------------------------|
              |--HCDR3--|

NSGALTSGVHTFPAVLQSSGLYSLSSVVTVPSSSLGTQTYICNVNHKPSNTKVDKRVEPKSCDKTHTCPPCPAPELLGGP

SVFLFPPKPKDTLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

>TPP-981 Light Chain (PRT)
DILLTQSPVILSVSPGERVSFSCRASQSIGTNIHWYQQRTNGSPRLLIKYASESISGIPSRFSGSGSGTDFTLSINSVES
|--------------------------------------------------VL--------------------------
                     |--LCDR1--|                 |-----|
                                                   LCDR2

EDIADYYCQQNNNWPTTFGAGTKLELKRTVAAPSVFIFPPSDEQLKSGTASVVCLLNNFYPREAKVQWKVDNALQSGNSQ
------------------------|
        |-LCDR3-|
```

FIG. 1B

```
ESVTEQDSKDSTYSLSSTLTLSKADYEKHKVYACEVTHQGLSSPVTKSFNRGEC

>TPP-1015 VH (PRT)
EVQLVESGGGLVQPGGSLRLSCAASGFNIKDTYIHWVRQAPGKGLEWVARIYPTNGYTRYADSVKGRFTISADTSKNTAY
                         |---|                  |-----HCDR2-----|
                         HCDR1

LQMNSLRAEDTAVYYCSRWGGDGFYAMDYWGQGTLVTVSS
              |--HCDR3--|

>TPP-1015 VL (PRT)
DIQMTQSPSSLSASVGDRVTITCRASQDVNTAVAWYQQKPGKAPKLLIYSASFLYSGVPSRFSGSRSGTDFTLTISSLQP
                   |--LCDR1--|              |-----|
                                              LCDR2

EDFATYYCQQHYTTPPTFGQGTKVEIK
        |-LCDR3-|

>TPP-1015 Heavy Chain (PRT)
EVQLVESGGGLVQPGGSLRLSCAASGFNIKDTYIHWVRQAPGKGLEWVARIYPTNGYTRYADSVKGRFTISADTSKNTAY
|------------------------------------------------------------VH------------------
                         |---|                  |-----HCDR2-----|
                         HCDR1

LQMNSLRAEDTAVYYCSRWGGDGFYAMDYWGQGTLVTVSSASTKGPSVFPLAPSSKSTSGGTAALGCLVKDYFPEPVTVS
--------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

>TPP-1015 Light Chain (PRT)
DIQMTQSPSSLSASVGDRVTITCRASQDVNTAVAWYQQKPGKAPKLLIYSASFLYSGVPSRFSGSRSGTDFTLTISSLQP
|--------------------------------------------------VL--------------------------
                   |--LCDR1--|              |-----|
                                              LCDR2
```

FIG. 1C

```
EDFATYYCQQHYTTPPTFGQGTKVEIKRTVAAPSVFIFPPSDEQLKSGTASVVCLLNNFYPREAKVQWKVDNALQSGNSQ
------------------------|
         |-LCDR3-|

ESVTEQDSKDSTYSLSSTLTLSKADYEKHKVYACEVTHQGLSSPVTKSFNRGEC

>TPP-6013 VH (PRT)
QVQLQESGPGLVKPSQSLSLTCSVTDYSITSGYYWNWIRQFPGNKLEWMGYISYDGSNNYNPSLKNRISITRDTSKNQFF
                            |----|             |----HCDR2-----|
                            HCDR1

LKLSSVTTEDTATYYCSRGEGFYFDSWGQGTTLTVSS
              |------|
              HCDR3

>TPP-6013 VL (PRT)
DIMMSQSPSSLAVSVGEKFTMTCKSSQSLFFGSTQKNYLAWYQQKPGQSPKLLIYWASTRESGVPDRFTGSGSGTDFTLA
                |-----LCDR1-----|              |-----|
                                                  LCDR2

ISSVMPEDLAVYYCQQYYNYPWTFGGGTKLEIK
            |-LCDR3-|

>TPP-6013 Heavy Chain (PRT)
QVQLQESGPGLVKPSQSLSLTCSVTDYSITSGYYWNWIRQFPGNKLEWMGYISYDGSNNYNPSLKNRISITRDTSKNQFF
|-----------------------------------------------------VH--------------------
                            |----|             |----HCDR2-----|
                            HCDR1

LKLSSVTTEDTATYYCSRGEGFYFDSWGQGTTLTVSSASTKGPSVFPLAPSSKSTSGGTAALGCLVKDYFPEPVTVSWNS
----------------------------------|
              |------|
              HCDR3

GALTSGVHTFPAVLQSSGLYSLSSVVTVPSSSLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

>TPP-6013 Light Chain (PRT)
DIMMSQSPSSLAVSVGEKFTMTCKSSQSLFFGSTQKNYLAWYQQKPGQSPKLLIYWASTRESGVPDRFTGSGSGTDFTLA
|---------------------------------------------------------VL-----------------
```

FIG. 1D

```
                        |-----LCDR1-----|              |-----|
                                                       LCDR2

ISSVMPEDLAVYYCQQYYNYPWTFGGGTKLEIKRTVAAPSVFIFPPSDEQLKSGTASVVCLLNNFYPREAKVQWKVDNAL
------------------------------|
             |-LCDR3-|

QSGNSQESVTEQDSKDSTYSLSSTLTLSKADYEKHKVYACEVTHQGLSSPVTKSFNRGEC

>TPP-7006 VH (PRT)
QVQLQQSGPELVKPGASVKMSCKASGYTFTDFIIAWVKQRTGQGLEWIGEIYPGTGRTYYSEKFRGKATLTADKSSNTAY
                           |---|                |-----HCDR2-----|
                           HCDR1

MQLSSLTSVDSAVYFCARRTIYYDYDGDYWGQGTTLTVSS
             |--HCDR3--|

>TPP-7006 VL (PRT)
DIVMTQAAFSNPVTLGTSASISCRSSKSLLHSNGITYLYWYLQKPGQSPQLLIYQMSNLASGVPDRFSSSGSGTDFTLRI
                |----LCDR1-----|                    |-----|
                                                     LCDR2

SRVEAEDVGVYYCAHNLELPWTFGGGTKLELK
         |-LCDR3-|

>TPP-7006 Heavy Chain (PRT)
QVQLQQSGPELVKPGASVKMSCKASGYTFTDFIIAWVKQRTGQGLEWIGEIYPGTGRTYYSEKFRGKATLTADKSSNTAY
|------------------------------------------------------------VH-------------------
                           |---|                |-----HCDR2-----|
                           HCDR1

MQLSSLTSVDSAVYFCARRTIYYDYDGDYWGQGTTLTVSSASTKGPSVFPLAPSSKSTSGGTAALGCLVKDYFPEPVTVS
--------------------------------------|
             |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

FIG. 1E

```
>TPP-7006 Light Chain (PRT)
DIVMTQAAFSNPVTLGTSASISCRSSKSLLHSNGITYLYWYLQKPGQSPQLLIYQMSNLASGVPDRFSSSGSGTDFTLRI
|----------------------------------------------------------VL-----------------------
                         |----LCDR1-----|                   |-----|
                                                             LCDR2

SRVEAEDVGVYYCAHNLELPWTFGGGTKLELKRTVAAPSVFIFPPSDEQLKSGTASVVCLLNNFYPREAKVQWKVDNALQ
-----------------------------|
         |-LCDR3-|

SGNSQESVTEQDSKDSTYSLSSTLTLSKADYEKHKVYACEVTHQGLSSPVTKSFNRGEC

>TPP-7007 VH (PRT)
QVQLVQSGAEVKKPGASVKVSCKASGYTFTDFIIAWVKQAPGQGLEWIGEIYPGTGRTYYSEKFRGKATLTADTSTSTAY
                         |---|                 |-----HCDR2-----|
                         HCDR1

MELSSLRSEDTAVYFCARRTIYYDYDGDYWGQGTLVTVSS
              |--HCDR3--|

>TPP-7007 VL (PRT)
DIVMTQSPLSLPVTPGEPASISCRSSKSLLHSNGITYLYWYLQKPGQSPQLLIYQMSNLASGVPDRFSGSGSGTDFTLKI
                         |----LCDR1-----|                   |-----|
                                                             LCDR2

SRVEAEDVGVYYCAHNLELPWTFGQGTKVEIK
         |-LCDR3-|

>TPP-7007 Heavy Chain (PRT)
QVQLVQSGAEVKKPGASVKVSCKASGYTFTDFIIAWVKQAPGQGLEWIGEIYPGTGRTYYSEKFRGKATLTADTSTSTAY
|--------------------------------------------------------------VH-------------------
                         |---|                 |-----HCDR2-----|
                         HCDR1

MELSSLRSEDTAVYFCARRTIYYDYDGDYWGQGTLVTVSSASTKGPSVFPLAPSSKSTSGGTAALGCLVKDYFPEPVTVS
--------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

FIG. 1F

```
>TPP-7007 Light Chain (PRT)
DIVMTQSPLSLPVTPGEPASISCRSSKSLLHSNGITYLYWYLQKPGQSPQLLIYQMSNLASGVPDRFSGSGSGTDFTLKI
|----------------------------------------------------------VL----------------------
                    |----LCDR1-----|                  |-----|
                                                        LCDR2

SRVEAEDVGVYYCAHNLELPWTFGQGTKVEIKRTVAAPSVFIFPPSDEQLKSGTASVVCLLNNFYPREAKVQWKVDNALQ
------------------------------|
          |-LCDR3-|

SGNSQESVTEQDSKDSTYSLSSTLTLSKADYEKHKVYACEVTHQGLSSPVTKSFNRGEC

>TPP-8382 VH (PRT)
EVQLLESGGGLVQPGGSLRLSCAASGFTFSSYAMSWVRQAPGKGLEWVSSISGSGGSTLYADSVKGRFTISRDNSKNTLY
                          |---|             |-----HCDR2-----|
                          HCDR1

LQMNSLRAEDTAVYYCAKLTGTSFDYWGQGTLVTVSS
              |------|
              HCDR3

>TPP-8382 VL (PRT)
QSVLTQPPSASGTPGQRVTISCSGSSSNIGSNPVNWYQQLPGTAPKLLIYSNNQRPSGVPDRFSGSKSGTSASLAITGLQ
                     |---LCDR1---|                |-----|
                                                    LCDR2

SEDEADYYCQSFDSSLKKVFGGGTKLTVL
        |-LCDR3--|

>TPP-8382 Heavy Chain (PRT)
EVQLLESGGGLVQPGGSLRLSCAASGFTFSSYAMSWVRQAPGKGLEWVSSISGSGGSTLYADSVKGRFTISRDNSKNTLY
|---------------------------------------------------------VH--------------------
                          |---|             |-----HCDR2-----|
                          HCDR1

LQMNSLRAEDTAVYYCAKLTGTSFDYWGQGTLVTVSSASTKGPSVFPLAPSSKSTSGGTAALGCLVKDYFPEPVTVSWNS
-----------------------------------|
              |------|
              HCDR3

GALTSGVHTFPAVLQSSGLYSLSSVVTVPSSSLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG
```

FIG. 1G

```
>TPP-8382 Light Chain (PRT)
QSVLTQPPSASGTPGQRVTISCSGSSSNIGSNPVNWYQQLPGTAPKLLIYSNNQRPSGVPDRFSGSKSGTSASLAITGLQ
|----------------------------------------------------VL------------------------
                       |---LCDR1---|                 |-----|
                                                      LCDR2

SEDEADYYCQSFDSSLKKVFGGGTKLTVLGQPKAAPSVTLFPPSSEELQANKATLVCLISDFYPGAVTVAWKADSSPVKA
---------------------------|
        |-LCDR3--|

GVETTTPSKQSNNKYAASSYLSLTPEQWKSHRSYSCQVTHEGSTVEKTVAPTECS

>TPP-8987 VH (PRT)
QVQLVQSGAEVKKPGSSVKVSCKASGGTFSDYYMKWVRQAPGQGLEWMGDIIPSNGATFYNQKFKGQVTITADESTSTAY
                            |---|                |-----HCDR2-----|
                            HCDR1

MELSSLRSEDTAVYYCARSHLLRASWFAYWGQGTLVTVSS
              |--HCDR3--|

>TPP-8987 VL (PRT)
DIVMTQSPDSLAVSLGERATINCESSQSVLNSGNQKNYLTWYQQKPGQPPKLLIYWASTRESGVPDRFSGSGSGTDFTLT
                    |-----LCDR1-----|              |-----|
                                                     LCDR2

ISSLQAEDVAVYYCQNDYSYPYTFGQGTKLEIK
            |-LCDR3-|

>TPP-8987 Heavy Chain (PRT)
QVQLVQSGAEVKKPGSSVKVSCKASGGTFSDYYMKWVRQAPGQGLEWMGDIIPSNGATFYNQKFKGQVTITADESTSTAY
|--------------------------------------------------------VH------------------
                            |---|                |-----HCDR2-----|
                            HCDR1

MELSSLRSEDTAVYYCARSHLLRASWFAYWGQGTLVTVSSASTKGPSVFPLAPSSKSTSGGTAALGCLVKDYFPEPVTVS
--------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV
```

FIG. 1H

```
LDSDGSFFLYSKLTVDKSRWQQGNVFSCSVMHEALHNHYTQKSLSLSPG

>TPP-8987 Light Chain (PRT)
DIVMTQSPDSLAVSLGERATINCESSQSVLNSGNQKNYLTWYQQKPGQPPKLLIYWASTRESGVPDRFSGSGSGTDFTLT
|--------------------------------------------------------VL----------------------
                  |-----LCDR1-----|                   |-----|
                                                       LCDR2

ISSLQAEDVAVYYCQNDYSYPYTFGQGTKLEIKRTVAAPSVFIFPPSDEQLKSGTASVVCLLNNFYPREAKVQWKVDNAL
------------------------------|
            |-LCDR3-|

QSGNSQESVTEQDSKDSTYSLSSTLTLSKADYEKHKVYACEVTHQGLSSPVTKSFNRGEC

>TPP-8988 VH (PRT)
EVQLLESGGGLVQPGGSLRLSCAVSDYSITSGYYWNWIRQAPGKKLEWMGYISYDGSNNYNPSLKNGRITISRDTSKNTF
                            |----|              |-----HCDR2-----|
                            HCDR1

YLQMNSLRAEDTAVYYCARGEGFYFDSWGQGTLVTVSS
                |------|
                HCDR3

>TPP-8988 VL (PRT)
EIVLTQSPGTLSLSPGERATLSCKSSQSLFFGSTQKNYLAWYQQKPGQAPRLLIYWASTRESGIPDRFSGSGSGTDFTLT
                  |-----LCDR1-----|                   |-----|
                                                       LCDR2

ISRLEPEDFAVYYCQQYYNYPWTFGQGTKLEIK
            |-LCDR3-|

>TPP-8988 Heavy Chain (PRT)
EVQLLESGGGLVQPGGSLRLSCAVSDYSITSGYYWNWIRQAPGKKLEWMGYISYDGSNNYNPSLKNGRITISRDTSKNTF
|---------------------------------------------------------VH-------------------
                            |----|              |-----HCDR2-----|
                            HCDR1

YLQMNSLRAEDTAVYYCARGEGFYFDSWGQGTLVTVSSASTKGPSVFPLAPSSKSTSGGTAALGCLVKDYFPEPVTVSWN
------------------------------------|
                |------|
                HCDR3

SGALTSGVHTFPAVLQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWESNGQPENNYKTTPPVLD
```

FIG. 1I

```
SDGSFFLYSKLTVDKSRWQQGNVFSCSVMHEALHNHYTQKSLSLSPG

>TPP-8988 Light Chain (PRT)
EIVLTQSPGTLSLSPGERATLSCKSSQSLFFGSTQKNYLAWYQQKPGQAPRLLIYWASTRESGIPDRFSGSGSGTDFTLT
|---------------------------------------------------VL----------------------
                    |-----LCDR1-----|               |-----|
                                                     LCDR2

ISRLEPEDFAVYYCQQYYNYPWTFGQGTKLEIKRTVAAPSVFIFPPSDEQLKSGTASVVCLLNNFYPREAKVQWKVDNAL
------------------------------|
            |-LCDR3-|

QSGNSQESVTEQDSKDSTYSLSSTLTLSKADYEKHKVYACEVTHQGLSSPVTKSFNRGEC

>TPP-9476 VH (PRT)
QVQLVQSGAEVKKPGSSVKVSCKASGGTFSDYYMKWVRQAPGQGLEWMGDIIPSNGATFYNQKFKGRVTITADESTSTAY
                        |---|                 |-----HCDR2-----|
                        HCDR1

MELSSLRSEDTAVYYCARSHLLRASWFAYWGQGTLVTVSS
              |--HCDR3--|

>TPP-9476 VL (PRT)
DIVMTQSPDSLAVSLGERATINCESSQSVLNSGNQKNYLTWYQQKPGQPPKLLIYWASTRESGVPDRFSGSGSGTDFTLT
                    |-----LCDR1-----|               |-----|
                                                     LCDR2

ISSLQAEDVAVYYCQNDYSYPYTFGQGTKLEIK
          |-LCDR3-|

>TPP-9476 Heavy Chain (PRT)
QVQLVQSGAEVKKPGSSVKVSCKASGGTFSDYYMKWVRQAPGQGLEWMGDIIPSNGATFYNQKFKGRVTITADESTSTAY
|-------------------------------------------------------VH------------------
                        |---|                 |-----HCDR2-----|
                        HCDR1

MELSSLRSEDTAVYYCARSHLLRASWFAYWGQGTLVTVSSASTKGPSVFPLAPSSKSTSGGTAALGCLVKDYFPEPVTVS
--------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV
```

FIG. 1J

```
LDSDGSFFLYSKLTVDKSRWQQGNVFSCSVMHEALHNHYTQKSLSLSPG

>TPP-9476 Light Chain (PRT)
DIVMTQSPDSLAVSLGERATINCESSQSVLNSGNQKNYLTWYQQKPGQPPKLLIYWASTRESGVPDRFSGSGSGTDFTLT
|--------------------------------------------------------VL----------------------
                        |-----LCDR1-----|                   |-----|
                                                             LCDR2

ISSLQAEDVAVYYCQNDYSYPYTFGQGTKLEIKRTVAAPSVFIFPPSDEQLKSGTASVVCLLNNFYPREAKVQWKVDNAL
-------------------------------|
            |-LCDR3-|

QSGNSQESVTEQDSKDSTYSLSSTLTLSKADYEKHKVYACEVTHQGLSSPVTKSFNRGEC

>TPP-9574 VH (PRT)
EVQLVESGGGLIQPGGSLRLSCAASGFTFSTSGMHWFRQAPGKGLEWVAYISSSSGFVYADAVKGRFTISRDNSKNTLYL
                            |---|                    |----HCDR2-----|
                            HCDR1

QMNSLRAEDTAVYYCARSEAAFWGQGTLVTVSS
              |---|
              HCDR3

>TPP-9574 VL (PRT)
DIVMTQSPLSLPVTPGEPASISCRSQKSRLSRMGITPLNWYLQKPGQSPQLLIYRMSNLASGVPDRFSGSGSGTDFTLKI
                        |----LCDR1-----|                   |-----|
                                                             LCDR2

SRVEAEDVGVYYCAQFLEYPPTFGQGTKLEIK
            |-LCDR3-|

>TPP-9574 Heavy Chain (PRT)
EVQLVESGGGLIQPGGSLRLSCAASGFTFSTSGMHWFRQAPGKGLEWVAYISSSSGFVYADAVKGRFTISRDNSKNTLYL
|---------------------------------------------------------VH----------------------
                            |---|                    |----HCDR2-----|
                            HCDR1

QMNSLRAEDTAVYYCARSEAAFWGQGTLVTVSSASTKGPSVFPLAPSSKSTSGGTAALGCLVKDYFPEPVTVSWNSGALT
-------------------------------|
              |---|
              HCDR3

SGVHTFPAVLQSSGLYSLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYPSDIAVEWESNGQPENNYKTTPPVLDSDGSF
```

FIG. 1K

```
FLYSKLTVDKSRWQQGNVFSCSVMHEALHNHYTQKSLSLSPG

>TPP-9574 Light Chain (PRT)
DIVMTQSPLSLPVTPGEPASISCRSQKSRLSRMGITPLNWYLQKPGQSPQLLIYRMSNLASGVPDRFSGSGSGTDFTLKI
|--------------------------------------------------------VL----------------------
                   |----LCDR1-----|                     |-----|
                                                         LCDR2

SRVEAEDVGVYYCAQFLEYPPTFGQTKLEIKRTVAAPSVFIFPPSDEQLKSGTASVVCLLNNFYPREAKVQWKVDNALQ
------------------------------|
            |-LCDR3-|

SGNSQESVTEQDSKDSTYSLSSTLTLSKADYEKHKVYACEVTHQGLSSPVTKSFNRGEC

>TPP-9580 VH (PRT)
EVQLVESGGGLIQPGGSLRLSCAASGFTFSTSGMHWVRQAPGKGLEWVSYISSSSGFVYADAVKGRFTISRDNSKNTLYL
                        |---|                 |----HCDR2-----|
                        HCDR1

QMNSLRAEDTAVYYCARSEAAFWGQGTLVTVSS
             |---|
             HCDR3

>TPP-9580 VL (PRT)
DIVMTQSPLSLPVTPGEPASISCRSQKSRLSRMGITPLNWYLQKPGQSPQLLIYRMSNLASGVPDRFSGSGSGTDFTLKI
                   |----LCDR1-----|                     |-----|
                                                         LCDR2

SRVEAEDVGVYYCAQFLEYPPTFGQTKLEIK
            |-LCDR3-|

>TPP-9580 Heavy Chain (PRT)
EVQLVESGGGLIQPGGSLRLSCAASGFTFSTSGMHWVRQAPGKGLEWVSYISSSSGFVYADAVKGRFTISRDNSKNTLYL
|---------------------------------------------------------VH----------------------
                        |---|                 |----HCDR2-----|
                        HCDR1

QMNSLRAEDTAVYYCARSEAAFWGQGTLVTVSSASTKGPSVFPLAPSSKSTSGGTAALGCLVKDYFPEPVTVSWNSGALT
-------------------------------|
             |---|
             HCDR3

SGVHTFPAVLQSSGLYSLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYPSDIAVEWESNGQPENNYKTTPPVLDSDGSF
```

FIG. 1L

```
FLYSKLTVDKSRWQQGNVFSCSVMHEALHNHYTQKSLSLSPG

>TPP-9580 Light Chain (PRT)
DIVMTQSPLSLPVTPGEPASISCRSQKSRLSRMGITPLNWYLQKPGQSPQLLIYRMSNLASGVPDRFSGSGSGTDFTLKI
|-----------------------------------------------------VL----------------------
                  |----LCDR1-----|                 |-----|
                                                    LCDR2

SRVEAEDVGVYYCAQFLEYPPTFGQGTKLEIKRTVAAPSVFIFPPSDEQLKSGTASVVCLLNNFYPREAKVQWKVDNALQ
------------------------------|
         |-LCDR3-|

SGNSQESVTEQDSKDSTYSLSSTLTLSKADYEKHKVYACEVTHQGLSSPVTKSFNRGEC
```

FIG. 2A

<SEQ ID NO:1>
QVQLKQSGPGLVQPSQSLSITCTVSGFSLTNYGVHWVRQSPGKGLEWLGVIWSGGNTDYNTPFTSR
LSINKDNSKSQVFFKMNSLQSNDTAIYYCARALTYYDYEFAYWGQGTLVTVSA

<SEQ ID NO:2>
NYGVH

<SEQ ID NO:3>
VIWSGGNTDYNTPFTS

<SEQ ID NO:4>
ALTYYDYEFAY

<SEQ ID NO:5>
DILLTQSPVILSVSPGERVSFSCRASQSIGTNIHWYQQRTNGSPRLLIKYASESISGIPSRFSGSG
SGTDFTLSINSVESEDIADYYCQQNNNWPTTFGAGTKLELK

<SEQ ID NO:6>
RASQSIGTNIH

<SEQ ID NO:7>
YASESIS

<SEQ ID NO:8>
QQNNNWPTT

<SEQ ID NO:9>
QVQLKQSGPGLVQPSQSLSITCTVSGFSLTNYGVHWVRQSPGKGLEWLGVIWSGGNTDYNTPFTSR
LSINKDNSKSQVFFKMNSLQSNDTAIYYCARALTYYDYEFAYWGQGTLVTVSAASTKGPSVFPLAP
SSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

<SEQ ID NO:10>
DILLTQSPVILSVSPGERVSFSCRASQSIGTNIHWYQQRTNGSPRLLIKYASESISGIPSRFSGSG
SGTDFTLSINSVESEDIADYYCQQNNNWPTTFGAGTKLELKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC

FIG. 2B

```
<SEQ ID NO:11>
EVQLVESGGGLVQPGGSLRLSCAASGFNIKDTYIHWVRQAPGKGLEWVARIYPTNGYTRYADSVKG
RFTISADTSKNTAYLQMNSLRAEDTAVYYCSRWGGDGFYAMDYWGQGTLVTVSS

<SEQ ID NO:12>
DTYIH

<SEQ ID NO:13>
RIYPTNGYTRYADSVKG

<SEQ ID NO:14>
WGGDGFYAMDY

<SEQ ID NO:15>
DIQMTQSPSSLSASVGDRVTITCRASQDVNTAVAWYQQKPGKAPKLLIYSASFLYSGVPSRFSGSR
SGTDFTLTISSLQPEDFATYYCQQHYTTPPTFGQGTKVEIK

<SEQ ID NO:16>
RASQDVNTAVA

<SEQ ID NO:17>
SASFLYS

<SEQ ID NO:18>
QQHYTTPPT

<SEQ ID NO:19>
EVQLVESGGGLVQPGGSLRLSCAASGFNIKDTYIHWVRQAPGKGLEWVARIYPTNGYTRYADSVKG
RFTISADTSKNTAYLQMNSLRAEDTAVYYCSRWGGDGFYAMDYWGQGTLVTVSSASTKGPSVFPLA
PSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK

<SEQ ID NO:20>
DIQMTQSPSSLSASVGDRVTITCRASQDVNTAVAWYQQKPGKAPKLLIYSASFLYSGVPSRFSGSR
SGTDFTLTISSLQPEDFATYYCQQHYTTPPTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC

<SEQ ID NO:21>
QVQLQESGPGLVKPSQSLSLTCSVTDYSITSGYYWNWIRQFPGNKLEWMGYISYDGSNNYNPSLKN
RISITRDTSKNQFFLKLSSVTTEDTATYYCSRGEGFYFDSWGQGTTLTVSS

<SEQ ID NO:22>
SGYYWN

<SEQ ID NO:23>
YISYDGSNNYNPSLKN
```

FIG. 2C

<SEQ ID NO:24>
GEGFYFDS

<SEQ ID NO:25>
DIMMSQSPSSLAVSVGEKFTMTCKSSQSLFFGSTQKNYLAWYQQKPGQSPKLLIYWASTRESGVPD
RFTGSGSGTDFTLAISSVMPEDLAVYYCQQYYNYPWTFGGGTKLEIK

<SEQ ID NO:26>
KSSQSLFFGSTQKNYLA

<SEQ ID NO:27>
WASTRES

<SEQ ID NO:28>
QQYYNYPWT

<SEQ ID NO:29>
QVQLQESGPGLVKPSQSLSLTCSVTDYSITSGYYWNWIRQFPGNKLEWMGYISYDGSNNYNPSLKN
RISITRDTSKNQFFLKLSSVTTEDTATYYCSRGEGFYFDSWGQGTTLTVSSASTKGPSVFPLAPSS
KSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG

<SEQ ID NO:30>
DIMMSQSPSSLAVSVGEKFTMTCKSSQSLFFGSTQKNYLAWYQQKPGQSPKLLIYWASTRESGVPD
RFTGSGSGTDFTLAISSVMPEDLAVYYCQQYYNYPWTFGGGTKLEIKRTVAAPSVFIFPPSDEQLK
SGTASVVCLLNNFYPREAKVQWKVDNALQSGNSQESVTEQDSKDSTYSLSSTLTLSKADYEKHKVY
ACEVTHQGLSSPVTKSFNRGEC

<SEQ ID NO:31>
QVQLQQSGPELVKPGASVKMSCKASGYTFTDFIIAWVKQRTGQGLEWIGEIYPGTGRTYYSEKFRG
KATLTADKSSNTAYMQLSSLTSVDSAVYFCARRTIYYDYDGDYWGQGTTLTVSS

<SEQ ID NO:32>
DFIIA

<SEQ ID NO:33>
EIYPGTGRTYYSEKFRG

<SEQ ID NO:34>
RTIYYDYDGDY

<SEQ ID NO:35>
DIVMTQAAFSNPVTLGTSASISCRSSKSLLHSNGITYLYWYLQKPGQSPQLLIYQMSNLASGVPDR
FSSSGSGTDFTLRISRVEAEDVGVYYCAHNLELPWTFGGGTKLELK

<SEQ ID NO:36>
RSSKSLLHSNGITYLY

FIG. 2D

<SEQ ID NO:37>
QMSNLAS

<SEQ ID NO:38>
AHNLELPWT

<SEQ ID NO:39>
QVQLQQSGPELVKPGASVKMSCKASGYTFTDFIIAWVKQRTGQGLEWIGEIYPGTGRTYYSEKFRG
KATLTADKSSNTAYMQLSSLTSVDSAVYFCARRTIYYDYDGDYWGQGTTLTVSSASTKGPSVFPLA
PSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPG

<SEQ ID NO:40>
DIVMTQAAFSNPVTLGTSASISCRSSKSLLHSNGITYLYWYLQKPGQSPQLLIYQMSNLASGVPDR
FSSSGSGTDFTLRISRVEAEDVGVYYCAHNLELPWTFGGGTKLELKRTVAAPSVFIFPPSDEQLKS
GTASVVCLLNNFYPREAKVQWKVDNALQSGNSQESVTEQDSKDSTYSLSSTLTLSKADYEKHKVYA
CEVTHQGLSSPVTKSFNRGEC

<SEQ ID NO:41>
QVQLVQSGAEVKKPGASVKVSCKASGYTFTDFIIAWVKQAPGQGLEWIGEIYPGTGRTYYSEKFRG
KATLTADTSTSTAYMELSSLRSEDTAVYFCARRTIYYDYDGDYWGQGTLVTVSS

<SEQ ID NO:42>
DFIIA

<SEQ ID NO:43>
EIYPGTGRTYYSEKFRG

<SEQ ID NO:44>
RTIYYDYDGDY

<SEQ ID NO:45>
DIVMTQSPLSLPVTPGEPASISCRSSKSLLHSNGITYLYWYLQKPGQSPQLLIYQMSNLASGVPDR
FSGSGSGTDFTLKISRVEAEDVGVYYCAHNLELPWTFGQGTKVEIK

<SEQ ID NO:46>
RSSKSLLHSNGITYLY

<SEQ ID NO:47>
QMSNLAS

<SEQ ID NO:48>
AHNLELPWT

<SEQ ID NO:49>
QVQLVQSGAEVKKPGASVKVSCKASGYTFTDFIIAWVKQAPGQGLEWIGEIYPGTGRTYYSEKFRG
KATLTADTSTSTAYMELSSLRSEDTAVYFCARRTIYYDYDGDYWGQGTLVTVSSASTKGPSVFPLA
PSSKSTSGGTAALGCLVKDYFPEPVTVSWNSGALTSGVHTFPAVLQSSGLYSLSSVVTVPSSSLGT

FIG. 2E

QTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPG

<SEQ ID NO:50>
DIVMTQSPLSLPVTPGEPASISCRSSKSLLHSNGITYLYWYLQKPGQSPQLLIYQMSNLASGVPDR
FSGSGSGTDFTLKISRVEAEDVGVYYCAHNLELPWTFGQGTKVEIKRTVAAPSVFIFPPSDEQLKS
GTASVVCLLNNFYPREAKVQWKVDNALQSGNSQESVTEQDSKDSTYSLSSTLTLSKADYEKHKVYA
CEVTHQGLSSPVTKSFNRGEC

<SEQ ID NO:51>
EVQLLESGGGLVQPGGSLRLSCAASGFTFSSYAMSWVRQAPGKGLEWVSSISGSGGSTLYADSVKG
RFTISRDNSKNTLYLQMNSLRAEDTAVYYCAKLTGTSFDYWGQGTLVTVSS

<SEQ ID NO:52>
SYAMS

<SEQ ID NO:53>
SISGSGGSTLYADSVKG

<SEQ ID NO:54>
LTGTSFDY

<SEQ ID NO:55>
QSVLTQPPSASGTPGQRVTISCSGSSSNIGSNPVNWYQQLPGTAPKLLIYSNNQRPSGVPDRFSGS
KSGTSASLAITGLQSEDEADYYCQSFDSSLKKVFGGGTKLTVL

<SEQ ID NO:56>
SGSSSNIGSNPVN

<SEQ ID NO:57>
SNNQRPS

<SEQ ID NO:58>
QSFDSSLKKV

<SEQ ID NO:59>
EVQLLESGGGLVQPGGSLRLSCAASGFTFSSYAMSWVRQAPGKGLEWVSSISGSGGSTLYADSVKG
RFTISRDNSKNTLYLQMNSLRAEDTAVYYCAKLTGTSFDYWGQGTLVTVSSASTKGPSVFPLAPSS
KSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG

<SEQ ID NO:60>
QSVLTQPPSASGTPGQRVTISCSGSSSNIGSNPVNWYQQLPGTAPKLLIYSNNQRPSGVPDRFSGS
KSGTSASLAITGLQSEDEADYYCQSFDSSLKKVFGGGTKLTVLGQPKAAPSVTLFPPSSEELQANK
ATLVCLISDFYPGAVTVAWKADSSPVKAGVETTTPSKQSNNKYAASSYLSLTPEQWKSHRSYSCQV
THEGSTVEKTVAPTECS

FIG. 2F

<SEQ ID NO:61>
QVQLVQSGAEVKKPGSSVKVSCKASGGTFSDYYMKWVRQAPGQGLEWMGDIIPSNGATFYNQKFKG
QVTITADESTSTAYMELSSLRSEDTAVYYCARSHLLRASWFAYWGQGTLVTVSS

<SEQ ID NO:62>
DYYMK

<SEQ ID NO:63>
DIIPSNGATFYNQKFKG

<SEQ ID NO:64>
SHLLRASWFAY

<SEQ ID NO:65>
DIVMTQSPDSLAVSLGERATINCESSQSVLNSGNQKNYLTWYQQKPGQPPKLLIYWASTRESGVPD
RFSGSGSGTDFTLTISSLQAEDVAVYYCQNDYSYPYTFGQGTKLEIK

<SEQ ID NO:66>
ESSQSVLNSGNQKNYLT

<SEQ ID NO:67>
WASTRES

<SEQ ID NO:68>
QNDYSYPYT

<SEQ ID NO:69>
QVQLVQSGAEVKKPGSSVKVSCKASGGTFSDYYMKWVRQAPGQGLEWMGDIIPSNGATFYNQKFKG
QVTITADESTSTAYMELSSLRSEDTAVYYCARSHLLRASWFAYWGQGTLVTVSSASTKGPSVFPLA
PSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPG

<SEQ ID NO:70>
DIVMTQSPDSLAVSLGERATINCESSQSVLNSGNQKNYLTWYQQKPGQPPKLLIYWASTRESGVPD
RFSGSGSGTDFTLTISSLQAEDVAVYYCQNDYSYPYTFGQGTKLEIKRTVAAPSVFIFPPSDEQLK
SGTASVVCLLNNFYPREAKVQWKVDNALQSGNSQESVTEQDSKDSTYSLSSTLTLSKADYEKHKVY
ACEVTHQGLSSPVTKSFNRGEC

<SEQ ID NO:71>
EVQLLESGGGLVQPGGSLRLSCAVSDYSITSGYYWNWIRQAPGKKLEWMGYISYDGSNNYNPSLKN
GRITISRDTSKNTFYLQMNSLRAEDTAVYYCARGEGFYFDSWGQGTLVTVSS

<SEQ ID NO:72>
SGYYWN

<SEQ ID NO:73>
YISYDGSNNYNPSLKNG

FIG. 2G

<SEQ ID NO:74>
GEGFYFDS

<SEQ ID NO:75>
EIVLTQSPGTLSLSPGERATLSCKSSQSLFFGSTQKNYLAWYQQKPGQAPRLLIYWASTRESGIPD
RFSGSGSGTDFTLTISRLEPEDFAVYYCQQYYNYPWTFGQGTKLEIK

<SEQ ID NO:76>
KSSQSLFFGSTQKNYLA

<SEQ ID NO:77>
WASTRES

<SEQ ID NO:78>
QQYYNYPWT

<SEQ ID NO:79>
EVQLLESGGGLVQPGGSLRLSCAVSDYSITSGYYWNWIRQAPGKKLEWMGYISYDGSNNYNPSLKN
GRITISRDTSKNTFYLQMNSLRAEDTAVYYCARGEGFYFDSWGQGTLVTVSSASTKGPSVFPLAPS
SKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG

<SEQ ID NO:80>
EIVLTQSPGTLSLSPGERATLSCKSSQSLFFGSTQKNYLAWYQQKPGQAPRLLIYWASTRESGIPD
RFSGSGSGTDFTLTISRLEPEDFAVYYCQQYYNYPWTFGQGTKLEIKRTVAAPSVFIFPPSDEQLK
SGTASVVCLLNNFYPREAKVQWKVDNALQSGNSQESVTEQDSKDSTYSLSSTLTLSKADYEKHKVY
ACEVTHQGLSSPVTKSFNRGEC

<SEQ ID NO:81>
QVQLVQSGAEVKKPGSSVKVSCKASGGTFSDYYMKWVRQAPGQGLEWMGDIIPSNGATFYNQKFKG
RVTITADESTSTAYMELSSLRSEDTAVYYCARSHLLRASWFAYWGQGTLVTVSS

<SEQ ID NO:82>
DYYMK

<SEQ ID NO:83>
DIIPSNGATFYNQKFKG

<SEQ ID NO:84>
SHLLRASWFAY

<SEQ ID NO:85>
DIVMTQSPDSLAVSLGERATINCESSQSVLNSGNQKNYLTWYQQKPGQPPKLLIYWASTRESGVPD
RFSGSGSGTDFTLTISSLQAEDVAVYYCQNDYSYPYTFGQGTKLEIK

<SEQ ID NO:86>
ESSQSVLNSGNQKNYLT

FIG. 2H

<SEQ ID NO:87>
WASTRES

<SEQ ID NO:88>
QNDYSYPYT

<SEQ ID NO:89>
QVQLVQSGAEVKKPGSSVKVSCKASGGTFSDYYMKWVRQAPGQGLEWMGDIIPSNGATFYNQKFKG
RVTITADESTSTAYMELSSLRSEDTAVYYCARSHLLRASWFAYWGQGTLVTVSSASTKGPSVFPLA
PSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPG

<SEQ ID NO:90>
DIVMTQSPDSLAVSLGERATINCESSQSVLNSGNQKNYLTWYQQKPGQPPKLLIYWASTRESGVPD
RFSGSGSGTDFTLTISSLQAEDVAVYYCQNDYSYPYTFGQGTKLEIKRTVAAPSVFIFPPSDEQLK
SGTASVVCLLNNFYPREAKVQWKVDNALQSGNSQESVTEQDSKDSTYSLSSTLTLSKADYEKHKVY
ACEVTHQGLSSPVTKSFNRGEC

<SEQ ID NO:91>
EVQLVESGGGLIQPGGSLRLSCAASGFTFSTSGMHWFRQAPGKGLEWVAYISSSSGFVYADAVKGR
FTISRDNSKNTLYLQMNSLRAEDTAVYYCARSEAAFWGQGTLVTVSS

<SEQ ID NO:92>
TSGMH

<SEQ ID NO:93>
YISSSSGFVYADAVKG

<SEQ ID NO:94>
SEAAF

<SEQ ID NO:95>
DIVMTQSPLSLPVTPGEPASISCRSQKSRLSRMGITPLNWYLQKPGQSPQLLIYRMSNLASGVPDR
FSGSGSGTDFTLKISRVEAEDVGVYYCAQFLEYPPTFGQGTKLEIK

<SEQ ID NO:96>
RSQKSRLSRMGITPLN

<SEQ ID NO:97>
RMSNLAS

<SEQ ID NO:98>
AQFLEYPPT

<SEQ ID NO:99>
EVQLVESGGGLIQPGGSLRLSCAASGFTFSTSGMHWFRQAPGKGLEWVAYISSSSGFVYADAVKGR
FTISRDNSKNTLYLQMNSLRAEDTAVYYCARSEAAFWGQGTLVTVSSASTKGPSVFPLAPSSKSTS
GGTAALGCLVKDYFPEPVTVSWNSGALTSGVHTFPAVLQSSGLYSLSSVVTVPSSSLGTQTYICNV

FIG. 2I

NHKPSNTKVDKKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG

<SEQ ID NO:100>
DIVMTQSPLSLPVTPGEPASISCRSQKSRLSRMGITPLNWYLQKPGQSPQLLIYRMSNLASGVPDR
FSGSGSGTDFTLKISRVEAEDVGVYYCAQFLEYPPTFGQGTKLEIKRTVAAPSVFIFPPSDEQLKS
GTASVVCLLNNFYPREAKVQWKVDNALQSGNSQESVTEQDSKDSTYSLSSTLTLSKADYEKHKVYA
CEVTHQGLSSPVTKSFNRGEC

<SEQ ID NO:101>
EVQLVESGGGLIQPGGSLRLSCAASGFTFSTSGMHWVRQAPGKGLEWVSYISSSSGFVYADAVKGR
FTISRDNSKNTLYLQMNSLRAEDTAVYYCARSEAAFWGQGTLVTVSS

<SEQ ID NO:102>
TSGMH

<SEQ ID NO:103>
YISSSSGFVYADAVKG

<SEQ ID NO:104>
SEAAF

<SEQ ID NO:105>
DIVMTQSPLSLPVTPGEPASISCRSQKSRLSRMGITPLNWYLQKPGQSPQLLIYRMSNLASGVPDR
FSGSGSGTDFTLKISRVEAEDVGVYYCAQFLEYPPTFGQGTKLEIK

<SEQ ID NO:106>
RSQKSRLSRMGITPLN

<SEQ ID NO:107>
RMSNLAS

<SEQ ID NO:108>
AQFLEYPPT

<SEQ ID NO:109>
EVQLVESGGGLIQPGGSLRLSCAASGFTFSTSGMHWVRQAPGKGLEWVSYISSSSGFVYADAVKGR
FTISRDNSKNTLYLQMNSLRAEDTAVYYCARSEAAFWGQGTLVTVSSASTKGPSVFPLAPSSKSTS
GGTAALGCLVKDYFPEPVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG

<SEQ ID NO:110>
DIVMTQSPLSLPVTPGEPASISCRSQKSRLSRMGITPLNWYLQKPGQSPQLLIYRMSNLASGVPDR
FSGSGSGTDFTLKISRVEAEDVGVYYCAQFLEYPPTFGQGTKLEIKRTVAAPSVFIFPPSDEQLKS
GTASVVCLLNNFYPREAKVQWKVDNALQSGNSQESVTEQDSKDSTYSLSSTLTLSKADYEKHKVYA
CEVTHQGLSSPVTKSFNRGEC

FIG. 2J

<SEQ ID NO:111>
MVLLWLTLLLIALPCLLQTKEDPNPPITNLRMKAKAQQLTWDLNRNVTDIECVKDADYSMPAVNNS
YCQFGAISLCEVTNYTVRVANPPFSTWILFPENSGKPWAGAENLTCWIHDVDFLSCSWAVGPGAPA
DVQYDLYLNVANRRQQYECLHYKTDAQGTRIGCRFDDISRLSSGSQSSHILVRGRSAAFGIPCTDK
FVVFSQIEILTPPNMTAKCNKTHSFMHWKMRSHFNRKFRYELQIQKRMQPVITEQVRDRTSFQLLN
PGTYTVQIRARERVYEFLSAWSTPQRFECDQEEGANTRAWRTSLLIALGTLLALVCVFVICRRYLV
MQRLFPRIPHMKDPIGDSFQNDKLVVWEAGKAGLEECLVTEVQVVQKT

<SEQ ID NO:112>
MNYPLTLEMDLENLEDLFWELDRLDNYNDTSLVENHLCPATEGPLMASFKAVFVPVAYSLIFLLGV
IGNVLVLVILERHRQTRSSTETFLFHLAVADLLLVFILPFAVAEGSVGWVLGTFLCKTVIALHKVN
FYCSSLLLACIAVDRYLAIVHAVHAYRHRRLLSIHITCGTIWLVGFLLALPEILFAKVSQGHHNNS
LPRCTFSQENQAETHAWFTSRFLYHVAGFLLPMLVMGWCYVGVVHRLRQAQRRPQRQKAVRVAILV
TSIFFLCWSPYHIVIFLDTLARLKAVDNTCKLNGSLPVAITMCEFLGLAHCCLNPMLYTFAGVKFR
SDLSRLLTKLGCTGPASLCQLFPSWRRSSLSESENATSLTTF

<SEQ ID NO:113>
MLRRRGSPGMGVHVGAALGALWFCLTGALEVQVPEDPVVALVGTDATLCCSFSPEPGFSLAQLNLI
WQLTDTKQLVHSFAEGQDQGSAYANRTALFPDLLAQGNASLRLQRVRVADEGSFTCFVSIRDFGSA
AVSLQVAAPYSKPSMTLEPNKDLRPGDTVTITCSSYQGYPEAEVFWQDGQGVPLTGNVTTSQMANE
QGLFDVHSILRVVLGANGTYSCLVRNPVLQQDAHSSVTITPQRSPTGAVEVQVPEDPVVALVGTDA
TLRCSFSPEPGFSLAQLNLIWQLTDTKQLVHSFTEGRDQGSAYANRTALFPDLLAQGNASLRLQRV
RVADEGSFTCFVSIRDFGSAAVSLQVAAPYSKPSMTLEPNKDLRPGDTVTITCSSYRGYPEAEVFW
QDGQGVPLTGNVTTSQMANEQGLFDVHSVLRVVLGANGTYSCLVRNPVLQQDAHGSVTITGQPMTF
PPEALWVTVGLSVCLIALLVALAFVCWRKIKQSCEEENAGAEDQDGEGEGSKTALQPLKHSDSKED
DGQEIA

<SEQ ID NO:114>
MARGSLRRLLRLLVLGLWLALLRSVAGEQAPGTAPCSRGSSWSADLDKCMDCASCRARPHSDFCLG
CAAAPPAPFRLLWPILGGALSLTFVLGLLSGFLVWRRCRRREKFTTPIEETGGEGCPAVALIQ

<SEQ ID NO:115>
MELAALCRWGLLLALLPPGAASTQVCTGTDMKLRLPASPETHLDMLRHLYQGCQVVQGNLELTYLP
TNASLSFLQDIQEVQGYVLIAHNQVRQVPLQRLRIVRGTQLFEDNYALAVLDNGDPLNNTTPVTGA
SPGGLRELQLRSLTEILKGGVLIQRNPQLCYQDTILWKDIFHKNNQLALTLIDTNRSRACHPCSPM
CKGSRCWGESSEDCQSLTRTVCAGGCARCKGPLPTDCCHEQCAAGCTGPKHSDCLACLHFNHSGIC
ELHCPALVTYNTDTFESMPNPEGRYTFGASCVTACPYNYLSTDVGSCTLVCPLHNQEVTAEDGTQR
CEKCSKPCARVCYGLGMEHLREVRAVTSANIQEFAGCKKIFGSLAFLPESFDGDPASNTAPLQPEQ
LQVFETLEEITGYLYISAWPDSLPDLSVFQNLQVIRGRILHNGAYSLTLQGLGISWLGLRSLRELG
SGLALIHHNTHLCFVHTVPWDQLFRNPHQALLHTANRPEDECVGEGLACHQLCARGHCWGPGPTQC
VNCSQFLRGQECVEECRVLQGLPREYVNARHCLPCHPECQPQNGSVTCFGPEADQCVACAHYKDPP
FCVARCPSGVKPDLSYMPIWKFPDEEGACQPCPINCTHSCVDLDDKGCPAEQRASPLTSIISAVVG
ILLVVVLGVVFGILIKRRQQKIRKYTMRRLLQETELVEPLTPSGAMPNQAQMRILKETELRKVKVL
GSGAFGTVYKGIWIPDGENVKIPVAIKVLRENTSPKANKEILDEAYVMAGVGSPYVSRLLGICLTS
TVQLVTQLMPYGCLLDHVRENRGRLGSQDLLNWCMQIAKGMSYLEDVRLVHRDLAARNVLVKSPNH
VKITDFGLARLLDIDETEYHADGGKVPIKWMALESILRRRFTHQSDVWSYGVTVWELMTFGAKPYD
GIPAREIPDLLEKGERLPQPPICTIDVYMIMVKCWMIDSECRPRFRELVSEFSRMARDPQRFVVIQ
NEDLGPASPLDSTFYRSLLEDDDMGDLVDAEEYLVPQQGFFCPDPAPGAGGMVHHRHRSSSTRSGG
GDLTLGLEPSEEEAPRSPLAPSEGAGSDVFDGDLGMGAAKGLQSLPTHDPSPLQRYSEDPTVPLPS
ETDGYVAPLTCSPQPEYVNQPDVRPQPPSPREGPLPAARPAGATLERPKTLSPGKNGVVKDVFAFG

FIG. 2K

GAVENPEYLTPQGGAAPQPHPPPAFSPAFDNLYYWDQDPPERGAPPSTFKGTPTAENPEYLGLDVPV

<SEQ ID NO:116>
MRPSGTAGAALLALLAALCPASRALEEKKVCQGTSNKLTQLGTFEDHFLSLQRMFNNCEVVLGNLE
ITYVQRNYDLSFLKTIQEVAGYVLIALNTVERIPLENLQIIRGNMYYENSYALAVLSNYDANKTGL
KELPMRNLQEILHGAVRFSNNPALCNVESIQWRDIVSSDFLSNMSMDFQNHLGSCQKCDPSCPNGS
CWGAGEENCQKLTKIICAQQCSGRCRGKSPSDCCHNQCAAGCTGPRESDCLVCRKFRDEATCKDTC
PPLMLYNPTTYQMDVNPEGKYSFGATCVKKCPRNYVVTDHGSCVRACGADSYEMEEDGVRKCKKCE
GPCRKVCNGIGIGEFKDSLSINATNIKHFKNCTSISGDLHILPVAFRGDSFTHTPPLDPQELDILK
TVKEITGFLLIQAWPENRTDLHAFENLEIIRGRTKQHGQFSLAVVSLNITSLGLRSLKEISDGDVI
ISGNKNLCYANTINWKKLFGTSGQKTKIISNRGENSCKATGQVCHALCSPEGCWGPEPRDCVSCRN
VSRGRECVDKCNLLEGEPREFVENSECIQCHPECLPQAMNITCTGRGPDNCIQCAHYIDGPHCVKT
CPAGVMGENNTLVWKYADAGHVCHLCHPNCTYGCTGPGLEGCPTNGPKIPSIATGMVGALLLLVV
ALGIGLFMRRRHIVRKRTLRRLLQERELVEPLTPSGEAPNQALLRILKETEFKKIKVLGSGAFGTV
YKGLWIPEGEKVKIPVAIKELREATSPKANKEILDEAYVMASVDNPHVCRLLGICLTSTVQLITQL
MPFGCLLDYVREHKDNIGSQYLLNWCVQIAKGMNYLEDRRLVHRDLAARNVLVKTPQHVKITDFGL
AKLLGAEEKEYHAEGGKVPIKWMALESILHRIYTHQSDVWSYGVTVWELMTFGSKPYDGIPASEIS
SILEKGERLPQPPICTIDVYMIMVKCWMIDADSRPKFRELIIEFSKMARDPQRYLVIQGDERMHLP
SPTDSNFYRALMDEEDMDDVVDADEYLIPQQGFFSSPSTSRTPLLSSLSATSNNSTVACIDRNGLQ
SCPIKEDSFLQRYSSDPTGALTEDSIDDTFLPVPEYINQSVPKRPAGSVQNPVYHNQPLNPAPSRD
PHYQDPHSTAVGNPEYLNTVQPTCVNSTFDSPAHWAQKGSHQISLDNPDYQQDFFPKEAKPNGIFK
GSTAENAEYLRVAPQSSEFIGA

SEQUENCE LISTING

<160> NUMBER OF SEQ ID NOS: 116

<210> SEQ ID NO 1
<211> LENGTH: 119
<212> TYPE: PRT
<213> ORGANISM: Artificial Sequence
<220> FEATURE:
<223> OTHER INFORMATION: Antibody Sequence

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 2
<211> LENGTH: 5
<212> TYPE: PRT
<213> ORGANISM: Artificial Sequence
<220> FEATURE:
<223> OTHER INFORMATION: Antibody Sequence

<400> SEQUENCE: 2

Asn Tyr Gly Val His
1               5

<210> SEQ ID NO 3
<211> LENGTH: 16
<212> TYPE: PRT
<213> ORGANISM: Artificial Sequence
<220> FEATURE:
<223> OTHER INFORMATION: Antibody Sequence

<400> SEQUENCE: 3

Val Ile Trp Ser Gly Gly Asn Thr Asp Tyr Asn Thr Pro Phe Thr Ser
1               5                   10                  15

```
<210> SEQ ID NO 4
<211> LENGTH: 11
<212> TYPE: PRT
<213> ORGANISM: Artificial Sequence
<220> FEATURE:
<223> OTHER INFORMATION: Antibody Sequence

<400> SEQUENCE: 4

Ala Leu Thr Tyr Tyr Asp Tyr Glu Phe Ala Tyr
1               5                   10

<210> SEQ ID NO 5
<211> LENGTH: 107
<212> TYPE: PRT
<213> ORGANISM: Artificial Sequence
<220> FEATURE:
<223> OTHER INFORMATION: Antibody Sequence

<400> SEQUENCE: 5

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: Antibody Sequence

<400> SEQUENCE: 6

Arg Ala Ser Gln Ser Ile Gly Thr Asn Ile His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Antibody Sequence

<400> SEQUENCE: 7

Tyr Ala Ser Glu Ser Ile Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Antibody Sequence
```

<400> SEQUENCE: 8

Gln Gln Asn Asn Asn Trp Pro Thr Thr
1               5

<210> SEQ ID NO 9
<211> LENGTH: 449
<212> TYPE: PRT
<213> ORGANISM: Artificial Sequence
<220> FEATURE:
<223> OTHER INFORMATION: Antibody Sequence

<400> SEQUENCE: 9

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 10
<211> LENGTH: 214
<212> TYPE: PRT
<213> ORGANISM: Artificial Sequence
<220> FEATURE:
<223> OTHER INFORMATION: Antibody Sequence

<400> SEQUENCE: 10

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 120
<212> TYPE: PRT
```

```
<213> ORGANISM: Artificial Sequence
<220> FEATURE:
<223> OTHER INFORMATION: Antibody Sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 12
<211> LENGTH: 5
<212> TYPE: PRT
<213> ORGANISM: Artificial Sequence
<220> FEATURE:
<223> OTHER INFORMATION: Antibody Sequence

<400> SEQUENCE: 12

Asp Thr Tyr Ile His
1               5

<210> SEQ ID NO 13
<211> LENGTH: 17
<212> TYPE: PRT
<213> ORGANISM: Artificial Sequence
<220> FEATURE:
<223> OTHER INFORMATION: Antibody Sequence

<400> SEQUENCE: 13

Arg Ile Tyr Pro Thr Asn Gly Tyr Thr Arg Tyr Ala Asp Ser Val Lys
1               5                   10                  15

Gly

<210> SEQ ID NO 14
<211> LENGTH: 11
<212> TYPE: PRT
<213> ORGANISM: Artificial Sequence
<220> FEATURE:
<223> OTHER INFORMATION: Antibody Sequence

<400> SEQUENCE: 14

Trp Gly Gly Asp Gly Phe Tyr Ala Met Asp Tyr
1               5                   10

<210> SEQ ID NO 15
<211> LENGTH: 107
<212> TYPE: PRT
<213> ORGANISM: Artificial Sequence
<220> FEATURE:
<223> OTHER INFORMATION: Antibody Sequence
```

```
<400> SEQUENCE: 15

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 16
<211> LENGTH: 11
<212> TYPE: PRT
<213> ORGANISM: Artificial Sequence
<220> FEATURE:
<223> OTHER INFORMATION: Antibody Sequence

<400> SEQUENCE: 16

Arg Ala Ser Gln Asp Val Asn Thr Ala Val Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Antibody Sequence

<400> SEQUENCE: 17

Ser Ala Ser Phe Leu Tyr Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Antibody Sequence

<400> SEQUENCE: 18

Gln Gln His Tyr Thr Thr Pro Pro Thr
1               5

<210> SEQ ID NO 19
<211> LENGTH: 450
<212> TYPE: PRT
<213> ORGANISM: Artificial Sequence
<220> FEATURE:
<223> OTHER INFORMATION: Antibody Sequence

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

```
Tyr Ile His Trp Val Arg Gln Ala Pro Gly Lys Gly Leu Glu Trp Val
         35                  40                  45
Ala Arg Ile Tyr Pro Thr Asn Gly Tyr Thr Arg Tyr Ala Asp Ser Val
     50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
             100                 105                 110
Gly Thr Leu Val Thr Val Ser Ser Ala Ser Thr Lys Gly Pro Ser Val
         115                 120                 125
Phe Pro Leu Ala Pro Ser Ser Lys Ser Thr Ser Gly Gly Thr Ala Ala
     130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
         195                 200                 205
Pro Ser Asn Thr Lys Val Asp Lys Lys Val Glu Pro Lys Ser Cys Asp
     210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
         275                 280                 285
Asn Ala Lys Thr Lys Pro Arg Glu Glu Gln Tyr Asn Ser Thr Tyr Arg
     290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
             340                 345                 350
Thr Leu Pro Pro Ser Arg Glu Glu Met Thr Lys Asn Gln Val Ser Leu
         355                 360                 365
Thr Cys Leu Val Lys Gly Phe Tyr Pro Ser Asp Ile Ala Val Glu Trp
     370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
         435                 440                 445
```

```
Gly Lys
    450

<210> SEQ ID NO 20
<211> LENGTH: 214
<212> TYPE: PRT
<213> ORGANISM: Artificial Sequence
<220> FEATURE:
<223> OTHER INFORMATION: Antibody Sequence

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 117
<212> TYPE: PRT
<213> ORGANISM: Artificial Sequence
<220> FEATURE:
<223> OTHER INFORMATION: Antibody Sequence

<400> SEQUENCE: 21

Gln Val Gln Leu Gln Glu Ser Gly Pro Gly Leu Val Lys Pro Ser Gln
1               5                   10                  15

Ser Leu Ser Leu Thr Cys Ser Val Thr Asp Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80
```

```
Leu Lys Leu Ser Ser Val Thr Thr Glu Asp Thr Ala Thr Tyr Tyr Cys
                85                  90                  95

Ser Arg Gly Glu Gly Phe Tyr Phe Asp Ser Trp Gly Gln Gly Thr Thr
            100                 105                 110

Leu Thr Val Ser Ser
        115

<210> SEQ ID NO 22
<211> LENGTH: 6
<212> TYPE: PRT
<213> ORGANISM: Artificial Sequence
<220> FEATURE:
<223> OTHER INFORMATION: Antibody Sequence

<400> SEQUENCE: 22

Ser Gly Tyr Tyr Trp Asn
1               5

<210> SEQ ID NO 23
<211> LENGTH: 16
<212> TYPE: PRT
<213> ORGANISM: Artificial Sequence
<220> FEATURE:
<223> OTHER INFORMATION: Antibody Sequence

<400> SEQUENCE: 23

Tyr Ile Ser Tyr Asp Gly Ser Asn Asn Tyr Asn Pro Ser Leu Lys Asn
1               5                   10                  15

<210> SEQ ID NO 24
<211> LENGTH: 8
<212> TYPE: PRT
<213> ORGANISM: Artificial Sequence
<220> FEATURE:
<223> OTHER INFORMATION: Antibody Sequence

<400> SEQUENCE: 24

Gly Glu Gly Phe Tyr Phe Asp Ser
1               5

<210> SEQ ID NO 25
<211> LENGTH: 113
<212> TYPE: PRT
<213> ORGANISM: Artificial Sequence
<220> FEATURE:
<223> OTHER INFORMATION: Antibody Sequence

<400> SEQUENCE: 25

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110
```

Lys

<210> SEQ ID NO 26
<211> LENGTH: 17
<212> TYPE: PRT
<213> ORGANISM: Artificial Sequence
<220> FEATURE:
<223> OTHER INFORMATION: Antibody Sequence

<400> SEQUENCE: 26

Lys Ser Ser Gln Ser Leu Phe Phe Gly Ser Thr Gln Lys Asn Tyr Leu
1               5                   10                  15
Ala

<210> SEQ ID NO 27
<211> LENGTH: 7
<212> TYPE: PRT
<213> ORGANISM: Artificial Sequence
<220> FEATURE:
<223> OTHER INFORMATION: Antibody Sequence

<400> SEQUENCE: 27

Trp Ala Ser Thr Arg Glu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Antibody Sequence

<400> SEQUENCE: 28

Gln Gln Tyr Tyr Asn Tyr Pro Trp Thr
1               5

<210> SEQ ID NO 29
<211> LENGTH: 446
<212> TYPE: PRT
<213> ORGANISM: Artificial Sequence
<220> FEATURE:
<223> OTHER INFORMATION: Antibody Sequence

<400> SEQUENCE: 29

Gln Val Gln Leu Gln Glu Ser Gly Pro Gly Leu Val Lys Pro Ser Gln
1               5                   10                  15

Ser Leu Ser Leu Thr Cys Ser Val Thr Asp Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Ser Ser Val Thr Thr Glu Asp Thr Ala Thr Tyr Tyr Cys
                85                  90                  95

Ser Arg Gly Glu Gly Phe Tyr Phe Asp Ser Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 30
<211> LENGTH: 220
<212> TYPE: PRT
<213> ORGANISM: Artificial Sequence
<220> FEATURE:
<223> OTHER INFORMATION: Antibody Sequence

<400> SEQUENCE: 30

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
                20                  25                  30

Ser Thr Gln Lys Asn Tyr Leu Ala Trp Tyr Gln Gln Lys Pro Gly Gln
                35                  40                  45

```
Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 31
<211> LENGTH: 120
<212> TYPE: PRT
<213> ORGANISM: Artificial Sequence
<220> FEATURE:
<223> OTHER INFORMATION: Antibody Sequence

<400> SEQUENCE: 31

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Phe
                20                  25                  30

Ile Ile Ala Trp Val Lys Gln Arg Thr Gly Gln Gly Leu Glu Trp Ile
            35                  40                  45

Gly Glu Ile Tyr Pro Gly Thr Gly Arg Thr Tyr Tyr Ser Glu Lys Phe
        50                  55                  60

Arg Gly Lys Ala Thr Leu Thr Ala Asp Lys Ser Ser Asn Thr Ala Tyr
65                  70                  75                  80

Met Gln Leu Ser Ser Leu Thr Ser Val Asp Ser Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Thr Leu Thr Val Ser Ser
        115                 120

<210> SEQ ID NO 32
<211> LENGTH: 5
<212> TYPE: PRT
<213> ORGANISM: Artificial Sequence
<220> FEATURE:
<223> OTHER INFORMATION: Antibody Sequence
```

-continued

<400> SEQUENCE: 32

Asp Phe Ile Ile Ala
1               5

<210> SEQ ID NO 33
<211> LENGTH: 17
<212> TYPE: PRT
<213> ORGANISM: Artificial Sequence
<220> FEATURE:
<223> OTHER INFORMATION: Antibody Sequence

<400> SEQUENCE: 33

Glu Ile Tyr Pro Gly Thr Gly Arg Thr Tyr Tyr Ser Glu Lys Phe Arg
1               5                   10                  15
Gly

<210> SEQ ID NO 34
<211> LENGTH: 11
<212> TYPE: PRT
<213> ORGANISM: Artificial Sequence
<220> FEATURE:
<223> OTHER INFORMATION: Antibody Sequence

<400> SEQUENCE: 34

Arg Thr Ile Tyr Tyr Asp Tyr Asp Gly Asp Tyr
1               5                   10

<210> SEQ ID NO 35
<211> LENGTH: 112
<212> TYPE: PRT
<213> ORGANISM: Artificial Sequence
<220> FEATURE:
<223> OTHER INFORMATION: Antibody Sequence

<400> SEQUENCE: 35

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gly Gly Thr Lys Leu Glu Leu Lys
            100                 105                 110

<210> SEQ ID NO 36
<211> LENGTH: 16
<212> TYPE: PRT
<213> ORGANISM: Artificial Sequence
<220> FEATURE:
<223> OTHER INFORMATION: Antibody Sequence

<400> SEQUENCE: 36

Arg Ser Ser Lys Ser Leu Leu His Ser Asn Gly Ile Thr Tyr Leu Tyr
1               5                   10                  15

```
<210> SEQ ID NO 37
<211> LENGTH: 7
<212> TYPE: PRT
<213> ORGANISM: Artificial Sequence
<220> FEATURE:
<223> OTHER INFORMATION: Antibody Sequence

<400> SEQUENCE: 37

Gln Met Ser Asn Leu Ala Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Antibody Sequence

<400> SEQUENCE: 38

Ala His Asn Leu Glu Leu Pro Trp Thr
1               5

<210> SEQ ID NO 39
<211> LENGTH: 449
<212> TYPE: PRT
<213> ORGANISM: Artificial Sequence
<220> FEATURE:
<223> OTHER INFORMATION: Antibody Sequence

<400> SEQUENCE: 39

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Phe
            20                  25                  30

Ile Ile Ala Trp Val Lys Gln Arg Thr Gly Gln Gly Leu Glu Trp Ile
        35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Lys Ser Ser Asn Thr Ala Tyr
65                  70                  75                  80

Met Gln Leu Ser Ser Leu Thr Ser Val Asp Ser Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 40
<211> LENGTH: 219
<212> TYPE: PRT
<213> ORGANISM: Artificial Sequence
<220> FEATURE:
<223> OTHER INFORMATION: Antibody Sequence

<400> SEQUENCE: 40

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gly Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 41
<211> LENGTH: 120
<212> TYPE: PRT
<213> ORGANISM: Artificial Sequence
<220> FEATURE:
<223> OTHER INFORMATION: Antibody Sequence

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ile Ile Ala Trp Val Lys Gln Ala Pro Gly Gln Gly Leu Glu Trp Ile
        35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Leu Val Thr Val Ser Ser
        115                 120

<210> SEQ ID NO 42
<211> LENGTH: 5
<212> TYPE: PRT
<213> ORGANISM: Artificial Sequence
<220> FEATURE:
<223> OTHER INFORMATION: Antibody Sequence

<400> SEQUENCE: 42

Asp Phe Ile Ile Ala
1               5

<210> SEQ ID NO 43
<211> LENGTH: 17
<212> TYPE: PRT
<213> ORGANISM: Artificial Sequence
<220> FEATURE:
<223> OTHER INFORMATION: Antibody Sequence

<400> SEQUENCE: 43

Glu Ile Tyr Pro Gly Thr Gly Arg Thr Tyr Tyr Ser Glu Lys Phe Arg
1               5                   10                  15

Gly

<210> SEQ ID NO 44
```

```
<211> LENGTH: 11
<212> TYPE: PRT
<213> ORGANISM: Artificial Sequence
<220> FEATURE:
<223> OTHER INFORMATION: Antibody Sequence

<400> SEQUENCE: 44

Arg Thr Ile Tyr Tyr Asp Tyr Asp Gly Asp Tyr
1               5                   10

<210> SEQ ID NO 45
<211> LENGTH: 112
<212> TYPE: PRT
<213> ORGANISM: Artificial Sequence
<220> FEATURE:
<223> OTHER INFORMATION: Antibody Sequence

<400> SEQUENCE: 45

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gln Gly Thr Lys Val Glu Ile Lys
            100                 105                 110

<210> SEQ ID NO 46
<211> LENGTH: 16
<212> TYPE: PRT
<213> ORGANISM: Artificial Sequence
<220> FEATURE:
<223> OTHER INFORMATION: Antibody Sequence

<400> SEQUENCE: 46

Arg Ser Ser Lys Ser Leu Leu His Ser Asn Gly Ile Thr Tyr Leu Tyr
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: Antibody Sequence

<400> SEQUENCE: 47

Gln Met Ser Asn Leu Ala Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Antibody Sequence
```

<400> SEQUENCE: 48

Ala His Asn Leu Glu Leu Pro Trp Thr
1               5

<210> SEQ ID NO 49
<211> LENGTH: 449
<212> TYPE: PRT
<213> ORGANISM: Artificial Sequence
<220> FEATURE:
<223> OTHER INFORMATION: Antibody Sequence

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ile Ile Ala Trp Val Lys Gln Ala Pro Gly Gln Gly Leu Glu Trp Ile
        35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 50
<211> LENGTH: 219
<212> TYPE: PRT
<213> ORGANISM: Artificial Sequence
<220> FEATURE:
<223> OTHER INFORMATION: Antibody Sequence

<400> SEQUENCE: 50

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 51
<211> LENGTH: 117
<212> TYPE: PRT
```

<213> ORGANISM: Artificial Sequence
<220> FEATURE:
<223> OTHER INFORMATION: Antibody Sequence

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Thr Ser Phe Asp Tyr Trp Gly Gln Gly Thr Leu
            100                 105                 110

Val Thr Val Ser Ser
        115

<210> SEQ ID NO 52
<211> LENGTH: 5
<212> TYPE: PRT
<213> ORGANISM: Artificial Sequence
<220> FEATURE:
<223> OTHER INFORMATION: Antibody Sequence

<400> SEQUENCE: 52

Ser Tyr Ala Met Ser
1               5

<210> SEQ ID NO 53
<211> LENGTH: 17
<212> TYPE: PRT
<213> ORGANISM: Artificial Sequence
<220> FEATURE:
<223> OTHER INFORMATION: Antibody Sequence

<400> SEQUENCE: 53

Ser Ile Ser Gly Ser Gly Gly Ser Thr Leu Tyr Ala Asp Ser Val Lys
1               5                   10                  15

Gly

<210> SEQ ID NO 54
<211> LENGTH: 8
<212> TYPE: PRT
<213> ORGANISM: Artificial Sequence
<220> FEATURE:
<223> OTHER INFORMATION: Antibody Sequence

<400> SEQUENCE: 54

Leu Thr Gly Thr Ser Phe Asp Tyr
1               5

<210> SEQ ID NO 55
<211> LENGTH: 109
<212> TYPE: PRT
<213> ORGANISM: Artificial Sequence
<220> FEATURE:
<223> OTHER INFORMATION: Antibody Sequence

```
<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Phe Asp Ser Ser Leu
                85                  90                  95

Lys Lys Val Phe Gly Gly Gly Thr Lys Leu Thr Val Leu
            100                 105

<210> SEQ ID NO 56
<211> LENGTH: 13
<212> TYPE: PRT
<213> ORGANISM: Artificial Sequence
<220> FEATURE:
<223> OTHER INFORMATION: Antibody Sequence

<400> SEQUENCE: 56

Ser Gly Ser Ser Ser Asn Ile Gly Ser Asn Pro Val Asn
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Antibody Sequence

<400> SEQUENCE: 57

Ser Asn Asn Gln Arg Pro Ser
1               5

<210> SEQ ID NO 58
<211> LENGTH: 10
<212> TYPE: PRT
<213> ORGANISM: Artificial Sequence
<220> FEATURE:
<223> OTHER INFORMATION: Antibody Sequence

<400> SEQUENCE: 58

Gln Ser Phe Asp Ser Ser Leu Lys Lys Val
1               5                   10

<210> SEQ ID NO 59
<211> LENGTH: 446
<212> TYPE: PRT
<213> ORGANISM: Artificial Sequence
<220> FEATURE:
<223> OTHER INFORMATION: Antibody Sequence

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
         35                  40                  45

Ser Ser Ile Ser Gly Ser Gly Gly Ser Thr Leu Tyr Ala Asp Ser Val
 50              55                  60

Lys Gly Arg Phe Thr Ile Ser Arg Asp Asn Ser Lys Asn Thr Leu Tyr
 65              70                  75                  80

Leu Gln Met Asn Ser Leu Arg Ala Glu Asp Thr Ala Val Tyr Tyr Cys
                 85                  90                  95

Ala Lys Leu Thr Gly Thr Ser Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445
```

```
<210> SEQ ID NO 60
<211> LENGTH: 215
<212> TYPE: PRT
<213> ORGANISM: Artificial Sequence
<220> FEATURE:
<223> OTHER INFORMATION: Antibody Sequence

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Phe Asp Ser Ser Leu
                85                  90                  95

Lys Lys Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 61
<211> LENGTH: 120
<212> TYPE: PRT
<213> ORGANISM: Artificial Sequence
<220> FEATURE:
<223> OTHER INFORMATION: Antibody Sequence

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 62
<211> LENGTH: 5
<212> TYPE: PRT
<213> ORGANISM: Artificial Sequence
<220> FEATURE:
<223> OTHER INFORMATION: Antibody Sequence

<400> SEQUENCE: 62

Asp Tyr Tyr Met Lys
1               5

<210> SEQ ID NO 63
<211> LENGTH: 17
<212> TYPE: PRT
<213> ORGANISM: Artificial Sequence
<220> FEATURE:
<223> OTHER INFORMATION: Antibody Sequence

<400> SEQUENCE: 63

Asp Ile Ile Pro Ser Asn Gly Ala Thr Phe Tyr Asn Gln Lys Phe Lys
1               5                   10                  15

Gly

<210> SEQ ID NO 64
<211> LENGTH: 11
<212> TYPE: PRT
<213> ORGANISM: Artificial Sequence
<220> FEATURE:
<223> OTHER INFORMATION: Antibody Sequence

<400> SEQUENCE: 64

Ser His Leu Leu Arg Ala Ser Trp Phe Ala Tyr
1               5                   10

<210> SEQ ID NO 65
<211> LENGTH: 113
<212> TYPE: PRT
<213> ORGANISM: Artificial Sequence
<220> FEATURE:
<223> OTHER INFORMATION: Antibody Sequence

<400> SEQUENCE: 65

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 66
<211> LENGTH: 17
<212> TYPE: PRT
<213> ORGANISM: Artificial Sequence
<220> FEATURE:
<223> OTHER INFORMATION: Antibody Sequence

<400> SEQUENCE: 66

Glu Ser Ser Gln Ser Val Leu Asn Ser Gly Asn Gln Lys Asn Tyr Leu
1               5                   10                  15

Thr

<210> SEQ ID NO 67
<211> LENGTH: 7
<212> TYPE: PRT
<213> ORGANISM: Artificial Sequence
<220> FEATURE:
<223> OTHER INFORMATION: Antibody Sequence

<400> SEQUENCE: 67

Trp Ala Ser Thr Arg Glu Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Antibody Sequence

<400> SEQUENCE: 68

Gln Asn Asp Tyr Ser Tyr Pro Tyr Thr
1               5

<210> SEQ ID NO 69
<211> LENGTH: 449
<212> TYPE: PRT
<213> ORGANISM: Artificial Sequence
<220> FEATURE:
<223> OTHER INFORMATION: Antibody Sequence

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 70
<211> LENGTH: 220
<212> TYPE: PRT
<213> ORGANISM: Artificial Sequence
<220> FEATURE:
<223> OTHER INFORMATION: Antibody Sequence

<400> SEQUENCE: 70

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Ser Tyr Pro Tyr Thr Phe Gly Gln Gly Thr Lys Leu Glu Ile
             100                 105                 110

Lys Arg Thr Val Ala Ala Pro Ser Val Phe Ile Phe Pro Pro Ser Asp
         115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 71
<211> LENGTH: 118
<212> TYPE: PRT
<213> ORGANISM: Artificial Sequence
<220> FEATURE:
<223> OTHER INFORMATION: Antibody Sequence

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
         35                  40                  45

Met Gly Tyr Ile Ser Tyr Asp Gly Ser Asn Asn Tyr Asn Pro Ser Leu
 50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                 85                  90                  95

Cys Ala Arg Gly Glu Gly Phe Tyr Phe Asp Ser Trp Gly Gln Gly Thr
            100                 105                 110

Leu Val Thr Val Ser Ser
        115

<210> SEQ ID NO 72
<211> LENGTH: 6
<212> TYPE: PRT
<213> ORGANISM: Artificial Sequence
<220> FEATURE:

<223> OTHER INFORMATION: Antibody Sequence

<400> SEQUENCE: 72

Ser Gly Tyr Tyr Trp Asn
1               5

<210> SEQ ID NO 73
<211> LENGTH: 17
<212> TYPE: PRT
<213> ORGANISM: Artificial Sequence
<220> FEATURE:
<223> OTHER INFORMATION: Antibody Sequence

<400> SEQUENCE: 73

Tyr Ile Ser Tyr Asp Gly Ser Asn Asn Tyr Asn Pro Ser Leu Lys Asn
1               5                   10                  15

Gly

<210> SEQ ID NO 74
<211> LENGTH: 8
<212> TYPE: PRT
<213> ORGANISM: Artificial Sequence
<220> FEATURE:
<223> OTHER INFORMATION: Antibody Sequence

<400> SEQUENCE: 74

Gly Glu Gly Phe Tyr Phe Asp Ser
1               5

<210> SEQ ID NO 75
<211> LENGTH: 113
<212> TYPE: PRT
<213> ORGANISM: Artificial Sequence
<220> FEATURE:
<223> OTHER INFORMATION: Antibody Sequence

<400> SEQUENCE: 75

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
                20                  25                  30

Ser Thr Gln Lys Asn Tyr Leu Ala Trp Tyr Gln Leu Lys Pro Gly Gln
            35                  40                  45

Ala Pro Arg Leu Leu Ile Tyr Trp Ala Ser Thr Arg Glu Ser Gly Ile
        50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys

<210> SEQ ID NO 76
<211> LENGTH: 17
<212> TYPE: PRT
<213> ORGANISM: Artificial Sequence
<220> FEATURE:
<223> OTHER INFORMATION: Antibody Sequence

<400> SEQUENCE: 76

Lys Ser Ser Gln Ser Leu Phe Phe Gly Ser Thr Gln Lys Asn Tyr Leu
1               5                   10                  15

Ala

<210> SEQ ID NO 77
<211> LENGTH: 7
<212> TYPE: PRT
<213> ORGANISM: Artificial Sequence
<220> FEATURE:
<223> OTHER INFORMATION: Antibody Sequence

<400> SEQUENCE: 77

Trp Ala Ser Thr Arg Glu Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Antibody Sequence

<400> SEQUENCE: 78

Gln Gln Tyr Tyr Asn Tyr Pro Trp Thr
1               5

<210> SEQ ID NO 79
<211> LENGTH: 447
<212> TYPE: PRT
<213> ORGANISM: Artificial Sequence
<220> FEATURE:
<223> OTHER INFORMATION: Antibody Sequence

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
                20                  25                  30

Tyr Tyr Trp Asn Trp Ile Arg Gln Ala Pro Gly Lys Lys Leu Glu Trp
            35                  40                  45

Met Gly Tyr Ile Ser Tyr Asp Gly Ser Asn Asn Tyr Asn Pro Ser Leu
        50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

```
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 80
<211> LENGTH: 220
<212> TYPE: PRT
<213> ORGANISM: Artificial Sequence
<220> FEATURE:
<223> OTHER INFORMATION: Antibody Sequence

<400> SEQUENCE: 80

Glu Ile Val Leu Thr Gln Ser Pro Gly Thr Leu Ser Leu Ser Pro Gly
1               5                   10                  15
Glu Arg Ala Thr Leu Ser Cys Lys Ser Ser Gln Ser Leu Phe Phe Gly
            20                  25                  30
Ser Thr Gln Lys Asn Tyr Leu Ala Trp Tyr Gln Gln Lys Pro Gly Gln
        35                  40                  45
Ala Pro Arg Leu Leu Ile Tyr Trp Ala Ser Thr Arg Glu Ser Gly Ile
    50                  55                  60
Pro Asp Arg Phe Ser Gly Ser Gly Ser Gly Thr Asp Phe Thr Leu Thr
65                  70                  75                  80
Ile Ser Arg Leu Glu Pro Glu Asp Phe Ala Val Tyr Tyr Cys Gln Gln
                85                  90                  95
Tyr Tyr Asn Tyr Pro Trp Thr Phe Gly Gln Gly Thr Lys Leu Glu Ile
                100                 105                 110
```

-continued

```
Lys Arg Thr Val Ala Ala Pro Ser Val Phe Ile Phe Pro Pro Ser Asp
    115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 81
<211> LENGTH: 120
<212> TYPE: PRT
<213> ORGANISM: Artificial Sequence
<220> FEATURE:
<223> OTHER INFORMATION: Antibody Sequence

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 82
<211> LENGTH: 5
<212> TYPE: PRT
<213> ORGANISM: Artificial Sequence
<220> FEATURE:
<223> OTHER INFORMATION: Antibody Sequence

<400> SEQUENCE: 82

Asp Tyr Tyr Met Lys
1               5

<210> SEQ ID NO 83
<211> LENGTH: 17
<212> TYPE: PRT
<213> ORGANISM: Artificial Sequence
<220> FEATURE:
<223> OTHER INFORMATION: Antibody Sequence
```

<400> SEQUENCE: 83

Asp Ile Ile Pro Ser Asn Gly Ala Thr Phe Tyr Asn Gln Lys Phe Lys
1               5                   10                  15

Gly

<210> SEQ ID NO 84
<211> LENGTH: 11
<212> TYPE: PRT
<213> ORGANISM: Artificial Sequence
<220> FEATURE:
<223> OTHER INFORMATION: Antibody Sequence

<400> SEQUENCE: 84

Ser His Leu Leu Arg Ala Ser Trp Phe Ala Tyr
1               5                   10

<210> SEQ ID NO 85
<211> LENGTH: 113
<212> TYPE: PRT
<213> ORGANISM: Artificial Sequence
<220> FEATURE:
<223> OTHER INFORMATION: Antibody Sequence

<400> SEQUENCE: 85

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 86
<211> LENGTH: 17
<212> TYPE: PRT
<213> ORGANISM: Artificial Sequence
<220> FEATURE:
<223> OTHER INFORMATION: Antibody Sequence

<400> SEQUENCE: 86

Glu Ser Ser Gln Ser Val Leu Asn Ser Gly Asn Gln Lys Asn Tyr Leu
1               5                   10                  15

Thr

<210> SEQ ID NO 87
<211> LENGTH: 7
<212> TYPE: PRT
<213> ORGANISM: Artificial Sequence
<220> FEATURE:
<223> OTHER INFORMATION: Antibody Sequence

<400> SEQUENCE: 87

Trp Ala Ser Thr Arg Glu Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Antibody Sequence

<400> SEQUENCE: 88

Gln Asn Asp Tyr Ser Tyr Pro Tyr Thr
1               5

<210> SEQ ID NO 89
<211> LENGTH: 449
<212> TYPE: PRT
<213> ORGANISM: Artificial Sequence
<220> FEATURE:
<223> OTHER INFORMATION: Antibody Sequence

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Tyr Met Lys Trp Val Arg Gln Ala Pro Gly Gln Gly Leu Glu Trp Met
            35                  40                  45

Gly Asp Ile Ile Pro Ser Asn Gly Ala Thr Phe Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 90
<211> LENGTH: 220
<212> TYPE: PRT
<213> ORGANISM: Artificial Sequence
<220> FEATURE:
<223> OTHER INFORMATION: Antibody Sequence

<400> SEQUENCE: 90

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

```
Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
    210                 215                 220
```

<210> SEQ ID NO 91
<211> LENGTH: 113
<212> TYPE: PRT
<213> ORGANISM: Artificial Sequence
<220> FEATURE:
<223> OTHER INFORMATION: Antibody Sequence

<400> SEQUENCE: 91

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Thr Ser
            20                  25                  30

Gly Met His Trp Phe Arg Gln Ala Pro Gly Lys Gly Leu Glu Trp Val
        35                  40                  45

Ala Tyr Ile Ser Ser Ser Gly Phe Val Tyr Ala Asp Ala Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Glu Ala Ala Phe Trp Gly Gln Gly Thr Leu Val Thr Val Ser
            100                 105                 110

Ser
```

<210> SEQ ID NO 92
<211> LENGTH: 5
<212> TYPE: PRT
<213> ORGANISM: Artificial Sequence
<220> FEATURE:
<223> OTHER INFORMATION: Antibody Sequence

<400> SEQUENCE: 92

```
Thr Ser Gly Met His
1               5
```

<210> SEQ ID NO 93
<211> LENGTH: 16
<212> TYPE: PRT
<213> ORGANISM: Artificial Sequence
<220> FEATURE:
<223> OTHER INFORMATION: Antibody Sequence

<400> SEQUENCE: 93

```
Tyr Ile Ser Ser Ser Gly Phe Val Tyr Ala Asp Ala Val Lys Gly
1               5                   10                  15
```

<210> SEQ ID NO 94
<211> LENGTH: 5
<212> TYPE: PRT
<213> ORGANISM: Artificial Sequence
<220> FEATURE:
<223> OTHER INFORMATION: Antibody Sequence

<400> SEQUENCE: 94

Ser Glu Ala Ala Phe
1               5

<210> SEQ ID NO 95
<211> LENGTH: 112
<212> TYPE: PRT
<213> ORGANISM: Artificial Sequence
<220> FEATURE:
<223> OTHER INFORMATION: Antibody Sequence

<400> SEQUENCE: 95

Asp Ile Val Met Thr Gln Ser Pro Leu Ser Leu Pro Val Thr Pro Gly
1               5                   10                  15

Glu Pro Ala Ser Ile Ser Cys Arg Ser Gln Lys Ser Arg Leu Ser Arg
            20                  25                  30

Met Gly Ile Thr Pro Leu Asn Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Glu Tyr Pro Pro Thr Phe Gly Gln Gly Thr Lys Leu Glu Ile Lys
            100                 105                 110

<210> SEQ ID NO 96
<211> LENGTH: 16
<212> TYPE: PRT
<213> ORGANISM: Artificial Sequence
<220> FEATURE:
<223> OTHER INFORMATION: Antibody Sequence

<400> SEQUENCE: 96

Arg Ser Gln Lys Ser Arg Leu Ser Arg Met Gly Ile Thr Pro Leu Asn
1               5                   10                  15

<210> SEQ ID NO 97
<211> LENGTH: 7
<212> TYPE: PRT
<213> ORGANISM: Artificial Sequence
<220> FEATURE:
<223> OTHER INFORMATION: Antibody Sequence

<400> SEQUENCE: 97

Arg Met Ser Asn Leu Ala Ser
1               5

<210> SEQ ID NO 98
<211> LENGTH: 9
<212> TYPE: PRT
<213> ORGANISM: Artificial Sequence
<220> FEATURE:
<223> OTHER INFORMATION: Antibody Sequence

<400> SEQUENCE: 98

Ala Gln Phe Leu Glu Tyr Pro Pro Thr
1               5

<210> SEQ ID NO 99
<211> LENGTH: 442

```
<212> TYPE: PRT
<213> ORGANISM: Artificial Sequence
<220> FEATURE:
<223> OTHER INFORMATION: Antibody Sequence

<400> SEQUENCE: 99

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Thr Ser
            20                  25                  30

Gly Met His Trp Phe Arg Gln Ala Pro Gly Lys Gly Leu Glu Trp Val
        35                  40                  45

Ala Tyr Ile Ser Ser Ser Ser Gly Phe Val Tyr Ala Asp Ala Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Glu Ala Ala Phe Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380
```

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly
        435                 440

<210> SEQ ID NO 100
<211> LENGTH: 219
<212> TYPE: PRT
<213> ORGANISM: Artificial Sequence
<220> FEATURE:
<223> OTHER INFORMATION: Antibody Sequence

<400> SEQUENCE: 100

Asp Ile Val Met Thr Gln Ser Pro Leu Ser Leu Pro Val Thr Pro Gly
1               5                   10                  15

Glu Pro Ala Ser Ile Ser Cys Arg Ser Gln Lys Ser Arg Leu Ser Arg
            20                  25                  30

Met Gly Ile Thr Pro Leu Asn Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Glu Tyr Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 101
<211> LENGTH: 113
<212> TYPE: PRT
<213> ORGANISM: Artificial Sequence
<220> FEATURE:
<223> OTHER INFORMATION: Antibody Sequence

<400> SEQUENCE: 101

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Thr Ser
            20                  25                  30

```
Gly Met His Trp Val Arg Gln Ala Pro Gly Lys Gly Leu Glu Trp Val
            35                  40                  45
Ser Tyr Ile Ser Ser Ser Ser Gly Phe Val Tyr Ala Asp Ala Val Lys
        50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                85                  90                  95
Arg Ser Glu Ala Ala Phe Trp Gly Gln Gly Thr Leu Val Thr Val Ser
            100                 105                 110
Ser

<210> SEQ ID NO 102
<211> LENGTH: 5
<212> TYPE: PRT
<213> ORGANISM: Artificial Sequence
<220> FEATURE:
<223> OTHER INFORMATION: Antibody Sequence

<400> SEQUENCE: 102

Thr Ser Gly Met His
 1               5

<210> SEQ ID NO 103
<211> LENGTH: 16
<212> TYPE: PRT
<213> ORGANISM: Artificial Sequence
<220> FEATURE:
<223> OTHER INFORMATION: Antibody Sequence

<400> SEQUENCE: 103

Tyr Ile Ser Ser Ser Ser Gly Phe Val Tyr Ala Asp Ala Val Lys Gly
 1               5                  10                  15

<210> SEQ ID NO 104
<211> LENGTH: 5
<212> TYPE: PRT
<213> ORGANISM: Artificial Sequence
<220> FEATURE:
<223> OTHER INFORMATION: Antibody Sequence

<400> SEQUENCE: 104

Ser Glu Ala Ala Phe
 1               5

<210> SEQ ID NO 105
<211> LENGTH: 112
<212> TYPE: PRT
<213> ORGANISM: Artificial Sequence
<220> FEATURE:
<223> OTHER INFORMATION: Antibody Sequence

<400> SEQUENCE: 105

Asp Ile Val Met Thr Gln Ser Pro Leu Ser Leu Pro Val Thr Pro Gly
 1               5                  10                  15
Glu Pro Ala Ser Ile Ser Cys Arg Ser Gln Lys Ser Arg Leu Ser Arg
            20                  25                  30
Met Gly Ile Thr Pro Leu Asn Trp Tyr Leu Gln Lys Pro Gly Gln Ser
        35                  40                  45
Pro Gln Leu Leu Ile Tyr Arg Met Ser Asn Leu Ala Ser Gly Val Pro
 50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Phe
                 85                  90                  95

Leu Glu Tyr Pro Pro Thr Phe Gly Gln Gly Thr Lys Leu Glu Ile Lys
            100                 105                 110
```

<210> SEQ ID NO 106
<211> LENGTH: 16
<212> TYPE: PRT
<213> ORGANISM: Artificial Sequence
<220> FEATURE:
<223> OTHER INFORMATION: Antibody Sequence

<400> SEQUENCE: 106

```
Arg Ser Gln Lys Ser Arg Leu Ser Arg Met Gly Ile Thr Pro Leu Asn
1               5                   10                  15
```

<210> SEQ ID NO 107
<211> LENGTH: 7
<212> TYPE: PRT
<213> ORGANISM: Artificial Sequence
<220> FEATURE:
<223> OTHER INFORMATION: Antibody Sequence

<400> SEQUENCE: 107

```
Arg Met Ser Asn Leu Ala Ser
1               5
```

<210> SEQ ID NO 108
<211> LENGTH: 9
<212> TYPE: PRT
<213> ORGANISM: Artificial Sequence
<220> FEATURE:
<223> OTHER INFORMATION: Antibody Sequence

<400> SEQUENCE: 108

```
Ala Gln Phe Leu Glu Tyr Pro Pro Thr
1               5
```

<210> SEQ ID NO 109
<211> LENGTH: 442
<212> TYPE: PRT
<213> ORGANISM: Artificial Sequence
<220> FEATURE:
<223> OTHER INFORMATION: Antibody Sequence

<400> SEQUENCE: 109

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Thr Ser
            20                  25                  30

Gly Met His Trp Val Arg Gln Ala Pro Gly Lys Gly Leu Glu Trp Val
        35                  40                  45

Ser Tyr Ile Ser Ser Ser Ser Gly Phe Val Tyr Ala Asp Ala Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Glu Ala Ala Phe Trp Gly Gln Gly Thr Leu Val Thr Val Ser
            100                 105                 110
```

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 110
<211> LENGTH: 219
<212> TYPE: PRT
<213> ORGANISM: Artificial Sequence
<220> FEATURE:
<223> OTHER INFORMATION: Antibody Sequence

<400> SEQUENCE: 110

Asp Ile Val Met Thr Gln Ser Pro Leu Ser Leu Pro Val Thr Pro Gly
1               5                   10                  15

Glu Pro Ala Ser Ile Ser Cys Arg Ser Gln Lys Ser Arg Leu Ser Arg
            20                  25                  30

Met Gly Ile Thr Pro Leu Asn Trp Tyr Leu Gln Lys Pro Gly Gln Ser
            35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Phe
                 85                  90                  95

Leu Glu Tyr Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 111
<211> LENGTH: 378
<212> TYPE: PRT
<213> ORGANISM: Homo sapiens

<400> SEQUENCE: 111

Met Val Leu Leu Trp Leu Thr Leu Leu Leu Ile Ala Leu Pro Cys Leu
 1               5                  10                  15

Leu Gln Thr Lys Glu Asp Pro Asn Pro Pro Ile Thr Asn Leu Arg Met
             20                  25                  30

Lys Ala Lys Ala Gln Gln Leu Thr Trp Asp Leu Asn Arg Asn Val Thr
         35                  40                  45

Asp Ile Glu Cys Val Lys Asp Ala Asp Tyr Ser Met Pro Ala Val Asn
 50                  55                  60

Asn Ser Tyr Cys Gln Phe Gly Ala Ile Ser Leu Cys Glu Val Thr Asn
 65                  70                  75                  80

Tyr Thr Val Arg Val Ala Asn Pro Pro Phe Ser Thr Trp Ile Leu Phe
                 85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
    130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

```
Ile Pro Cys Thr Asp Lys Phe Val Phe Ser Gln Ile Glu Ile Leu
        195                 200                 205

Thr Pro Pro Asn Met Thr Ala Lys Cys Asn Lys Thr His Ser Phe Met
210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Gly Ala Asn Thr Arg Ala Trp
        290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
        355                 360                 365

Val Thr Glu Val Gln Val Val Gln Lys Thr
370                 375

<210> SEQ ID NO 112
<211> LENGTH: 372
<212> TYPE: PRT
<213> ORGANISM: Homo sapiens

<400> SEQUENCE: 112

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
                20                  25                  30

Val Glu Asn His Leu Cys Pro Ala Thr Glu Gly Pro Leu Met Ala Ser
            35                  40                  45

Phe Lys Ala Val Phe Val Pro Val Ala Tyr Ser Leu Ile Phe Leu Leu
        50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175
```

-continued

```
Gly Phe Leu Leu Ala Leu Pro Glu Ile Leu Phe Ala Lys Val Ser Gln
                180                 185                 190

Gly His His Asn Asn Ser Leu Pro Arg Cys Thr Phe Ser Gln Glu Asn
            195                 200                 205

Gln Ala Glu Thr His Ala Trp Phe Thr Ser Arg Phe Leu Tyr His Val
210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Pro Gln Arg Gln Lys
                245                 250                 255

Ala Val Arg Val Ala Ile Leu Val Thr Ser Ile Phe Phe Leu Cys Trp
                260                 265                 270

Ser Pro Tyr His Ile Val Ile Phe Leu Asp Thr Leu Ala Arg Leu Lys
            275                 280                 285

Ala Val Asp Asn Thr Cys Lys Leu Asn Gly Ser Leu Pro Val Ala Ile
            290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
                340                 345                 350

Pro Ser Trp Arg Arg Ser Ser Leu Ser Glu Ser Glu Asn Ala Thr Ser
                355                 360                 365

Leu Thr Thr Phe
    370

<210> SEQ ID NO 113
<211> LENGTH: 534
<212> TYPE: PRT
<213> ORGANISM: Homo sapiens

<400> SEQUENCE: 113

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
                100                 105                 110

Arg Val Ala Asp Glu Gly Ser Phe Thr Cys Phe Val Ser Ile Arg Asp
            115                 120                 125

Phe Gly Ser Ala Ala Val Ser Leu Gln Val Ala Ala Pro Tyr Ser Lys
        130                 135                 140

Pro Ser Met Thr Leu Glu Pro Asn Lys Asp Leu Arg Pro Gly Asp Thr
145                 150                 155                 160
```

```
Val Thr Ile Thr Cys Ser Ser Tyr Gln Gly Tyr Pro Glu Ala Glu Val
                165                 170                 175
Phe Trp Gln Asp Gly Gln Gly Val Pro Leu Thr Gly Asn Val Thr Thr
            180                 185                 190
Ser Gln Met Ala Asn Glu Gln Gly Leu Phe Asp Val His Ser Ile Leu
        195                 200                 205
Arg Val Val Leu Gly Ala Asn Gly Thr Tyr Ser Cys Leu Val Arg Asn
    210                 215                 220
Pro Val Leu Gln Gln Asp Ala His Ser Ser Val Thr Ile Thr Pro Gln
225                 230                 235                 240
Arg Ser Pro Thr Gly Ala Val Glu Val Gln Val Pro Glu Asp Pro Val
                245                 250                 255
Val Ala Leu Val Gly Thr Asp Ala Thr Leu Arg Cys Ser Phe Ser Pro
            260                 265                 270
Glu Pro Gly Phe Ser Leu Ala Gln Leu Asn Leu Ile Trp Gln Leu Thr
        275                 280                 285
Asp Thr Lys Gln Leu Val His Ser Phe Thr Glu Gly Arg Asp Gln Gly
    290                 295                 300
Ser Ala Tyr Ala Asn Arg Thr Ala Leu Phe Pro Asp Leu Leu Ala Gln
305                 310                 315                 320
Gly Asn Ala Ser Leu Arg Leu Gln Arg Val Arg Val Ala Asp Glu Gly
                325                 330                 335
Ser Phe Thr Cys Phe Val Ser Ile Arg Asp Phe Gly Ser Ala Ala Val
            340                 345                 350
Ser Leu Gln Val Ala Ala Pro Tyr Ser Lys Pro Ser Met Thr Leu Glu
        355                 360                 365
Pro Asn Lys Asp Leu Arg Pro Gly Asp Thr Val Thr Ile Thr Cys Ser
    370                 375                 380
Ser Tyr Arg Gly Tyr Pro Glu Ala Glu Val Phe Trp Gln Asp Gly Gln
385                 390                 395                 400
Gly Val Pro Leu Thr Gly Asn Val Thr Thr Ser Gln Met Ala Asn Glu
                405                 410                 415
Gln Gly Leu Phe Asp Val His Ser Val Leu Arg Val Val Leu Gly Ala
            420                 425                 430
Asn Gly Thr Tyr Ser Cys Leu Val Arg Asn Pro Val Leu Gln Gln Asp
        435                 440                 445
Ala His Gly Ser Val Thr Ile Thr Gly Gln Pro Met Thr Phe Pro Pro
    450                 455                 460
Glu Ala Leu Trp Val Thr Val Gly Leu Ser Val Cys Leu Ile Ala Leu
465                 470                 475                 480
Leu Val Ala Leu Ala Phe Val Cys Trp Arg Lys Ile Lys Gln Ser Cys
                485                 490                 495
Glu Glu Glu Asn Ala Gly Ala Glu Asp Gln Asp Gly Glu Gly Glu Gly
            500                 505                 510
Ser Lys Thr Ala Leu Gln Pro Leu Lys His Ser Asp Ser Lys Glu Asp
        515                 520                 525
Asp Gly Gln Glu Ile Ala
    530
```

<210> SEQ ID NO 114
<211> LENGTH: 129
<212> TYPE: PRT
<213> ORGANISM: Homo sapiens

<400> SEQUENCE: 114

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Glu Lys Phe Thr Thr
            100                 105                 110

Pro Ile Glu Glu Thr Gly Gly Glu Gly Cys Pro Ala Val Ala Leu Ile
            115                 120                 125

Gln
```

<210> SEQ ID NO 115
<211> LENGTH: 1255
<212> TYPE: PRT
<213> ORGANISM: Homo sapiens

<400> SEQUENCE: 115

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
        130                 135                 140

Leu Thr Glu Ile Leu Lys Gly Gly Val Leu Ile Gln Arg Asn Pro Gln
145                 150                 155                 160
```

```
Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540
```

```
Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
        930                 935                 940

Pro Ile Cys Thr Ile Asp Val Tyr Met Ile Met Val Lys Cys Trp Met
945                 950                 955                 960
```

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 116
<211> LENGTH: 1210
<212> TYPE: PRT
<213> ORGANISM: Homo sapiens

<400> SEQUENCE: 116

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

-continued

```
Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
        210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460
```

-continued

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

```
Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210
```

ANTIBODY DRUG CONJUGATES (ADCS) HAVING ENZYMATICALLY CLEAVABLE GROUPS

CROSS REFERENCE TO RELATED APPLICATIONS

This application is the national stage of International Application No. PCT/EP2017/082789, filed internationally on Dec. 14, 2017, which claims the benefit of European Application No. 16205868.9, filed Dec. 21, 2016.

SUBMISSION OF SEQUENCE LISTING

The content of the following submission on ASCII text file is incorporated herein by reference in its entirety: a computer readable form (CRF) of the Sequence Listing (file name: 777052035700SEQLIST.TXT, date recorded: Jun. 19, 2019, size: 134 KB).

INTRODUCTION AND STATE OF THE ART

The invention relates to novel binder-drug conjugates (ADCs) having improved properties, to active metabolites of these ADCs and to processes for their preparation. The present invention furthermore relates to the use of these conjugates for the treatment and/or prevention of diseases and to the use of these conjugates for preparing medicaments for treatment and/or prevention of diseases, in particular hyperproliferative and/or angiogenic disorders such as, for example, cancer diseases. Such treatments can be effected as monotherapy or else in combination with other medicaments or further therapeutic measures. According to the invention, the binder is preferably an antibody.

Cancers are the consequence of uncontrolled cell growth of the most diverse tissues. In many cases the new cells penetrate into existing tissue (invasive growth), or they metastasize into remote organs. Cancers occur in a wide variety of different organs and often have tissue-specific courses. The term "cancer" as a generic term therefore describes a large group of defined diseases of different organs, tissue and cell types.

Some tumours at early stages can be removed by surgical and radiotherapy measures. Metastasized tumours as a rule can only be treated palliatively by chemotherapeutics. The aim here is to achieve the optimum combination of an improvement in the quality of life and prolonging of life.

Conjugates of binder proteins with one or more drug molecules are known, in particular in the form of antibody drug conjugates (ADCs) in which an internalizing antibody directed against a tumour-associated antigen is covalently attached via a linker to a cytotoxic agent. Following introduction of the ADCs into the tumour cell and subsequent dissociation of the conjugate, either the cytotoxic agent itself or a cytotoxic metabolite formed therefrom is released within the tumour cell and can unfold its action therein directly and selectively. In this manner, in contrast to conventional cancer chemotherapy, damage to normal tissue is contained in significantly narrower limits [see, for example, J. M. Lambert, Curr. Opin. Pharmacol. 5, 543-549 (2005); A. M. Wu and P. D. Senter, Nat. Biotechnol. 23, 1137-1146 (2005); P. D. Senter, Curr. Opin. Chem. Biol. 13, 235-244 (2009); L. Ducry and B. Stump, Bioconjugate Chem. 21, 5-13 (2010)]. Thus, WO2012/171020 describes ADCs in which a plurality of toxophore molecules are attached via a polymeric linker to an antibody. As possible toxophores, WO2012/171020 mentions, among others, the substances SB 743921, SB 715992 (Ispinesib), MK-0371, AZD8477, AZ3146 and ARRY-520.

The substances mentioned last are kinesin spindle protein inhibitors. Kinesin spindle protein (KSP, also known as Eg5, HsEg5, KNSL1 or KIF11) is a kinesin-like motorprotein which is essential for the bipolar mitotic spindle to function. Inhibition of KSP leads to mitotic arrest and, over a relatively long term, to apoptosis (Tao et al., Cancer Cell 2005 Jul. 8(1), 39-59). After the discovery of the first cell-penetrating KSP inhibitor, Monastrol, KSP inhibitors have established themselves as a class of novel chemotherapeutics (Mayer et al., Science 286: 971-974, 1999), and they are subject matter of a number of patent applications (e.g. WO2006/044825; WO2006/002236; WO2005/051922; WO2006/060737; WO03/060064; WO03/040979; and WO03/049527). However, since KSP is active only during a relatively short period of time during the mitosis phase, KSP inhibitors have to be present in a sufficiently high concentration during this phase. WO2014/151030 discloses ADCs including certain KSP inhibitors. ADCs with KSP inhibitors which also comprise enzymatically cleavable linkers which, however, do not have an optimum activity profile, have already been disclosed in the patent applications WO2015/096982 and WO2016/096610.

Legumain is a tumour-associated asparaginyl endopeptidase (S. Ishii, Methods Enzymol. 1994, 244, 604; J. M. Chen et al. J. Biol. Chem. 1997, 272, 8090) and has been utilized for processing of prodrugs of small cytotoxic molecules, for example of doxorubicin and etoposide derivatives among others (W. Wu et al. Cancer Res. 2006, 66, 970; L. Stern et al. Bioconjugate Chem. 2009, 20, 500; K. M. Bajjuri et al. ChemMedChem 2011, 6, 54).

Other lysosomal enzymes are, for example, cathepsin or glycosidases, for example β-glucuronidases, which have also been utilized for release of the active compounds by enzymatic cleavage of prodrugs. Groups cleavable enzymatically in vivo are especially 2-8-oligopeptide groups or glycosides. Peptide cleaving sites are disclosed in *Bioconjugate Chem.* 2002, 13, 855-869 and *Bioorganic & Medicinal Chemistry Letters* 8 (1998) 3341-3346 and also *Bioconjugate Chem.* 1998, 9, 618-626. These include, for example, valine-alanine, valine-lysine, valine-citrulline, alanine-lysine and phenylalanine-lysine (optionally with additional amide group).

SUMMARY OF THE INVENTION

The prior art discloses various antibody-drug conjugates with enzymatically cleavable linkers which, however, do not have an optimum activity profile, for example with respect to their broad activity on different cells. It is therefore an object of the present invention to provide more effective compounds which, after administration at a relatively low concentration, exhibit long-lasting apoptotic action and are therefore of benefit for cancer therapy. Here, on the one hand, the profile of the metabolites released intracellularly from the ADCs plays an important role. Frequently, the metabolites formed from ADCs are substrates of efflux pumps and/or have high cell membrane permeability. Both phenomena may contribute to a short residence time and thus suboptimal apoptotic action in the tumour cell.

Accordingly, the present invention provides binder-drug conjugates (ADCs) having a specific toxophore-linker composition which, in association with antibodies, have a particularly interesting activity profile with respect to potency and activity spectrum. In order to further improve the tumour selectivity of ADCs and the metabolites thereof, binder conjugates have been provided with peptide linkers which can be released by lysosomal tumour-associated enzymes such as legumain or cathepsin. The tumour selectivity is thus determined not just by the choice of antibody but additionally by the enzymatic cleavage of the peptide derivative, for example by tumour-associated enzymes such as legumain. Furthermore, the metabolites released from the binder-drug conjugates (ADCs) according to the invention in the tumour cells are distinguished by a particularly interesting property profile. They exhibit low efflux from the tumour cell and lead to high active compound exposition in tumours. Thus, a high activity is achieved in the tumour cell whereas, owing to poor permeability, there is only low systemic cytotoxic activity, resulting in lower off-target toxicity.

The kinesin spindle protein inhibitors used in accordance with the invention have an amino group which is essential to the effect. By modification of this amino group with peptide derivatives, the effect with respect to the kinesin spindle protein is blocked and hence the development of a cytotoxic effect is also inhibited. These peptide derivatives may also be components of the linker to the antibody. If this peptide residue or peptide linker, however, can be released from the active compound by tumour-associated enzymes such as legumain or cathepsin, the effect can be re-established in a controlled manner in the tumour tissue. The particular property profile of the metabolites formed in the tumour is ensured by a further modification of the kinesin spindle protein inhibitor at a position different from the amino group in the molecule which, however, does not adversely affect the high potency at the target.

Furthermore, the structure of the ADCs according to the invention allows, for certain embodiments, high loading of the antibody (referred to as DAR, drug-to-antibody ratio) which, surprisingly, has no negative effect on the physico-chemical and pharmakokinetic behaviour of the ADCs.

Surprisingly, it has now been found that binder-drug conjugates of the formula (I)

(I)

in which
$X_1$ represents N,
$X_2$ represents N and
$X_3$ represents C;
or
$X_1$ represents N,
$X_2$ represents C and
$X_3$ represents N;
or
$X_1$ represents CH or CF,
$X_2$ represents C and
$X_3$ represents N;
or
$X_1$ represents NH,
$X_2$ represents C and
$X_3$ represents C;
or
$X_1$ represents CH,
$X_2$ represents N and
$X_3$ represents C,
$R^1$ represents hydrogen or methyl,
$R^2$ represents methyl, ethyl, —CH$_2$—CH(CH$_3$)$_2$, —CH$_2$—C(=O)OH or isopropyl,
$R^3$ represents methyl, ethyl, —CH$_2$—CH(CH$_3$)$_2$ or —CH$_2$—C(=O)—NH$_2$,
M represents the group
  #-C(=O)—CH(CH$_3$)—NH—C(=O)—CH$_2$—NH—C(=O)—CH$_2$—CH(##)-COOH,
  #-C(=O)—CH(CH$_3$)—NH—C(=O)—CH$_2$—NH—C(=O)—CH(##)-CH$_2$—COOH,
  #-C(=O)—CH(CH$_3$)—NH—C(=O)—CH$_2$—W,
  #-C(=O)—CH$_2$—NH—C(=O)—CH$_2$—CH(##)-COOH,
  #-C(=O)—CH$_2$—NH—C(=O)—CH(##)-CH$_2$—COOH,
  #-C(=O)—CH$_2$—W,
  #-C(=O)—CH(CH$_3$)—NH—C(=O)—(CH$_2$)$_{2-8}$—C(=O)-###,
  #-C(=O)—(CH$_2$)$_3$—C(=O)-###,
  #-C(=O)—CH(CH$_3$)—NH—C(=O)—(CH$_2$)$_5$—W,
  #-C(=O)—CH(CH$_3$)—NH—C(=O)—(CH$_2$)-## or
  #-C(=O)—CH(CH$_3$)—NH—C(=O)—(CH$_2$—CH$_2$—O)$_{1-8}$—(CH$_2$)$_2$—NH—C(=O)—CH$_2$-##,
W represents the group n represents a number from 1 to 50,
AK represents a binder or a derivative thereof, preferably an antibody or an
antigen-binding fragment,
# represents the bond to the compound,
## represents the bond to a sulfur atom of a cysteine side-chain of the binder,
### represents the bond to a nitrogen atom of a lysine side-chain of the binder,
and their salts, solvates and salts of these solvates, have superior properties compared to the known conjugates.

Preference is given to those binder-drug conjugates of the formula (I), in which
$X_1$ represents CH,
$X_2$ represents C, X$_3$ represents N,
R$^1$ represents hydrogen or methyl,
R$^2$ represents methyl, —CH$_2$—CH(CH$_3$)$_2$, —CH$_2$—C(=O)OH or isopropyl,
R$^3$ represents methyl, —CH$_2$—CH(CH$_3$)$_2$ or —CH$_2$—C(=O)—NH$_2$,
M represents the group
  #-C(=O)—CH(CH$_3$)—NH—C(=O)—CH$_2$—NH—C(=O)—CH$_2$—CH(##)-COOH,
  #-C(=O)—CH(CH$_3$)—NH—C(=O)—CH$_2$—NH—C(=O)—CH(##)-CH$_2$—COOH,
  #-C(=O)—CH(CH$_3$)—NH—C(=O)—CH$_2$—W,
  #-C(=O)—CH$_2$—NH—C(=O)—CH$_2$—CH(##)-COOH,
  #-C(=O)—CH$_2$—NH—C(=O)—CH(##)-CH$_2$—COOH,
  #-C(=O)—CH$_2$—W,
  #-C(=O)—CH(CH$_3$)—NH—C(=O)—(CH$_2$)$_3$—C(=O)-###,
  #-C(=O)—(CH$_2$)$_3$—C(=O)-###,
  #-C(=O)—CH(CH$_3$)—NH—C(=O)—(CH$_2$)$_5$—W,
  #-C(=O)—CH(CH$_3$)—NH—C(=O)—(CH$_2$)-## or
  #-C(=O)—CH(CH$_3$)—NH—C(=O)—(CH$_2$—CH$_2$—O)$_4$—(CH$_2$)$_2$—NH—C(=O)—CH$_2$-##,
W represents the group

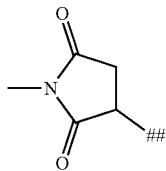

n represents a number from 1 to 50,
AK represents a binder or a derivative thereof, preferably an antibody or an antigen-binding fragment,
# represents the bond to the compound,
## represents the bond to a sulfur atom of a cysteine side-chain of the binder,
### represents the bond to a nitrogen atom of a lysine side-chain of the binder, and their salts, solvates and salts of these solvates.

Particular preference is given to those binder-drug conjugates of the formula (I), in which
R$^1$ represents hydrogen or methyl,
R$^2$ represents methyl or isopropyl,
R$^3$ represents methyl or —CH$_2$—C(=O)—NH$_2$,
M represents the group
  #-C(=O)—CH(CH$_3$)—NH—C(=O)—(CH$_2$)$_3$—C(=O)-###,
n represents a number from 1 to 50,
AK represents a binder or a derivative thereof, preferably an antibody or an antigen-binding fragment,
# represents the bond to the compound,
### represents the bond to a nitrogen atom of a lysine side-chain of the binder, and their salts, solvates and salts of these solvates.

Very particular preference is given to those binder-drug conjugates of the formula (I), in which
R$^1$ represents methyl,
R$^2$ represents methyl,
R$^3$ represents —CH$_2$—C(=O)—NH$_2$,
M represents the group
  #-C(=O)—CH(CH$_3$)—NH—C(=O)—(CH$_2$)$_3$—C(=O)-###,
n represents a number from 1 to 50,
AK represents a binder or a derivative thereof, preferably an antibody or an antigen-binding fragment,
# represents the bond to the compound,
### represents the bond to a nitrogen atom of a lysine side-chain of the binder, and their salts, solvates and salts of these solvates.

Special preference is given to those binder-drug conjugates of the formula (I), in which
R$^1$ represents methyl,
R$^2$ represents methyl,
R$^3$ represents —CH$_2$—C(=O)—NH$_2$,
M represents the group
  #-C(=O)—CH(CH$_3$)—NH—C(=O)—(CH$_2$)$_3$—C(=O)-###,
n represents a number from 1 to 20,
AK represents a binder or a derivative thereof, preferably an antibody or an antigen-binding fragment,
# represents the bond to the compound,
### represents the bond to a nitrogen atom of a lysine side-chain of the binder, and their salts, solvates and salts of these solvates.

Selected are those binder-drug conjugates of the formula (I),
in which
R$^1$ represents methyl,
R$^2$ represents methyl,
R$^3$ represents —CH$_2$—C(=O)—NH$_2$,
M represents the group
  #-C(=O)—CH(CH$_3$)—NH—C(=O)—(CH$_2$)$_3$—C(=O)-###,
n represents a number from 1 to 20 and
AK represents an anti-CD123 antibody, an anti-CXCR5 antibody, an anti-B7H3 antibody, an anti-TWEAKR antibody, an anti-Her2 antibody or an anti-EGFR antibody or represents an antigen-binding antibody fragment of these,
# represents the bond to the compound,
### represents the bond to a nitrogen atom of a lysine side-chain of the antibody (AK) or of the antigen-binding antibody fragment thereof,
and their salts, solvates and salts of these solvates.

Selected are in particular those binder-drug conjugates of the formula (I),
in which
R$^1$ represents methyl,
R$^2$ represents methyl,
R$^3$ represents —CH$_2$—C(=O)—NH$_2$,
M represents the group
  #-C(=O)—CH(CH$_3$)—NH—C(=O)—(CH$_2$)$_3$—C(=O)-###,
n represents a number from 1 to 20 and
AK represents an anti-CD123 antibody selected from the group consisting of TPP-9476, TPP-8988, TPP-8987 and TPP-6013, represents an anti-CXCR5 antibody selected from the group consisting of TPP-9574 and TPP-9580, represents an anti-B7H3 antibody TPP-8382, represents an anti-TWEAKR antibody selected from the group consisting of TPP-7006 and TPP-7007, represents an anti- Her2 antibody TPP-1015 or represents an anti-EGFR antibody TPP-981 or represents an antigen-binding antibody fragment of these, # represents the bond to the compound, ### represents the bond to a nitrogen atom of a lysine side-chain of the antibody (AK) or of the antigen-binding antibody fragment thereof, and their salts, solvates and salts of these solvates.

Preference is given to those binder-drug conjugates of the formulae mentioned above in which AK represents a binder which specifically binds to an extracellular cancer target molecule. In a preferred embodiment, the binder, after binding to its extracellular target molecule on the target cell, is internalized by the target cell through the binding. Preferably, the binder is an antibody or an antigen-binding fragment.

In a preferred subject of the invention, the extracellular cancer target molecule is selected from the group consisting of the cancer target molecules EGFR, CD123, HER2, B7H3, TWEAKR and CXCR5; particular preference is given to CD123, CXCR5 and B7H3.

In a preferred subject of the invention, the binder AK is an anti-CD123 antibody, an anti-CXCR5 antibody, an anti-B7H3 antibody, an anti-TWEAKR antibody, an anti-Her2 antibody or an anti-EGFR antibody, or an antigen-binding antibody fragment of these. Especially preferred are those binder-drug conjugates of the formulae mentioned in which AK (AK1, AK2) represents an antibody selected from the group consisting of TPP-8382 (anti B7H3), TPP-6013 (anti-CD123), TPP-8987 (anti-CD123), TPP-8988 (anti-CD123), TPP 9476 (anti-CD123), TPP-9574 (anti-CXCR5) and TPP 9580 (anti-CXCR5), or an antigen-binding fragment of these. Here, preference is given to the antibodies TPP-6013, TPP-8987, TPP-8988 and TPP-9476 (in each case anti-CD123). The exact structure (sequence) of these antibodies can be found in the table: Protein sequences of the antibodies, the text following this table and the sequence listing.

Especially preferred are those binder-drug conjugates of the formula (I) in which AK represents an antibody selected from the group consisting of TPP-8382 (anti B7H3), TPP-6013 (anti-CD123), TPP-8987 (anti-CD123), TPP-8988 (anti-CD123), TPP 9476 (anti-CD123), TPP-9574 (anti-CXCR5) and TPP 9580 (anti-CXCR5). Here, preference is given to the antibodies (AK) TPP-6013, TPP-8987, TPP-8988 and TPP-9476 (in each case anti-CD123).

DESCRIPTION OF THE FIGURES

FIGS. 1A-1L: Annotated sequences of preferred antibodies for binder-drug conjugates. What are shown are the protein sequences of the heavy and light chains of the IgGs, and the VH and VL regions of these antibodies. Below the sequences, important regions are annotated (VH and VL regions in IgGs, and the CDR regions (H-CDR1, H-CDR2, H-CDR3, L-CDR1, L-CDR2, L-CDR3)). SEQ ID NOs of annotated sequences are as follows: TPP-981 VH (PRT)—SEQ ID NO: 1, TPP-981 VL (PRT)—SEQ ID NO: 5, TPP-981 Heavy Chain (PRT)—SEQ ID NO: 9, TPP-981 Light Chain (PRT)—SEQ ID NO: 10, TPP-1015 VH (PRT)—SEQ ID NO: 11, TPP-1015 VL (PRT)—SEQ ID NO: 15, TPP-1015 Heavy Chain (PRT)—SEQ ID NO: 19, TPP-1015 Light Chain (PRT)—SEQ ID NO: 20, TPP-6013 VH (PRT)—SEQ ID NO: 21, TPP-6013 VL (PRT)—SEQ ID NO: 25, TPP-6013 Heavy Chain (PRT)—SEQ ID NO: 29, TPP-6013 Light Chain (PRT)—SEQ ID NO: 30, TPP-7006 VH (PRT)—SEQ ID NO: 31, TPP-7006 VL (PRT)—SEQ ID NO: 35, TPP-7006 Heavy Chain (PRT)—SEQ ID NO: 39, TPP-7006 Light Chain (PRT)—SEQ ID NO: 40, TPP-7007 VH (PRT)—SEQ ID NO: 41, TPP-7007 VL (PRT)—SEQ ID NO: 45, TPP-7007 Heavy Chain (PRT)—SEQ ID NO: 49, TPP-7007 Light Chain (PRT)—SEQ ID NO: 50, TPP-8382 VH (PRT)—SEQ ID NO: 51, TPP-8382 VL (PRT)—SEQ ID NO: 55, TPP-8382 Heavy Chain (PRT)—SEQ ID NO: 59, TPP-8382 Light Chain (PRT)—SEQ ID NO: 60, TPP-8987 VH (PRT)—SEQ ID NO: 61, TPP-8987 VL (PRT)—SEQ ID NO: 65, TPP-8987 Heavy Chain (PRT)—SEQ ID NO: 69, TPP-8987 Light Chain (PRT)—SEQ ID NO: 70, TPP-8988 VH (PRT)—SEQ ID NO: 71, TPP-8988 VL (PRT)—SEQ ID NO: 75, TPP-8988 Heavy Chain (PRT)—SEQ ID NO: 79, TPP-8988 Light Chain (PRT)—SEQ ID NO: 80, TPP-9476 VH (PRT)—SEQ ID NO: 81, TPP-9476 VL (PRT)—SEQ ID NO: 85, TPP-9476 Heavy Chain (PRT)—SEQ ID NO: 89, TPP-9476 Light Chain (PRT)—SEQ ID NO: 90, TPP-9574 VH (PRT)—SEQ ID NO: 91, TPP-9574 VL (PRT)—SEQ ID NO: 95, TPP-9574 Heavy Chain (PRT)—SEQ ID NO: 99, TPP-9574 Light Chain (PRT)—SEQ ID NO: 100, TPP-9580 VH (PRT)—SEQ ID NO: 101, TPP-9580 VL (PRT)—SEQ ID NO: 105, TPP-9580 Heavy Chain (PRT)—SEQ ID NO: 109, and TPP-9580 Light Chain (PRT)—SEQ ID NO: 110.

FIGS. 2A-2K: Sequence listing of sequences of the preferred antibodies for binder-drug conjugates and of sequences of the target proteins.

DETAILED DESCRIPTION OF THE INVENTION

The invention provides conjugates of a binder or derivative thereof with one or more drug molecules, the drug molecule being a kinesin spindle protein inhibitor (KSP inhibitor).

Binders which can be used according to the invention, KSP inhibitors thereof which can be used according to the invention and linkers which can be used according to the invention which can be used in combination without any limitation are described below. In particular, the binders represented in each case as preferred or particularly preferred can be employed in combination with the KSP inhibitors represented in each case as preferred or particularly preferred, optionally in combination with the linkers represented in each case as preferred or particularly preferred.

Particularly Preferred KSP-Inhibitor Conjugates (Binder-Drug Conjugates)

Particular preference is given in accordance with the invention to the KSP inhibitor conjugates which follow, where AK (AK$_1$, AK$_2$) represents binders or a derivative thereof (preferably an antibody), and n represents a number from 1 to 20, preferably 1 to 8 and more preferably 4 to 8. AK$_1$ preferably represents an antibody bonded via a cysteine residue to the KSP inhibitor; AK$_2$ preferably represents an antibody bonded via a lysine residue to the KSP inhibitor. The binders or antibodies used here are preferably the binders and antibodies described as preferred in the description.

Here, particular preference is given to the following binder-drug conjugates:
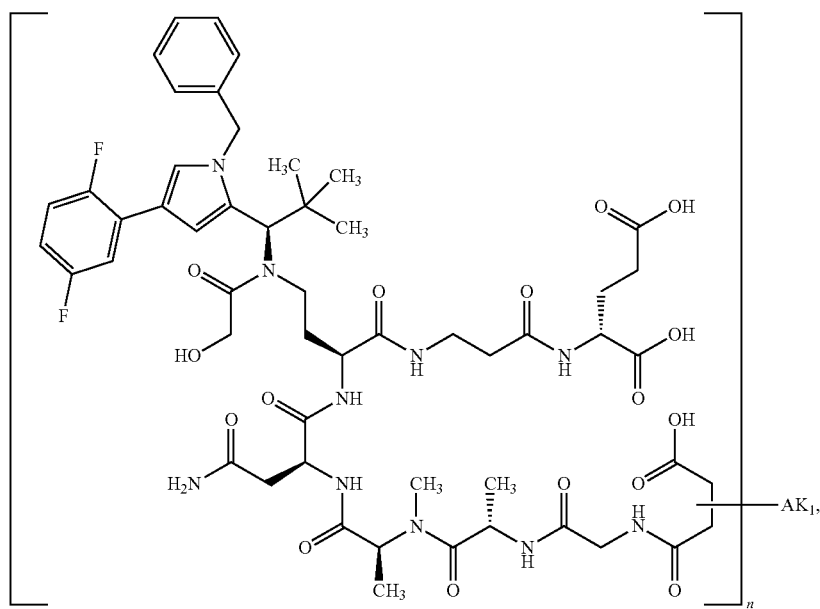
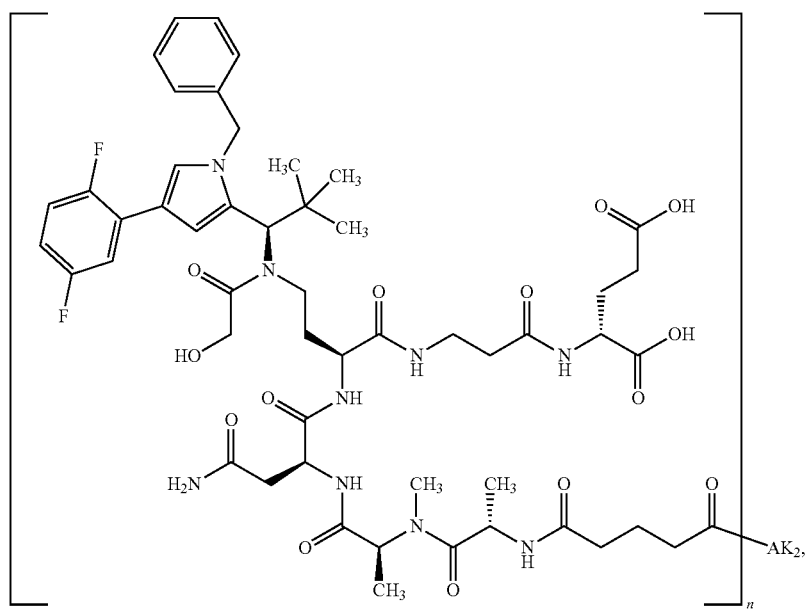

-continued
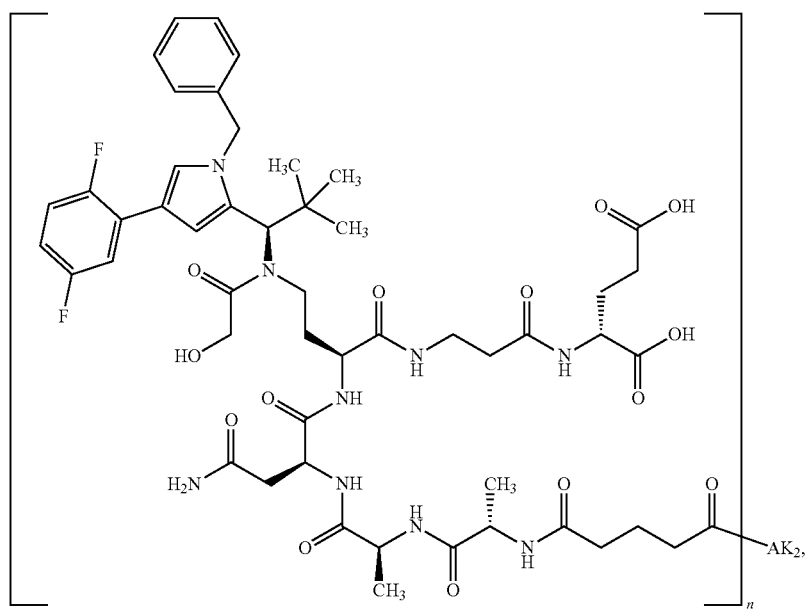
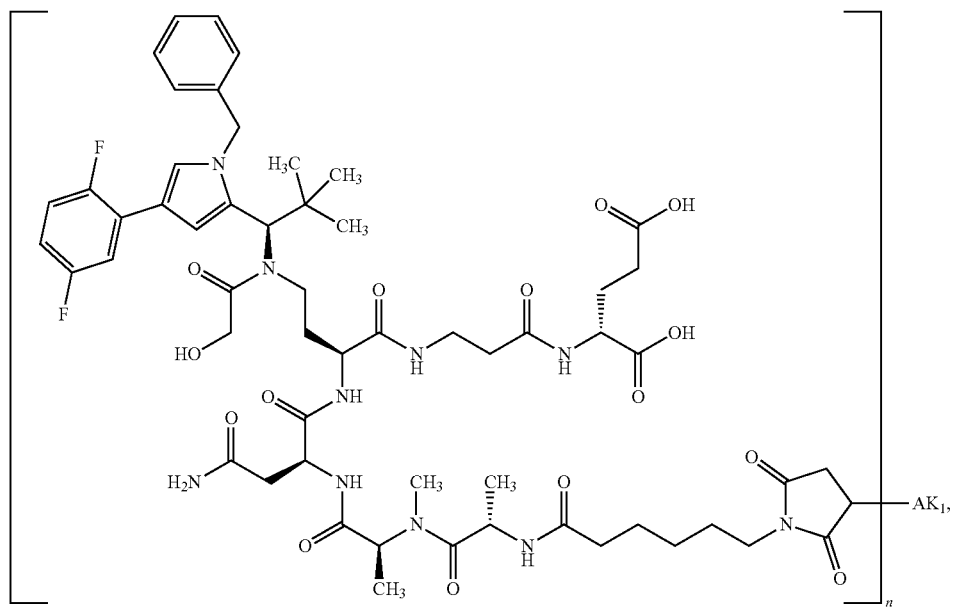

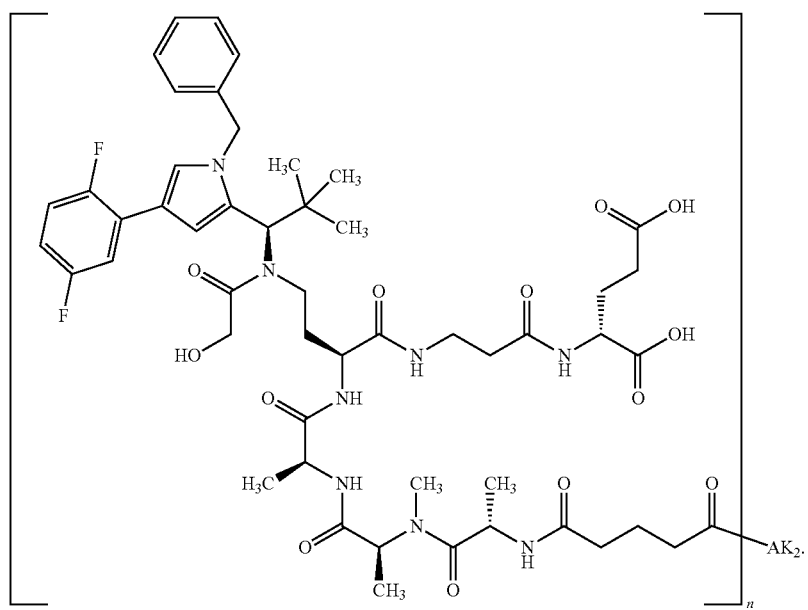
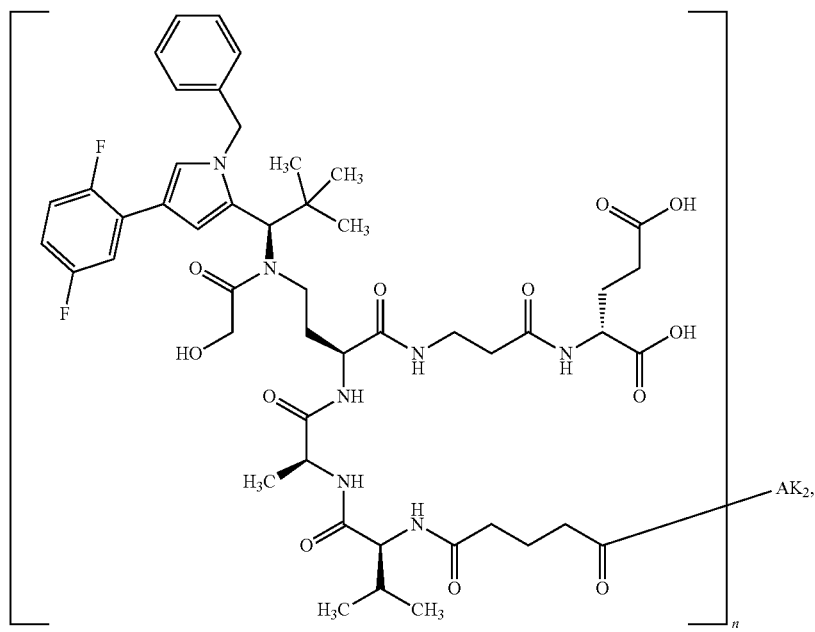

-continued
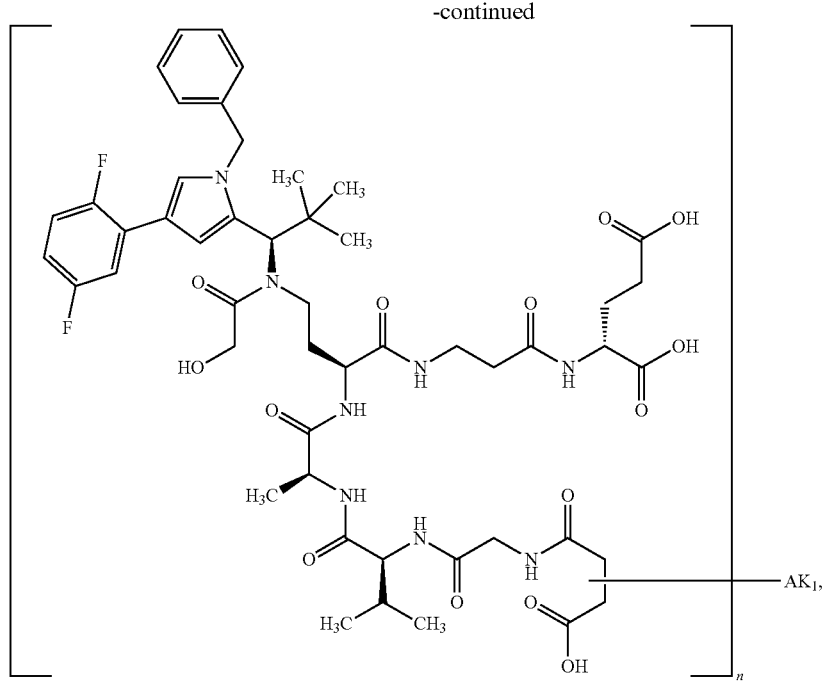
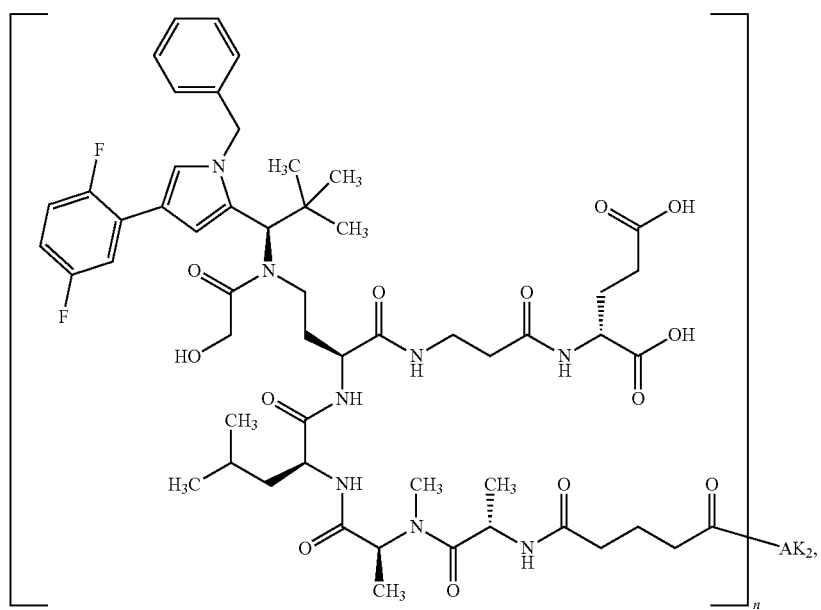

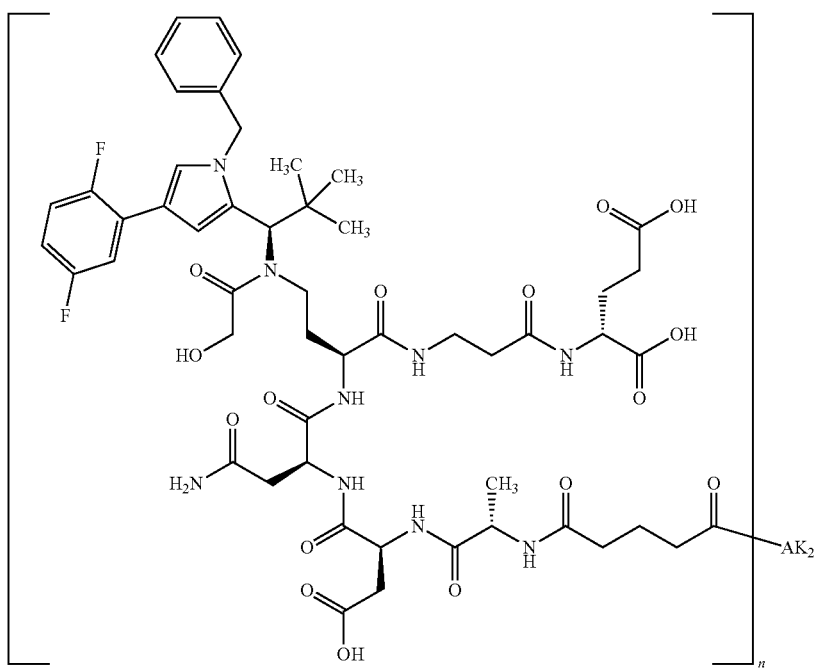
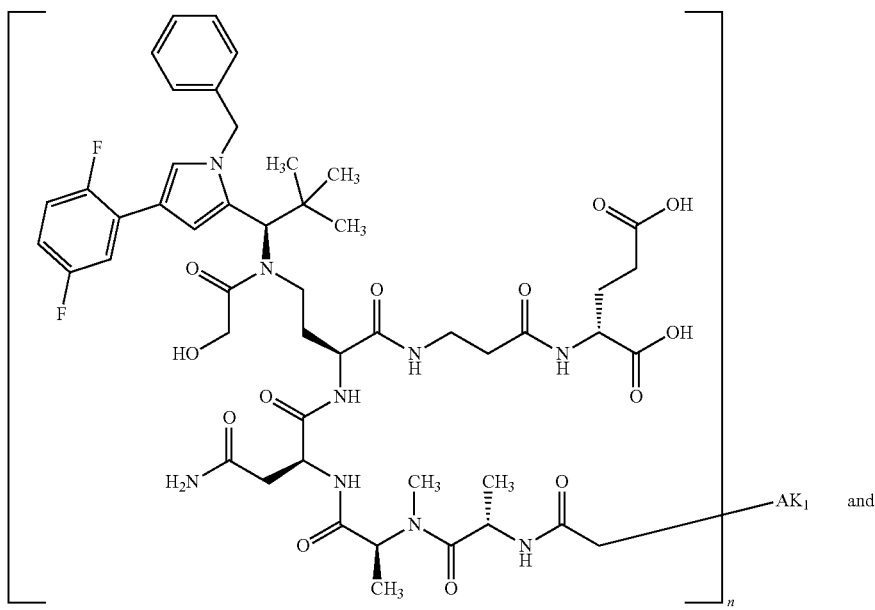

-continued

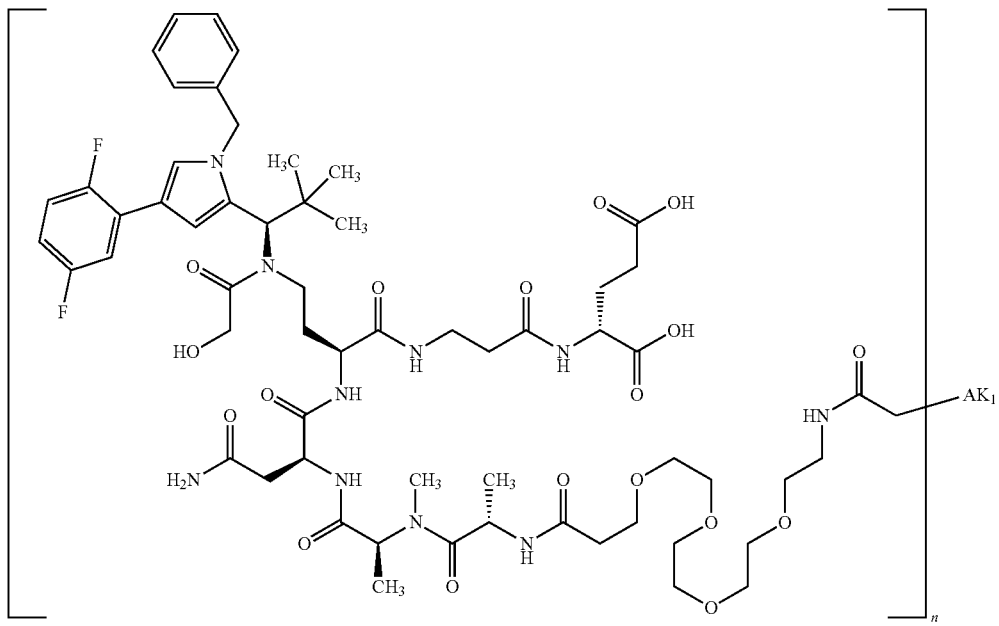

Preference is given to those binder-drug conjugates of the formulae mentioned in which AK (AK1, AK2) represents a binder which specifically binds to an extracellular cancer target molecule. In a preferred embodiment, the binder, after binding to its extracellular target molecule on the target cell, is internalized by the target cell through the binding.

In a preferred subject of the invention, the extracellular cancer target molecule is selected from the group consisting of the cancer target molecules EGFR, CD123, Her2, B7H3, TWEAKR and CXCR5, in particular CD123, CXCR5 and B7H3.

In a preferred subject of the invention, the binder AK (AK$_1$, AK$_2$) is an anti-CD123 antibody, an anti-CXCR5 antibody, an anti-B7H3 antibody, an anti-TWEAKR antibody, an anti-Her2 antibody or an anti-EGFR antibody, or an antigen-binding antibody fragment of these.

Especially preferred are those binder-drug conjugates of the formulae mentioned in which AK (AK1, AK2) represents an antibody selected from the group consisting of TPP-8382 (anti B7H3), TPP-6013 (anti-CD123), TPP-8987 (anti-CD123), TPP-8988 (anti-CD123), TPP-9476 (anti-CD123), TPP-9574 (anti-CXCR5) and TPP-9580 (anti-CXCR5), or an antigen-binding fragment of these. Here, preference is given to the antibodies TPP-6013, TPP-8987, TPP-8988 and TPP-9476 (in each case anti-CD123). The exact structure (sequence) of these antibodies can be found in the table: Protein sequences of the antibodies, the text following this table and the sequence listing.

KSP Inhibitor—Linker-Intermediates and Preparation of the Conjugates

The conjugates according to the invention are prepared by initially providing the low-molecular weight KSP inhibitor thereof with a linker. The intermediate obtained in this manner is then reacted with the binder (preferably antibody).

For an intermediate that couples to a lysine residue and the subsequent coupling with the antibody, the reaction can be illustrated as follows:

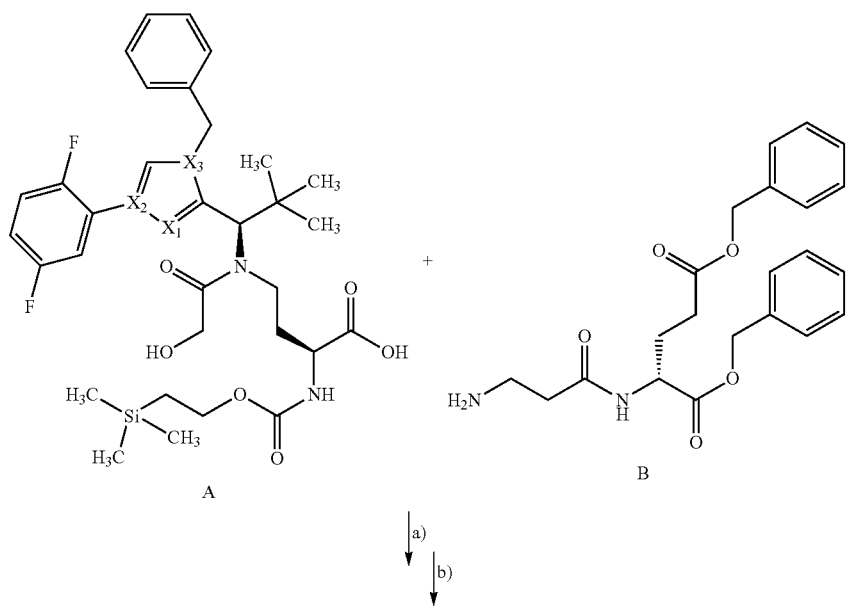
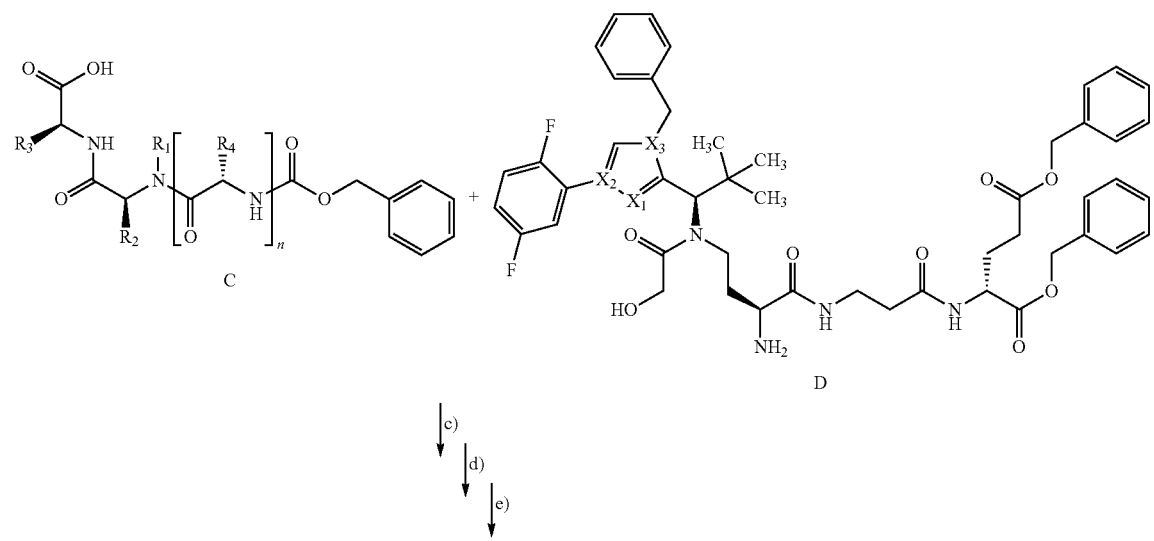

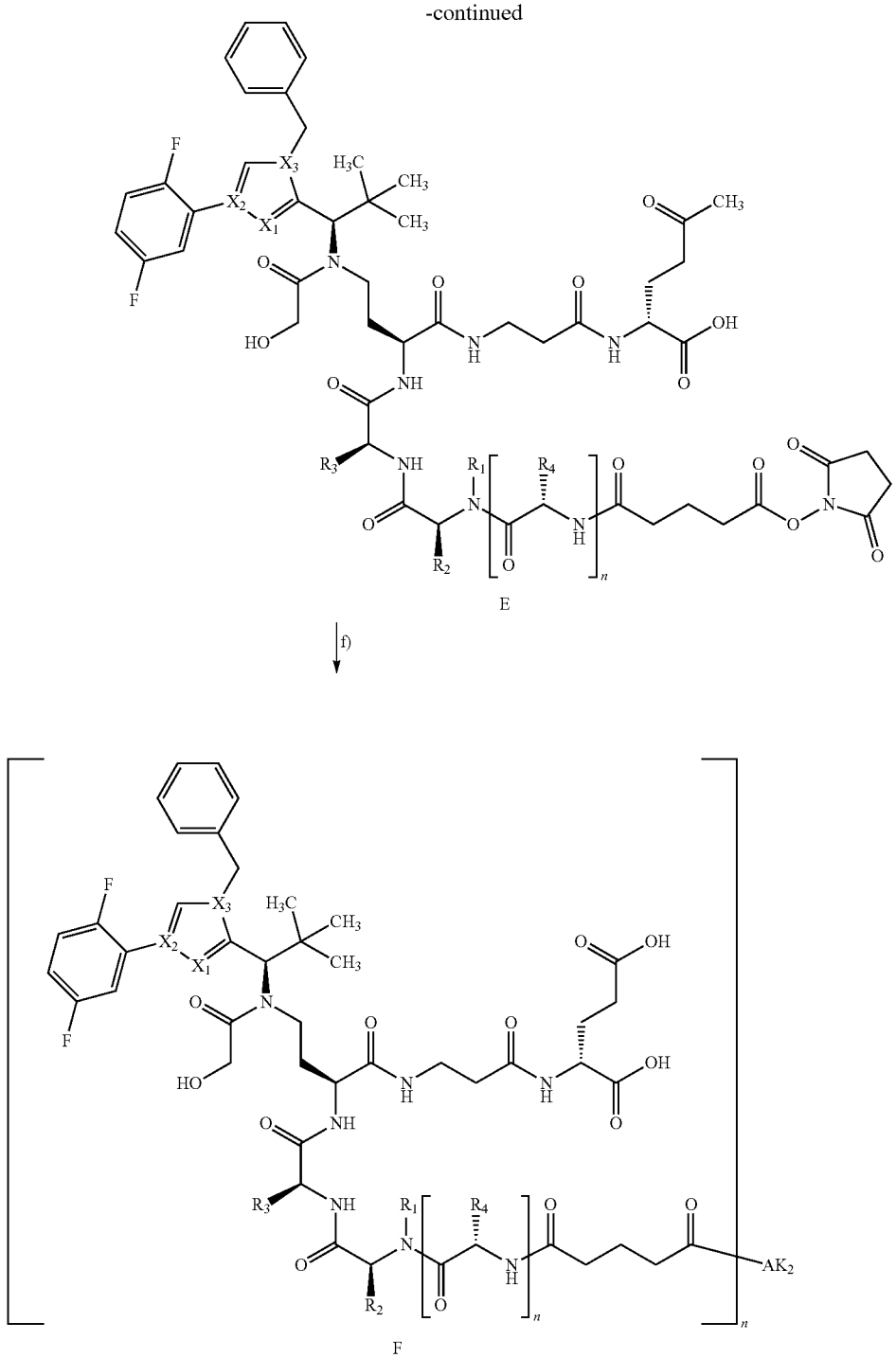

In the above reaction scheme, $X_1$, $X_2$, $X_3$, $R^1$, $R^2$, $R^3$ and $AK_2$ have the meanings given in the formula (I) and here $R^4$ represents methyl and n represents 0 or 1.

The synthesis of building block A has been described in WO2015/096982. The peptide derivatives B and C were prepared by classical methods of peptide chemistry. Intermediates C and D were coupled using HATU in DMF in the presence of N,N-diisopropylethylamine at RT. Subsequently, both the benzyloxycarbonyl protective group and the benzyl ester were removed hydrogenolytically over 10% palladium on activated carbon. The completely deprotected intermediate was then reacted with 1,1'-[(1,5-dioxopentan-1,5-diyl)bis(oxy)]dipyrrolidine-2,5-dione in DMF in the presence of N,N-diisopropylethylamine at RT to give the ADC precursor molecule E. This activated ester was then coupled with the respective antibodies as described in Chapter B-5.

For an intermediate that couples to a cysteine residue and the subsequent coupling with the antibody, the reaction can be illustrated as follows:

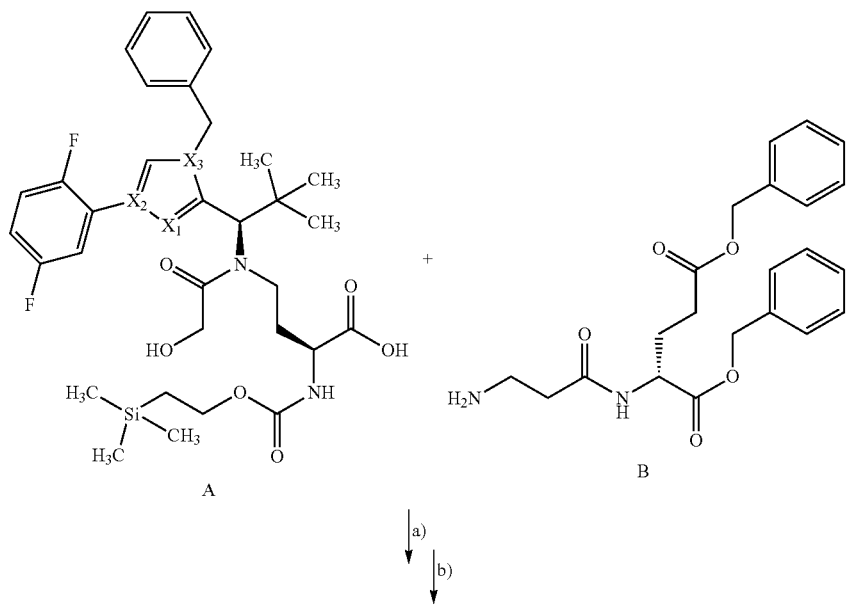
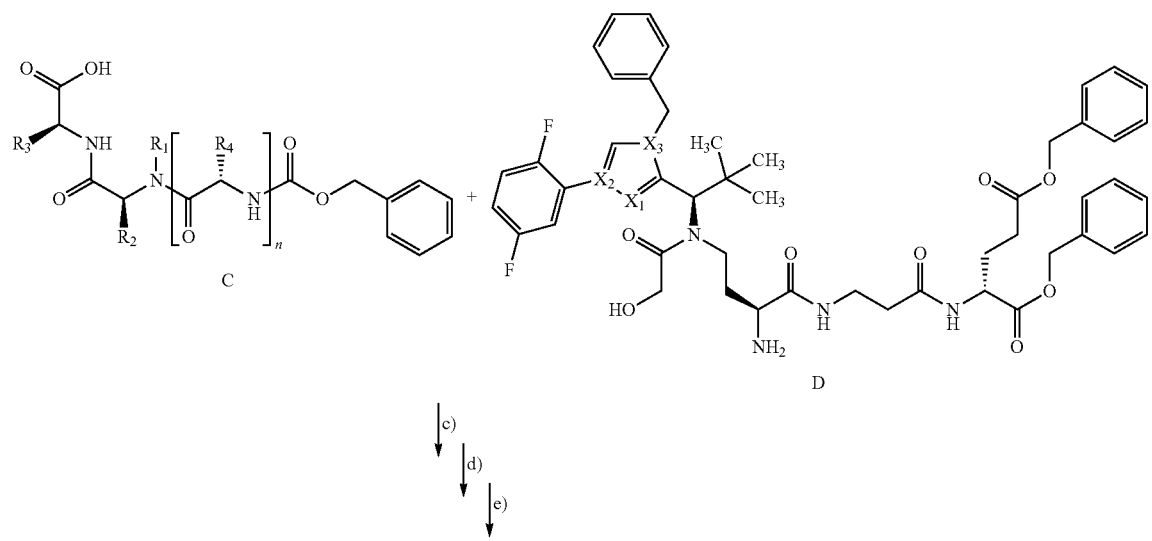

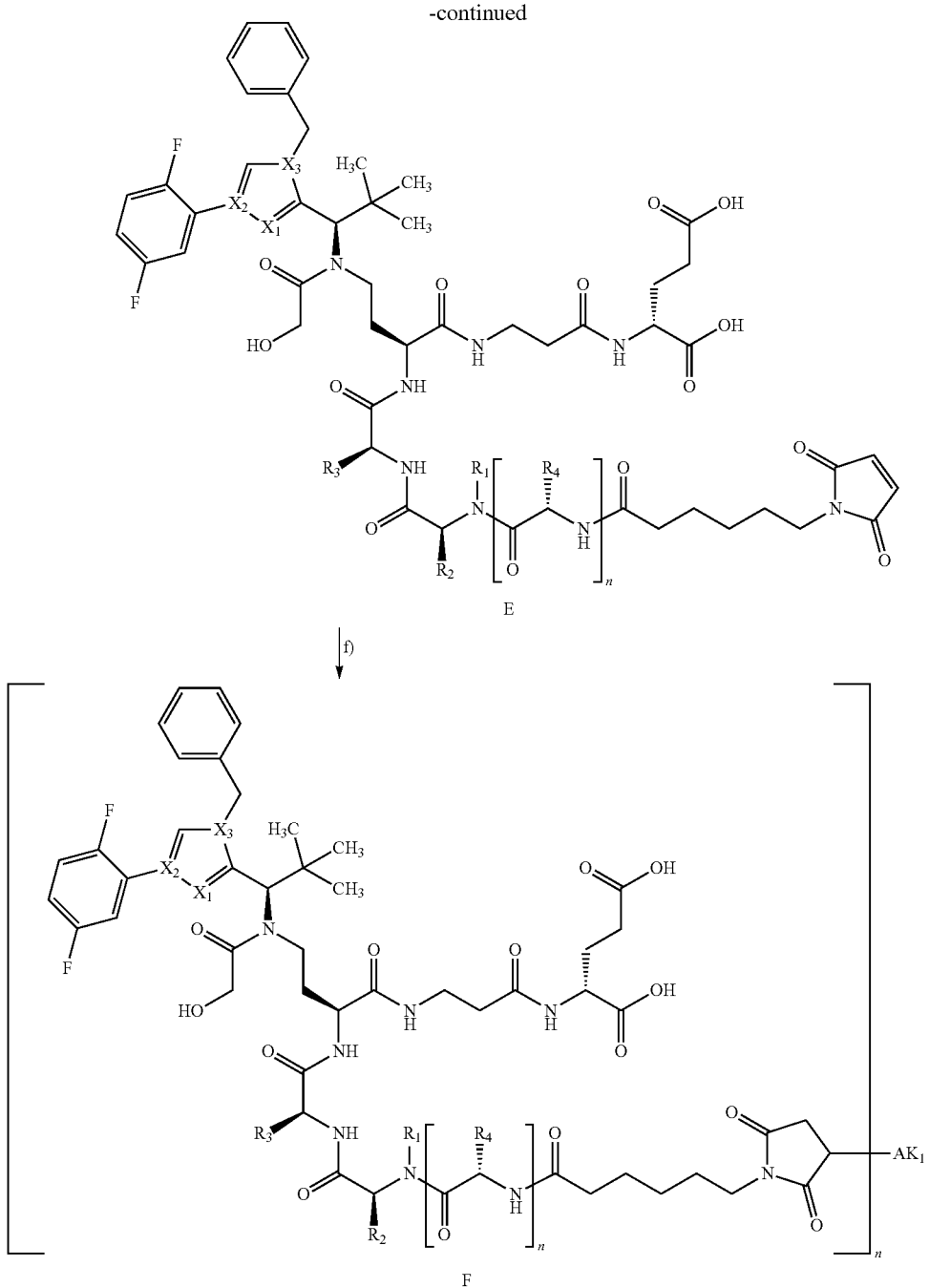

In the above reaction scheme, $X_1$, $X_2$, $X_3$, $R^1$, $R^2$, $R^3$ and $AK_1$ have the meanings given in the formula (I) and here $R^4$ represents methyl and n represents 1.

Using an analogous procedure, it is also possible to prepare compounds in which n represents 0.

The synthesis of building block A has been described in WO2015/096982. The peptide derivatives B and C were prepared by classical methods of peptide chemistry. Intermediates C and D were coupled using HATU in DMF in the presence of N,N-diisopropylethylamine at RT. Subsequently, both the benzyloxycarbonyl protective group and the benzyl ester were removed hydrogenolytically over 10% palladium on activated carbon. The completely deprotected intermediate was then reacted with 1-{6-[(2,5-dioxopyrrolidin-1-yl)oxy]-6-oxohexyl}-1H-pyrrole-2,5-dione in DMF in the presence of N,N-diisopropylethylamine at RT to give the ADC precursor molecule E. This maleimide derivative was then coupled with the respective antibodies as described in Chapter B-4.

Depending on the linker, succinimide-linked ADCs may, after conjugation, be converted into the open-chain succinamides, which have an advantageous stability profile.

This reaction (ring opening) can be effected at pH 7.5 to 9, preferably at pH 8, at a temperature of 25° C. to 37° C., for example by stirring. The preferred stirring time is 8 to 30 hours.

For an intermediate that couples to a cysteine residue and the subsequent coupling with the antibody followed by ring opening of the succinimide ring, the reaction can be illustrated as follows:
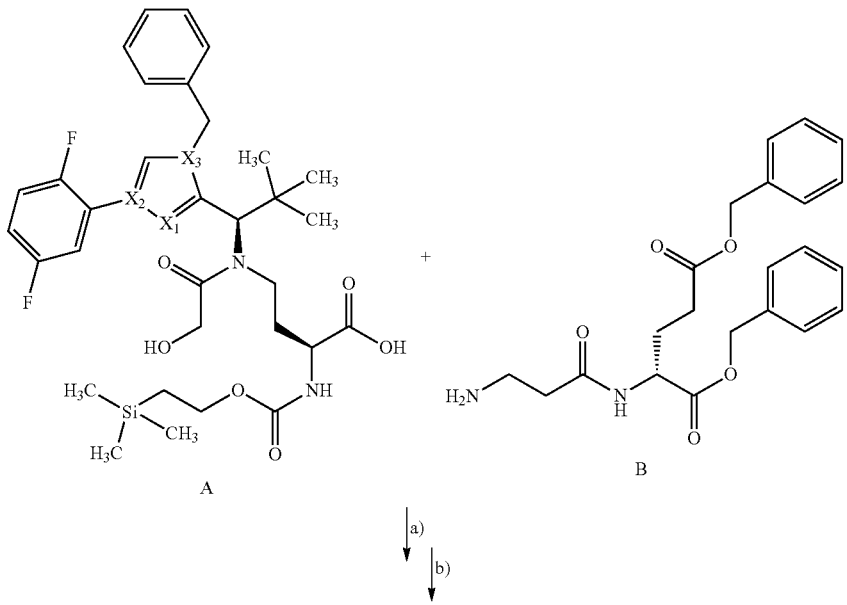
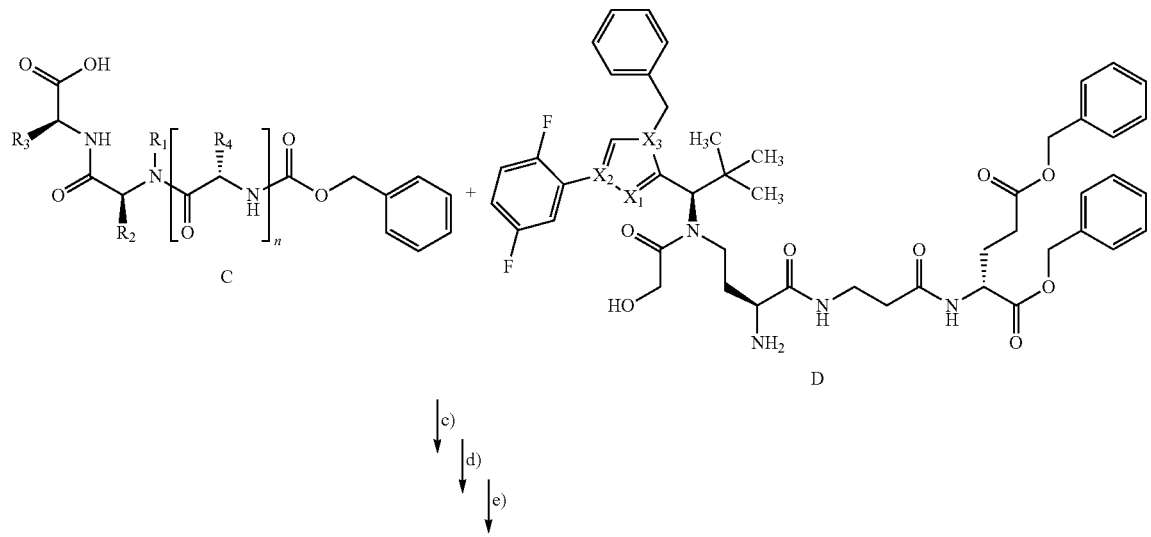

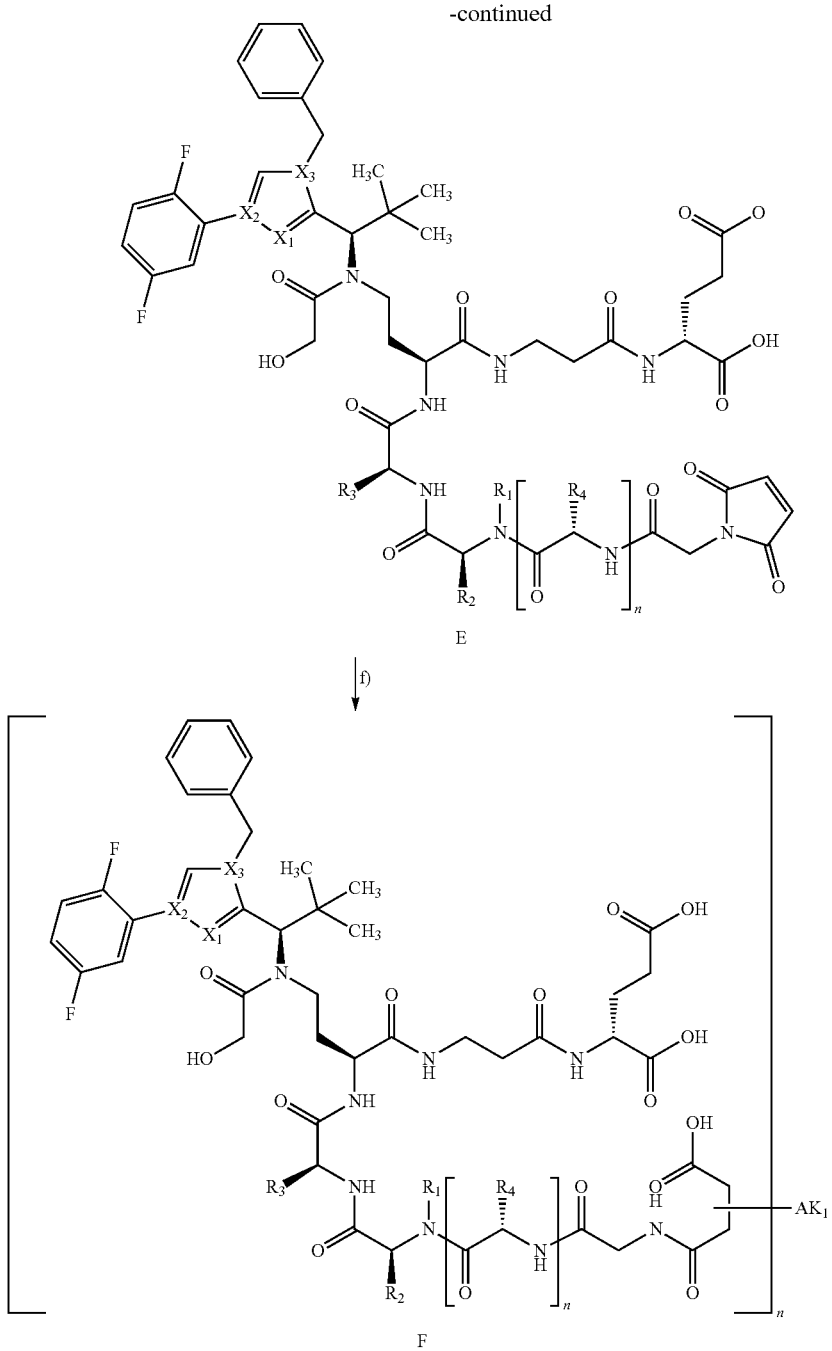

In the above reaction scheme, $X_1$, $X_2$, $X_3$, $R^1$, $R^2$, $R^3$ and AK, have the meanings given in the formula (I) and here $R^4$ represents methyl and n represents 0 or 1.

The synthesis of building block A has been described in WO2015/096982. The peptide derivatives B and C were prepared by classical methods of peptide chemistry. Intermediates C and D were coupled using HATU in DMF in the presence of N,N-diisopropylethylamine at RT. Subsequently, both the benzyloxycarbonyl protective group and the benzyl ester were removed hydrogenolytically over 10% palladium on activated carbon. The completely deprotected intermediate was then reacted with 1-{2-[(2,5-dioxopyrrolidin-1-yl)oxy]-2-oxoethyl}-1H-pyrrole-2,5-dione in the presence of N,N-diisopropylethylamine at RT to give the ADC precursor molecule E. This maleimide derivative was then coupled with the respective antibodies as described in Chapter B-4 under small scale coupling or under medium scale coupling.

Binders

In the broadest sense, the term "binder" is understood to mean a molecule which binds to a target molecule present at a certain target cell population to be addressed by the binder-drug conjugate. The term binder is to be understood in its broadest meaning and also comprises, for example, lectins, proteins capable of binding to certain sugar chains, or phospholipid-binding proteins. Such binders include, for example, high-molecular weight proteins (binding proteins), polypeptides or peptides (binding peptides), non-peptidic (e.g. aptamers (U.S. Pat. No. 5,270,163) review by Keefe A D., et al., Nat. Rev. Drug Discov. 2010; 9:537-550), or vitamins) and all other cell-binding molecules or substances. Binding proteins are, for example, antibodies and antibody fragments or antibody mimetics, for example affibodies, adnectins, anticalins, DARPins, avimers, nanobodies (review by Gebauer M. et al., Curr. Opinion in Chem. Biol. 2009; 13:245-255; Nuttall S. D. et al., Curr. Opinion in Pharmacology 2008; 8:608-617). Binding peptides are, for example, ligands of a ligand/receptor pair such as, for example, VEGF of the ligand/receptor pair VEGF/KDR, such as transferrin of the ligand/receptor pair transferrin/transferrin receptor or cytokine/cytokine receptor, such as TNFalpha of the ligand/receptor pair TNFalpha/TNFalpha receptor.

The binder may be a binding protein. Preferred embodiments of the binders are an antibody, an antigen-binding antibody fragment, a multispecific antibody or an antibody mimetic.

The literature also discloses various options of covalent coupling (conjugation) of organic molecules to binders and in particular antibodies. Preference according to the invention is given to the conjugation of the toxophores to the antibody via one or more sulfur atoms of cysteine residues of the antibody and/or via one or more NH groups of lysine residues of the antibody. However, it is also possible to bind the toxophore to the antibody via free carboxyl groups or via sugar residues of the antibody.

A "target molecule" in the broadest sense is understood to mean a molecule which is present in the target cell population and which may be a protein (for example a receptor of a growth factor) or a non-peptidic molecule (for example a sugar or phospholipid). It is preferably a receptor or an antigen.

The term "extracellular" target molecule describes a target molecule, attached to the cell, which is located at the outside of a cell, or the part of a target molecule which is located at the outside of a cell, i.e. a binder may bind on an intact cell to its extracellular target molecule. An extracellular target molecule may be anchored in the cell membrane or be a component of the cell membrane. The person skilled in the art is aware of methods for identifying extracellular target molecules. For proteins, this may be by determining the transmembrane domain(s) and the orientation of the protein in the membrane. These data are usually deposited in protein databases (e.g. SwissProt).

The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

The binder can be attached to the linker via a bond. The binder can be linked by means of a heteroatom of the binder. Heteroatoms according to the invention of the binder which can be used for attachment are sulfur (in one embodiment via a sulfhydryl group of the binder), oxygen (according to the invention by means of a carboxyl or hydroxyl group of the binder) and nitrogen (in one embodiment via a primary or secondary amine group or amide group of the binder). These heteroatoms may be present in the natural binder or are introduced by chemical methods or methods of molecular biology. According to the invention, the attachment of the binder to the toxophore has only a minor effect on the binding activity of the binder with respect to the target molecule. In a preferred embodiment, the linkage has no effect on the binding activity of the binder with respect to the target molecule.

In accordance with the present invention, the term "antibody" is to be understood in its broadest meaning and comprises immunoglobulin molecules, for example intact or modified monoclonal antibodies, polyclonal antibodies or multispecific antibodies (e.g. bispecific antibodies). An immunoglobulin molecule preferably comprises a molecule having four polypeptide chains, two heavy chains (H chains) and two light chains (L chains) which are typically linked by disulfide bridges. Each heavy chain comprises a variable domain of the heavy chain (abbreviated VH) and a constant domain of the heavy chain. The constant domain of the heavy chain may, for example, comprise three domains CH1, CH2 and CH3. Each light chain comprises a variable domain (abbreviated VL) and a constant domain. The constant domain of the light chain comprises a domain (abbreviated CL). The VH and VL domains may be subdivided further into regions having hypervariability, also referred to as complementarity determining regions (abbreviated CDR) and regions having low sequence variability (framework region, abbreviated FR). Typically, each VH and VL region is composed of three CDRs and up to four FRs. For example from the amino terminus to the carboxy terminus in the following order: FR1, CDR1, FR2, CDR2, FR3, CDR3, FR4. An antibody may be obtained from any suitable species, e.g. rabbit, llama, camel, mouse or rat. In one embodiment, the antibody is of human or murine origin. An antibody may, for example, be human, humanized or chimeric.

The term "monoclonal" antibody refers to antibodies obtained from a population of substantially homogeneous antibodies, i.e. individual antibodies of the population are identical except for naturally occurring mutations, of which there may be a small number. Monoclonal antibodies recognize a single antigenic binding site with high specificity. The term monoclonal antibody does not refer to a particular preparation process.

The term "intact" antibody refers to antibodies comprising both an antigen-binding domain and the constant domain of the light and heavy chain. The constant domain may be a naturally occurring domain or a variant thereof having a number of modified amino acid positions, and may also be aglycosylated.

The term "modified intact" antibody refers to intact antibodies fused via their amino terminus or carboxy terminus by means of a covalent bond (e.g. a peptide bond) with a further polypeptide or protein not originating from an antibody. Furthermore, antibodies may be modified such that, at defined positions, reactive cysteines are introduced to facilitate coupling to a toxophore (see Junutula et al. Nat Biotechnol. 2008 August; 26(8):925-32).

"Amino acid modification" or "mutation" here means an amino acid substitution, insertion and/or deletion in a polypeptide sequence. The preferred amino acid modification here is a substitution. "Amino acid substitution" or "substitution" here means an exchange of an amino acid at a given position in a protein sequence for another amino acid. For example, the substitution Y50W describes a variant of a parent polypeptide in which the tyrosine at position 50 has been exchanged for a tryptophan. A "variant" of a polypeptide describes a polypeptide having an amino acid sequence substantially identical to a reference polypeptide, typically a native or "parent" polypeptide. The polypeptide variant may have one or more amino acid exchanges, deletions and/or insertions at particular positions in the native amino acid sequence.

The term "human" antibody refers to antibodies which can be obtained from a human or which are synthetic human antibodies. A "synthetic" human antibody is an antibody which is partially or entirely obtainable in silico from synthetic sequences based on the analysis of human antibody sequences. A human antibody can be encoded, for example, by a nucleic acid isolated from a library of antibody sequences of human origin. An example of such an antibody can be found in Söderlind et al., Nature Biotech. 2000, 18:853-856. Such "human" and "synthetic" antibodies also include aglycosylated variants which have been produced either by deglycosylation by PNGaseF or by mutation of N297 (Kabat numbering) of the heavy chain to any other amino acid.

The term "humanized" or "chimeric" antibody describes antibodies consisting of a non-human and a human portion of the sequence. In these antibodies, part of the sequences of the human immunoglobulin (recipient) is replaced by sequence portions of a non-human immunoglobulin (donor). In many cases, the donor is a murine immunoglobulin. In the case of humanized antibodies, amino acids of the CDR of the recipient are replaced by amino acids of the donor. Sometimes, amino acids of the framework, too, are replaced by corresponding amino acids of the donor. In some cases the humanized antibody contains amino acids present neither in the recipient nor in the donor, which were introduced during the optimization of the antibody. In the case of chimeric antibodies, the variable domains of the donor immunoglobulin are fused with the constant regions of a human antibody. Such "humanized" and "chimeric" antibodies also include aglycosylated variants which have been produced either by deglycosylation by PNGaseF or by mutation of N297 (Kabat numbering) of the heavy chain to any other amino acid.

The term complementarity determining region (CDR) as used herein refers to those amino acids of a variable antibody domain which are required for binding to the antigen. Typically, each variable region has three CDR regions referred to as CDR1, CDR2 and CDR3. Each CDR region may embrace amino acids according to the definition of Kabat and/or amino acids of a hypervariable loop defined according to Chotia. The definition according to Kabat comprises, for example, the region from about amino acid position 24-34 (CDR1), 50-56 (CDR2) and 89-97 (CDR3) of the variable light chain/domain (VL) and 31-35 (CDR1), 50-65 (CDR2) and 95-102 (CDR3) of the variable heavy chain/domain (VH) (Kabat et al., Sequences of Proteins of Immunological Interest, 5th Ed. Public Health Service, National Institutes of Health, Bethesda, Md. (1991)). The definition according to Chotia comprises, for example, the region from about amino acid position 26-32 (CDR1), 50-52 (CDR2) and 91-96 (CDR3) of the variable light chain (VL) and 26-32 (CDR1), 53-55 (CDR2) and 96-101 (CDR3) of the variable heavy chain (VH) (Chothia and Lesk; J Mol Biol 196: 901-917 (1987)). In some cases, a CDR may comprise amino acids from a CDR region defined according to Kabat and Chotia.

Depending on the amino acid sequence of the constant domain of the heavy chain, antibodies may be categorized into different classes. There are five main classes of intact antibodies: IgA, IgD, IgE, IgG and IgM, and several of these can be divided into further subclasses. (Isotypes), e.g. IgG1, IgG2, IgG3, IgG4, IgA1 and IgA2. The constant domains of the heavy chain, which correspond to the different classes, are referred to as [alpha/a], [delta/S], [epsilon/s], [gamma/y] and [my/p]. Both the three-dimensional structure and the subunit structure of antibodies are known.

The term "functional fragment" or "antigen-binding antibody fragment" of an antibody/immunoglobulin is defined as a fragment of an antibody/immunoglobulin (e.g. the variable domains of an IgG) which still comprise the antigen binding domains of the antibody/immunoglobulin. The "antigen binding domain" of an antibody typically comprises one or more hypervariable regions of an antibody, for example the CDR, CDR2 and/or CDR3 region. However, the "framework" or "skeleton" region of an antibody may also play a role during binding of the antibody to the antigen. The framework region forms the skeleton of the CDRs. Preferably, the antigen binding domain comprises at least amino acids 4 to 103 of the variable light chain and amino acids 5 to 109 of the variable heavy chain, more preferably amino acids 3 to 107 of the variable light chain and 4 to 111 of the variable heavy chain, especially preferably the complete variable light and heavy chains, i.e. amino acids 1-109 of the VL and 1 to 113 of the VH (numbering according to WO97/08320).

"Functional fragments" or "antigen-binding antibody fragments" of the invention encompass, non-conclusively, Fab, Fab', F(ab')$_2$ and Fv fragments, diabodies, Single Domain Antibodies (DAbs), linear antibodies, individual chains of antibodies (single-chain Fv, abbreviated to scFv); and multispecific antibodies, such as bi- and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag. Antibodies other than "multispecific" or "multifunctional" antibodies are those having identical binding sites. Multispecific antibodies may be specific for different epitopes of an antigen or may be specific for epitopes of more than one antigen (see, for example, WO 93/17715; WO 92/08802; WO 91/00360; WO 92/05793; Tutt, et al., 1991, J. Immunol. 14760 69; U. S. Pat. Nos. 4,474,893; 4,714,681; 4,925,648; 5,573,920; 5,601,819; or Kostelny et al., 1992, J. Immunol. 148 1547 1553). An F(ab')$_2$ or Fab molecule may be constructed such that the number of intermolecular disulfide interactions occurring between the Ch1 and the CL domains can be reduced or else completely prevented.

"Epitopes" refer to protein determinants capable of binding specifically to an immunoglobulin or T cell receptors. Epitopic determinants usually consist of chemically active surface groups of molecules such as amino acids or sugar side chains or combinations thereof, and usually have specific 3-dimensional structural properties and also specific charge properties.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et al. Nat Biotechnol. 2008 August; 26(8):925-32).

Polyclonal antibodies can be prepared by methods known to a person of ordinary skill in the art. Monoclonal antibodies may be prepared by methods known to a person of ordinary skill in the art (Kohler and Milstein, Nature, 256, 495-497, 1975). Human and humanized monoclonal antibodies may be prepared by methods known to a person of ordinary skill in the art (Olsson et al., Meth Enzymol. 92, 3-16 or Cabilly et al U.S. Pat. No. 4,816,567 or Boss et al U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1): 65-93) or Phage Display Technologien (Clackson et al., Nature. 1991 Aug. 15; 352(6336):624-8). Antibodies of the invention may be obtained from recombinant antibody libraries consisting for example on the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of a cell. A preferred antibody or binder is one which has been purified to an extent of more than 95% by weight, relative to the antibody or binder (determined for example by Lowry method, UV-Vis spectroscopy or by SDS capillary gel electrophoresis). Moreover an antibody which has been purified to such an extent that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blue staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with Kd values smaller than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. Specific binding of an antibody or binder does not exclude the antibody or binder binding to a plurality of antigens/target molecules (e.g. orthologs of different species). The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-11}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$ M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Antibodies Directed Against a Cancer Target Molecule

The target molecule towards which the binder, for example an antibody or an antigen-binding fragment thereof, is directed is preferably a cancer target molecule. The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

Antibodies which are specific against an antigen, for example cancer cell antigen, can be prepared by a person of ordinary skill in the art by means of methods with which he or she is familiar (such as recombinant expression, for example) or may be acquired commercially (as for example from Merck KGaA, Germany). Examples of known commercially available antibodies in cancer therapy are Erbitux® (cetuximab, Merck KGaA), Avastin® (bevacizumab, Roche) and Herceptin® (trastuzumab, Genentech). Trastuzumab is a recombinant humanized monoclonal antibody of the IgG1kappa type which in a cell-based assay (Kd=5 nM) binds the extracellular domains of the human epidermal growth receptor with high affinity. The antibody is produced recombinantly in CHO cells. All these antibodies can also be produced as aglycosylated variants of these antibodies, either by deglycosylation by means of PNGase F or by mutation of N297 (Kabat numbering) of the heavy chain to any amino acid.

In a preferred embodiment, the target molecule is a selective cancer target molecule.

In a particularly preferred embodiment, the target molecule is a protein.

In one embodiment, the target molecule is an extracellular target molecule. In a preferred embodiment, the extracellular target molecule is a protein.

Cancer target molecules are known to those skilled in the art. Examples of these are listed below.

Examples of cancer target molecules are:

(1) EGFR (EGF receptor, NCBI Reference Sequence NP_005219.2, NCBI Gene ID: 1956)

(2) mesothelin (SwissProt Reference Q13421-3), mesothelin being encoded by amino acids 296-598. Amino acids 37-286 code for megakaryocyte-potentiating factor.

Mesothelin is anchored in the cell membrane by a GPI anchor and is localized extracellularly.

(3) Carboanhydrase IX (CA9, SwissProt Reference Q16790), NCBI Gene ID: 768)

(4) C4.4a (NCBI Reference Sequence NP_055215.2; synonym LYPD3, NCBI Gene ID: 27076)

(5) CD52 (NCBI Reference Sequence NP_001794.2)

(6) Her2 (ERBB2; NCBI Reference Sequence NP_004439.2; NCBI Gene ID: 2064)

(7) CD20 (NCBI Reference Sequence NP_068769.2)

(8) the lymphocyte activation antigen CD30 (SwissProt ID P28908)

(9) the lymphocyte adhesion molecule CD22 (SwissProt ID P20273; NCBI Gene ID: 933)

(10) the myloid cell surface antigen CD33 (SwissProt ID P20138; NCBI Gene ID: 945)

(11) the transmembrane glycoprotein NMB (GPNMB, SwissProt ID Q14956, NCBI Gene ID: 10457)

(12) the adhesion molecule CD56 (SwissProt ID P13591)

(13) the surface molecule CD70 (SwissProt ID P32970, NCBI Gene ID: 970)

(14) the surface molecule CD74 (SwissProt ID P04233, NCBI Gene ID: 972)

(15) the B-lymphocyte antigen CD19 (SwissProt ID P15391, NCBI Gene ID: 930)

(16) the surface protein Mucin-1 (MUC1, SwissProt ID P15941, NCBI Gene ID: 4582)

(17) the surface protein CD138 (SwissProt ID P18827)

(18) the integrin alphaV (NCBI reference sequence: NP_002201.1, NCBI Gene ID: 3685)

(19) the teratocarcinoma-derived growth factor 1 protein TDGF1 (NCBI Reference Sequence: NP_003203.1, NCBI Gene ID: 6997)

(20) the prostate-specific membrane antigen PSMA (Swiss Prot ID: Q04609; NCBI Gene ID: 2346)

(21) the tyrosine protein kinase EPHA2 (Swiss Prot ID: P29317, NCBI Gene ID: 1969)

(22) the surface protein SLC44A4 (NCBI Reference Sequence: NP_001171515.1, NCBI Gene ID: 80736)

(23) the surface protein BMPR1B (SwissProt: 000238)

(24) the transport protein SLC7A5 (SwissProt: Q01650)

(25) the epithelial prostate antigen STEAP1 (SwissProt: Q9UHE8, Gene ID: 26872)

(26) the ovarian carcinoma antigen MUC16 (SwissProt: Q8WX17, Gene ID: 94025)

(27) the transport protein SLC34A2 (SwissProt: 095436, Gene ID: 10568)

(28) the surface protein SEMA5b (SwissProt: Q9P283)

(29) the surface protein LYPD1 (SwissProt: Q8N2G4)

(30) the endothelin receptor type B EDNRB (SwissProt: P24530, NCBI Gene ID: 1910)

(31) the ring finger protein RNF43 (SwissProt: Q68DV7)

(32) the prostate carcinoma-associated protein STEAP2 (SwissProt: Q8NFT2)

(33) the cation channel TRPM4 (SwissProt: Q8TD43)

(34) the complement receptor CD21 (SwissProt: P20023)

(35) the B-cell antigen receptor complex-associated protein CD79b (SwissProt: P40259, NCBI Gene ID: 974)

(36) the cell adhesion antigen CEACAM6 (SwissProt: P40199)

(37) the dipeptidase DPEP1 (SwissProt: P16444)

(38) the interleukin receptor IL20Ralpha (SwissProt: Q9UHF4, NCBI Gene ID: 3559)

(39) the proteoglycan BCAN (SwissProt: Q96GW7)

(40) the ephrin receptor EPHB2 (SwissProt: P29323)

(41) the prostate stem cell-associated protein PSCA (NCBI Reference Sequence: NP_005663.2)

(42) the surface protein LHFPL3 (SwissProt: Q86UP9)

(43) the receptor protein TNFRSF13C (SwissProt: Q96RJ3)

(44) the B-cell antigen receptor complex-associated protein CD79a (SwissProt: P11912)

(45) the receptor protein CXCR5 (CD185; SwissProt: P32302; NCBI Gene ID 643, NCBI Reference Sequence: NP_001707.1)

(46) the ion channel P2X5 (SwissProt: Q93086)

(47) the lymphocyte antigen CD180 (SwissProt: Q99467)

(48) the receptor protein FCRL1 (SwissProt: Q96LA6)

(49) the receptor protein FCRL5 (SwissProt: Q96RD9)

(50) the MHC class II molecule Ia antigen HLA-DOB (NCBI Reference Sequence: NP_002111.1)

(51) the T-cell protein VTCN1 (SwissProt: Q7Z7D3)

(52) TWEAKR (FN14, TNFRSF12A, NCBI Reference Sequence: NP_057723.1, NCBI Gene ID: 51330)

(53) the lymphocyte antigen CD37 (Swiss Prot: P11049, NCBI Gene ID: 951)

(54) the FGF receptor 2; FGFR2 (NCBI Gene ID: 2263; Official Symbol: FGFR2). FGFR2 receptor occurs in different splice variants (alpha, beta, IIIb, IIIc). All splice variants can act as target molecule.

(55) the transmembrane glycoprotein B7H3 (CD276; NCBI Gene ID: 80381 NCBI Reference Sequence: NP_001019907.1, Swiss Prot: Q5ZPR3-1)

(56) the B cell receptor BAFFR (CD268; NCBI Gene ID: 115650)

(57) the receptor protein ROR 1 (NCBI Gene ID: 4919)

(58) the surface receptor CD123 (IL3RA; NCBI Gene ID: 3563; NCBI Reference Sequence: NP_002174.1; SwissProt: P26951)

(59) the receptor protein syncytin (NCBI Gene ID 30816)

(60) aspartate beta-hydroxylase (ASPH; NCBI Gene ID 444)

(61) the cell surface glycoprotein CD44 (NCBI Gene ID: 960)

(62) CDH15 (Cadherin 15, NCBI Gene ID: 1013)

(63) the cell surface glycoprotein CEACAM5 (NCBI Gene ID: 1048)

(64) the cell adhesion molecule L1-like (CHL1, NCBI Gene ID: 10752)

(65) the receptor tyrosine kinase c-Met (NCBI Gene ID: 4233)

(66) the notch ligand DLL3 (NCBI Gene ID: 10683)

(67) the ephrin A4 (EFNA4, NCBI Gene ID: 1945)

(68) ectonucleotide pyrophosphatase/phosphodiesterase 3 (ENPP3, NCBI Gene ID: 5169)

(69) coagulation factor III (F3, NCBI Gene ID: 2152)

(70) FGF receptor 3 (FGFR3, NCBI Gene ID: 2261)

(71) the folate hydrolase FOLH1 (NCBI Gene ID: 2346)

(72) the folate receptor 1 (FOLR1; NCBI Gene ID: 2348)

(73) the guanylate cyclase 2C (GUCY2C, NCBI Gene ID: 2984)

(74) the KIT proto-oncogen receptor tyrosine kinase (NCBI Gene ID: 3815)

(75) lysosomal-associated membrane protein 1 (LAMP1, NCBI Gene ID: 3916)

(76) lymphocyte antigen 6 complex, locus E (LY6E, NCBI Gene ID: 4061)

(77) the protein NOTCH3 (NCBI Gene ID: 4854)

(78) protein tyrosine kinase 7 (PTK7, NCBI Gene ID: 5754)

(79) nectin cell adhesion molecule 4 (PVRL4, NECTIN4, NCBI Gene ID: 81607)

(80) the transmembrane protein syndecan 1 (SDC1, NCBI Gene ID: 6382)

(81) SLAM family member 7 (SLAMF7, NCBI Gene ID: 57823)

(82) the transport protein SLC39A6 (NCBI Gene ID: 25800)

(83) SLIT- and NTRK-like family member 6 (SLITRK6, NCBI Gene ID: 84189)

(84) the cell surface receptor TACSTD2 (NCBI Gene ID: 4070)

(85) the receptor protein TNFRSF8 (NCBI Gene ID: 943)

(86) the receptor protein TNFSF13B (NCBI Gene ID: 10673)

(87) the glycoprotein TPBG (NCBI Gene ID: 7162)

(88) the cell surface receptor TROP2 (TACSTD2, NCBI Gene ID: 4070)

(89) the galanin-like G protein-coupled receptor KISS1R (GPR54, NCBI Gene ID: 84634)

(90) the transport protein SLAMF6 (NCBI Gene ID: 114836)

In a preferred subject of the invention, the cancer target molecule is selected from the group consisting of the cancer target molecules EGFR, CD123, Her2, B7H3, TWEAKR and CXCR5, in particular CD123, CXCR5 and B7H3.

In a further particularly preferred subject of the invention, the binder binds to an extracellular cancer target molecule selected from the group consisting of the cancer target molecules EGFR, CD123, Her2, B7H3, TWEAKR and CXCR5, in particular CD123, CXCR5 and B7H3.

In a further particularly preferred subject of the invention, the binder binds specifically to an extracellular cancer target molecule selected from the group consisting of the cancer target molecules EGFR, CD123, Her2, B7H3, TWEAKR and CXCR5, in particular CD123, CXCR5 and B7H3. In a preferred embodiment, the binder, after binding to its extracellular target molecule on the target cell, is internalized by the target cell through the binding. This causes the binder-drug conjugate, which may be an immunoconjugate or an ADC, to be taken up by the target cell. The binder is then processed, preferably intracellularly, with preference lysosomally.

In one embodiment the binder is a binding protein. In a preferred embodiment the binder is an antibody, an antigen-binding antibody fragment, a multispecific antibody or an antibody mimetic.

Preferred antibody mimetics are affibodies, adnectins, anticalins, DARPins, avimers, or nanobodies. Preferred multispecific antibodies are bispecific and trispecific antibodies.

In a preferred embodiment the binder is an antibody or an antigen-binding antibody fragment, more preferably an isolated antibody or an isolated antigen-binding antibody fragment.

Preferred antigen-binding antibody fragments are Fab, Fab', F(ab')2 and Fv fragments, diabodies, DAbs, linear antibodies and scFv. Particularly preferred are Fab, diabodies and scFv.

In a particularly preferred embodiment the binder is an antibody. Particularly preferred are monoclonal antibodies or antigen-binding antibody fragments thereof. Further particularly preferred are human, humanized or chimeric antibodies or antigen-binding antibody fragments thereof.

Antibodies or antigen-binding antibody fragments which bind cancer target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK Example 2 on page 72). Further processes for preparing antibodies that use DNA libraries from B cells are described for example on page 26 (WO 2007/070538).

Processes for humanizing antibodies are described on page 30-32 of WO2007070538 and in detail in Queen, et al., Pros. Natl. Acad. Sci. USA 8610029-10033,1989 or in WO 90/0786. Furthermore, processes for recombinant expression of proteins in general and of antibodies in particular are known to the person skilled in the art (see, for example, in Berger and Kimrnel (Guide to Molecular Cloning Techniques, Methods in Enzymology, Vol. 152, Academic Press, Inc.); Sambrook, et al., (Molecular Cloning A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, Green Publishing Associates, Inc./John Wiley & Sons, Inc.); Harlow et al., (Monoclonal Antibodies A Laboratory Manual, Cold Spring Harbor Laboratory Press (19881, Paul [Ed.]); Fundamental Immunology, (Lippincott Williams & Wilkins (1998)); and Harlow, et al., (Using Antibodies A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

Bacterial Expression

The person skilled in the art is aware of the way in which antibodies, antigen-binding fragments thereof or variants thereof can be produced with the aid of bacterial expression. Suitable expression vectors for bacterial expression of desired proteins are constructed by insertion of a DNA sequence which encodes the desired protein within the functional reading frame together with suitable translation initiation and translation termination signals and with a functional promoter. The vector comprises one or more phenotypically selectable markers and a replication origin in order to enable the retention of the vector and, if desired, the amplification thereof within the host. Suitable prokaryotic hosts for transformation include but are not limited to *E. coli, Bacillus subtilis, Salmonella typhimurium* and various species from the genus *Pseudomonas, Streptomyces*, and *Staphylococcus*. Bacterial vectors may be based, for example, on bacteriophages, plasmids, or phagemids. These vectors may contain selectable markers and a bacterial replication origin, which are derived from commercially available plasmids. Many commercially available plasmids typically contain elements of the well-known cloning vector pBR322 (ATCC 37017). In bacterial systems, a number of advantageous expression vectors can be selected on the basis of the intended use of the protein to be expressed.

After transformation of a suitable host strain and growth of the host strain to an appropriate cell density, the selected promoter is de-reprimed/induced by suitable means (for example a change in temperature or chemical induction), and the cells are cultivated for an additional period. The cells are typically harvested by centrifugation and if necessary digested in a physical manner or by chemical means, and the resulting raw extract is retained for further purification.

Therefore, a further embodiment of the present invention is an expression vector comprising a nucleic acid which encodes a novel antibody of the present invention.

Antibodies of the present invention or antigen-binding fragments thereof include naturally purified products, products which originate from chemical syntheses, and products which are produced by recombinant technologies in prokaryotic hosts, for example *E. coli, Bacillus subtilis, Salmonella typhimurium* and various species from the genus *Pseudomonas, Streptomyces*, and *Staphylococcus*, preferably *E. coli*.

Mammalian Cell Expression

The person skilled in the art is aware of the way in which antibodies, antigen-binding fragments thereof or variants thereof can be produced with the aid of mammalian cell expression.

Preferred regulatory sequences for expression in mammalian cell hosts include viral elements which lead to high expression in mammalian cells, such as promoters and/or expression amplifiers derived from cytomegalovirus (CMV) (such as the CMV promoter/enhancer), simian virus 40 (SV40) (such as the SV40 promoter/enhancer), from adenovirus, (for example the adenovirus major late promoter (AdMLP)) and from polyoma. The expression of the antibodies may be constitutive or regulated (for example induced by addition or removal of small molecule inductors such as tetracycline in combination with the Tet system).

For further description of viral regulatory elements and sequences thereof, reference is made, for example, to U.S. Pat. No. 5,168,062 by Stinski, U.S. Pat. No. 4,510,245 by Bell et al. and U.S. Pat. No. 4,968,615 by Schaffner et al. The recombinant expression vectors may likewise include a replication origin and selectable markers (see, for example, U.S. Pat. Nos. 4,399,216, 4,634,665 and 5,179,017). Suitable selectable markers include genes which impart resistance to substances such as G418, puromycin, hygromycin, blasticidin, zeocin/bleomycin, or methotrexate, or selectable markers which lead to auxotrophy of a host cell, such as glutamine synthetase (Bebbington et al., Biotechnology (N Y). 1992 February; 10(2):169-75), when the vector has been introduced into the cell.

For example, the dihydrofolate reductase (DHFR) gene imparts resistance to methotrexate, the neo gene imparts resistance to G418, the bsd gene from *Aspergillus terreus* imparts resistance to blasticidin, puromycin N-acetyltransferase imparts resistance to puromycin, the Sh ble gene product imparts resistance to zeocin, and resistance to hygromycin is imparted by the *E. coli* hygromycin resistance gene (hyg or hph). Selectable markers such as DHFR or glutamine synthetase are also helpful for amplification techniques in conjunction with MTX and MSX.

The transfection of an expression vector into a host cell can be executed with the aid of standard techniques, including by electroporation, nucleofection, calcium phosphate precipitation, lipofection, polycation-based transfection such as polyethyleneimine (PEI)-based transfection and DEAE-dextran transfection.

Suitable mammalian host cells for the expression of antibodies, antigen-binding fragments thereof, or variants thereof include Chinese hamster ovary (CHO) cells such as CHO-K1, CHO-S, CHO-K1SV [including DHFR-CHO cells, described in Urlaub and Chasin, (1980) Proc. Natl. Acad. Sci. USA 77:4216-4220 and Urlaub et al., Cell. 1983 June; 33(2):405-12, used with a DHFR-selectable marker, as described in R. J. Kaufman and P. A. Sharp (1982) Mol. Biol. 159:601-621, and other knockout cells, as detailed in Fan et al., Biotechnol Bioeng. 2012 April; 109(4):1007-15), NS0 myeloma cells, COS cells, HEK293 cells, HKB11 cells, BHK21 cells, CAP cells, EB66 cells, and SP2 cells.

The expression of antibodies, antigen-binding fragments thereof, or variants thereof can also be effected in a transient or semi-stable manner in expression systems such as HEK293, HEK293T, HEK293-EBNA, HEK293E, HEK293-6E, HEK293 Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for example like Durocher et al., Nucleic Acids Res. 2002 Jan. 15; 30(2):E9)

In some embodiments, the expression vector is constructed in such a way that the protein to be expressed is secreted into the cell culture medium in which the host cells are growing. The antibodies, the antigen-binding fragments thereof, or the variants thereof can be obtained from the cell culture medium with the aid of protein purification methods known to those skilled in the art.

Purification

The antibodies, the antigen-binding fragments thereof, or the variants thereof can be obtained and purified from recombinant cell cultures with the aid of well-known methods, examples of which include ammonium sulfate or ethanol precipitation, acid extraction, protein A chromatography, protein G chromatography, anion or cation exchange chromatography, phosphocellulose chromatography, hydrophobic interaction chromatography (HIC), affinity chromatography, hydroxyapatite chromatography and lectin chromatography. High-performance liquid chromatography ("HPLC") can likewise be employed for purification. See, for example, Colligan, Current Protocols in Immunology, or Current Protocols in Protein Science, John Wiley & Sons, NY, N.Y., (1997-2001), e.g., Chapters 1, 4, 6, 8, 9, 10.

Antibodies of the present invention or antigen-binding fragments thereof, or variants thereof include naturally purified products, products from chemical synthesis methods and products which are produced with the aid of recombinant techniques in prokaryotic or eukaryotic host cells. Eukaryotic hosts include, for example, yeast cells, higher plant cells, insect cells and mammalian cells. Depending on the host cell chosen for the recombinant expression, the protein expressed may be in glycosylated or non-glycosylated form.

In a preferred embodiment, the antibody is purified (1) to an extent of more than 95% by weight, measured, for example, by the Lowry method, by UV-vis spectroscopy or by SDS capillary gel electrophoresis (for example with a Caliper LabChip GXII, GX 90 or Biorad Bioanalyzer instrument), and in more preferred embodiments more than 99% by weight, (2) to a degree suitable for determination of at least 15 residues of the N-terminal or internal amino acid sequence, or (3) to homogeneity determined by SDS-PAGE under reducing or non-reducing conditions with the aid of Coomassie blue or preferably silver staining.

Usually, an isolated antibody is obtained with the aid of at least one protein purification step.

Anti-CD123 Antibodies

According to the invention, it is possible to use anti-CD123 antibodies.

The expression "anti-CD123 antibody" or "an antibody which binds specifically to CD123" relates to an antibody which binds the cancer target molecule CD123 (IL3RA; NCBI-Gene ID: 3563; NCBI Reference sequence: NP_002174.1; Swiss-Prot: P26951; SEQ ID NO: 111), preferably with an affinity sufficient for a diagnostic and/or therapeutic application. In particular embodiments, the antibody binds CD123 with a dissociation constant ($K_D$) of ≤1 µM, ≤100 nM, ≤10 nM, ≤1 nM, ≤0.1 nM, ≤0.01 nM, or ≤0.001 nM.

Sun et al. (Sun et al., 1996, Blood 87(1)83-92) describe the generation and properties of the monoclonal antibody 7G3, which binds the N-terminal domain of IL-3Rα, CD123. U.S. Pat. No. 6,177,078 (Lopez) relates to the anti-CD123 antibody 7G3. A chimeric variant of this antibody (CSL360) is described in WO 2009/070844, and a humanized version (CSL362) in WO 2012/021934. The sequence of the 7G3 antibody is disclosed in EP2426148. This sequence constitutes the starting point for the humanized antibodies obtained by CDR grafting.

An antibody which, after cell surface antigen binding, is internalized particularly well is the anti-CD123 antibody 12F1 disclosed by Kuo et al. (Kuo et al., 2009, Bioconjug Chem. 20(10):1975-82). The antibody 12F1 binds with higher affinity to CD123 than the antibody 7G3 and, after cell surface antigen binding, is internalized markedly faster than 7G3. Bispecific scFv immunofusion proteins based on 12F1 are disclosed in WO 2013/173820. Antibody TPP-6013 is a chimeric variant of 12F1.

The invention relates in particular to conjugates with antibodies or antigen-binding antibody fragments thereof or variants thereof derived from the antibodies 7G3 (Sun et al., 1996, Blood 87(1):83-92) and 12F1 (Kuo et al., 2009, Bioconjug Chem. 20(10):1975-82) originating from the mouse, or to conjugates with antibodies or antigen-binding antibody fragments thereof or variants thereof derived from the antibody 12F1 (Kuo et al., 2009, Bioconjug Chem. 20(10):1975-82) originating from the mouse.

Humanized variants of the murine 7G3 antibody and the murine 12F1 antibody were generated by CDR grafting into a human framework and subsequent optimization and are preferred examples in the context of the present invention.

Particular preference is given in the context of the present invention to the anti-CD123 antibodies TPP-9476, TPP-8988, TPP-8987 and TPP-6013.

Anti-CXCR5 Antibodies

According to the invention, it is possible to use anti-CXCR5 antibodies.

The expression "anti-CXCR5 antibody" or "an antibody which binds specifically to CXCR5" relates to an antibody which binds the cancer target molecule CXCR5 (NCBI Reference Sequence: NP_001707.1; SEQ ID NO: 112), preferably with an affinity sufficient for a diagnostic and/or therapeutic application. In particular embodiments, the antibody binds CXCR5 with a dissociation constant ($K_D$) of ≤1 µM, ≤100 nM, ≤10 nM, ≤1 nM, ≤0.1 nM, ≤0.01 nM, or ≤0.001 nM.

Examples of antibodies and antigen-binding fragments which bind to CXCR5 are known to those skilled in the art and are described, for example, in EP2195023.

The hybridoma cells for the rat antibody RF8B2 (ACC2153) were purchased from DSMZ and the sequence of the antibody was identified by standard methods. This sequence constitutes the starting point for the humanized antibodies obtained by CDR grafting.

Humanized variants of this antibody were generated by CDR grafting into germline sequences.

These antibodies and antigen-binding fragments can be used in the context of this invention.

Particular preference is given in the context of the present invention to the anti-CXCR5 antibodies TPP-9574 and TPP-9580.

Anti-B7H3 Antibodies

According to the invention, it is possible to use anti-B7H3 antibodies.

The expression "anti-B7H3 antibody" or "an antibody which binds specifically to B7H3" relates to an antibody which binds the cancer target molecule B7H3 (NCBI Reference Sequence: NP_001019907.1 SEQ ID NO: 113), preferably with an affinity sufficient for a diagnostic and/or therapeutic application. In particular embodiments, the antibody binds B7H3 with a dissociation constant ($K_D$) of ≤1 µM, ≤100 nM, ≤10 nM, ≤1 nM, ≤0.1 nM, ≤0.01 nM, or ≤0.001 nM.

Examples of antibodies and antigen-binding fragments which bind to B7H3 are known to those skilled in the art and are described, for example, in WO201109400, EP1773884 and WO2014061277. EP2121008 describes the anti-B7H3 antibody 8H9 and the CDR sequences thereof.

These antibodies and antigen-binding fragments can be used in the context of this invention.

A preferred embodiment of the anti-B7H3 antibodies was obtained by screening an antibody phage display library for cells that express recombinant mouse B7H3 (mouse CD276; Gene ID: 102657) and human B7H3 (human CD276; Gene ID: 80381). The antibodies obtained were transformed to the human IgG1 format. The anti-B7H3 antibody TPP-8382 is a preferred example.

Particular preference is given in the context of the present invention to the anti-B7H3 antibody TPP-8382.

Anti-TWEAKR Antibodies

According to the invention, it is possible to use anti-TWEAKR antibodies.

The expression "anti-TWEAKR antibody" or "an antibody which binds specifically to TWEAKR" relates to an antibody which binds the cancer target molecule TWEAKR (NCBI Reference Sequence: NP_057723.1 SEQ ID NO: 114), preferably with an affinity sufficient for a diagnostic and/or therapeutic application. In particular embodiments, the antibody binds TWEAKR with a dissociation constant ($K_D$) of ≤≤1 µM, ≤100 nM, ≤10 nM, ≤1 nM, ≤0.1 nM, ≤0.01 nM, or ≤0.001 nM.

Examples of antibodies which bind to TWEAKR are disclosed, for example, in WO2009/020933(A2), WO2009/140177 (A2), WO 2014/198817 (A1) and WO 2015/189143 (A1). These antibodies and antigen-binding fragments can be used in the context of this invention.

ITEM-4 is an anti-TWEAKR antibody which was described by Nakayama et al. (Nakayama, et al., 2003, Biochem Biophy Res Comm, 306:819-825). Humanized variants of this antibody based on CDR grafting are described by Zhou et al. (Zhou et al., 2013, J Invest Dermatol. 133(4):1052-62) and in WO 2009/020933. These antibodies and antigen-binding fragments can be used in the context of this invention.

Particular preference is given in the context of the present invention to the anti-TWEAKR antibodies TPP-7006 and TPP-7007. These are humanized variants of the antibody ITEM-4. These antibodies and antigen-binding fragments can be used with preference in the context of this invention.

Anti-HER2 Antibodies:

According to the invention, it is possible to use anti-HER2 antibodies.

The expression "anti-HER2 antibody" or "an antibody which binds specifically to HER2" relates to an antibody which binds the cancer target molecule HER2 (NCBI Reference Sequence: NP_004439.2 SEQ ID NO: 115), preferably with an affinity sufficient for a diagnostic and/or therapeutic application. In particular embodiments, the antibody binds HER2 with a dissociation constant ($K_D$) of ≤1 µM, ≥100 nM, ≥10 nM, ≥1 nM, ≥0.1 nM, ≥0.01 nM, or ≥0.001 nM.

An example of an antibody binding to the cancer target molecule Her2 is trastuzumab (Genentech). Trastuzumab is a humanized antibody used inter alia for the treatment of breast cancer. In a particularly preferred embodiment, the anti-HER2 antibody is TPP-1015 (trastuzumab analogue).

Further examples of antibodies binding to HER2 are, in addition to trastuzumab (INN 7637, CAS No.: RN: 180288-69-1) and pertuzumab (CAS No.: 380610-27-5), the antibodies disclosed in WO 2009/123894-A2, WO 200/8140603-A2 or in WO 2011/044368-A2. An example of an anti-HER2 conjugate is trastuzumab-emtansine (INN-No. 9295). These antibodies and antigen-binding fragments can be used in the context of this invention.

Particular preference is given in the context of this invention to the anti-HER2 antibody TPP-1015 (analogous to trastuzumab).

Anti-EGFR Antibodies

According to the invention, it is possible to use anti-EGFR antibodies.

The expression "anti-EGFR antibody" or "an antibody which binds specifically to EGFR" relates to an antibody which binds the cancer target molecule EGFR (NCBI Reference Sequence: NP_005219.2 SEQ ID NO: 116), preferably with an affinity sufficient for a diagnostic and/or therapeutic application. In particular embodiments, the antibody binds EGFR with a dissociation constant ($K_D$) of ≤1 µM, ≤100 nM, ≤10 nM, ≤1 nM, ≤0.1 nM, ≤0.01 nM, or ≥0.001 nM.

In a preferred embodiment, the anti-EGFR antibodies are selected from the group consisting of TPP-981, Cetuximab, panitumumab, nimotuzumab. In a particularly preferred embodiment, the anti-EGFR antibody is TPP-981.

Further embodiments of EGFR antibodies are as follows:

zalutumumab/2F8/HuMax-EGFr, from Genmab A/S (WO 02/100348, WO 2004/056847, INN number 8605)

necitumumab/11F8, ImClone/IMC-11F8, from ImClone Systems Inc. [Eli Lilly & Co] (WO 2005/090407 (EP 01735348-A1, US 2007/0264253-A1, U.S. Pat. No. 7,598,350, WO 2005/090407-A1), INN number 9083)

matuzumab/anti-EGFR MAb, Merck KGaA/anti-EGFR MAb, Takeda/EMD 72000/EMD-6200/EMD-72000 and EMD-55900/MAb 425/monoclonal antibody 425, from Merck KGaA/Takeda (WO 92/15683, INN number 8103 (matuzumab))

RG-7160/GA-201/GA201/R-7160/R7160/RG7160/RO-4858696/RO-5083945/R04858696/R05083945, from Glycart Biotechnology AG (Roche Holding AG) (WO 2010/112413-A1, WO 2010/115554)

GT-MAB 5.2-GEX/CetuGEX, from Glycotope GmbH (WO 2008/028686-A2 (EP 01900750-A1, EP 01911766-A1, EP 02073842-A2, US 2010/0028947-A1)

ISU-101, from Isu Abxis Inc (ISU Chemical Co Ltd)/Scancell (WO 2008/004834-A1)

ABT-806/mAb-806/ch-806/anti-EGFR monoclonal antibody 806, from Ludwig Institute for Cancer Research/Abbott/Life Science Pharmaceuticals (WO 02/092771, WO 2005/081854 and WO 2009/023265)

SYM-004 (consists of two chimeric IgG1 antibodies (992 and 1024)), from Symphogen A/S (WO 2010/022736-A2)

MR1-1/MR1-1KDEL, from IVAX Corp (Teva Pharmaceutical Industries Ltd) (Duke University), (patent: WO2001/062931-A2)

Antibody against the deletion mutant, EGFRvIII, from Amgen/Abgenix (WO 2005/010151, U.S. Pat. No. 7,628,986)

SC-100, from Scancell Ltd (WO 01/088138-A1)

MDX-447/EMD 82633/BAB-447/H 447/MAb, EGFR, Medarex/Merck KgaA, from Bristol-Myers Squibb (US)/Merck KGaA (DE)/Takeda (JP), (WO 91/05871, WO 92/15683)

anti-EGFR-Mab, from Xencor (WO 2005/056606)

DXL-1218/anti-EGFR monoclonal antibody (cancer), InNexus, from InNexus Biotechnology Inc, Pharmaprojects PH048638

Anti-Carboanhydrase IX Antibodies

Examples of antibodies which bind the cancer target molecule carbonanhydrase IX are described in WO 2007/070538-A2 (e.g. Claims 1-16).

Anti-C4.4a Antibodies:

Examples of C4.4a antibodies and antigen-binding fragments are described in WO 2012/143499 A2. The sequences of the antibodies are given in Table 1 of WO 2012/143499 A2, where each row shows the respective CDR amino acid sequences of the variable light chain or the variable heavy chain of the antibody listed in column 1.

Anti-CD20 Antibodies:

An example of an antibody binding to the cancer target molecule CD20 is rituximab (Genentech). Rituximab (CAS Number: 174722-31-7) is a chimeric antibody used for the treatment of non-Hodgkin's lymphoma. These antibodies and antigen-binding fragments thereof can be used in the context of this invention.

Anti-CD52 Antibodies:

An example of an antibody binding to the cancer target molecule CD52 is alemtuzumab (Genzyme). Alemtuzumab (CAS Number: 216503-57-0) is a humanized antibody used for the treatment of chronic lymphocytic leukaemia. These antibodies and antigen-binding fragments thereof can be used in the context of this invention.

Anti-Mesothelin Antibodies:

Examples of anti-mesothelin antibodies are described, for example, in WO2009/068204. All WO2009/068204 disclosed antibodies and antigen-binding fragments can be used in the context of the invention disclosed herein. More preferably, the antibody disclosed in WO2009/068204 is MF-T.

Anti-CD30 Antibodies

Examples of antibodies which bind the cancer target molecule CD30 and can be used for the treatment of cancer, for example Hodgkin's lymphoma, are brentuximab, iratumumab and antibodies disclosed in WO 2008/092117, WO 2008/036688 or WO 2006/089232. An example of an anti-CD30 conjugate is brentuximab vedotin (INN No. 9144). These antibodies and antigen-binding fragments thereof can be used in the context of this invention.

Anti-CD22 Antibodies

Examples of antibodies which bind the cancer target molecule CD22 and can be used for the treatment of cancer, for example lymphoma, are inotuzumab and epratuzumab.

Examples of anti-CD22 conjugates are inotuzumab ozagamycin (INN No. 8574) or anti-CD22-MMAE and anti-CD22-MC-MMAE (CAS RN: 139504-50-0 and 474645-27-7, respectively). These antibodies and antigen-binding fragments thereof can be used in the context of this invention.

Anti-CD33 Antibodies

Examples of antibodies which bind the cancer target molecule CD33 and can be used for the treatment of cancer, for example leukaemia, are gemtuzumab and lintuzumab (INN 7580). An example of an anti-CD33 conjugate is gemtuzumab-ozagamycin. These antibodies and antigen-binding fragments can be used in the context of this invention.

Anti-NMB Antibodies

An example of an antibody which binds the cancer target molecule NMB and can be used for the treatment of cancer, for example melanoma or breast cancer, is glembatumumab (INN 9199). An example of an anti-NMB conjugate is glembatumumab vedotin (CAS RN: 474645-27-7). These antibodies and antigen-binding fragments thereof can be used in the context of this invention.

Anti-CD56 Antibodies

An example of an antibody which binds the cancer target molecule CD56 and can be used for the treatment of cancer, for example multiple myeloma, small-cell lung carcinoma, MCC or ovarial carcinoma is lorvotuzumab. An example of an anti-CD57 conjugate is lorvotuzumab mertansine (CAS RN: 139504-50-0). These antibodies and antigen-binding fragments can be used in the context of this invention.

Anti-CD70 Antibodies

Examples of antibodies which bind the cancer target molecule CD70 and can be used for the treatment of cancer, for example non-Hodgkin's lymphoma or renal cell cancer, are disclosed in WO 2007/038637-A2 and WO 2008/070593-A2. An example of an anti-CD70 conjugate is SGN-75 (CD70 MMAF). These antibodies and antigen-binding fragments can be used in the context of this invention.

Anti-CD74 Antibodies

An example of an antibody which binds the cancer target molecule CD74 and can be used for treatment of cancer, for example multiple myeloma, is milatuzumab. An example of an anti-CD74 conjugate is milatuzumab-doxorubicin (CAS RN: 23214-92-8). These antibodies and antigen-binding fragments can be used in the context of this invention.

Anti-CD19 Antibodies

An example of an antibody which binds the cancer target molecule CD19 and can be used for the treatment of cancer, for example non-Hodgkin's lymphoma, is disclosed in WO 2008/031056-A2. Further antibodies and examples of an anti-CD19 conjugate (SAR3419) are disclosed in WO 2008/047242-A2. These antibodies and antigen-binding fragments thereof can be used in the context of this invention.

Anti-Mucin Antibodies

Examples of antibodies which bind the cancer target molecule mucin-1 and can be used for the treatment of cancer, for example non-Hodgkin's lymphoma, are clivatuzumab and the antibodies disclosed in WO 2003/106495-A2, WO 2008/028686-A2. Examples of anti-mucin conjugates are disclosed in WO 2005/009369-A2. These antibodies and antigen-binding fragments thereof can be used in the context of this invention.

Anti-CD138 Antibodies

Examples of antibodies which bind the cancer target molecule CD138 and conjugates thereof, which can be used for the treatment of cancer, for example multiple myeloma, are disclosed in WO 2009/080829-A1, WO 2009/080830-A1. These antibodies and antigen-binding fragments thereof can be used in the context of this invention.

Anti-Integrin-AlphaV Antibodies

Examples of antibodies which bind the cancer target molecule integrin alphaV and can be used for the treatment of cancer, for example melanoma, sarcoma or carcinoma, are intetumumab (CAS RN: 725735-28-4), abciximab (CAS RN: 143653-53-6), etaracizumab (CAS RN: 892553-42-3) and the antibodies disclosed in U.S. Pat. No. 7,465,449, EP 719859-A1, WO 2002/012501-A1 and WO2006/062779-A2. Examples of anti-integrin AlphaV conjugates are intetumumab-DM4 and other ADCs disclosed in WO 2007/024536-A2.

These antibodies and antigen-binding fragments thereof can be used in the context of this invention.

Anti-TDGF1 Antibodies

Examples of antibodies which bind the cancer target molecule TDGF1 and can be used for the treatment of cancer are the antibodies disclosed in WO 02/077033-A1, U.S. Pat. No. 7,318,924, WO 2003/083041-A2 and WO 2002/088170-A2. Examples of anti-TDGF1 conjugates are disclosed in WO 2002/088170-A2. These antibodies and antigen-binding fragments thereof can be used in the context of this invention.

Anti-PSMA Antibodies

Examples of antibodies which bind the cancer target molecule PSMA and can be used for the treatment of cancer, for example prostate carcinoma, are the antibodies disclosed in WO 97/35616-A1, WO 99/47554-A1, WO 01/009192-A1 and WO2003/034903. Examples of anti-PSMA conjugates are disclosed in WO 2009/026274-A1 and WO 2007/002222. These antibodies and antigen-binding fragments can be used in the context of this invention.

Anti-EPHA2 Antibodies

Examples of antibodies which bind the cancer target molecule EPHA2 and can be used for preparing a conjugate and for the treatment of cancer are disclosed in WO 2004/091375-A2. These antibodies and antigen-binding fragments can be used in the context of this invention.

Anti-SLC44A4 Antibodies

Examples of antibodies which bind the cancer target molecule SLC44A4 and can be used for preparing a conjugate and for the treatment of cancer, for example pancreas or prostate carcinoma, are disclosed in WO2009/033094-A2 and US2009/0175796-A1.

These antibodies and antigen-binding fragments thereof can be used in the context of this invention.

Anti-HLA-DOB Antibodies

An example of an antibody binding to the cancer target molecule HLA-DOB is the antibody Lym-1 (CAS RN: 301344-99-0) which can be used for treatment of cancer, for example non-Hodgkin's lymphoma. Examples of anti-HLA-DOB conjugates are disclosed, for example, in WO 2005/081711-A2. These antibodies and antigen-binding fragments thereof can be used in the context of this invention.

Anti-VTCN1 Antibodies

Examples of antibodies which bind the cancer target molecule VTCN1 and can be used for preparing a conjugate and for the treatment of cancer, for example ovarial carcinoma, pancreas, lung or breast cancer, are disclosed in WO 2006/074418-A2. These antibodies and antigen-binding fragments thereof can be used in the context of this invention.

Anti-FGFR2 Antibodies

Examples of anti-FGFR2 antibodies and antigen-binding fragments are described in WO2013076186. The sequences of the antibodies are shown in Table 9 and Table 10 of WO2013076186. Preference is given to antibodies, antigen-binding fragments and variants of the antibodies derived from the antibodies referred to as M048-D01 and M047-D08.

Preferred Antibodies and Antigen-Binding Antibody Fragments for Binder-Drug Conjugates According to the Invention In this application, in the context of the binder-drug conjugates, reference is made to the following preferred antibodies as shown in the following table: TPP-981, TPP-1015, TPP-6013, TPP-7006, TPP-7007, TPP-8382, TPP-8987, TPP-8988, TPP-9476, TPP-9574 and TPP-9580.

SEQ ID NO: 2, the variable CDR2 sequence of the heavy chain (H-CDR2), as shown by SEQ ID NO: 3 and the variable CDR3 sequence of the heavy chain (H-CDR3), as shown by SEQ ID NO: 4, and a variable region of the light chain (VL) comprising the variable CDR1 sequence of the light chain (L-CDR1), as shown by SEQ ID NO: 6, the variable CDR2 sequence of the light chain (L-CDR2), as shown by SEQ ID NO: 7 and the variable CDR3 sequence of the light chain (L-CDR3), as shown by SEQ ID NO: 8.

TPP-1015 is an anti-HER2 antibody comprising a variable region of the heavy chain (VH) comprising the variable CDR1 sequence of the heavy chain (H-CDR1), as shown by SEQ ID NO: 12, the variable CDR2 sequence of the heavy chain (H-CDR2), as shown by SEQ ID NO: 13 and the variable CDR3 sequence of the heavy chain (H-CDR3), as shown by SEQ ID NO: 14, and a variable region of the light chain (VL) comprising the variable CDR1 sequence of the light chain (L-CDR1), as shown by SEQ ID NO: 16, the variable CDR2 sequence of the light chain (L-CDR2), as shown by SEQ ID NO: 17 and the variable CDR3 sequence of the light chain (L-CDR3), as shown by SEQ ID NO: 18.

TPP-6013 is an anti-CD123 antibody comprising a variable region of the heavy chain (VH) comprising the variable CDR1 sequence of the heavy chain (H-CDR1), as shown by SEQ ID NO: 22, the variable CDR2 sequence of the heavy chain (H-CDR2), as shown by SEQ ID NO: 23 and the variable CDR3 sequence of the heavy chain (H-CDR3), as shown by SEQ ID NO: 24, and a variable region of the light chain (VL) comprising the variable CDR1 sequence of the light chain (L-CDR1), as shown by SEQ ID NO: 26, the variable CDR2 sequence of the light chain (L-CDR2), as shown by SEQ ID NO: 27 and the variable CDR3 sequence of the light chain (L-CDR3), as shown by SEQ ID NO: 28.

TABLE

Protein sequences of the antibodies:

| Antibody TPP-XXX | Antigen | SEQ ID NO: VH | SEQ ID NO: H-CDR1 | SEQ ID NO: H-CDR2 | SEQ ID NO: H-CDR3 | SEQ ID NO: VL | SEQ ID NO: L-CDR1 | SEQ ID NO: L-CDR2 | SEQ ID NO: L-CDR3 | SEQ ID NO: IgG heavy chain | SEQ ID NO: IgG light chain |
|---|---|---|---|---|---|---|---|---|---|---|---|
| TPP-981 | EGFR | 1 | 2 | 3 | 4 | 5 | 6 | 7 | 8 | 9 | 10 |
| TPP-1015 | HER2 | 11 | 12 | 13 | 14 | 15 | 16 | 17 | 18 | 19 | 20 |
| TPP-6013 | CD123 | 21 | 22 | 23 | 24 | 25 | 26 | 27 | 28 | 29 | 30 |
| TPP-7006 | TWEAKR | 31 | 32 | 33 | 34 | 35 | 36 | 37 | 38 | 39 | 40 |
| TPP-7007 | TWEAKR | 41 | 42 | 43 | 44 | 45 | 46 | 47 | 48 | 49 | 50 |
| TPP-8382 | B7H3 | 51 | 52 | 53 | 54 | 55 | 56 | 57 | 58 | 59 | 60 |
| TPP-8987 | CD123 | 61 | 62 | 63 | 64 | 65 | 66 | 67 | 68 | 69 | 70 |
| TPP-8988 | CD123 | 71 | 72 | 73 | 74 | 75 | 76 | 77 | 78 | 79 | 80 |
| TPP-9476 | CD123 | 81 | 82 | 83 | 84 | 85 | 86 | 87 | 88 | 89 | 90 |
| TPP-9574 | CXCR5 | 91 | 92 | 93 | 94 | 95 | 96 | 97 | 98 | 99 | 100 |
| TPP-9580 | CXCR5 | 101 | 102 | 103 | 104 | 105 | 106 | 107 | 108 | 109 | 110 |

TPP-981, TPP-1015, TPP-6013, TPP-7006, TPP-7007, TPP-8382, TPP-8987, TPP-8988, TPP-9476, TPP-9574 and TPP-9580 are antibodies comprising one or more of the CDR sequences specified in the above table (H-CDR1, H-CDR2, H-CDR3, L-CDR1, L-CDR2, L-CDR3) in the variable region of the heavy chain (VH) or the variable region of the light chain (VL). Preferably, the antibodies comprise the specified variable region of the heavy chain (VH) and/or the variable region of the light chain (VL). Preferably, the antibodies comprise the specified region of the heavy chain (IgG heavy chain) and/or the specified region of the light chain (IgG light chain).

TPP-981 is an anti-EGFR antibody comprising a variable region of the heavy chain (VH) comprising the variable CDR1 sequence of the heavy chain (H-CDR1), as shown by TPP-7006 is an anti-TWEAKR antibody comprising a variable region of the heavy chain (VH) comprising the variable CDR1 sequence of the heavy chain (H-CDR1), as shown by SEQ ID NO: 32, the variable CDR2 sequence of the heavy chain (H-CDR2), as shown by SEQ ID NO: 33 and the variable CDR3 sequence of the heavy chain (H-CDR3), as shown by SEQ ID NO: 34, and a variable region of the light chain (VL) comprising the variable CDR1 sequence of the light chain (L-CDR1), as shown by SEQ ID NO: 36, the variable CDR2 sequence of the light chain (L-CDR2), as shown by SEQ ID NO: 37 and the variable CDR3 sequence of the light chain (L-CDR3), as shown by SEQ ID NO: 38.

TPP-7007 is an anti-TWEAKR antibody comprising a variable region of the heavy chain (VH) comprising the variable CDR1 sequence of the heavy chain (H-CDR1), as shown by SEQ ID NO: 42, the variable CDR2 sequence of the heavy chain (H-CDR2), as shown by SEQ ID NO: 43 and the variable CDR3 sequence of the heavy chain (H-CDR3), as shown by SEQ ID NO: 44, and a variable region of the light chain (VL) comprising the variable CDR1 sequence of the light chain (L-CDR1), as shown by SEQ ID NO: 46, the variable CDR2 sequence of the light chain (L-CDR2), as shown by SEQ ID NO: 47 and the variable CDR3 sequence of the light chain (L-CDR3), as shown by SEQ ID NO: 48.

TPP-8382 is an anti-B7H3 antibody comprising a variable region of the heavy chain (VH) comprising the variable CDR1 sequence of the heavy chain (H-CDR1), as shown by SEQ ID NO: 52, the variable CDR2 sequence of the heavy chain (H-CDR2), as shown by SEQ ID NO: 53 and the variable CDR3 sequence of the heavy chain (H-CDR3), as shown by SEQ ID NO: 54, and a variable region of the light chain (VL) comprising the variable CDR1 sequence of the light chain (L-CDR1), as shown by SEQ ID NO: 56, the variable CDR2 sequence of the light chain (L-CDR2), as shown by SEQ ID NO: 57 and the variable CDR3 sequence of the light chain (L-CDR3), as shown by SEQ ID NO: 58.

TPP-8987 is an anti-CD123 antibody comprising a variable region of the heavy chain (VH) comprising the variable CDR1 sequence of the heavy chain (H-CDR1), as shown by SEQ ID NO: 62, the variable CDR2 sequence of the heavy chain (H-CDR2), as shown by SEQ ID NO: 63 and the variable CDR3 sequence of the heavy chain (H-CDR3), as shown by SEQ ID NO: 64, and a variable region of the light chain (VL) comprising the variable CDR1 sequence of the light chain (L-CDR1), as shown by SEQ ID NO: 66, the variable CDR2 sequence of the light chain (L-CDR2), as shown by SEQ ID NO: 67 and the variable CDR3 sequence of the light chain (L-CDR3), as shown by SEQ ID NO: 68.

TPP-8988 is an anti-CD123 antibody comprising a variable region of the heavy chain (VH) comprising the variable CDR1 sequence of the heavy chain (H-CDR1), as shown by SEQ ID NO: 72, the variable CDR2 sequence of the heavy chain (H-CDR2), as shown by SEQ ID NO: 73 and the variable CDR3 sequence of the heavy chain (H-CDR3), as shown by SEQ ID NO: 74, and a variable region of the light chain (VL) comprising the variable CDR1 sequence of the light chain (L-CDR1), as shown by SEQ ID NO: 76, the variable CDR2 sequence of the light chain (L-CDR2), as shown by SEQ ID NO: 77 and the variable CDR3 sequence of the light chain (L-CDR3), as shown by SEQ ID NO: 78.

TPP-9476 is an anti-CD123 antibody comprising a variable region of the heavy chain (VH) comprising the variable CDR1 sequence of the heavy chain (H-CDR1), as shown by SEQ ID NO: 82, the variable CDR2 sequence of the heavy chain (H-CDR2), as shown by SEQ ID NO: 83 and the variable CDR3 sequence of the heavy chain (H-CDR3), as shown by SEQ ID NO: 84, and a variable region of the light chain (VL) comprising the variable CDR1 sequence of the light chain (L-CDR1), as shown by SEQ ID NO: 86, the variable CDR2 sequence of the light chain (L-CDR2), as shown by SEQ ID NO: 87 and the variable CDR3 sequence of the light chain (L-CDR3), as shown by SEQ ID NO: 88.

TPP-9574 is an anti-CXCR5 antibody comprising a variable region of the heavy chain (VH) comprising the variable CDR1 sequence of the heavy chain (H-CDR1), as shown by SEQ ID NO: 92, the variable CDR2 sequence of the heavy chain (H-CDR2), as shown by SEQ ID NO: 93 and the variable CDR3 sequence of the heavy chain (H-CDR3), as shown by SEQ ID NO: 94, and a variable region of the light chain (VL) comprising the variable CDR1 sequence of the light chain (L-CDR1), as shown by SEQ ID NO: 96, the variable CDR2 sequence of the light chain (L-CDR2), as shown by SEQ ID NO: 97 and the variable CDR3 sequence of the light chain (L-CDR3), as shown by SEQ ID NO: 98.

TPP-9580 is an anti-CXCR5 antibody comprising a variable region of the heavy chain (VH) comprising the variable CDR1 sequence of the heavy chain (H-CDR1), as shown by SEQ ID NO: 102, the variable CDR2 sequence of the heavy chain (H-CDR2), as shown by SEQ ID NO: 103 and the variable CDR3 sequence of the heavy chain (H-CDR3), as shown by SEQ ID NO: 104, and a variable region of the light chain (VL) comprising the variable CDR1 sequence of the light chain (L-CDR1), as shown by SEQ ID NO: 106, the variable CDR2 sequence of the light chain (L-CDR2), as shown by SEQ ID NO: 107 and the variable CDR3 sequence of the light chain (L-CDR3), as shown by SEQ ID NO: 108.

TPP-981 is an anti-EGFR antibody comprising preferably a variable region of the heavy chain (VH) as shown in SEQ ID NO: 1 and a variable region of the light chain (VL) as shown in SEQ ID NO: 5.

TPP-1015 is an anti-HER2 antibody comprising preferably a variable region of the heavy chain (VH) as shown in SEQ ID NO: 11 and a variable region of the light chain (VL) as shown in SEQ ID NO: 15.

TPP-6013 is an anti-CD123 antibody comprising preferably a variable region of the heavy chain (VH) as shown in SEQ ID NO: 21 and a variable region of the light chain (VL) as shown in SEQ ID NO: 25.

TPP-7006 is an anti-TWEAKR antibody comprising preferably a variable region of the heavy chain (VH) as shown in SEQ ID NO: 31 and a variable region of the light chain (VL) as shown in SEQ ID NO: 35.

TPP-7007 is an anti-TWEAKR antibody comprising preferably a variable region of the heavy chain (VH) as shown in SEQ ID NO: 41 and a variable region of the light chain (VL) as shown in SEQ ID NO: 45.

TPP-8382 is an anti-B7H3 antibody comprising preferably a variable region of the heavy chain (VH) as shown in SEQ ID NO: 51 and a variable region of the light chain (VL) as shown in SEQ ID NO: 55.

TPP-8987 is an anti-CD123 antibody comprising preferably a variable region of the heavy chain (VH) as shown in SEQ ID NO: 61 and a variable region of the light chain (VL) as shown in SEQ ID NO: 65.

TPP-8988 is an anti-CD123 antibody comprising preferably a variable region of the heavy chain (VH) as shown in SEQ ID NO: 71 and a variable region of the light chain (VL) as shown in SEQ ID NO: 75.

TPP-9476 is an anti-CD123 antibody comprising preferably a variable region of the heavy chain (VH) as shown in SEQ ID NO: 81 and a variable region of the light chain (VL) as shown in SEQ ID NO: 85.

TPP-9574 is an anti-CXCR5 antibody comprising preferably a variable region of the heavy chain (VH) as shown in SEQ ID NO: 91 and a variable region of the light chain (VL) as shown in SEQ ID NO: 95.

TPP-9580 is an anti-CXCR5 antibody comprising preferably a variable region of the heavy chain (VH) as shown in SEQ ID NO: 101 and a variable region of the light chain (VL) as shown in SEQ ID NO: 105.

TPP-981 is an anti-EGFR antibody comprising preferably a region of the heavy chain as shown in SEQ ID NO: 9 and a region of the light chain as shown in SEQ ID NO: 10.

TPP-1015 is an anti-HER2 antibody comprising preferably a region of the heavy chain as shown in SEQ ID NO: 19 and a region of the light chain as shown in SEQ ID NO: 20.

TPP-6013 is an anti-CD123 antibody comprising preferably a region of the heavy chain as shown in SEQ ID NO: 29 and a region of the light chain as shown in SEQ ID NO: 30.

TPP-7006 is an anti-TWEAKR antibody comprising preferably a region of the heavy chain as shown in SEQ ID NO: 39 and a region of the light chain as shown in SEQ ID NO: 40.

TPP-7007 is an anti-TWEAKR antibody comprising preferably a region of the heavy chain as shown in SEQ ID NO: 49 and a region of the light chain as shown in SEQ ID NO: 50.

TPP-8382 is an anti-B7H3 antibody comprising preferably a region of the heavy chain as shown in SEQ ID NO: 59 and a region of the light chain as shown in SEQ ID NO: 60.

TPP-8987 is an anti-CD123 antibody comprising preferably a region of the heavy chain as shown in SEQ ID NO: 69 and a region of the light chain as shown in SEQ ID NO: 70.

TPP-8988 is an anti-CD123 antibody comprising preferably a region of the heavy chain as shown in SEQ ID NO: 79 and a region of the light chain as shown in SEQ ID NO: 80.

TPP-9476 is an anti-CD123 antibody comprising preferably a region of the heavy chain as shown in SEQ ID NO: 89 and a region of the light chain as shown in SEQ ID NO: 90.

TPP-9574 is an anti-CXCR5 antibody comprising preferably a region of the heavy chain as shown in SEQ ID NO: 99 and a region of the light chain as shown in SEQ ID NO: 100.

TPP-9580 is an anti-CXCR5 antibody comprising preferably a region of the heavy chain as shown in SEQ ID NO: 109 and a region of the light chain as shown in SEQ ID NO: 110.

Isotopes, Salts, Solvates, Isotopic Variants

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labelled with $^{3}H$ or $^{14}C$ isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described further down and the procedures described in the working examples, by using corresponding isotopic modifications of the respective reagents and/or starting compounds.

Preferred salts in the context of the present invention are physiologically acceptable salts of the compounds of the invention. Also encompassed are salts which are not themselves suitable for pharmaceutical applications but can be used, for example, for isolation or purification of the compounds of the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

Therapeutic Use

The hyper-proliferative diseases, for the treatment of which the compounds according to the invention may be employed, include in particular the group of cancer and tumour diseases. In the context of the present invention, these are understood to mean especially the following diseases, but without any limitation thereto: mammary carcinomas and mammary tumours (mammary carcinomas including ductal and lobular forms, also in situ), tumours of the respiratory tract (small-cell and non-small cell carcinoma, bronchial carcinoma), cerebral tumours (e.g. of the brain stem and of the hypothalamus, astrocytoma, ependymoma, glioblastoma, glioma, medulloblastoma, meningioma and neuro-ectodermal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of connective tissue (inter alia soft tissue sarcomas, osteosarcomas, malignant fibrous histiocytomas, chondrosarcomas, fibrosarcomas, haemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative diseases of the blood, the lymph system and the spinal cord, in solid form and as circulating cells, such as leukaemias, lymphomas and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-characterized diseases in humans can also occur with a comparable aetiology in other mammals and can likewise be treated there with the compounds of the present invention.

The binder- or antibody-drug conjugates (ADCs) described herein and directed against CD123 can preferably be used for the treatment of CD123-expressing disorders, such as CD123-expressing cancer diseases. Typically, such cancer cells exhibit measurable amounts of CD123 measured at the protein (e.g. using an immunoassay) or RNA level. Some of these cancer tissues show an elevated level of CD123 compared to non-cancerogenous tissue of the same type, preferably measured in the same patient. Optionally, the CD123 content is measured prior to the start of the cancer treatment with an antibody-drug conjugate (ADC) according to the invention (patient stratification). The binder-drug conjugates (ADCs) directed against CD123 can preferably be used for the treatment of CD123-expressing disorders, such as CD123-expressing cancer diseases, such as tumours of the haematopoietic and lymphatic tissue or haematopoietic and lymphatic malignant tumours. Examples of cancer diseases associated with CD123 expression include myeloid diseases such as acute myeloid leukaemia (AML) and myelodysplastic syndrome (MDS). Other types of cancer include B-cell acute lymphoblastic leukaemia (B-ALL), hairy cell leukaemia, blastic plasmacytoid dendritic cell neoplasm (BPDCN), Hodgkin's lymphoma, immature T-cell acute lymphoblastic leukaemia (immature T-ALL), Burkitt's lymphoma, follicular lymphoma, chronic lymphocytic leukaemia (CLL), mantle cell lymphoma (MCL). Methods of the described invention comprise the treatment of patients suffering from CD123-expressing cancer, the method comprising the administration of an antibody-drug conjugate (ADC) according to the invention.

The treatment of the cancer diseases mentioned above with the compounds according to the invention comprises both a treatment of the solid tumours and a treatment of metastasizing or circulating forms thereof.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides for the use of the compounds of the invention in a method for treatment and/or prevention of disorders, especially of the aforementioned disorders.

The present invention further provides a method of treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders.

For example, the compounds of the present invention can be combined with known anti-hyper-proliferative, cytostatic, cytotoxic or immunotherapeutic substances for the treatment of cancer diseases. Examples of suitable combination drugs include:

131I-chTNT, abarelix, abiraterone, aclarubicin, adalimumab, ado-trastuzumab emtansine, afatinib, aflibercept, aldesleukin, alemtuzumab, alendronic acid, alitretinoin, altretamine, amifostine, aminoglutethimide, hexyl-5-aminolevulinate, amrubicin, amsacrine, anastrozole, ancestim, anethole dithiolethione, anetumab ravtansine, angiotensin 11, antithrombin III, aprepitant, arcitumomab, arglabin, arsenic trioxide, asparaginase, atezolizumab, avelumab, axitinib, azacitidine, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonin, calcium folinate, calcium levofolinate, capecitabine, capromab, carbomazepine, carboplatin, carboquon, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, dabrafenib, darolutamide, dasatinib, daunorubicin, decitabine, degarelix, denileukin-diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, durvalumab, edrecolomab, elliptinium acetate, endostatin, enocitabine, enzalutamide, epacadostat, epirubicin, epitiostanol, epoetin-alfa, epoetin-beta, epoetin-zeta, eptaplatin, eribulin, erlotinib, esomeprazole, estramustine, etoposide, ethylnyl oestradiol, everolimus, exemestane, fadrozole, fentanyl, fluoxymesterone, floxuridine, fludarabine, fluorouracil, flutamide, folic acid, formestane, fosaprepitant, fotemustine, fulvestrant, gadobutrol, gadoteridol, gadoteric acid meglumine salt, gadoversetamide, gadoxetic acid disodium salt (gd-EOB-DTPA disodium salt), gallium nitrate, ganirelix, gefitinib, gemcitabine, gemtuzumab, glucarpidase, glutoxim, goserelin, granisetron, granulocyte colony stimulating factor (G-CSF), granulocyte macrophage colony stimulating factor (GM-CSF), histamine dihydrochloride, histrelin, hydroxycarbamide, I-125 seeds, ibandronic acid, ibritumomab-tiuxetan, ibrutinib, idarubicin, ifosfamide, imatinib, imiquimod, improsulfan, indisetron, incadronic acid, ingenol mebutate, interferon-alfa, interferon-beta, interferon-gamma, iobitridol, iobenguane (123I), iomeprol, ipilimumab, irinotecan, itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxin-sodium, lipegfilgrastim, lisuride, lobaplatin, lomustine, lonidamine, masoprocol, medroxyprogesteron, megestrol, melarsoprol, melphalan, mepitiostan, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotan, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxin mepesuccinate, omeprazole, ondansetron, orgotein, orilotimod, osimertinib, oxaliplatin, oxycodone, oxymetholone, ozogamicin, p53 gene therapy, paclitaxel, palbociclib, palifermine, palladium-103 seed, palonosetron, pamidronic acid, panitumumab, panobinostat, pantoprazole, pazopanib, pegaspargase, pembrolizumab, Peg-interferon alfa-2b, pembrolizumab, pemetrexed, pentostatin, peplomycin, perflubutane, perfosfamide, pertuzumab, picibanil, pilocarpine, pirarubicin, pixantron, plerixafor, plicamycin, poliglusam, polyoestradiol phosphate, polyvinylpyrrolidone+sodium hyaluronate, polysaccharide-K, pomalidomide, ponatinib, porfimer-sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxan, refametinib, regorafenib, risedronic acid, rhenium-186 etidronate, rituximab, rogaratinib, rolapitant, romidepsin, romurtid, roniciclib, samarium (153Sm) lexidronam, satumomab, secretin, siltuximab, sipuleucel-T, sizofiran, sobuzoxane, sodium glycididazole, sonidegib, sorafenib, stanozolol, streptozocin, sunitinib, talaporfin, talimogen laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, treosulfan, tretinoin, trifluridine+tipiracil, trametinib, trilostane, triptorelin, trofosfamide, thrombopoietin, ubenimex, valrubicin, vandetanib, vapreotide, vatalanib, vemurafenib, vinblastine, vincristine, vindesine, vinflunine, vinorelbine, vismodegib, vorinostat, yttrium-90 glass microbeads, zinostatin, zinostatin stimalamer, zoledronic acid, zorubicin In addition, the compounds of the present invention can be combined, for example, with binders (e.g. antibodies) which, by way of example, can bind to the following targets: OX-40, CD137/4-1BB, DR3, IDO1/IDO2, LAG-3, CD40.

Since a non-cell-permeable toxophore metabolite of a binder-drug conjugate (ADC) should have no damaging effect on the cells of the adaptive immune system, the invention furthermore provides the combination of a binder-drug conjugate (ADC) according to the invention with a cancer immunotherapy for use in the treatment of cancer or tumours. The intrinsic mechanism of action of cytotoxic binder-drug conjugates comprises the direct triggering of cell death of the tumour cells and thus the release of tumour antigens which may stimulate an immune response. Furthermore, there are indications that the KSP inhibitor toxophore class induces markers of immunogenic cell death (ICD) in vitro. Thus, the combination of the binder-drug conjugates (ADCs) of the present invention with one or more therapeutic approaches of cancer immunotherapy or with one or more active compounds, preferably antibodies, directed against a molecular target of cancer immunotherapy represents a preferred method for treating cancer or tumours. i) Examples of therapeutic approaches of cancer immunotherapy comprise immunomodulatory monoclonal antibodies and low-molecular weight substances directed against targets of cancer immunotherapy, vaccines, CAR T cells, bispecific T-cell-recruiting antibodies, oncolytical viruses, cell-based vaccination approaches. ii) Examples of selected targets of cancer immunotherapy suitable for immunomodulatory monoclonal antibodies comprise CTLA-4, PD-1/PDL-1, OX-40, CD137, DR3, IDO1, IDO2, TDO2, LAG-3, TIM-3 CD40, ICOS/ICOSL, TIGIT; GITR/GITRL, VISTA, CD70, CD27, HVEM/BTLA, CEACAMI, CEACAM6, ILDR2, CD73, CD47, B7H3, TLRs. Accordingly, combination of a binder-drug conjugate (ADC) according to the invention with cancer immunotherapy could, on the one hand, render tumours with weak immunogenic properties more immunogenic and enhance the effectiveness of cancer immunotherapy, and furthermore unfold long-lasting therapeutic action.

In addition, the compounds according to the invention can also be used in combination with radiotherapy and/or surgical intervention.

Generally, the following aims can be pursued with the combination of compounds of the present invention with other cytostatically, cytotoxically or immunotherapeutically active agents:

improved efficacy in slowing the growth of a tumour, in reducing its size or even in completely eliminating it, compared with treatment with an individual active ingredient;

the possibility of using the chemotherapeutics used in a lower dosage than in the case of monotherapy;

the possibility of a more tolerable therapy with fewer side effects compared with individual administration;

the possibility of treatment of a broader spectrum of neoplastic disorders;

the achievement of a higher rate of response to the therapy;

a longer survival time of the patient compared with present-day standard therapy.

In addition, the compounds according to the invention can also be used in combination with radiotherapy and/or surgical intervention.

The present invention further provides medicaments which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example parenterally, possibly inhalatively or as implants or stents.

The compounds of the invention can be administered in administration forms suitable for these administration routes.

Parenteral administration can bypass an absorption step (for example intravenously, intraarterially, intracardially, intraspinally or intralumbally) or include an absorption (for example intramuscularly, subcutaneously, intracutaneously, percutaneously or intraperitoneally). Administration forms suitable for parenteral administration include preparations for injection and infusion in the form of solutions, suspensions, emulsions or lyophilizates. Preference is given to parenteral administration, especially intravenous administration.

In general, it has been found to be advantageous in the case of parenteral administration to administer amounts of about 0.1 to 20 mg/kg, preferably about 0.3 to 7 mg/kg, of body weight to achieve effective results.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

EXAMPLES

The examples which follow illustrate the invention. The invention is not restricted to these examples.

Unless stated otherwise, the percentages in the tests and examples which follow are percentages by weight; parts are parts by weight. Solvent ratios, dilution ratios and concentration data for the liquid/liquid solutions are based in each case on volume.

Synthesis Routes:

By way of example for the working examples, the following schemes show illustrative synthesis routes leading to the working examples:

Scheme 1: Synthesis of Lysine-Bonded ADCs with Legumain-Cleavable Linker

Scheme 1: Synthesis of lysine-bonded ADCs with legumain-cleavable linker

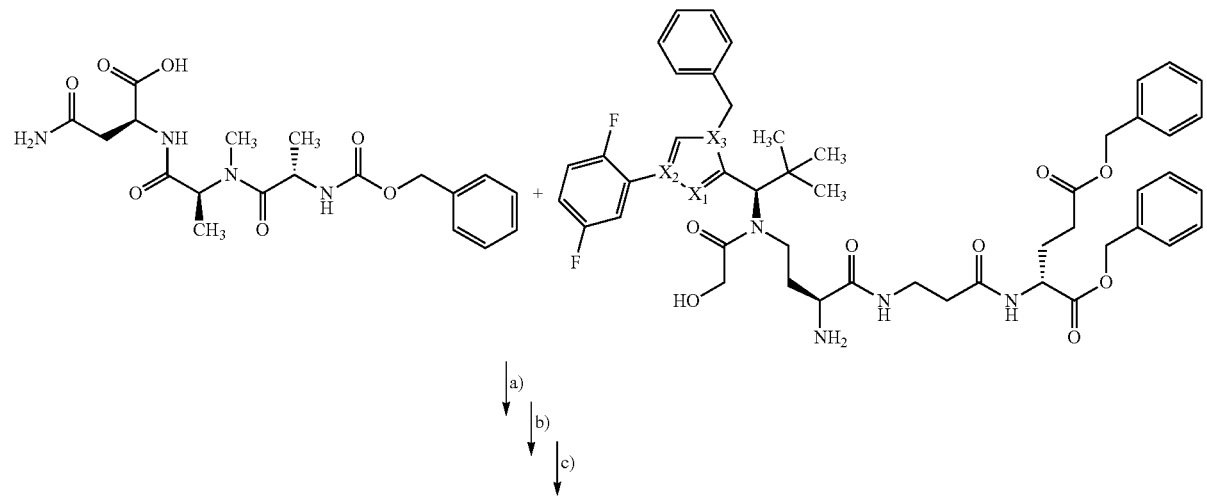

-continued

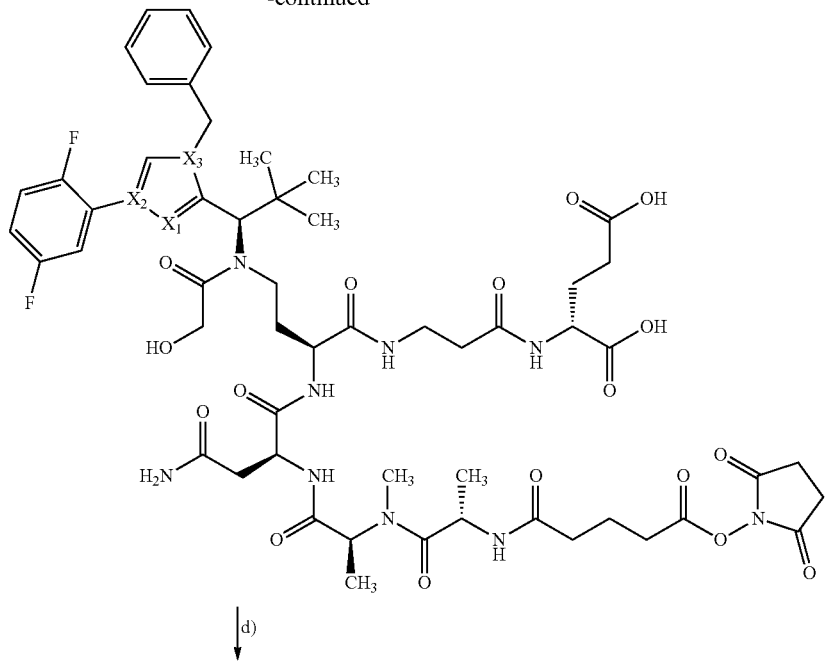

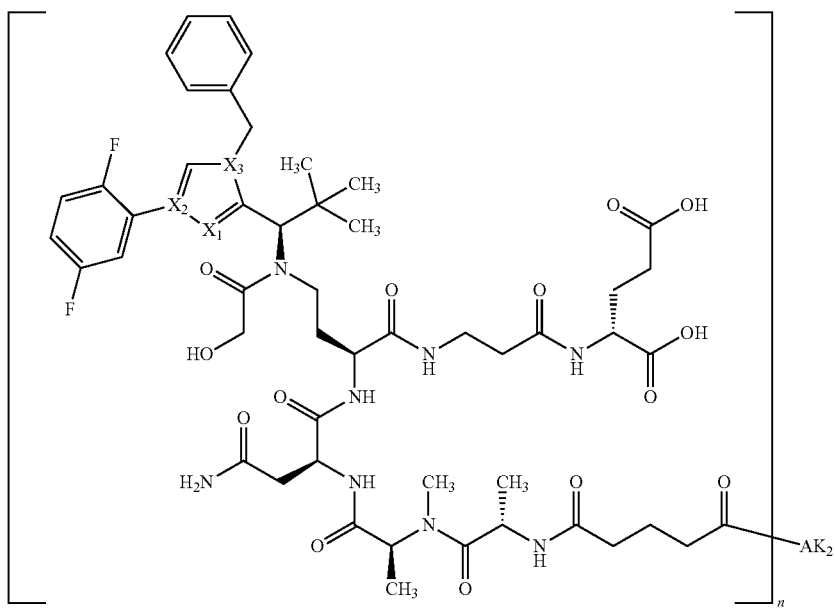

In the above reaction scheme, $X_1$, $X_2$, $X_3$, n and $AK_2$ have the meanings given in formula (I).

a): HATU, DMF, N,N-diisopropylethylamine, RT; b) $H_2$, 10% Pd—C, methanol 1.5 h, RT; c) 1,1'-[(1,5-dioxopentane-1,5-diyl)bis(oxy)]dipyrrolidine-2,5-dione, N,N-diisopropylethylamine, DMF, stirring at RT overnight; d) AK2 in PBS, under argon addition of 3-5 equiv. of active ester dissolved in DMSO, stirring at RT under argon for 60 min, addition of another 3-5 equiv. of active ester dissolved in DMSO, stirring at RT under argon for 60 min, then purification by means of PD 10 columns equilibrated with PBS buffer (pH 7.2) (Sephadex® G-25, GE Healthcare) and subsequent concentration by means of ultracentrifugation and setting of the concentration desired with PBS buffer (pH 7.2)]. In the case of in vivo batches, this is optionally followed by sterile filtration.

Scheme 2: Synthesis of cysteine-linked ADCs
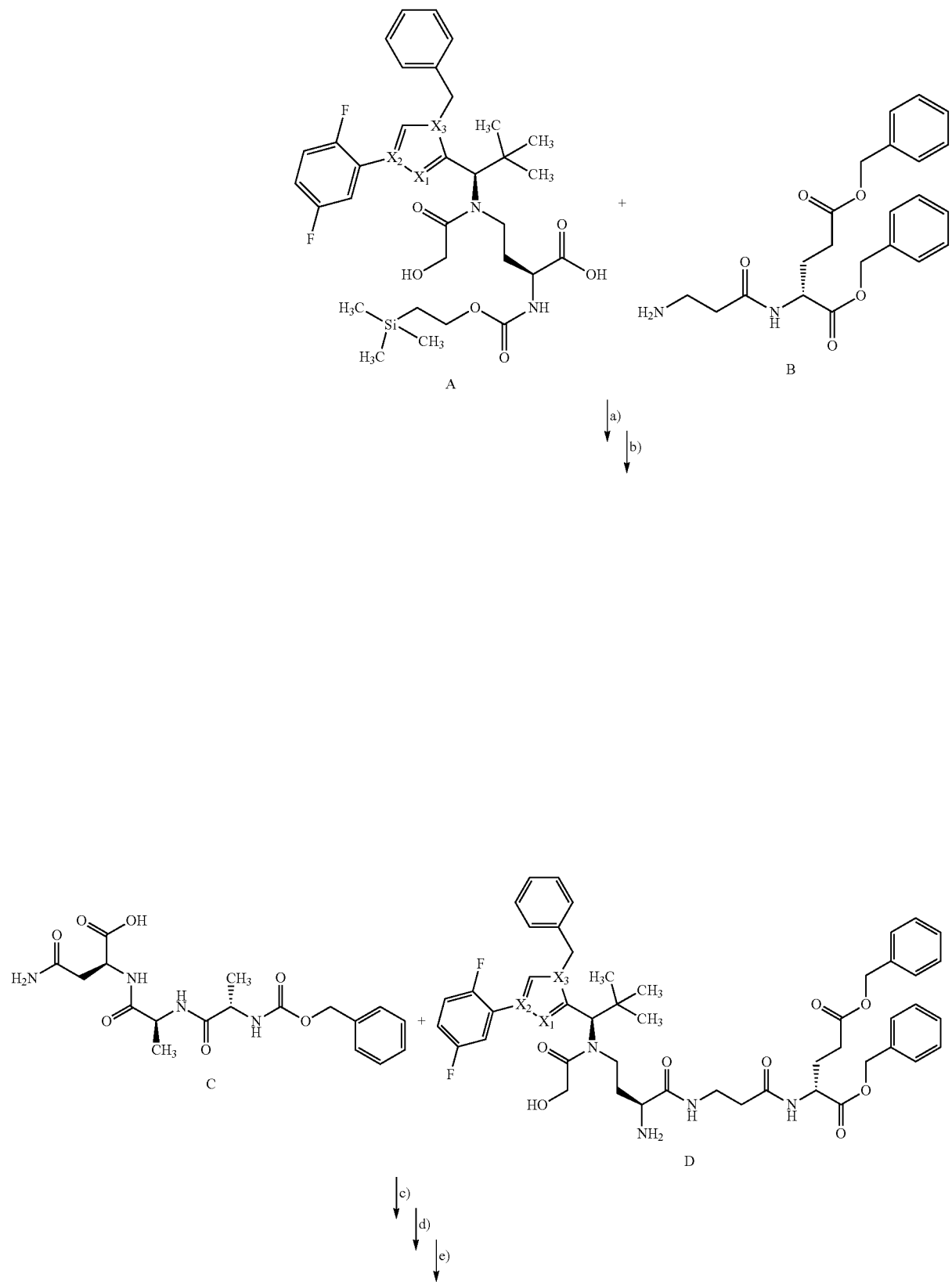

-continued

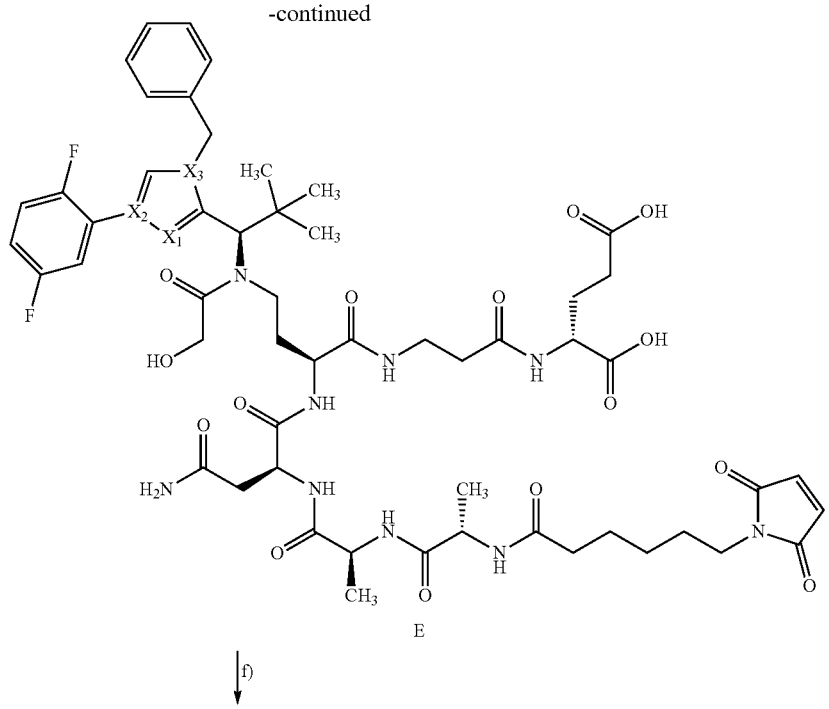

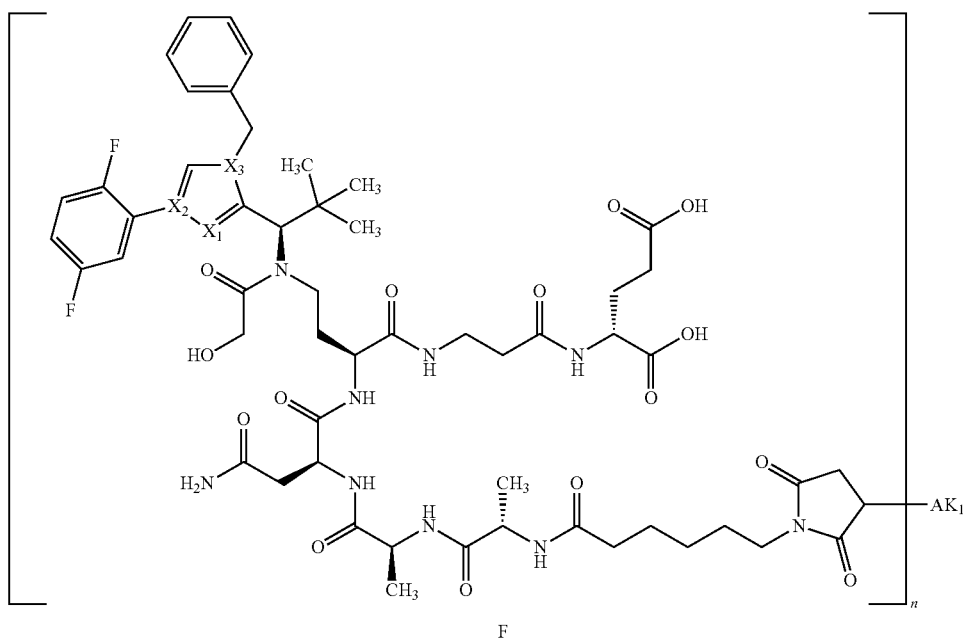

In the above reaction scheme, $X_1$, $X_2$, $X_3$, n and $AK_1$ have the meanings given in formula (I).

a): HATU, DMF, N,N-diisopropylethylamine, RT; b) zinc chloride, trifluoroethanol, 50° C., EDTA c): HATU, DMF, N,N-diisopropylethylamine, RT; d) $H_2$, 10% Pd—C, methanol 1.5 h, RT; e) 1-{6-[(2,5-dioxopyrrolidin-1-yl)oxy]-6-oxohexyl}-1H-pyrrole-2,5-dione, N,N-diisopropylethylamine, DMF, stirring at RT; f) AK1 dissolved in PBS, under argon addition of 3-4 equivalents of TCEP in PBS buffer and about 30 min stirring at RT, then addition of 5-10 equivalents of compound E dissolved in DMSO, about 90 min of stirring at RT, then purification by means of PD 10 columns equilibrated with PBS buffer (pH 7.2) (Sephadex® G-25, GE Healthcare) and subsequent concentration by means of ultracentrifugation and setting of the concentration desired with PBS buffer (pH 7.2)]. In the case of in vivo batches, this is optionally followed by sterile filtration.

Scheme 3: Synthesis of cysteine-linked ADCs via ring-opened succinimides
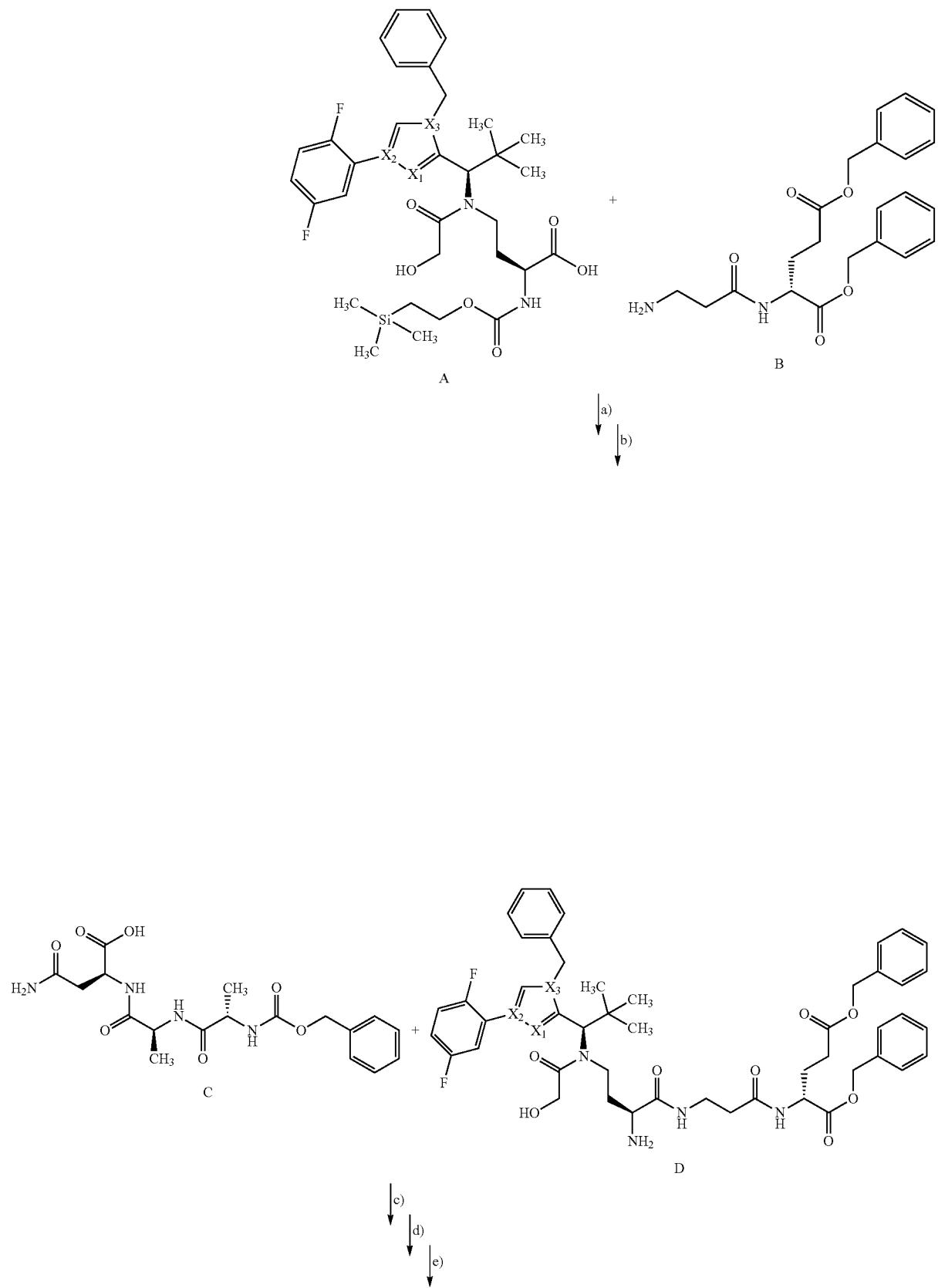

-continued

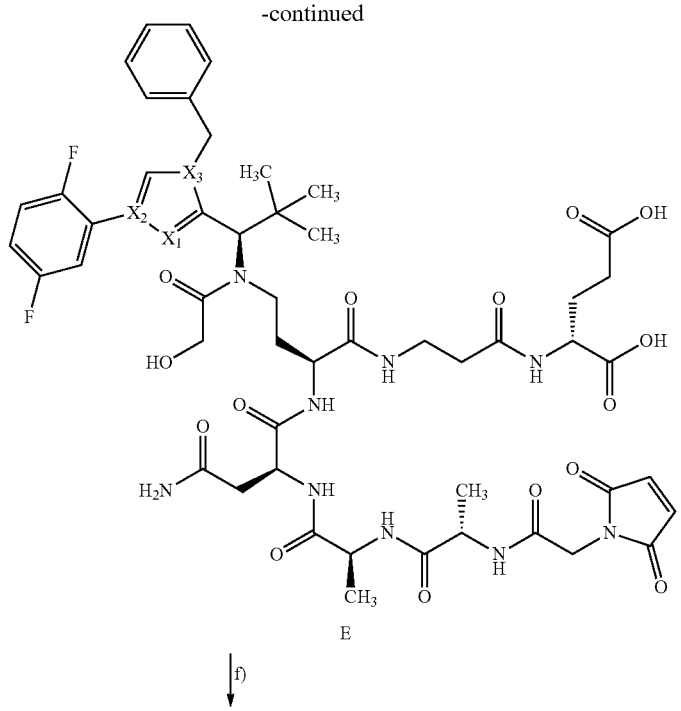

E

↓ f)

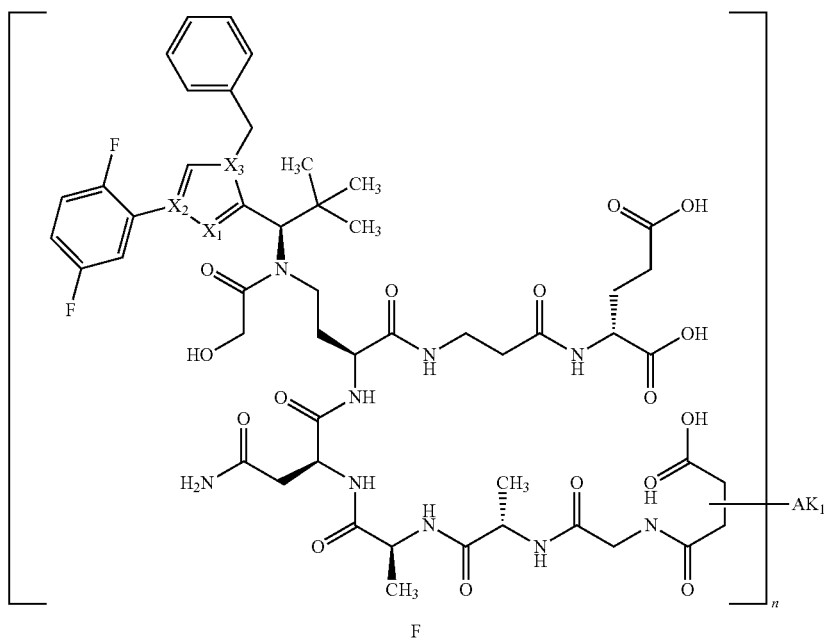

F

In the above reaction scheme, $X_1$, $X_2$, $X_3$, n and $AK_1$ have the meanings given in formula (I).

a): HATU, DMF, N,N-diisopropylethylamine, RT; b) zinc chloride, trifluoroethanol, 50° C., EDTA c): HATU, DMF, N,N-diisopropylethylamine, RT; d) $H_2$, 10% Pd—C, methanol 1.5 h, RT; e) 1-{2-[(2,5-dioxopyrrolidin-1-yl)oxy]-2-oxoethyl}-1H-pyrrole-2,5-dione, N,N-diisopropylethylamine, DMF, stirring at RT; f) AK1 dissolved in PBS, under argon addition of 3-4 equivalents of TCEP in PBS buffer and about 30 min stirring at RT, then addition of 5-10 equivalents of compound E dissolved in DMSO, about 90 min of stirring at RT, then rebuffering to pH 8 by means of PD 10 columns equilibrated with PBS buffer (pH 8) (Sephadex® G-25, GE Healthcare), then stirring at RT overnight, then optionally purification by means of PD 10 columns equilibrated with PBS buffer (pH 7.2) (Sephadex® G-25, GE Healthcare) and subsequent concentration by means of ultracentrifugation and setting of the concentration desired with PBS buffer (pH 7.2)]. In the case of in vivo batches, this is optionally followed by sterile filtration.

A. Examples

Abbreviations and Acronyms

ABCB1 ATP-binding cassette sub-family B member 1 (synonym for P-gp and MDR1)
abs. absolute
Ac acetyl
ACN acetonitrile
aq. aqueous, aqueous solution
ATP adenosine triphosphate
BCRP breast cancer resistance protein, an efflux transporter
BEP 2-bromo-1-ethylpyridinium tetrafluoroborate
Boc tert-butoxycarbonyl
br. broad (in NMR)
Ex. Example
BxPC3 human tumour cell line
C concentration
ca. circa, about
CI chemical ionization (in MS)
DAR drug-to-antibody ratio
d doublet (in NMR)
d day(s)
TLC thin layer chromatography
DCI direct chemical ionization (in MS)
DCM dichloromethane
dd doublet of doublets (in NMR)
DMAP 4-N,N-dimethylaminopyridine
DME 1,2-dimethoxyethane
DMEM Dulbecco's Modified Eagle Medium (standardized nutrient medium for cell culture)
DMF N,N-dimethylformamide
DMSO dimethyl sulfoxide
D/P dye (fluorescent dye)/protein ratio
DPBS, D-PBS, Dulbecco's phosphate-buffered salt solution
DSMZ Deutsche Sammlung von Mikroorganismen und Zellkulturen (German Collection of Microorganisms and Cell Cultures)
PBS PBS=DPBS=D-PBS, pH 7.4, from Sigma, No D8537
  Composition:
  0.2 g KCl
  0.2 g $KH_2PO_4$ (anhyd)
  8.0 g NaCl
  1.15 g $Na_2HPO_4$ (anhyd)
  made up ad 1 l with $H_2O$
dt doublet of triplets (in NMR)
DTT DL-dithiothreitol
EDC N'-(3-dimethylaminopropyl)-N-ethylcarbodiimide hydrochloride
EGFR epidermal growth factor receptor
EI electron impact ionization (in MS)
ELISA enzyme-linked immunosorbent assay
eq. equivalent(s)
ESI electrospray ionization (in MS)
ESI-MicroTofq ESI-MicroTofq (name of the mass spectrometer with Tof=time of flight and q=quadrupole)
FCS foetal calf serum
Fmoc (9H-fluoren-9-ylmethoxy)carbonyl
sat. saturated
GTP guanosine-5'-triphosphate
H hour(s)
HATU O-(7-azabenzotriazol-1-yl)-N,N,N',N'-tetramethyluronium hexafluorophosphate
HEPES 4-(2-hydroxyethyl)piperazine-1-ethanesulfonic acid
HOAc acetic acid
HOAt 1-hydroxy-7-azabenzotriazole
HOBt 1-hydroxy-1H-benzotriazole hydrate
HOSu N-hydroxysuccinimide
HPLC high-pressure, high-performance liquid chromatography
$IC_{50}$ half-maximal inhibitory concentration
i.m. intramuscularly, administration into the muscle
i.v. intravenously, administration into the vein
conc. concentrated
KPL-4 human tumour cell line
KU-19-19 human tumour cell line
LC-MS liquid chromatography-coupled mass spectrometry
LLC-PK1 cells Lewis lung carcinoma pork kidney cell line
L-MDR human MDR1 transfected LLC-PK1 cells
LoVo human tumour cell line
M multiplet (in NMR)
Me methyl
MDR1 Multidrug resistance protein 1
MeCN acetonitrile
min minute(s)
MOLM-13 human tumour cell line
MS mass spectrometry
MTT 3-(4,5-dimethylthiazol-2-yl)-2,5-diphenyl-2H-tetrazolium bromide
MV-4-11 human tumour cell line
NB4 human tumour cell line
NCI-H292 human tumour cell line
NMM N-methylmorpholine
NMP N-methyl-2-pyrrolidinone
NMR nuclear magnetic resonance spectrometry
NMRI mouse strain originating from the Naval Medical Research Institute (NMRI)
Nude mice experimental animals
NSCLC non small cell lung cancer
PBS phosphate-buffered salt solution
Pd/C palladium on activated charcoal
P-gp P-glycoprotein, a transporter protein
PNGaseF enzyme for cleaving sugar
quant. quantitative (in yield)
quart quartet (in NMR)
quint quintet (in NMR)
Rec-1 human tumour cell line
Rf retention index (in TLC)
RT room temperature
$R_t$ retention time (in HPLC)
S singlet (in NMR)
s.c. subcutaneously, administration under the skin
SCID mice test mice with severe combined immunodeficiency
SK-HEP-1 human tumour cell line
t triplet (in NMR)
TBAF tetra-n-butylammonium fluoride
TCEP tris(2-carboxyethyl)phosphine
TEMPO (2,2,6,6-tetramethylpiperidin-1-yl)oxyl
Teoc trimethylsilylethoxycarbonyl
tert tertiary
TFA trifluoroacetic acid
TH F tetrahydrofuran
T3P© 2,4,6-tripropyl-1,3,5,2,4,6-trioxatriphosphinane 2,4,6-trioxide
U251 human tumour cell line
UV ultraviolet spectrometry
v/v volume to volume ratio (of a solution)
Z benzyloxycarbonyl
  HPLC and LC-MS Methods:
  Method 1 (LC-MS):
  Instrument: Waters ACQUITY SQD UPLC System; column: Waters Acquity UPLC HSS T3 1.8µ 50×1 mm; mobile phase A: 1 l of water+0.25 ml of 99% strength formic acid;

mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2 (LC-MS):

MS instrument type: Waters Synapt G2S; UPLC instrument type: Waters Acquity I-CLASS; column: Waters, BEH300, 2.1×150 mm, C18 1.7 µm; mobile phase A: 1 l of water+0.01% formic acid; mobile phase B: 1 l of acetonitrile+0.01% formic acid; gradient: 0.0 min 2% B→1.5 min 2% B→8.5 min 95% B→10.0 min 95% B; oven: 50° C.; flow rate: 0.50 ml/min; UV detection: 220 nm Method 3 (LC-MS):

MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm Method 4 (LC-MS):

MS instrument type: Waters Synapt G2S; UPLC instrument type: Waters Acquity I-CLASS; column: Waters, HSST3, 2.1×50 mm, C18 1.8 µm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm Method 5 (LC-MS):

Instrument: Waters ACQUITY SQD UPLC System; column: Waters Acquity UPLC HSS T3 1.8µ 50×1 mm; mobile phase A: 1 l of water+0.25 ml of 99% strength formic acid; mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 6 (LC-MS):

Instrument: Micromass Quattro Premier with Waters UPLC Acquity; column: Thermo Hypersil GOLD 1.9µ, 50×1 mm; mobile phase A: 1 l of water+0.5 ml of 50% strength formic acid; mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV detection: 210 nm.

Method 7 (LC-MS):

Instrument: Agilent MS Quad 6150; HPLC: Agilent 1290; column: Waters Acquity UPLC HSS T3 1.8µ 50×2.1 mm; mobile phase A: 1 l of water+0.25 ml of 99% strength formic acid; mobile phase B: 1 l of acetonitrile+0.25 ml of 99% strength formic acid; gradient: 0.0 min 90% A→0.3 min 90% A→1.7 min 5% A→3.0 min 5% A oven: 50° C.; flow rate: 1.20 ml/min; UV detection: 205-305 nm.

Method 8 (LC-MS):

MS instrument type: Waters Synapt G2S; UPLC instrument type: Waters Acquity I-CLASS; column: Waters, HSST3, 2.1×50 mm, C18 1.8 µm; mobile phase A: 1 l of water+0.01% formic acid; mobile phase B: 1 l of acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 210 nm.

Method 9: (LC-MS Prep. Purification Method)

MS instrument: Waters, HPLC instrument: Waters (column Waters X-Bridge C18, 19 mm×50 mm, 5 µm, eluent A: water+0.05% ammonia, mobile phase B: acetonitrile (ULC) with gradient; flow rate: 40 ml/min; UV detection: DAD; 210-400 nm).

or

MS instrument: Waters, HPLC instrument: Waters (column Phenomenex Luna 5p C18(2) 100A, AXIA Tech. 50×21.2 mm, eluent A: water+0.05% formic acid, eluent B: acetonitrile (ULC) with gradient; flow rate: 40 ml/min; UV detection: DAD; 210-400 nm).

Method 10: (LC-MS Analysis Method)

MS instrument: Waters SQD; HPLC instrument: Waters UPLC; column: Zorbax SB-Aq (Agilent), 50 mm×2.1 mm, 1.8 µm; mobile phase A: water+0,025% formic acid, eluent B: acetonitrile (ULC)+0,025% formic acid; gradient: 0.0 min 98% A—0.9 min 25% A—1.0 min 5% A—1.4 min 5% A—1.41 min 98% A—1.5 min 98% A; oven: 40° C.; flow rate: 0,600 ml/min; UV detection: DAD; 210 nm.

Method 11 (HPLC):

Instrument: HP1100 Series

Column: Merck Chromolith SpeedROD RP-18e, 50-4.6 mm, Cat.
  No. 1.51450.0001, precolumn Chromolith Guard Cartridge Kit, RP-18e, 5-4.6 mm, Cat. No. 1.51470.0001

Gradient: flow rate 5 ml/min injection volume 5 µl solvent A: HClO4 (70%) in water (4 ml/l)

solvent B: acetonitrile start 20% B 0.50 min 20% B 3.00 min 90% B 3.50 min 90% B 3.51 min 20% B 4.00 min 20% B Column temperature: 40° C.

Wavelength: 210 nm

Method 12 (LC-MS):

MS instrument type: Thermo Scientific FT-MS; instrument type UHPLC+: Thermo Scientific UltiMate 3000; column: Waters, HSST3, 2.1×75 mm, C18 1.8 µm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Method 13: (LC-MS):

MS instrument: Waters (Micromass) Quattro Micro; instrument Waters UPLC Acquity; column: Waters BEH C18 1.7µ 50×2.1 mm; mobile phase A: 1 l of water+0.01 mol of ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm.

Method 14: (LC-MS) (MCW-LTQ-POROSHELL-TFA98-10 min)

MS instrument type: ThermoFisherScientific LTQ-Orbitrap-XL; HPLC instrument type: Agilent 1200SL; column: Agilent, POROSHELL 120, 3×150 mm, SB—C18 2.7 µm; mobile phase A: 1 l of water+0.1% trifluoroacetic acid; mobile phase B: 1 l of acetonitrile+0.1% trifluoroacetic acid; gradient: 0.0 min 2% B→0.3 min 2% B→5.0 min 95% B→10.0 min 95% B; oven: 40° C.; flow rate: 0.75 ml/min; UV detection: 210 nm All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Compounds and Intermediates:
Intermediate C52

(1R)-1-[1-Benzyl-4-(2,5-difluorophenyl)-1H-pyrrol-2-yl]-2,2-dimethylpropan-1-amine

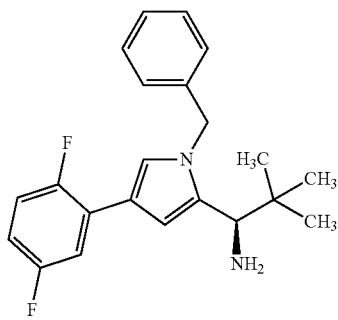 [SMILES: CC(C)(C)[C@@H](N)c1cc(-c2cc(F)ccc2F)cn1Cc1ccccc1]

10.00 g (49.01 mmol) of methyl 4-bromo-1H-pyrrole-2-carboxylate were initially charged in 100.0 ml of DMF, and 20.76 g (63.72 mmol) of caesium carbonate and 9.22 g (53.91 mmol) of benzyl bromide were added. The reaction mixture was stirred at RT overnight. The reaction mixture was partitioned between water and ethyl acetate and the aqueous phase was extracted with ethyl acetate. The combined organic phases were dried over magnesium sulfate and the solvent was evaporated under reduced pressure. The reaction was repeated with 90.0 g of methyl 4-bromo-1H-pyrrole-2-carboxylate. The two combined reactions were purified by preparative RP-HPLC (column: Daiso 300×100; 10μ, flow rate: 250 ml/min, MeCN/water). The solvents were evaporated under reduced pressure and the residue was dried under high vacuum. This gave 125.15 g (87% of theory) of the compound methyl 1-benzyl-4-bromo-1H-pyrrole-2-carboxylate.

LC-MS (Method 1): $R_t$=1.18 min; MS (ESIpos): m/z=295 [M+H]$^+$.

Under argon, 4.80 g (16.32 mmol) of methyl 1-benzyl-4-bromo-1H-pyrrole-2-carboxylate were initially charged in DMF, and 3.61 g (22.85 mmol) of (2,5-difluorophenyl)boronic acid, 19.20 ml of saturated sodium carbonate solution and 1.33 g (1.63 mmol) of [1,1'-bis(diphenylphosphino)ferrocene]-dichloropalladium(II):dichloromethane were added. The reaction mixture was stirred at 85° C. overnight. The reaction mixture was filtered through Celite and the filter cake was washed with ethyl acetate. The organic phase was extracted with water and then washed with saturated NaCl solution. The organic phase was dried over magnesium sulfate and the solvent was evaporated under reduced pressure. The residue was purified on silica gel (mobile phase: cyclohexane/ethyl acetate 100:3). The solvents were evaporated under reduced pressure and the residue was dried under high vacuum. This gave 3.60 g (67% of theory) of the compound methyl 1-benzyl-4-(2,5-difluorophenyl)-1H-pyrrole-2-carboxylate.

LC-MS (Method 7): $R_t$=1.59 min; MS (ESIpos): m/z=328 [M+H]$^+$.

3.60 g (11.00 mmol) of methyl 1-benzyl-4-(2,5-difluorophenyl)-1H-pyrrole-2-carboxylate were initially charged in 90.0 ml of THF, and 1.04 g (27.50 mmol) of lithium aluminium hydride (2.4 M in THF) were added at 0° C. The reaction mixture was stirred at 0° C. for 30 minutes. Saturated potassium sodium tartrate solution was added at 0° C. and the reaction mixture was admixed with ethyl acetate. The organic phase was extracted three times with saturated potassium sodium tartrate solution. The organic phase was washed once with saturated NaCl solution and dried over magnesium sulfate. The solvent was evaporated under reduced pressure and the residue was dissolved in 30.0 ml of dichloromethane. 3.38 g (32.99 mmol) of manganese(IV) oxide were added, and the mixture was stirred at RT for 48 h. Another 2.20 g (21.47 mmol) of manganese(IV) oxide were added, and the mixture was stirred at RT overnight. The reaction mixture was filtered through Celite and the filter cake was washed with dichloromethane. The solvent was evaporated under reduced pressure and the residue 2.80 g of (1-benzyl-4-(2,5-difluorophenyl)-1H-pyrrole-2-carbaldehyde) was used without further purification in the next step of the synthesis.

LC-MS (Method 7): $R_t$=1.48 min; MS (ESIpos): m/z=298 [M+H]$^+$.

28.21 g (94.88 mmol) of 1-benzyl-4-(2,5-difluorophenyl)-1H-pyrrole-2-carbaldehyde together with 23.00 g (189.77 mmol) of (R)-2-methylpropane-2-sulfinamide were initially charged in 403.0 ml of absolute THF, and 67.42 g (237.21 mmol) of titanium(IV) isopropoxide were added and the mixture was stirred at RT overnight. 500 ml of saturated NaCl solution and 1000.0 ml of ethyl acetate were added, and the mixture was stirred at RT for 1 h. The mixture was filtered through kieselguhr and the filtrate was washed twice with saturated NaCl solution. The organic phase was dried over magnesium sulfate, the solvent was evaporated under reduced pressure and the residue was purified using Biotage Isolera (silica gel, column 1500+340 g SNAP, flow rate 200 ml/min, ethyl acetate/cyclohexane 1:10).

LC-MS (Method 7): $R_t$=1.63 min; MS (ESIpos): m/z=401 [M+H]$^+$.

25.00 g (62.42 mmol) of (R)—N-{(E/Z)-[1-benzyl-4-(2,5-difluorophenyl)-1H-pyrrol-2-yl]methylene}-2-methylpropane-2-sulfinamide were initially charged in absolute THF under argon and cooled to −78° C. 12.00 g (187.27 mmol) of tert-butyllithium (1.7 M solution in pentane) were then added at −78° C. and the mixture was stirred at this temperature for 3 h. At −78° C., 71.4 ml of methanol and 214.3 ml of saturated ammonium chloride solution were then added successively and the reaction mixture was allowed to warm to RT and stirred at RT for 1 h. The mixture was diluted with ethyl acetate and washed with water. The organic phase was dried over magnesium sulfate and the solvent was evaporated under reduced pressure. The residue (R)—N-{(1R)-1-[1-benzyl-4-(2,5-difluorophenyl)-1H-pyrrol-2-yl]-2,2-dimethylpropyl}-2-methylpropane-2-sulfinamide was used without further purification in the next step of the synthesis.

LC-MS (Method 6): $R_t$=2.97 min; MS (ESIpos): m/z=459 [M+H]$^+$.

28.00 g (61.05 mmol) of (R)—N-{(1R)-1-[1-benzyl-4-(2,5-difluorophenyl)-1H-pyrrol-2-yl]-2,2-dimethylpropyl}-2-methylpropane-2-sulfinamide were initially charged in 186.7 ml of 1,4-dioxane, and 45.8 ml of HCl in 1,4-dioxane solution (4.0 M) were then added. The reaction mixture was stirred at RT for 2 h and the solvent was evaporated under reduced pressure. The residue was purified by preparative HPLC (column: Kinetix 100×30; flow rate: 60 ml/min, MeCN/water). The acetonitrile was evaporated under reduced pressure and dichloromethane was added to the aqueous residue. The organic phase was washed with sodium bicarbonate solution and dried over magnesium sulfate. The solvent was evaporated under reduced pressure and the residue was dried under high vacuum. This gave 16.2 g (75% of theory) of the title compound.

LC-MS (Method 6): R$_t$=2.10 min; MS (ESIpos): m/z=338 [M-NH$_2$]+, 709 [2M+H]$^+$.

$^1$H-NMR (400 MHz, DMSO-d$_6$): δ [ppm]=0.87 (s, 9H), 1.53 (s, 2H), 3.59 (s, 1H), 5.24 (d, 2H), 6.56 (s, 1H), 6.94 (m, 1H), 7.10 (d, 2H), 7.20 (m, 1H), 7.26 (m, 2H), 7.34 (m, 2H), 7.46 (m, 1H).

Intermediate C58

(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic acid

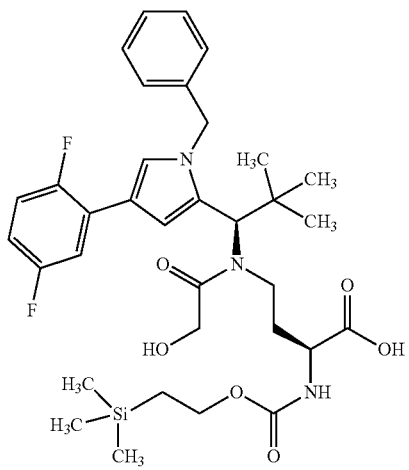 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CO]

4.3 g (12.2 mmol) of Intermediate C52 were dissolved in 525 ml of DCM, and 3.63 g (17.12 mmol) of sodium triacetoxyborohydride and 8.4 ml of acetic acid were added. After 5 min of stirring at RT, 8.99 g (24.5 mmol) of Intermediate L57 dissolved in 175 ml of DCM were added and the reaction was stirred at RT for a further 45 min. The reaction was then diluted with 300 ml of DCM and washed twice with 100 ml of sodium bicarbonate solution and once with saturated NaCl solution. The organic phase was dried over magnesium sulfate, the solvent was evaporated under reduced pressure and the residue was dried under high vacuum. The residue was then purified by preparative RP-HPLC (column: Chromatorex C18). After combination of the appropriate fractions, the solvent was evaporated under reduced pressure and the residue was dried under high vacuum. This gave 4.6 g (61% of theory) of methyl (2S)-4-({(1R)-1-[1-benzyl-4-(2,5-difluorophenyl)-1H-pyrrol-2-yl]-2,2-dimethylpropyl}amino)-2-({[2-(trimethylsilyl)ethoxy]carbonyl}amino)butanoate.

LC-MS (Method 12): R$_t$=1.97 min; MS (ESIpos): m/z=614 (M+H)$^+$. 2.06 g (3.36 mmol) of this intermediate were initially charged in 76 ml of DCM and acylated with 0.81 ml (7.17 mmol) of 2-chloro-2-oxoethyl acetate in the presence of 2.1 ml of triethylamine. After 20 h of stirring at RT, 0.36 ml of 2-chlor-2-oxoethyl acetate and 0.94 ml of triethylamine were added and the reaction was stirred at RT for a further 15 min. The mixture was then diluted with 500 ml of ethyl acetate and extracted successively twice with 300 ml of 5% citric acid, twice with 300 ml of saturated sodium hydrogencarbonate solution and once with 100 ml of saturated sodium chloride solution and then dried over magnesium sulfate and concentrated. Drying under high vacuum gave 2.17 g (79% of theory) of the protected intermediate.

LC-MS (Method 1): R$_t$=1.48 min; MS (ESIpos): m/z=714 (M+H)$^+$.

2.17 mg (2.64 mmol) of this intermediate were dissolved in 54 ml of THF and 27 ml of water, and 26 ml of a 2-molar lithium hydroxide solution were added. The mixture was stirred at RT for 30 min and then adjusted to a pH between 3 and 4 using 1.4 ml of TFA. The mixture was concentrated under reduced pressure. Once most of the THF had been distilled off, the aqueous solution was extracted twice with DCM and then concentrated to dryness under reduced pressure. The residue was purified by preparative HPLC (column: Chromatorex C18). After combination of the appropriate fractions, the solvent was evaporated under reduced pressure and the residue was lyophilized from acetonitrile/water. This gave 1.1 g (63% of theory) of the title compound.

LC-MS (Method 1): R$_t$=1.34 min; MS (ESIpos): m/z=656 (M−H)$^-$.

$^1$H-NMR (400 MHz, DMSO-d$_6$): δ [ppm]=0.03 (s, 9H), 0.58 (m, 1H), 0.74-0.92 (m, 11H), 1.40 (m, 1H), 3.3 (m, 2H), 3.7 (m, 1H), 3.8-4.0 (m, 2H), 4.15 (q, 2H), 4.9 and 5.2 (2d, 2H), 5.61 (s, 1H), 6.94 (m, 2H), 7.13-7.38 (m, 7H), 7.48 (s, 1H), 7.60 (m, 1H), 12.35 (s, 1H).

Intermediate C61

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-beta-alanine

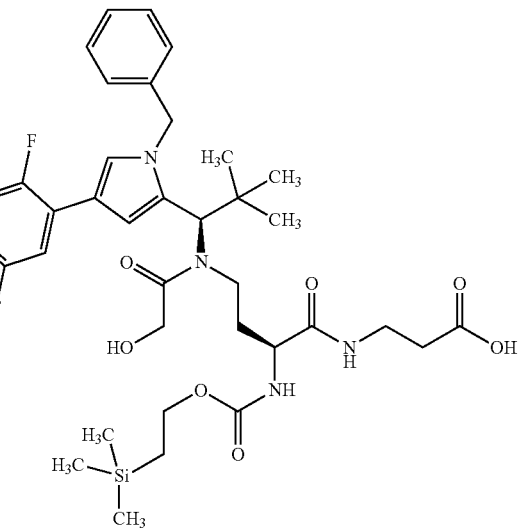

The title compound was prepared by coupling 60 mg (0.091 mmol) of Intermediate C58 with methyl β-alaninate, followed by ester cleavage with 2M lithium hydroxide solution.

This gave 67 mg (61% of theory) of the title compound over 2 steps.

LC-MS (Method 1): R$_t$=1.29 min; MS (ESIpos): m/z=729 (M+H)$^+$.

Intermediate C102

(2S)-4-[{(1R)-1-[1-Benzyl-4-(2,5-difluorophenyl)-1H-pyrrol-2-yl]-2,2-dimethylpropyl}(glycoloyl)amino]-2-{[(benzyloxy)carbonyl]amino}butanoic acid

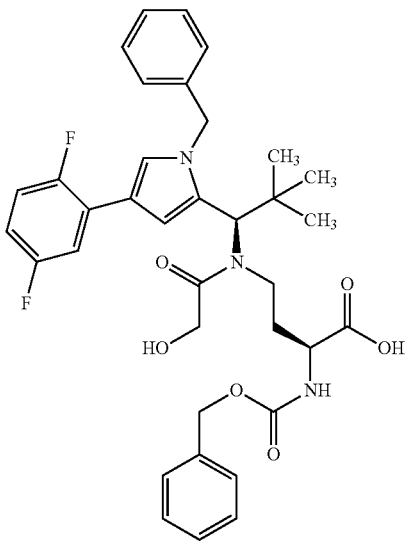 [SMILES: CC(C)(C)[C@H](c1cc(-c2cc(F)ccc2F)cn1Cc1ccccc1)N(CC[C@H](NC(=O)OCc1ccccc1)C(=O)O)C(=O)CO]

First, intermediate C52 was reductively alkylated with benzyl (2S)-2-{[(benzyloxy)carbonyl]amino}-4-oxobutanoate analogously to Intermediate C2. The secondary amino group was then acylated with 2-chloro-2-oxoethyl acetate, and the two ester groups were then hydrolysed with 2M lithium hydroxide solution in methanol.

LC-MS (Method 1): $R_t$=1.31 min; MS (ESIpos): m/z=646 (M−H)⁻.

Intermediate C110(D)

Dibenzyl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamate The title compound was prepared by coupling dibenzyl D-glutamate, which had been released beforehand from its p-toluenesulfonic acid salt by partitioning between ethyl acetate and 5% sodium hydrogencarbonate solution, with Intermediate C61 in the presence of HATU and N,N-diisopropylethylamine and subsequent detachment of the Teoc protecting group by means of zinc chloride in trifluoroethanol.

LC-MS (Method 1): $R_t$=1.08 min; MS (ESIpos): m/z=894 [M+H]⁺.

Intermediate C111

Di-tert-butyl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamate

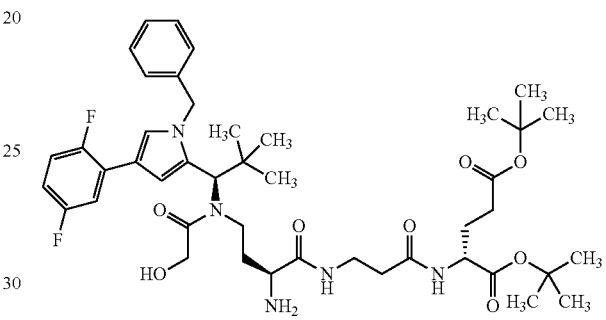

First of all, the dipeptide derivative di-tert-butyl beta-alanyl-D-glutamate was prepared by conventional methods of peptide chemistry by coupling of commercially available N-[(benzyloxy)carbonyl]-beta-alanine and di-tert-butyl D-glutamate hydrochloride (1:1) in the presence of HATU and subsequent hydrogenolytic detachment of the Z protecting group. The title compound was then prepared by coupling this intermediate with Intermediate C102 in the presence of HATU and N,N-diisopropylethylamine and subsequent detachment of the Z protecting group by hydrogenation over 10% palladium on activated carbon in DCM/methanol 1:1 at RT under standard hydrogen pressure for 1 hour.

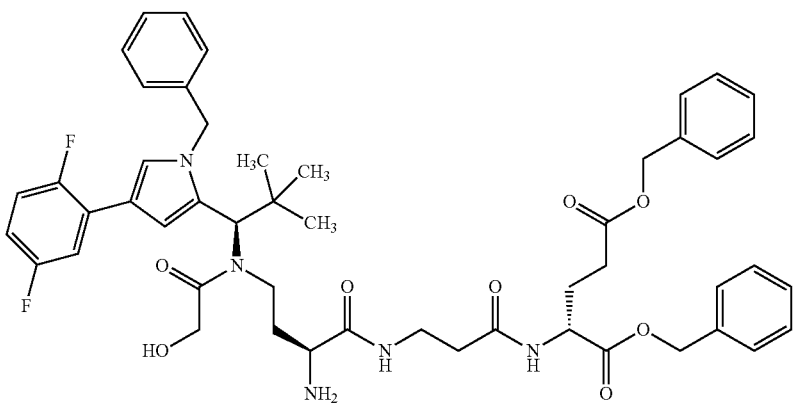 [SMILES: CC(C)(C)[C@H](c1cc(-c2cc(F)ccc2F)cn1Cc1ccccc1)N(CC[C@H](N)C(=O)NCCC(=O)N[C@H](CCC(=O)OCc1ccccc1)C(=O)OCc1ccccc1)C(=O)CO]

LC-MS (Method 1): $R_t$=1.06 min; MS (ESIpos): m/z=826 [M+H]$^+$.

Intermediate C117

Trifluoroacetic acid dibenzyl N-{(2S)-2-(L-asparaginylamino)-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamate salt

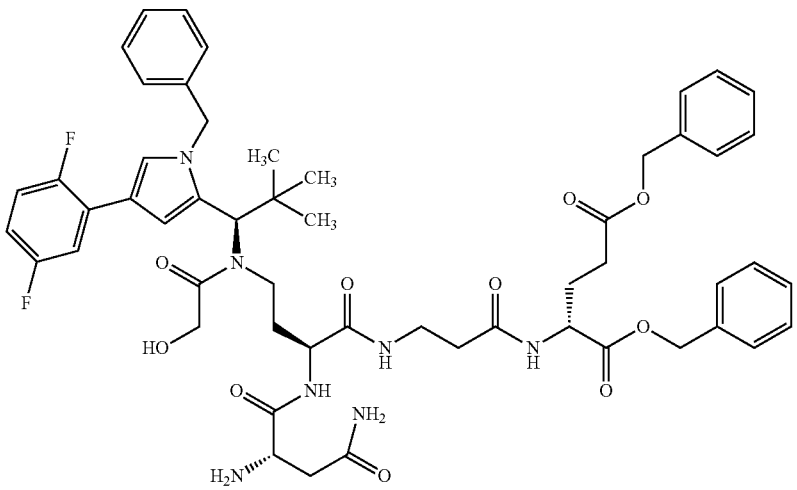 [SMILES: CC(C)(C)[C@H](c1cc(-c2cc(F)ccc2F)cn1Cc1ccccc1)N(CC[C@H](NC(=O)[C@@H](N)CC(N)=O)C(=O)NCCC(=O)N[C@H](CCC(=O)OCc1ccccc1)C(=O)OCc1ccccc1)C(=O)CO]

Intermediate C110D and 2,5-dioxopyrrolidin-1-yl-N$^2$-(tert-butoxycarbonyl)-L-asparaginate (251 mg, 764 µmol) were dissolved in 21 ml of DMF and N,N-diisopropylethylamine (363 µl, 2.01 mmol) was added. The reaction was stirred at RT and then purified directly by prep. RP-HPLC (column: Chromatorex C18-10). The solvents were evaporated under reduced pressure and the residue was lyophilized.

The intermediate obtained (578 mg, 52 µmol) was dissolved in 20.0 ml of trifluoroethanol. The reaction mixture was admixed with zinc chloride (426 mg, 3.13 mmol) and stirred at 50° C. for 40 min. The mixture was admixed with ethylenediamine-N,N,N',N'-tetraacetic acid (914 mg, 3.13 mmol) and diluted with 20 ml of water, TFA (200 µl) was added and the mixture was stirred briefly. The mixture was filtered and purified by preparative RP-HPLC (column: Chromatorex C18-5; 125×40, flow rate: 100 ml/min, MeCN/water, 0.1% TFA gradient). Lyophilization gave the title compound.

Intermediate L57

Methyl (2S)-4-oxo-2-({[2-(trimethylsilyl)ethoxy]carbonyl}amino)butanoate

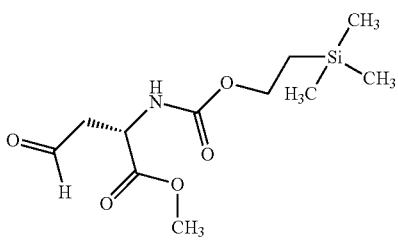 [SMILES: COC(=O)[C@H](CC=O)NC(=O)OCC[Si](C)(C)C]

500.0 mg (2.72 mmol) of methyl L-asparaginate hydrochloride and 706.3 mg (2.72 mmol) of 2-(trimethylsilyl)ethyl 2,5-dioxopyrrolidine-1-carboxylate were initially charged in 5.0 ml of 1,4-dioxane, and 826.8 mg (8.17 mmol) of triethylamine were added. The reaction mixture was stirred at RT overnight. The reaction mixture was purified directly by preparative RP-HPLC (column: Reprosil 250× 40; 10µ, flow rate 50 ml/min, MeCN/water, 0.1% TFA). The solvents were then evaporated under reduced pressure and the residue was dried under high vacuum. This gave 583.9 mg (74% of theory) of the compound (3S)-4-methoxy-4-oxo-3-({[2-(trimethylsilyl)ethoxy]carbonyl}amino)butanoic acid. LC-MS (Method 1): $R_t$=0.89 min; MS (ESIneg): m/z=290 (M−H)$^-$.

592.9 mg of (3S)-4-methoxy-4-oxo-3-({[2-(trimethylsilyl)ethoxy]carbonyl}amino)butanoic acid were initially charged in 10.0 ml of 1,2-dimethoxyethane, the mixture was cooled to −15° C. and 205.8 mg (2.04 mmol) of 4-methylmorpholine and 277.9 mg (2.04 mmol) of isobutyl chloroformate were added. The precipitate was filtered off with suction after 15 min and twice with in each case 10.0 ml of 1,2-dimethoxyethane. The filtrate was cooled to −10° C., and 115.5 mg (3.05 mmol) of sodium borohydride dissolved in 10 ml of water were added with vigorous stirring. The phases were separated and the organic phase was washed once each with saturated sodium hydrogencarbonate solution and saturated NaCl solution. The organic phase was dried over magnesium sulfate, the solvent was evaporated under reduced pressure and the residue was dried under high vacuum. This gave 515.9 mg (91% of theory) of the compound methyl N-{[2-(trimethylsilyl)ethoxy]carbonyl}-L-homoserinate.

LC-MS (Method 1): $R_t$=0.87 min; MS (ESIpos): m/z=278 (M+H)$^+$.

554.9 mg (2.00 mmol) of methyl N-{[2-(trimethylsilyl)ethoxy]carbonyl}-L-homoserinate were initially charged in 30.0 ml of dichloromethane, and 1.27 g (3.0 mmol) of Dess-Martin periodinane and 474.7 mg (6.00 mmol) of pyridine were added. The mixture was stirred at RT overnight. After 4 h, the reaction was diluted with dichloromethane and the organic phase was washed in each case three times with 10% strength Na$_2$S$_2$O$_3$ solution, 10% strength citric acid solution and saturated sodium hydrogencarbonate solution. The organic phase was dried over magnesium sulfate and the solvent was evaporated under reduced pressure. This gave 565.7 mg (97% of theory) of the title compound.

¹H-NMR (400 MHz, DMSO-d₆): δ [ppm]=0.03 (s, 9H), 0.91 (m, 2H), 2.70-2.79 (m, 1H), 2.88 (dd, 1H), 3.63 (s, 3H), 4.04 (m, 2H), 4.55 (m, 1H), 7.54 (d, 1H), 9.60 (t, 1H).

Intermediate L95

N-[(Benzyloxy)carbonyl]-L-valyl-L-alanine

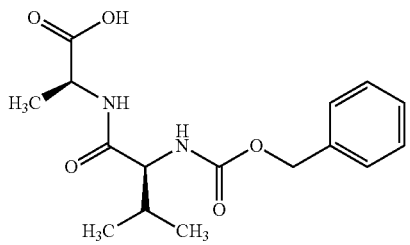 [SMILES: CC(C)[C@H](NC(=O)OCc1ccccc1)C(=O)N[C@@H](C)C(=O)O]

This intermediate was prepared proceeding from N-[(benzyloxy)carbonyl]-L-valine and tert-butyl L-alaninate hydrochloride by conventional methods of peptide chemistry.

LC-MS (Method 12): $R_t$=1.34 min; MS (ESIpos): m/z=323.16 (M+H)⁺.

Intermediate L103

N-(Pyridin-4-ylacetyl)-L-alanyl-L-alanyl-L-asparagine trifluoroacetate

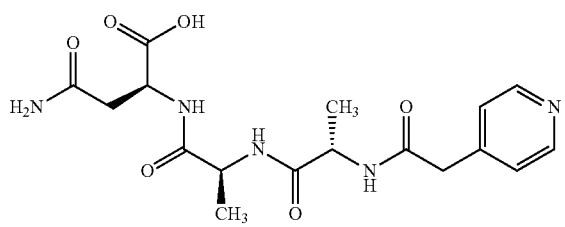

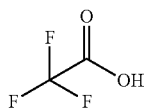

The title compound was prepared by conventional methods of peptide chemistry commencing with the coupling of 4-pyridineacetic acid with commercially available tert-butyl L-alanyl-L-alaninate in the presence of HATU and N,N-diisopropylethylamine, followed by deprotection with trifluoroacetic acid, coupling to tert-butyl L-asparaginate and subsequent deprotection of the carboxyl group with trifluoroacetic acid.

LC-MS (Method 1): $R_t$=0.15 min; MS (ESIpos): m/z=394 (M+H)+.

Intermediate L116

N-[(Benzyloxy)carbonyl]-L-alanyl-N-methyl-L-alanine

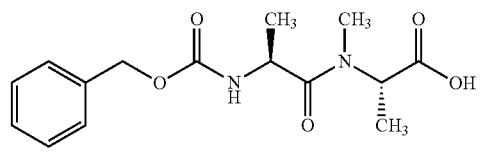 [SMILES: C[C@H](NC(=O)OCc1ccccc1)C(=O)N(C)[C@@H](C)C(=O)O]

The title compound was prepared from commercially available N-[(benzyloxy)carbonyl]-L-alanine by classical methods of peptide chemistry via coupling with tert-butyl N-methyl-L-alaninate hydrochloride salt in the presence of HATU and finally by removal of the tert-butyl ester protective group with TFA.

LC-MS (Method 1): $R_t$=0.68 min; MS (ESIpos): m/z=309 [M+H]⁺

Intermediate L117

N-[(Benzyloxy)carbonyl]-L-alanyl-N-methyl-L-alanyl-L-asparagine trifluoroacetic acid salt

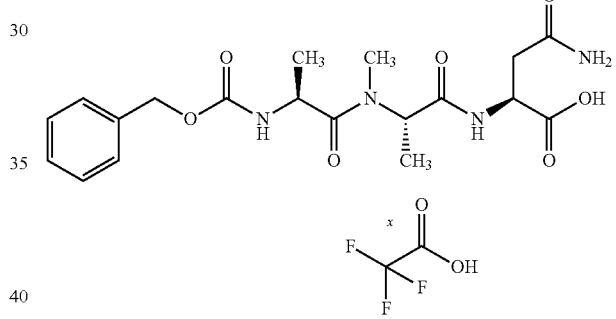

The title compound was prepared from commercially available 4-tert-butyl L-asparaginate by classical methods of peptide chemistry via coupling with N-[(benzyloxy)carbonyl]-L-alanyl-N-methyl-L-alanine (Intermediate L116) in the presence of HATU and finally by removal of the tert-butyl ester protective group with TFA.

LC-MS (Method 1): $R_t$=0.57 min; MS (ESIneg): m/z=421 [M−H]⁻

Intermediate L118

N-[(Benzyloxy)carbonyl]-L-alanyl-N-methyl-L-alanyl-L-alanine

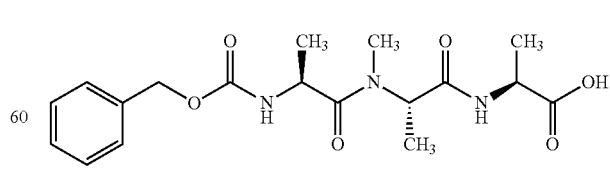

The title compound was prepared from commercially available tert-butyl L-alaninate hydrochloride salt by classical methods of peptide chemistry via coupling with N-[(benzyloxy)carbonyl]-L-alanyl-N-methyl-L-alanine (Intermediate L116) in the presence of HATU and finally by removal of the tert-butyl ester protective group with TFA.

LC-MS (Method 12): $R_t$=1.25 min; MS (ESIneg): m/z=378 [M−H]⁻

Intermediate L121

N-[(Benzyloxy)carbonyl]-L-alanyl-N-methyl-L-alanyl-L-leucine

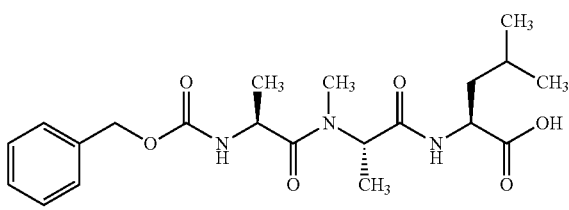 [SMILES: CC(C)C[C@H](NC(=O)[C@H](C)N(C)C(=O)[C@H](C)NC(=O)OCc1ccccc1)C(=O)O]

The title compound was prepared from commercially available tert-butyl L-leucinate hydrochloride salt by classical methods of peptide chemistry via coupling with N-[(benzyloxy)carbonyl]-L-alanyl-N-methyl-L-alanine (Intermediate L116) in the presence of HATU and finally by removal of the tert-butyl ester protective group with TFA.

LC-MS (Method 12): $R_t$=0.83 min; MS (ESIneg): m/z=420 [M−H]⁻

Intermediate L122

(5S,8S,11S)-11-(2-Amino-2-oxoethyl)-8-[2-(benzyloxy)-2-oxoethyl]-5-methyl-3,6,9-trioxo-1-phenyl-2-oxa-4,7,10-triazadodecan-12-oic acid

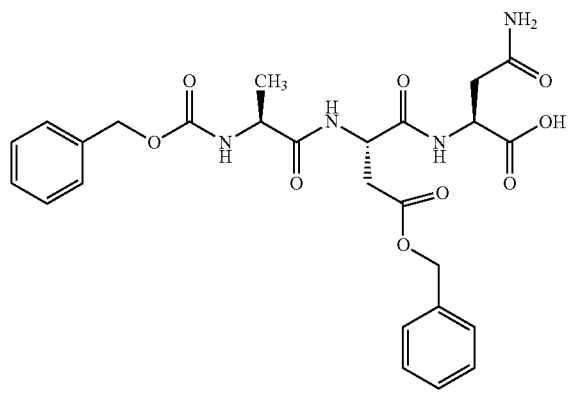 [SMILES: C[C@H](NC(=O)OCc1ccccc1)C(=O)N[C@@H](CC(=O)OCc1ccccc1)C(=O)N[C@@H](CC(N)=O)C(=O)O]

The title compound was prepared from commercially available 4-benzyl-1-tert-butyl-L-aspartate hydrochloride (1:1) by classical methods of peptide chemistry via initially coupling with 2,5-dioxopyrrolidin-1-yl-N-[(benzyloxy)carbonyl]-L-alaninate, then removing the tert-butyl ester protective group with TFA, then subsequent coupling with 4-tert-butyl L-asparaginate in the presence of HATU and finally by once more removing the tert-butyl ester protective group with TFA.

LC-MS (Method 1): $R_t$=0.76 min; MS (ESIpos): m/z=543 [M+H]⁺

Intermediate L138

1-Bromo-2-oxo-6,9,12,15-tetraoxa-3-azaoctadecan-18-oic acid

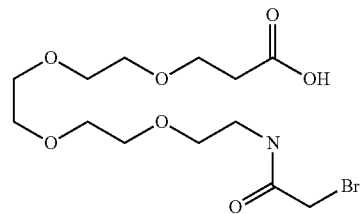 [SMILES: O=C(O)CCOCCOCCOCCOCCNC(=O)CBr]

The title compound was prepared by coupling of 1-amino-3,6,9,12-tetraoxapentadecan-15-oic acid with bromoacetic anhydride in the presence of N,N-diisopropylethylamine.

LC-MS (Method 5): $R_t$=1.05 min; MS (ESIpos): m/z=386 and 388 (M+H)⁺.

Intermediate Q1

N-[(2,5-Dioxo-2,5-dihydro-1H-pyrrol-1-yl)acetyl]-L-alanyl-N-methyl-L-alanyl-N-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1R)-1,3-dicarboxypropyl]amino}-3-oxopropyl)amino]-1-oxobutan-2-yl}-L-aspartamide

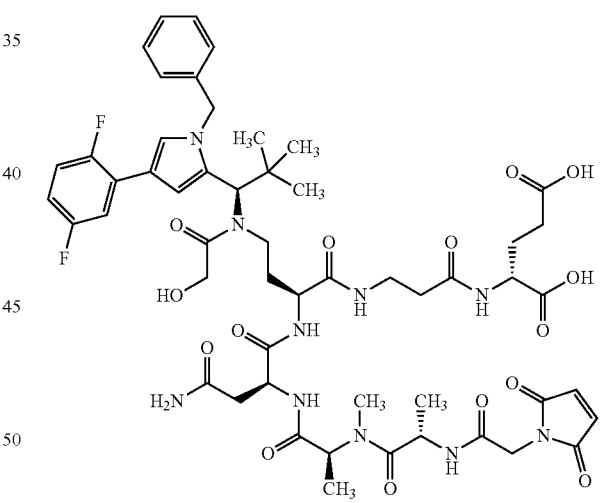

The title compound was prepared proceeding from compound C110D, first by coupling to Intermediate L117 in the presence of HATU and N,N-diisopropylethylamine. In the next step, all protecting groups were removed by hydrogenation over 10% palladium on activated carbon in DCM-methanol 1:1 under standard hydrogen pressure at RT for 1 hour and the deprotected intermediate was then converted to the title compound by reaction with 1-{2-[(2,5-dioxopyrrolidin-1-yl)oxy]-2-oxoethyl}-1H-pyrrole-2,5-dione in the presence of N,N-diisopropylethylamine.

LC-MS (Method 12): $R_t$=1.66 min; MS (ESIneg): m/z=1119 [M−H]⁻.

Intermediate Q2

N-{5-[(2,5-Dioxopyrrolidin-1-yl)oxy]-5-oxopentanoyl}-L-alanyl-N-methyl-L-alanyl-N$^1$-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1R)-1,3-dicarboxypropyl]amino}-3-oxopropyl)amino]-1-oxobutan-2-yl}-L-aspartamide

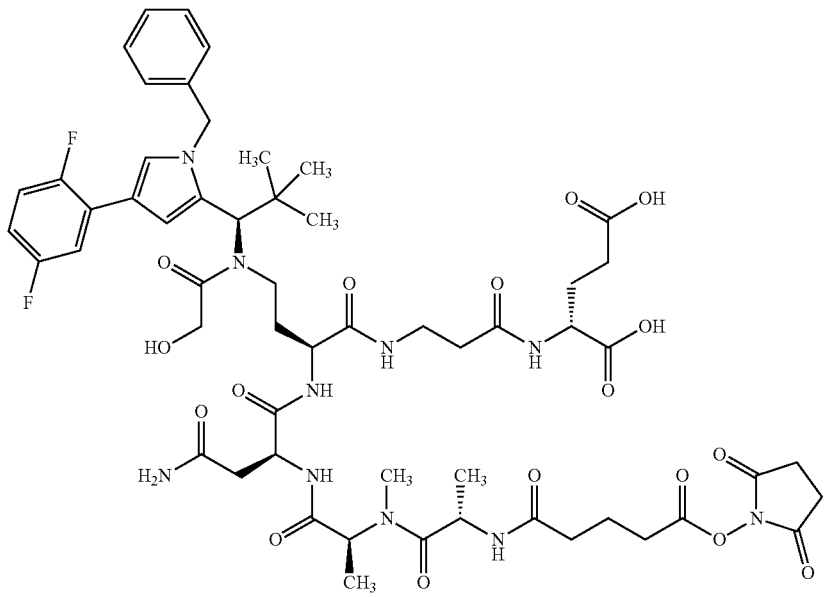 [SMILES: C[C@H](NC(=O)CCCC(=O)ON1C(=O)CCC1=O)C(=O)N(C)[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The title compound was prepared proceeding from compound C110D, first by coupling to Intermediate L117 in the presence of HATU and N,N-diisopropylethylamine. In the next step, all protecting groups were removed by hydrogenation over 10% palladium on activated carbon in DCM-methanol 1:1 under standard hydrogen pressure at RT for 1 hour and the deprotected intermediate was then converted to the title compound by reaction with 1,1'-[(1,5-dioxopentane-1,5-diyl)bis(oxy)]dipyrrolidine-2,5-dione in the presence of N,N-diisopropylethylamine.

LC-MS (Method 1): R$_t$=0.93 min; MS (ESIpos): m/z=1195 [M+H]$^+$.

Intermediate Q3

N-{5-[(2,5-Dioxopyrrolidin-1-yl)oxy]-5-oxopentanoyl}-L-alanyl-L-alanyl-N¹-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1R)-1,3-dicarboxypropyl]amino}-3-oxopropyl)amino]-1-oxobutan-2-yl}-L-aspartamide

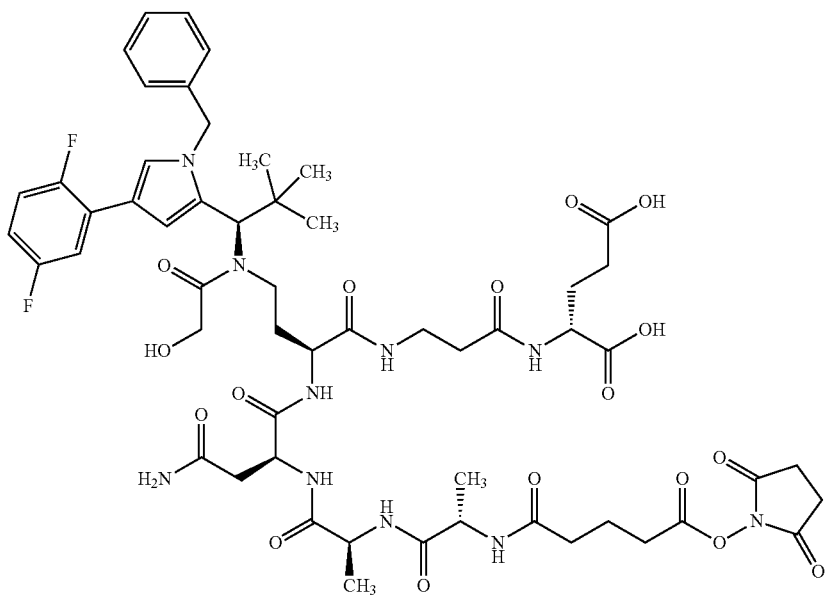 [SMILES: C[C@H](NC(=O)CCCC(=O)ON1C(=O)CCC1=O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The title compound was prepared from Compound C117 first by coupling to N-(tert-butoxycarbonyl)-L-alanyl-L-alanine in the presence of HATU and N,N-diisopropylethylamine. The intermediate was then taken up in trifluoroethanol and the tert-butoxycarbonyl-protected amine was released by stirring at 50° C. in the presence of zinc chloride. In the next step, all benzyl protecting groups were removed by hydrogenation over 10% palladium on activated carbon in DCM-methanol 1:1 under standard hydrogen pressure at RT for 1 hour and the deprotected intermediate was then converted to the title compound by reaction with 1,1'-[(1,5-dioxopentane-1,5-diyl)bis(oxy)]dipyrrolidine-2,5-dione in the presence of N,N-diisopropylethylamine.

LC-MS (Method 1): $R_f$=0.90 min; MS (ESIneg): m/z=1181 [M−H]⁻.

Intermediate Q4

N-[(2,5-Dioxo-2,5-dihydro-1H-pyrrol-1-yl)hexanoyl]-L-alanyl-N-methyl-L-alanyl-N$^1$-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1R)-1,3-dicarboxypropyl]amino}-3-oxopropyl)amino]-1-oxobutan-2-yl}-L-aspartamide

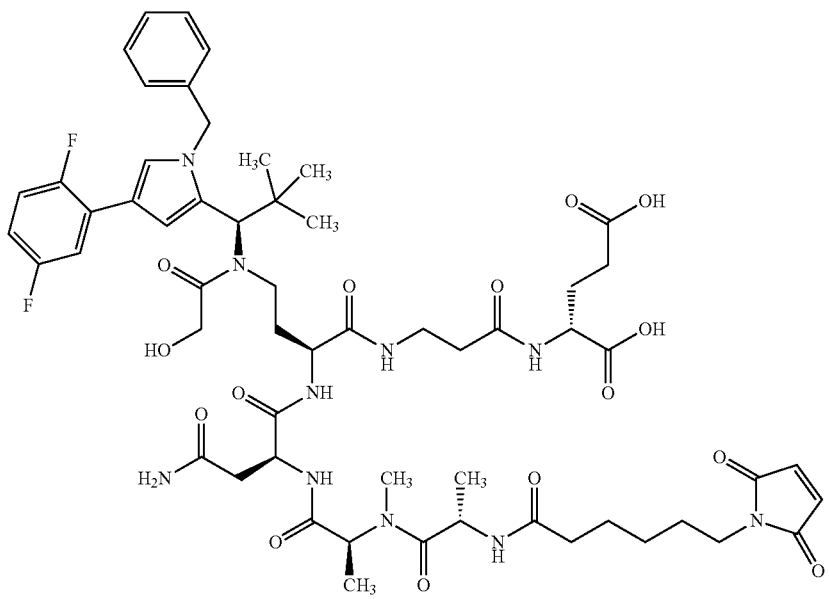 [SMILES: C[C@H](NC(=O)CCCCCN1C(=O)C=CC1=O)C(=O)N(C)[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The title compound was prepared proceeding from compound C110D, first by coupling to Intermediate L117 in the presence of HATU and N,N-diisopropylethylamine. In the next step, all protecting groups were removed by hydrogenation over 10% palladium on activated carbon in DCM-methanol 1:1 under standard hydrogen pressure at RT for 1 hour and the deprotected intermediate was then converted to the title compound by reaction with 1-{6-[(2,5-dioxopyrrolidin-1-yl)oxy]-6-oxohexyl}-1H-pyrrole-2,5-dione in the presence of N,N-diisopropylethylamine.

LC-MS (Method 1): $R_t$=3.2 min; MS (ESIpos): m/z=1177 [M+H]$^+$.

Intermediate Q5

N-{5-[(2,5-Dioxopyrrolidin-1-yl)oxy]-5-oxopentanoyl}-L-alanyl-N-methyl-L-alanyl-N-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1R)-1,3-dicarboxypropyl]amino}-3-oxopropyl)amino]-1-oxobutan-2-yl}-L-alaninamide

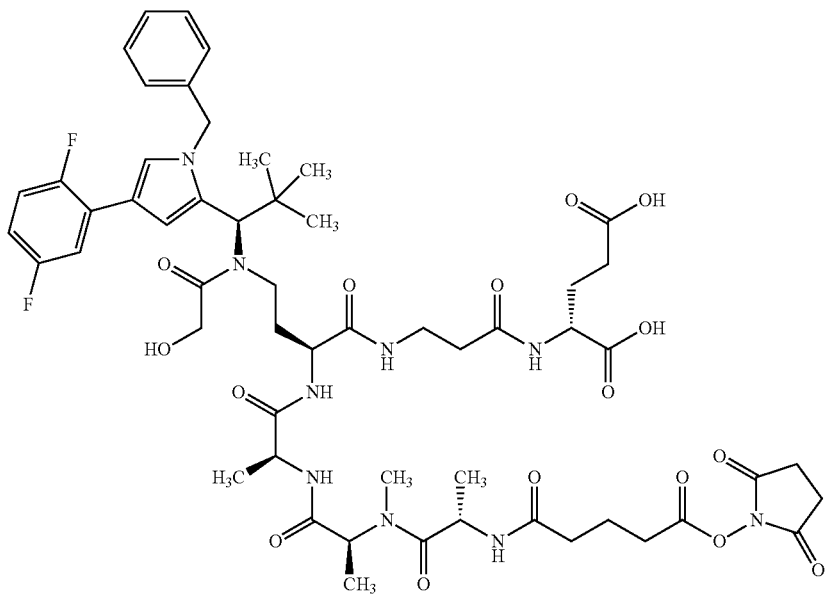 [SMILES: C[C@H](NC(=O)[C@H](C)N(C)C(=O)[C@H](C)NC(=O)CCCC(=O)ON1C(=O)CCC1=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The title compound was prepared proceeding from compound C110D, first by coupling to Intermediate L118 in the presence of HATU and N,N-diisopropylethylamine. In the next step, all protecting groups were removed by hydrogenation over 10% palladium on activated carbon in DCM-methanol 1:1 under standard hydrogen pressure at RT for 1 hour and the deprotected intermediate was then converted to the title compound by reaction with 1,1'-[(1,5-dioxopentane-1,5-diyl)bis(oxy)]dipyrrolidine-2,5-dione in the presence of N,N-diisopropylethylamine.

LC-MS (Method 1): $R_t$=0.96 min; MS (ESIpos): m/z=1152 [M+H]$^+$.

Intermediate Q6

N-{(2S)-4-[{(1R)-1-[1-Benzyl-4-(2,5-difluorophenyl)-1H-pyrrol-2-yl]-2,2-dimethylpropyl}(glycoloyl)amino]-2-[(N-{5-[(2,5-dioxopyrrolidin-1-yl)oxy]-5-oxopentanoyl}-L-valyl-L-alanyl)amino]butanoyl}-beta-alanyl-D-glutamic acid

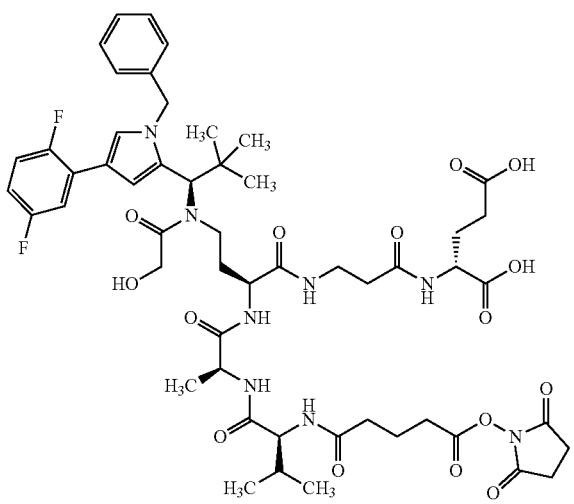 [SMILES: CC(C)[C@H](NC(=O)CCCC(=O)ON1C(=O)CCC1=O)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The title compound was prepared proceeding from compound C110D, first by coupling to Intermediate L95 in the presence of HATU and N,N-diisopropylethylamine. In the next step, all protecting groups were removed by hydrogenation over 10% palladium on activated carbon in DCM-methanol 1:1 under standard hydrogen pressure at RT for 1 hour and the deprotected intermediate was then converted to the title compound by reaction with 1,1'-[(1,5-dioxopentane-1,5-diyl)bis(oxy)]dipyrrolidine-2,5-dione in the presence of N,N-diisopropylethylamine.

LC-MS (Method 1): $R_t$=0.98 min; MS (ESIpos): m/z=1095 [M+H]$^+$.

Intermediate Q7

N-[(2S)-4-[{(1R)-1-[1-Benzyl-4-(2,5-difluorophenyl)-1H-pyrrol-2-yl]-2,2-dimethylpropyl}(glycoloyl)amino]-2-({N-[(2,5-dioxo-2,5-dihydro-1H-pyrrol-1-yl)acetyl]-L-valyl-L-alanyl}amino)butanoyl]-beta-alanyl-D-glutamic acid

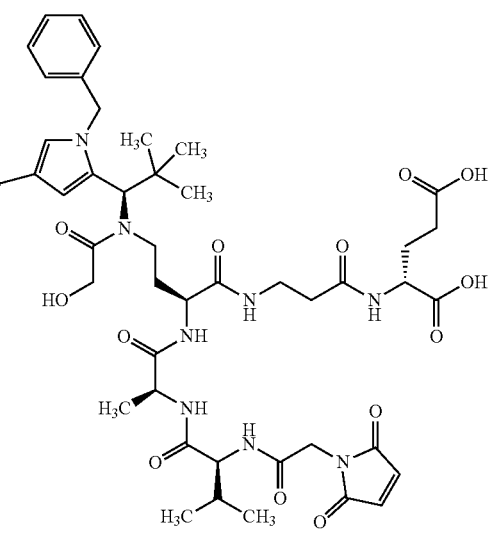

The title compound was prepared proceeding from compound C110D, first by coupling to Intermediate L95 in the presence of HATU and N,N-diisopropylethylamine. In the next step, all protecting groups were removed by hydrogenation over 10% palladium on activated carbon in DCM-methanol 1:1 under standard hydrogen pressure at RT for 1 hour and the deprotected intermediate was then converted to the title compound by reaction with 1-{2-[(2,5-dioxopyrrolidin-1-yl)oxy]-2-oxoethyl}-1H-pyrrole-2,5-dione in the presence of N,N-diisopropylethylamine.

LC-MS (Method 1): $R_t$=0.98 min; MS (ESIpos): m/z=1021 [M+H]$^+$.

Intermediate Q8

N-{5-[(2,5-Dioxopyrrolidin-1-yl)oxy]-5-oxopentanoyl}-L-alanyl-N-methyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1R)-1,3-dicarboxypropyl]amino}-3-oxopropyl)amino]-1-oxobutan-2-yl}-L-leucinamide

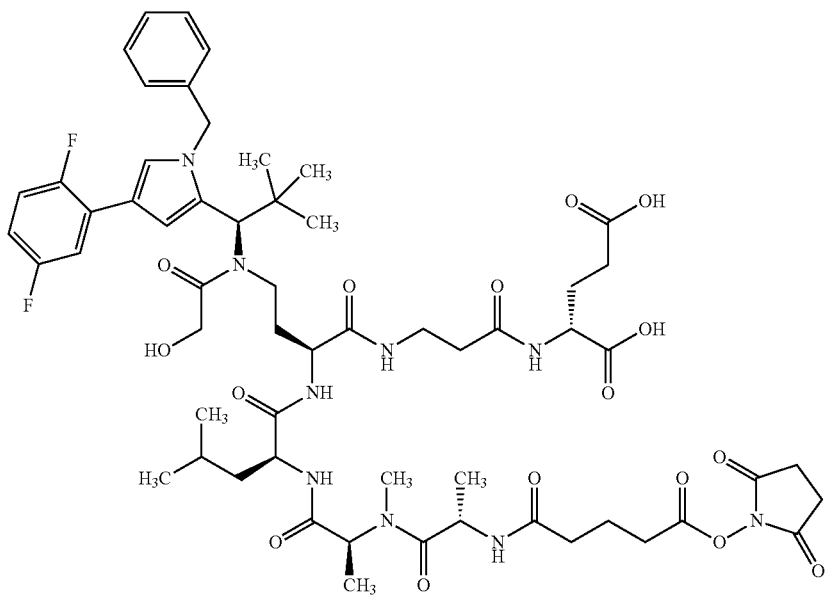 [SMILES: CC(C)C[C@H](NC(=O)[C@H](C)N(C)C(=O)[C@H](C)NC(=O)CCCC(=O)ON1C(=O)CCC1=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The title compound was prepared proceeding from compound C110D, first by coupling to Intermediate L121 in the presence of HATU and N,N-diisopropylethylamine. In the next step, all protecting groups were removed by hydrogenation over 10% palladium on activated carbon in ethanol under standard hydrogen pressure at RT for 1 hour and the deprotected intermediate was then converted to the title compound by reaction with 1,1'-[(1,5-dioxopentane-1,5-diyl)bis(oxy)]dipyrrolidine-2,5-dione in the presence of N,N-diisopropylethylamine.

LC-MS (Method 1): $R_t$=1.02 min; MS (ESIpos): m/z=1194 [M+H]$^+$.

Intermediate Q9

N-{5-[(2,5-Dioxopyrrolidin-1-yl)oxy]-5-oxopentanoyl}-L-alanyl-N-methyl-L-alpha-aspartyl-N$^1$-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1R)-1,3-dicarboxypropyl]amino}-3-oxopropyl)amino]-1-oxobutan-2-yl}-L-aspartamide

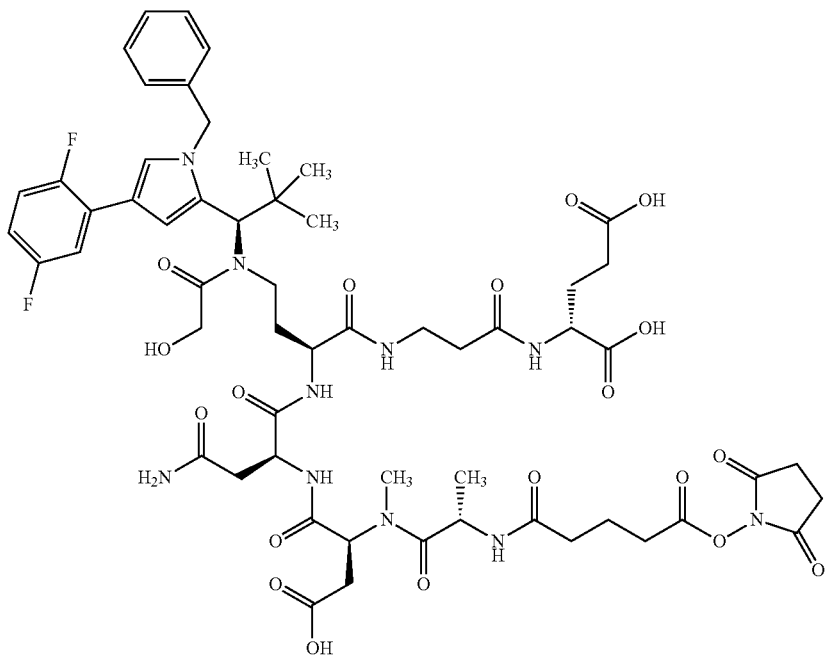 [SMILES: C[C@H](NC(=O)CCCC(=O)ON1C(=O)CCC1=O)C(=O)N(C)[C@@H](CC(=O)O)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The title compound was prepared proceeding from compound C110D, first by coupling to Intermediate L122 in the presence of HATU and N,N-diisopropylethylamine. In the next step, all protecting groups were removed by hydrogenation over 10% palladium on activated carbon in methanol under standard hydrogen pressure at RT for 1 hour and the deprotected intermediate was then converted to the title compound by reaction with 3 equiv. of 1,1'-[(1,5-dioxopentane-1,5-diyl)bis(oxy)]dipyrrolidine-2,5-dione in the presence of N,N-diisopropylethylamine.

LC-MS (Method 1): $R_1$=0.89 min; MS (ESIpos): m/z=1225 [M+H]$^+$.

Intermediate Q10

N-(Bromoacetyl)-L-alanyl-N-methyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1R)-1,3-dicarboxypropyl]amino}-3-oxopropyl)amino]-1-oxobutan-2-yl}-L-aspartamide

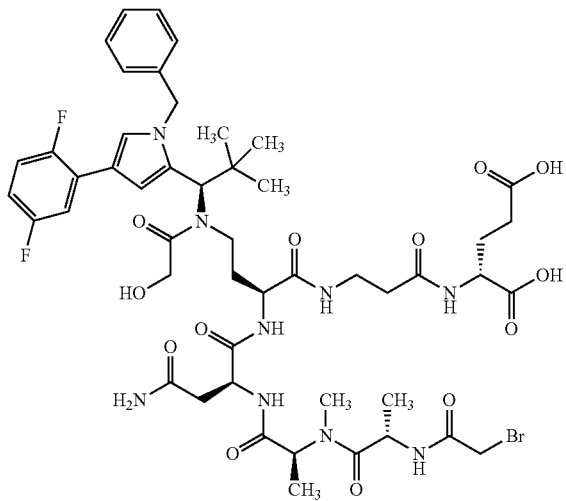 [SMILES: C[C@H](NC(=O)CBr)C(=O)N(C)[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The title compound was prepared proceeding from compound C110D, first by coupling to Intermediate L117 in the presence of HATU and N,N-diisopropylethylamine. In the next step, all protecting groups were removed by hydrogenation over 10% palladium on activated carbon in DCM-methanol 1:1 under standard hydrogen pressure at RT for 1 hour and the deprotected intermediate was then converted to the title compound by reaction with bromoacetic anhydride in the presence of 3 equiv. of N,N-diisopropylethylamine.

LC-MS (Method 1): $R_t$=0.95 min; MS (ESIpos): m/z=1104 and 1106 $[M+H]^+$.

Intermediate Q11

N-(18-Bromo-17-oxo-4,7,10,13-tetraoxa-16-azaoctadecan-1-oyl)-L-alanyl-N-methyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1R)-1,3-dicarboxypropyl]amino}-3-oxopropyl)amino]-1-oxobutan-2-yl}-L-aspartamide

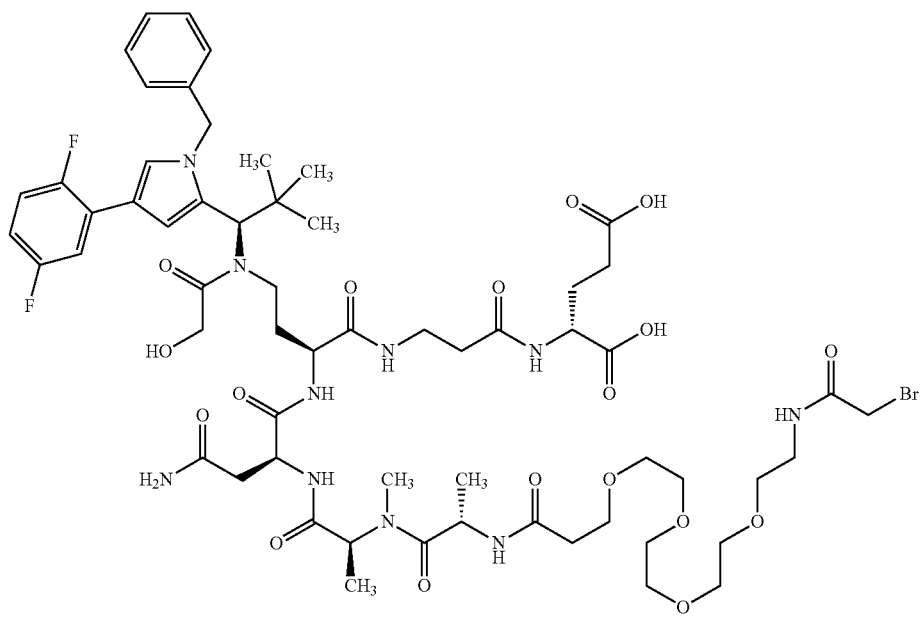 [SMILES: C[C@H](NC(=O)CCOCCOCCOCCOCCNC(=O)CBr)C(=O)N(C)[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The synthesis of the title compound was carried out by initially coupling Intermediate C111 with intermediate L117 in DMF in the presence of 1.5 equiv. HATU and 3 equiv. of N,N-diisopropylethylamine. Subsequently, the Z protective group was removed by a 2-hour hydrogenation over 10% palladium on activated carbon in ethanol under hydrogen standard pressure at RT. The deprotected intermediate was then reacted with Intermediate L138 in DMF in the presence of 1.5 equiv. of HATU and 3 equiv. of N,N-diisopropylethylamine. In the last step, cleavage of the tert-butyl ester groups by 2 h of stirring at 50° C. with 8 equivalents of zinc chloride in trifluoroethanol gave the title compound.

LC-MS (Method 8): $R_t$=4.06 min; MS (ESI-pos): m/z=1353 [M+H]$^+$.

B: Preparation of Antibody-Drug Conjugates (ADC)

B-1. General Method for Generation of Antibodies

The protein sequence (amino acid sequence) of the antibodies used, for example TPP-981, TPP-1015, TPP-6013, TPP-7006, TPP-7007, TPP-8382, TPP-8987, TPP-8988, TPP-9476, TPP-9574 and TPP-9580, was transformed into a DNA sequence that encodes the corresponding protein by a method known to those skilled in the art and inserted into an expression vector suitable for transient mammalian cell culture (as described by Tom et al., Chapter 12 in Methods Express: Expression Systems, edited by Michael R. Dyson and Yves Durocher, Scion Publishing Ltd, 2007).

B-2. General Method for Expression of Antibodies in Mammalian Cells

The antibodies, for example TPP-981, TPP-1015, TPP-6013, TPP-7006, TPP-7007, TPP-8382, TPP-8987, TPP-8988, TPP-9476, TPP-9574 and TPP-9580, were produced in transient mammalian cell cultures, as described by Tom et al., Chapter 12 in Methods Express: Expression Systems, edited by Michael R. Dyson and Yves Durocher, Scion Publishing Ltd, 2007.

B-3. General Method for Purification of Antibodies from Cell Supernatants

The antibodies, for example TPP-981, TPP-1015, TPP-6013, TPP-7006, TPP-7007, TPP-8382, TPP-8987, TPP-8988, TPP-9476, TPP-9574 and TPP-9580, were obtained from the cell culture supernatants. The cell supernatants were clarified by centrifugation of cells. The cell supernatant was then purified by affinity chromatography on a MabSelect Sure (GE Healthcare) chromatography column. To this end, the column was equilibrated in DPBS pH 7.4 (Sigma/Aldrich), the cell supernatant was applied and the column was washed with about 10 column volumes of DPBS pH 7.4+500 mM sodium chloride. The antibodies were eluted in 50 mM sodium acetate pH 3.5+500 mM sodium chloride and then purified further by gel filtration chromatography on a Superdex 200 column (GE Healthcare) in DPBS pH 7.4.

Commercially available antibodies were purified by standard chromatography methods (protein A chromatography, preparative gel filtration chromatography (SEC—size exclusion chromatography)) from the commercial products.

B-4. General Method for Coupling to Cysteine Side Chains

The following antibodies were used in the coupling reactions:

Examples a: TPP-981 cetuximab (anti-EGFR AK)
Examples c: TPP-6013 (anti-CD123 AK)
TPP-8987 (anti-CD123 AK)
TPP-8988 (anti-CD123 AK)
TPP-9476 (anti-CD123 AK)
Examples h: TPP-8382 (anti-B7H3 AK)
Examples e: TPP-1015 (anti-Her2 AK)
Examples k: TPP-7006 (anti-TWEAKR AK)
TPP-7007 (anti-TWEAKR AK)
Examples x: TPP-9574 (anti-CXCR5 AK)
TPP-9580 (anti-CXCR5 AK)

The coupling reactions were usually carried out under argon.

Between 2 and 5 equivalents of tris(2-carboxyethyl)phosphine hydrochloride (TCEP), dissolved in PBS buffer, were added to a solution of the appropriate antibody in PBS buffer in the concentration range between 1 mg/ml and 20 mg/ml, preferably in the range of about 10 mg/ml to 15 mg/ml, and the mixture was stirred at RT for 1 h. For this purpose, the solution of the respective antibody used can be employed at the concentrations stated in the working examples, or it may optionally also be diluted with PBS buffer to about half of the stated starting concentration in order to get into the preferred concentration range. Subsequently, depending on the intended loading, from 2 to 12 equivalents, preferably about 5-10 equivalents of the maleimide precursor compound or halide precursor compound to be coupled were added as a solution in DMSO. Here, the amount of DMSO should not exceed 10% of the total volume. The mixture was stirred in the case of maleimide precursors for 60-240 min at RT and in the case of halide precursors between 8 and 24 h at RT and then applied to PBS-equilibrated PD 10 columns (Sephadex® G-25, GE Healthcare) and eluted with PBS buffer. Generally, unless indicated otherwise, 5 mg of the antibody in question in PBS buffer were used for the reduction and the subsequent coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution. The respective protein concentrations, stated in the working examples, of the ADC solutions were determined. Furthermore, antibody loading (drug/mAb ratio) was determined using the methods described under B-6.

Depending on the linker, the ADCs shown in the examples may also be present to a lesser or higher degree in the form of the hydrolysed open-chain succinamides linked to the antibodies.

Particularly the KSP-I-ADCs linked via the linker substructure

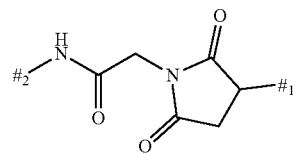

to thiol groups of the antibodies can optionally also be prepared selectively by rebuffering after the coupling and stirring at pH 8 for about 20-24 h according to Scheme 28 in the ADCs linked via open-chain succinamides.

1 represents the sulfur bridge to the antibody, and #2 the point of attachment to the modified KSP inhibitor Such ADCs where the linker is attached to the antibodies through hydrolysed open-chain succinamides can optionally also be prepared selectively by the small scale and large scale couplings shown here by way of example:

Between 2 and 7 equivalents of tris(2-carboxyethyl)phosphine hydrochloride (TCEP), dissolved in PBS buffer, were added to a solution of 2-5 mg of the appropriate antibody in PBS buffer in the concentration range between 1 mg/ml and 20 mg/ml, preferably in the range of about 5 mg/ml to 15 mg/ml, and the mixture was stirred at RT for 30 min to 1 h. Subsequently, depending on the intended loading, from 2 to 20 equivalents, preferably about 5-10 equivalents of the maleimide precursor compound to be coupled were added as a solution in DMSO. To achieve higher DARs, it is also possible to use 15-20 equivalents. Here, the amount of DMSO should not exceed 10% of the total volume. The mixture was stirred at RT for 60-240 min. The eluate was diluted with PBS buffer pH 8 to a concentration of 1-5 mg/ml and then passed through a PD 10 column (Sephadex® G-25, GE Healthcare) equilibrated with PBS buffer pH 8, and eluted with PBS buffer pH 8. The eluate was stirred at RT under argon overnight. Subsequently, the solution was concentrated by ultracentrifugation and rediluted with PBS buffer (pH 7.2).

Medium-Scale Coupling:

Under argon, a solution of 2-7 equivalents, preferably 3 equivalents, of TCEP in PBS buffer (c~0.2-0.8 mg/ml, preferably 0.5 mg/ml) was added to 20-200 mg of the antibody in question in PBS buffer (c~5-15 mg/ml). The mixture was stirred at RT for 30 min, and then 2-20, preferably 5-10, equivalents of a maleimide precursor compound dissolved in DMSO were added. To achieve higher DARs, it is also possible to use 15-20 equivalents. After stirring at RT for a further 1.5 h-2 h, the mixture was diluted with PBS buffer which had been adjusted to pH 8 beforehand. This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a concentration of 2-7 mg/ml. This solution was stirred at RT under argon overnight. If required, the solution was then rebuffered to pH 7.2. The ADC solution was concentrated by ultracentrifugation, rediluted with PBS buffer (pH 7.2) and then optionally concentrated again to a concentration of about 10 mg/ml.

In the structural formulae shown, $AK_1$ can have the meaning

Examples a: TPP-981 cetuximab (partially reduced)-S§$^1$

Examples c: TPP-6013 (anti-CD123 AK) (partially reduced)-S§$^1$

TPP-8987 (anti-CD123 AK) (partially reduced)-S§$^1$

TPP-8988 (anti-CD123 AK) (partially reduced)-S§$^1$

TPP-9476 (anti-CD123 AK) (partially reduced)-S§$^1$

Examples e: TPP-1015 (anti-Her2 AK) (partially reduced)-S§$^1$

Examples h: TPP-8382 (anti-B7H3 AK) (partially reduced)-S§$^1$

Examples k: TPP-7006 (anti-TWEAKR) (partially reduced)-S§$^1$

TPP-7007 (anti-TWEAKR) (partially reduced)-S§$^1$

Examples x: TPP-9574 (anti-CXCR5 AK) (partially reduced)-S§$^1$

TPP-9580 (anti-CXCR5 AK) (partially reduced)-S§$^1$ wherein

§$^1$ represents the linkage to the succinimide group or to any isomeric hydrolysed open-chain succinamides or the alkylene radical resulting therefrom, and S represents the sulfur atom of a cysteine residue of the partially reduced antibody.

B-5. General Process for Coupling to Lysine Side Chains

The following antibodies were used for the coupling reactions:

Examples a: TPP-981 cetuximab (anti-EGFR AK)

Examples c: TPP-6013 (anti-CD123 AK)

TPP-8987 (anti-CD123 AK)

TPP-8988 (anti-CD123 AK)

TPP-9476 (anti-CD123 AK)

Examples e: TPP-1015 (anti-Her2 AK)

Examples k: TPP-7006 (anti-TWEAKR AK)

TPP-7007 (anti-TWEAKR AK)

Examples x: TPP-9574 (anti-CXCR5 AK)

TPP-9580 (anti-CXCR5 AK)

The coupling reactions were usually carried out under argon.

From 2 to 8 equivalents of the precursor compound to be coupled were added as a solution in DMSO to a solution of the antibody in question in PBS buffer in a concentration range between 1 mg/ml and 20 mg/ml, preferably about 10 mg/ml, depending on the intended loading. After stirring at RT for 30 min to 6 h, the same amount of precursor compound in DMSO was added again. Here, the amount of DMSO should not exceed 10% of the total volume. After stirring at RT for a further 30 min to 6 h, the mixture was applied to PD 10 columns (Sephadex® G-25, GE Healthcare) equilibrated with PBS and eluted with PBS buffer. Purification on the PD10 column thus in each case afforded solutions of the respective ADCs in PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution.

The respective protein concentrations, stated in the working examples, of the ADC solutions were determined. Furthermore, antibody loading (drug/mAb ratio) was determined using the methods described under B-6.

In the structural formulae shown, $AK_2$ has the meaning

Examples a: TPP-981 cetuximab (anti-EGFR AK)-NH§$^2$

Examples c: TPP-6013 (anti-CD123 AK)-NH§$^2$

TPP-8987 (anti-CD123 AK)-NH§$^2$

TPP-8988 (anti-CD123 AK)-NH§$^2$

TPP-9476 (anti-CD123 AK)-NH§$^2$

Examples e: TPP-1015 (anti-Her2 AK)-NH§$^2$

Examples k: TPP-7006 (anti-TWEAKR AK)-NH§$^2$

TPP-7007 (anti-TWEAKR AK)-NH§$^2$

Examples x: TPP-9574 (anti-CXCR5 AK)-NH§$^2$

TPP-9580 (anti-CXCR5 AK)-NH§$^2$ wherein

§$^2$ represents the linkage to the carbonyl group and

NH represents the side-chain amino group of a lysine residue of the antibody.

Further Purification and Characterization of the Conjugates According to the Invention After the reaction, in some instances the reaction mixture was concentrated, for example by ultrafiltration, and then desalted and purified by chromatography, for example using a Sephadex® G-25 column. Elution was carried out, for example, with phosphate-buffered saline (PBS). The solution was then sterile filtered and frozen. Alternatively, the conjugate can be lyophilized.

B-6. Determination of the Antibody, the Toxophore Loading and the Proportion of Open Cysteine Adducts For protein identification in addition to molecular weight determination after deglycosylation and/or denaturing, a tryptic digestion was carried out which, after denaturing, reduction and derivatization, confirms the identity of the protein via the tryptic peptides found.

toxophore loading (in the tables referred to as DAR, drug-to-antibody ratio) of the PBS buffer solutions obtained of the conjugates described in the working examples was determined as follows:

Determination of toxophore loading of lysine-linked ADCs was carried out by mass spectrometry determination of the molecular weights of the individual conjugate species. Here, the antibody conjugates were first deglycosylated with PNGaseF, and the sample was acidified and, after HPLC separation/desalting, analysed by mass spectrometry using ESI-MicroTof$_a$(Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species. For this purpose, the sum total of the integration results for all species weighted by the toxophore count was divided by the sum total of the simply weighted integration results for all species.

The toxophore loading of cysteine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 μl) were added to the ADC solution (1 mg/ml, 50 μl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL1912-3802) (2.1×150 mm, 8 μm particle size, 1000 Å) was used at a flow rate of 1 ml/min with the following gradient: 0 min, 25% B; 3 min, 25% B; 28 min, 50% B. Eluent A consisted of 0.05% trifluoroacetic acid (TFA) in water, eluent B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the light chain with one toxophore (L1) and the heavy chains with one, two and three toxophores (H1, H2, H3).

Average loading of the antibody with toxophores (referred to as DAR, drug-to-antibody ratio) was calculated from the peak areas determined by integration as double the sum of HC load and LC load, where LC load is calculated from the sum of the toxophore number-average weighed integration results of all LC peaks divided by the sum of the singly weighed integration results of all LC peaks, and where the HC load is calculated from the sum of the toxophore number-average weighed integration results of all HC peaks divided by the sum of the singly weighed integration results of all HC peaks. In individual cases, it was be possible that, owing to co-elution of some peaks, it was not possible to determine toxophore loading accurately.

In the cases where light and heavy chains could not be separated sufficiently by HPLC, determination of toxophore loading of cysteine-linked conjugates was carried out by mass spectrometry determination of the molecular weights of the individual conjugate species at light and heavy chain.

For this purpose, guanidinium hydrochloride (GuHCl) (28.6 mg) and a solution of DL-dithiothreitol (DTT) (500 mM, 3 μl) were added to the ADC solution (1 mg/ml, 50 μl). The mixture was incubated for one hour at 55° C. and analysed by mass spectrometry after online desalting using ESI-MicroTofQ (Bruker Daltonik).

For the DAR (drug-to-antibody ratio) determination, all spectra were added over the signal in the TIC (Total Ion Chromatogram), and the molecular weight of the different conjugate species at light and heavy chain was calculated based on MaxEnt deconvolution. The average loading of the antibody with toxophores was determined from the peak areas determined by integration as twice the sum total of the HC loading and the LC loading. In this context, the LC loading is calculated from the sum total of the integration results for all LC peaks weighted by the toxophore count, divided by the sum total of the simply weighted integration results for all LC peaks, and the HC loading from the sum total of the integration results for all HC peaks weighted by the toxophore count, divided by the sum total of the simply weighted integration results for all HC peaks.

In the case of the open constructs, to determine the proportion of the open cysteine adduct, the molecular weight area ratio of closed to open cysteine adduct (molecular weight delta 18 daltons) of all singly conjugated light and heavy chain variants was determined. The mean of all variants yielded the proportion of the open cysteine adduct.

B-7. Verification of the Antigen Binding of the ADCs

The capability of the binder of binding to the target molecule was checked after coupling had taken place. The person skilled in the art is familiar with various methods which can be used for this purpose; for example, the affinity of the conjugate can be checked using ELISA technology or surface plasmon resonance analysis (BIAcore™ measurement). The conjugate concentration can be measured by the person skilled in the art using customary methods, for example for antibody conjugates by protein determination. (see also Doronina et al.; Nature Biotechnol. 2003; 21:778-784 and Polson et al., Blood 2007; 1102:616-623).

Working Examples of Metabolites

Example M1

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamic acid

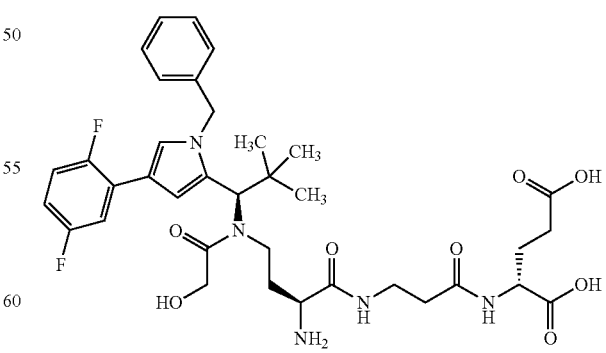

Intermediate C110D was converted into the title compound by a 1-hour hydrogenation over 10% palladium on activated carbon in ethanol under hydrogen standard pressure at RT.

LC-MS (Method 1): $R_t$=1.78 min; MS (ESIpos): m/z=714 [M+H]$^+$.

The ADCs shown below in an exemplary manner are capable of releasing the preferred metabolite M1, which has preferred pharmacological properties.

Working Examples ADCs

The ADCs shown in the structural formulae of the working examples, which were coupled to the cysteine side chains of the antibodies via maleimide radicals, are, depending on the linker and the coupling procedure, mainly present in the ring-opened or ring-closed forms shown in each case. However, the preparation may comprise a small proportion of the respective other form.

The coupling reactions were carried out under argon. All the larger batches for in vivo tests were sterile-filtered at the end of the preparation.

Examples 1

Exemplary Procedure A:

Under argon, a solution of 0.029 mg of TCEP in 0.05 ml of PBS buffer was added to 5 mg of the antibody in question in 0.5 ml of PBS (c=10 mg/ml). The mixture was stirred at RT for 30 min, and then 0.26 mg (0.00023 mmol) of Intermediate Q1 dissolved in 50 µl of DMSO was added. After stirring at RT for a further 90 min, the mixture was diluted to a volume of 2.5 ml with PBS buffer which had been adjusted to pH 8 beforehand and then passed through a PD 10 column (Sephadex® G-25, GE Healthcare) equilibrated with PBS buffer pH 8, and eluted with PBS buffer pH 8. The eluate was stirred at RT under argon overnight. This was followed by concentration by ultracentrifugation and redilution with PBS buffer (pH 7.2).

Exemplary Procedure B:

Under argon, a solution of 0.172 mg of TCEP in 0.3 ml of PBS buffer was added to 30 mg of the antibody in question in 3 ml of PBS (c=10 mg/ml). The mixture was stirred at RT for 30 min, and then 1.57 mg (0.0014 mmol) of Intermediate Q1 dissolved in 300 µl of DMSO was added. After stirring at RT for a further 90 min, the mixture was diluted to a volume of 5 ml with PBS buffer which had been adjusted to pH 8 beforehand and then passed through a PD 10 column (Sephadex® G-25, GE Healthcare) equilibrated with PBS buffer pH 8, and eluted with PBS buffer pH 8. The eluate was diluted with PBS buffer pH 8 to a volume of 7.5 ml and stirred at RT under argon overnight. This solution was then applied to a PD 10 column (Sephadex® G-25, GE Healthcare) which had been equilibrated with PBS buffer pH 7.2 and was eluted with PBS buffer pH 7.2. The eluate was then concentrated by ultracentrifugation, rediluted with PBS buffer (pH 7.2) and reconcentrated and sterile-filtered again.

The following ADCs were prepared analogously to these procedures and characterized as indicated in the table:

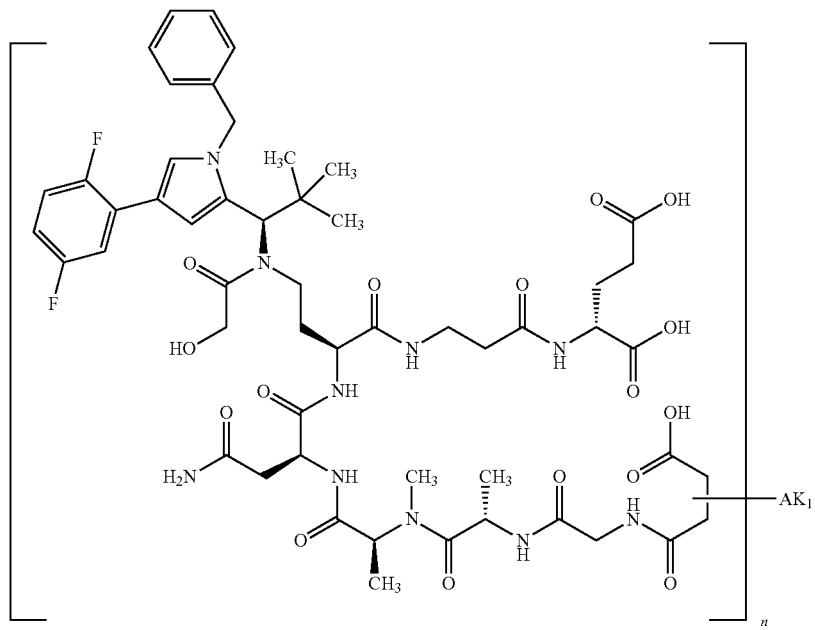

| Example | Antibody Target | TPP- | Procedure | C [mg/ml] | DAR |
|---|---|---|---|---|---|
| 1a-981 | EGFR | 981 | A | 1.85 | 2.5 |
| 1c-6013 | CD123 | 6013 | A | 2.0 | 2.4 |
| 1c-9476 | CD123 | 9476 | A | 1.96 | 3.1 |
| 1e-1015 | HER2 | 1015 | A | 1.75 | 3.3 |
| 1h-8382 | B7H3 | 8382 | B | 11.01 | 3.5 |
| 1k-7006 | TWEAKR | 7006 | A | 1.8 | 2.9 |
| 1k-7007 | TWEAKR | 7007 | B | 7.84 | 3.3 |
| 1x-9574 | CXCR5 | 9574 | A | 1.26 | 2.9 |

Examples 2

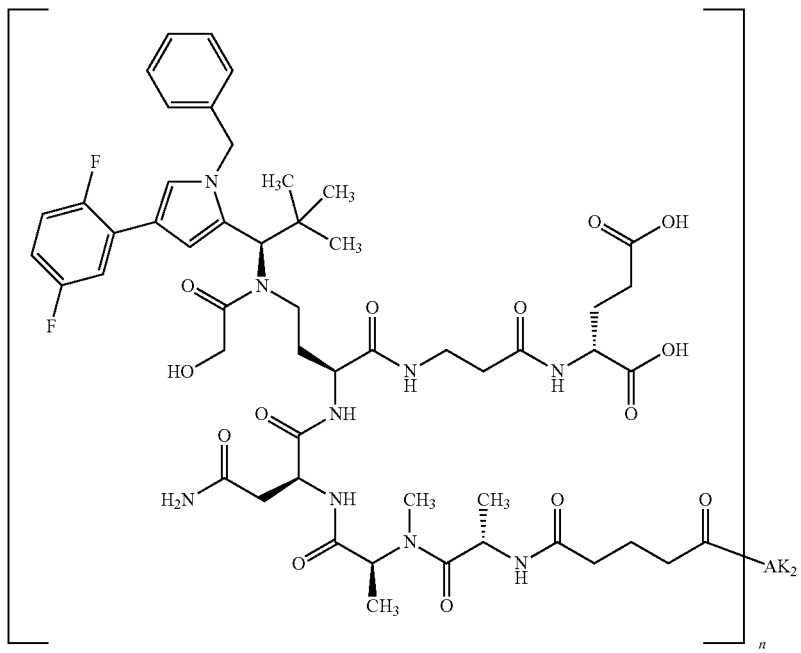

Exemplary Procedure A:

Under argon, 5 eq (0.2 mg) of Intermediate Q2 dissolved in 50 µl of DMSO were added to 5 mg of the antibody in question in 0.5 ml of PBS (c=10 mg/ml). After stirring at RT for 1 h, the same amount again was added and the mixture was stirred at RT for a further hour.

The reaction mixture was subsequently diluted to 2.5 ml with PBS buffer (pH 7.2), purified on a Sephadex column, then concentrated by ultracentrifugation and rediluted with PBS (pH 7.2).

Exemplary Procedure B:

Under argon, 4 eq (1 mg) of Intermediate Q2 dissolved in 50 µl of DMSO were added to 30 mg of the antibody in question in 3 ml of PBS buffer (pH 7.2) (c=10 mg/ml). After stirring at RT for 1 h, the same amount again was added and the mixture was stirred at RT for a further hour. Then the mixture was diluted to 5 ml with PBS buffer (pH 7.2), purified on a Sephadex column, then concentrated by ultracentrifugation, rediluted with PBS (pH 7.2) and reconcentrated and sterile-filtered again.

Exemplary Procedure C:

Under argon, 2.5 eq (1 mg) of Intermediate Q2 dissolved in 250 µl of DMSO were added to 50 mg of the antibody in question in 5 ml of PBS buffer (pH 7.2) (c=10 mg/ml). After stirring at RT for 1 h, the same amount again was added and the mixture was stirred at RT for a further hour. Then the mixture was diluted to 7.5 ml with PBS buffer (pH 7.2), purified on a Sephadex column, then concentrated by ultracentrifugation, rediluted with PBS (pH 7.2) and reconcentrated and sterile-filtered again.

Exemplary Procedure D:

Under argon, 4.5 eq (36 mg) of Intermediate Q2 dissolved in 7.5 ml of DMSO were added to 1000 mg of the antibody in question in 150 ml of PBS buffer (pH7.2) (c=6.7 mg/ml). After stirring at RT for 1 h, the same amount again was added and the mixture was stirred at RT for a further hour. The batch was then purified by cross-flow filtration, concentrated and sterile-filtered.

| Example | Target | Antibody TPP- | Procedure | C [mg/ml] | DAR |
|---|---|---|---|---|---|
| 2a-981 | EGFR | 981 | A | 2.23 | 4.5 |
| 2c-6013 | CD123 | 6013 | A | 2.32 | 4.9 |
| 2c-8987 | CD123 | 8987 | B | 8.86 | 5.8 |
| 2c-8988 | CD123 | 8988 | B | 9.81 | 3.6 |
| 2c-9476B | CD123 | 9476 | B | 10.27 | 4.2 |
| 2c-9476C | CD123 | 9476 | C | 9.22 | 3.4 |
| 2c-9476D | CD123 | 9476 | D | 15.83 | 6.3 |
| 2e-1015 | HER2 | 1015 | A | 2.05 | 5.4 |
| 2k-7006 | TWEAKR | 7006 | A | 2.09 | 5.9 |
| 2k-7007 | TWEAKR | 7007 | B | 9.32 | 3.4 |
| 2x-9574 | CXCR5 | 9574 | B | 9.5 | 4.8 |
| 2x-9580 | CXCR5 | 9580 | B | 10.12 | 4.8 |

Examples 3

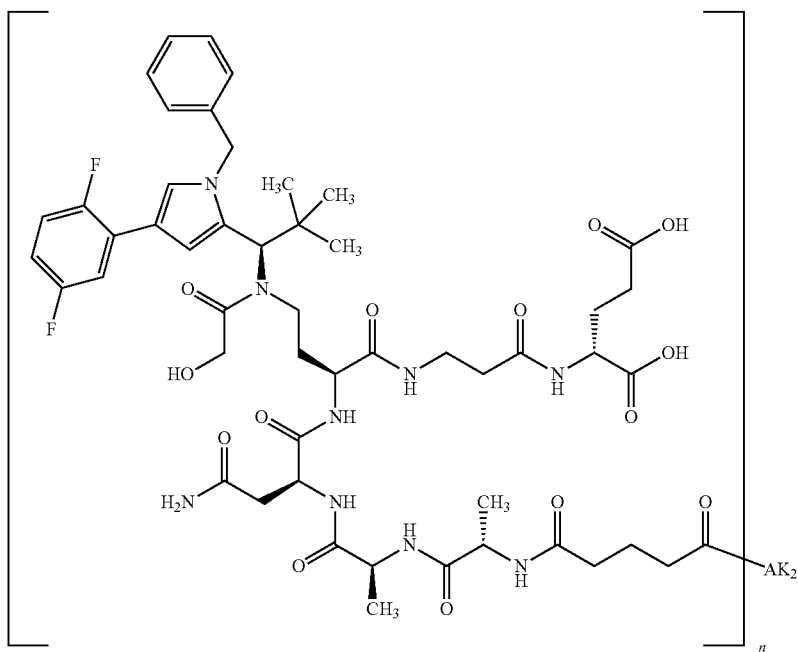

Exemplary Procedure A:

Under argon, 5 eq (0.2 mg) of Intermediate Q3 dissolved in 50 μl of DMSO were added to 5 mg of the antibody in question in 0.5 ml of PBS (c=10 mg/ml). After stirring at RT for 1 h, the same amount again was added and the mixture was stirred at RT for a further hour.

The reaction mixture was subsequently diluted to 2.5 ml with PBS buffer (pH 7.2), purified on a Sephadex column, then concentrated by ultracentrifugation and rediluted with PBS (pH 7.2).

Exemplary Procedure B:

Under argon, 4 eq (1 mg) of Intermediate Q3 dissolved in 50 μl of DMSO were added to 30 mg of the antibody in question in 3 ml of PBS buffer (pH 7.2) (c=10 mg/ml). After stirring at RT for 1 h, the same amount again was added and the mixture was stirred at RT for a further hour. Then the mixture was diluted to 2.5 ml with PBS buffer (pH 7.2), purified on a Sephadex column, then concentrated by ultracentrifugation, rediluted with PBS (pH 7.2) and reconcentrated and sterile-filtered again.

| Example | Target | Antibody TPP- | Procedure | C [mg/ml] | DAR |
|---|---|---|---|---|---|
| 3a-981 | EGFR | 981 | A | 1.99 | 5.0 |
| 3c-9476 | CD123 | 9476 | A | 2.09 | 5.8 |
| 3e-1015 | HER2 | 1015 | A | 2.06 | 6.3 |
| 3k-7007 | TWEAKR | 7007 | A | 2.11 | 5.3 |
| 3x-9574 | CXCR5 | 9574 | A | 2.02 | 4.5 |

Examples 4

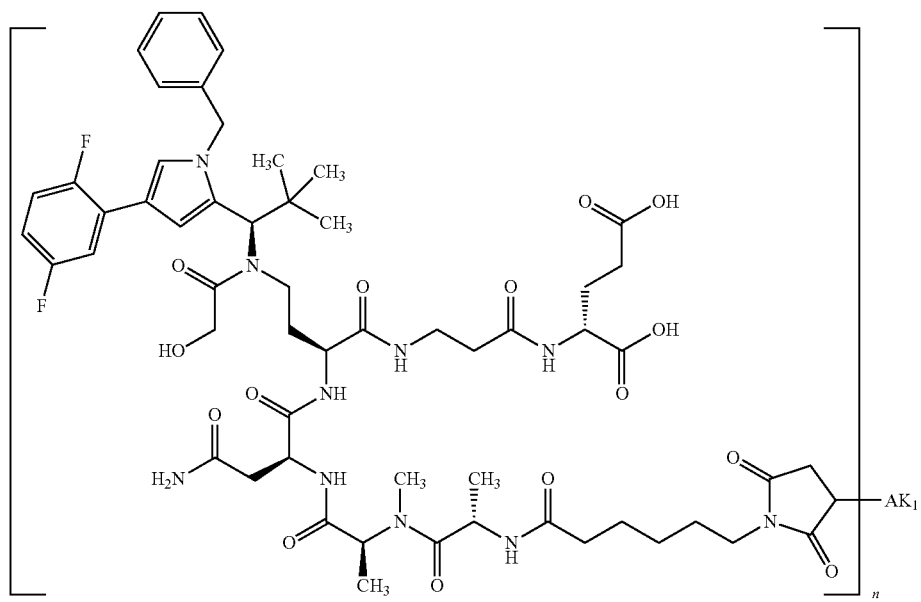

Exemplary Procedure A:

Under argon, a solution of 0.029 mg of TCEP in 0.05 ml of PBS buffer was added to 5 mg of the antibody in question in 0.4 ml of PBS buffer (pH 7.2) (c=12.5 mg/ml). The mixture was stirred at RT for 30 min, and then 0.275 mg (0.00023 mmol) of Intermediate Q4 dissolved in 50 µl of DMSO was added. After a further 90 min of stirring at RT, the reaction was diluted to a total volume of 2.5 ml with PBS buffer. This solution was then applied to a PD 10 column (Sephadex® G-25, GE Healthcare) which had been equilibrated with PBS buffer (pH 7.2) and was eluted with PBS buffer (pH 7.2). This was followed by concentration by ultracentrifugation and redilution with PBS buffer (pH 7.2).

| Example | Target | Antibody TPP- | Procedure | C [mg/ml] | DAR |
|---|---|---|---|---|---|
| 4c-9476 | CD123 | 9476 | A | 2.06 | 3.5 |
| 4k-7007 | TWEAKR | 7007 | A | 1.87 | 4.0 |
| 4x-9574 | CXCR5 | 9574 | A | 1.93 | 3.6 |

Examples 5

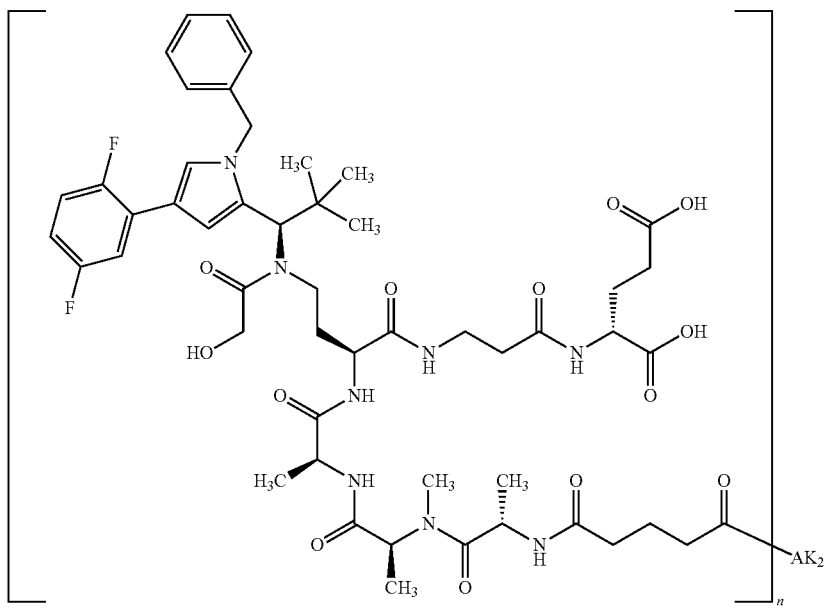

Exemplary Procedure A:

Under argon, 5 eq (0.2 mg) of Intermediate Q5 dissolved in 50 µl of DMSO were added to 5 mg of the antibody in question in 0.5 ml of PBS (c=10 mg/ml). After stirring at RT for 1 h, the same amount again was added and the mixture was stirred at RT for a further hour.

The reaction mixture was subsequently diluted to 2.5 ml with PBS buffer (pH 7.2), purified on a Sephadex column, then concentrated by ultracentrifugation and rediluted with PBS (pH 7.2).

| Example | Target | Antibody TPP- | Procedure | C [mg/ml] | DAR |
|---|---|---|---|---|---|
| 5c-9476 | CD123 | 9476 | A | 2.37 | 5.3 |
| 5e-1015 | HER2 | 1015 | A | 2.33 | 5.5 |
| 5k-7007 | TWEAKR | 7007 | A | 2.18 | 5.6 |
| 5x-9574 | CXCR5 | 9574 | A | 1.88 | 6.8 |

Examples 6

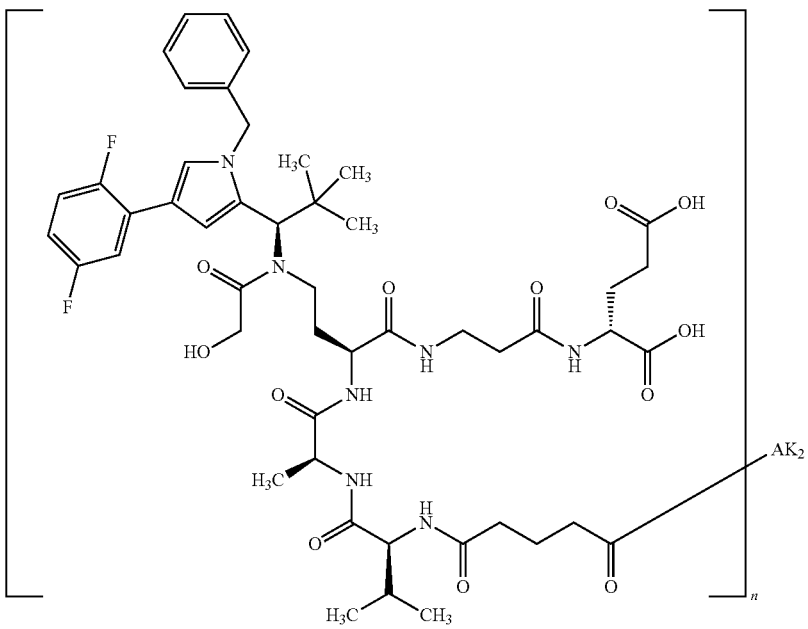

Exemplary Procedure A:

Under argon, 5 eq (0.18 mg) of Intermediate Q6 dissolved in 50 μl of DMSO were added to 5 mg of the antibody in question in 0.4 ml of PBS (c=12.5 mg/ml). After stirring at RT for 1 h, the same amount again was added and the mixture was stirred at RT for a further hour. The reaction mixture was subsequently diluted to 2.5 ml with PBS buffer (pH 7.2), purified on a Sephadex column, then concentrated by ultracentrifugation and rediluted with PBS (pH 7.2).

| Example | Target | Antibody TPP- | Procedure | C [mg/ml] | DAR |
|---------|--------|---------------|-----------|-----------|-----|
| 6a-981  | EGFR   | 981           | A         | 2.39      | 4.9 |
| 6c-9476 | CD123  | 9476          | A         | 1.8       | 5.3 |
| 6e-1015 | HER2   | 1015          | A         | 2.23      | 6.2 |
| 6k-7007 | TWEAKR | 7007          | A         | 2.57      | 5.6 |

Examples 7

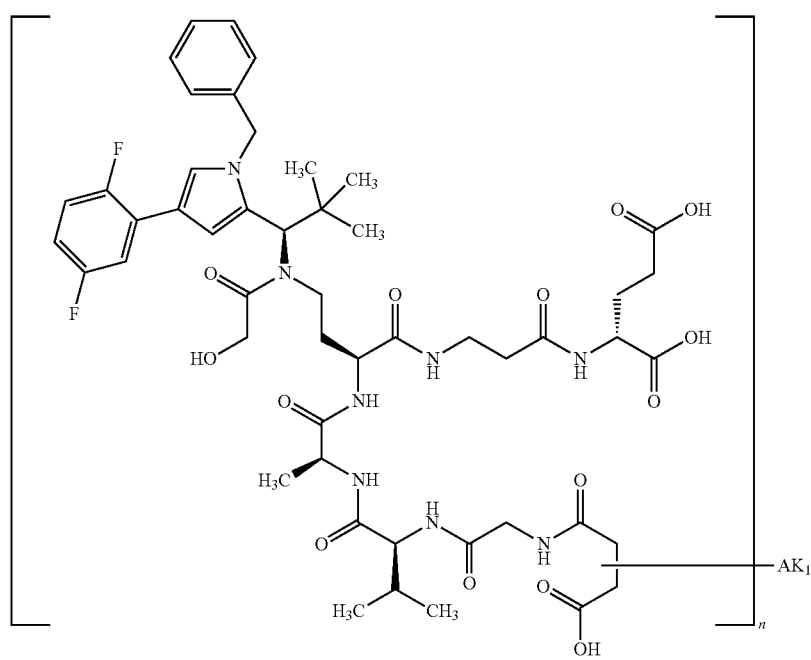

Exemplary Procedure A:

Under argon, a solution of 0.029 mg of TCEP in 0.05 ml of PBS buffer was added to 5 mg of the antibody in question in 0.4 ml of PBS (c=12.5 mg/ml). The mixture was stirred at RT for 30 min, and then 0.24 mg (0.00023 mmol) of Intermediate Q7 dissolved in 50 μl of DMSO was added. After stirring at RT for a further 90 min, the mixture was diluted to a volume of 2.5 ml with PBS buffer which had been adjusted to pH 8 beforehand and then passed through a PD 10 column (Sephadex© G-25, GE Healthcare) equilibrated with PBS buffer pH 8, and eluted with PBS buffer pH 8. The eluate was stirred at RT under argon overnight. This was followed by concentration by ultracentrifugation and redilution with PBS buffer (pH 7.2).

| Example | Target | Antibody TPP- | Procedure | C [mg/ml] | DAR |
|---|---|---|---|---|---|
| 7a-981 | EGFR | 981 | A | 2.03 | 3.4 |
| 7c-9476 | CD123 | 9476 | A | 1.53 | 4.0 |
| 7e-1015 | HER2 | 1015 | A | 1.88 | 3.8 |
| 7k-7007 | TWEAKR | 7007 | A | 1.99 | 3.6 |

Examples 8

Exemplary Procedure A:

Under argon, 5 eq (0.2 mg) of Intermediate Q8 dissolved in 50 μl of DMSO were added to 5 mg of the antibody in question in 0.5 ml of PBS (c=10 mg/ml). After stirring at RT for 1 h, the same amount again was added and the mixture was stirred at RT for a further hour.

The reaction mixture was subsequently diluted to 2.5 ml with PBS buffer (pH 7.2), purified on a Sephadex column, then concentrated by ultracentrifugation and rediluted with PBS (pH 7.2).

| Example | Target | Antibody TPP- | Procedure | C [mg/ml] | DAR |
|---|---|---|---|---|---|
| 8a-981 | EGFR | 981 | A | 2.32 | 6.5 |
| 8c-9476 | CD123 | 9476 | A | 2.37 | 6.9 |
| 8e-1015 | HER2 | 1015 | A | 1.46 | 6.6 |
| 8k-7007 | TWEAKR | 7007 | A | 2.43 | 6.7 |

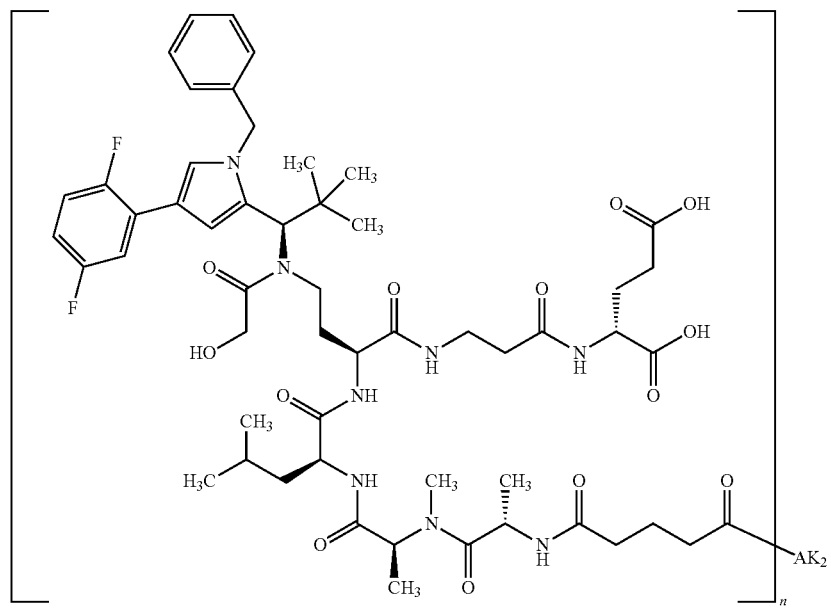

Examples 9

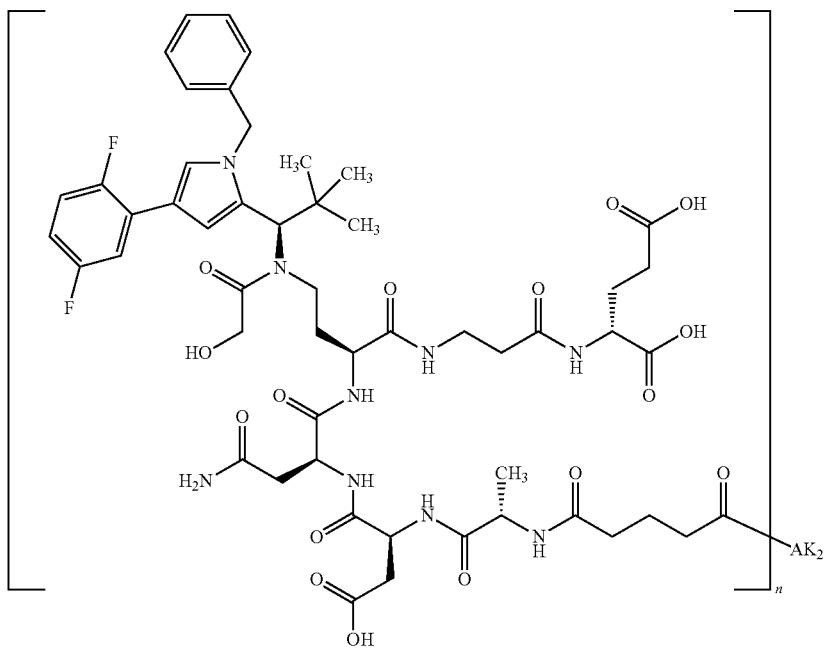

Exemplary Procedure A:

Under argon, 5 eq (0.2 mg) of Intermediate Q9 dissolved in 50 µl of DMSO were added to 5 mg of the antibody in question in 0.5 ml of PBS (c=10 mg/ml). After stirring at RT for 1 h, the same amount again was added and the mixture was stirred at RT for a further hour.

The reaction mixture was subsequently diluted to 2.5 ml with PBS buffer (pH 7.2), purified on a Sephadex column, then concentrated by ultracentrifugation and rediluted with PBS (pH 7.2).

| Example | Target | Antibody TPP- | Procedure | C [mg/ml] | DAR |
|---------|--------|---------------|-----------|-----------|-----|
| 9a-981  | EGFR   | 981           | A         | 2.34      | 4.4 |
| 9c-9476 | CD123  | 9476          | A         | 2.65      | 4.2 |
| 9e-1015 | HER2   | 1015          | A         | 2.22      | 4.8 |
| 9k-7007 | TWEAKR | 7007          | A         | 2.14      | 3.8 |

Examples 10

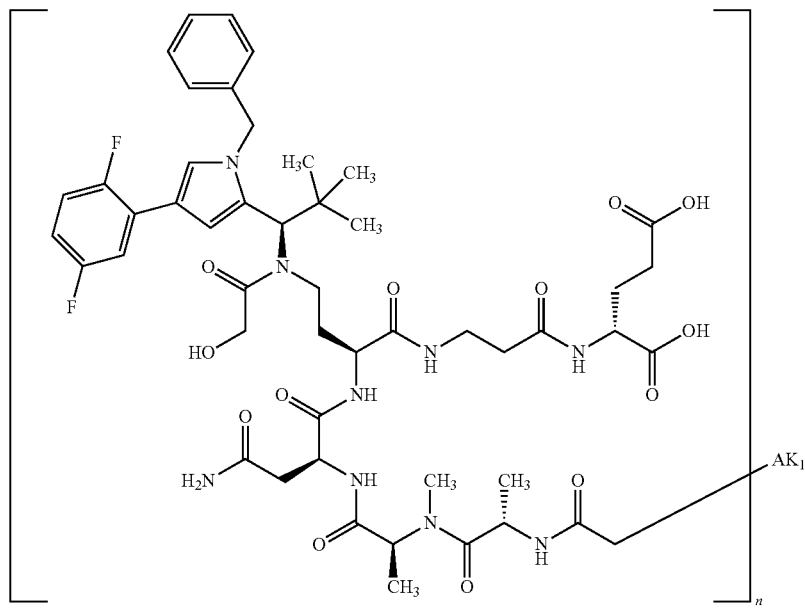

Exemplary Procedure A:

Under argon, a solution of 0.029 mg of TCEP in 0.05 ml of PBS buffer was added to 5 mg of the antibody in question in 0.5 ml of PBS buffer (pH 7.2) (c=10 mg/ml). The mixture was stirred at RT for 30 min, and then 0.295 mg (0.00023 mmol) of Intermediate Q10 dissolved in 50 μl of DMSO was added. After a further 20 h of stirring at RT, the reaction was diluted to a total volume of 2.5 ml with PBS buffer. This solution was then applied to a PD 10 column (Sephadex® G-25, GE Healthcare) which had been equilibrated with PBS buffer (pH 7.2) and was eluted with PBS buffer (pH 7.2). This was followed by concentration by ultracentrifugation and redilution with PBS buffer (pH 7.2).

Exemplary Procedure C for Obtaining a Higher DAR:

Under argon, a solution of 0.057 mg of TCEP in 0.05 ml of PBS buffer was added to 5 mg of the antibody in question in 0.5 ml of PBS buffer (pH 7.2) (c=10 mg/ml). The mixture was stirred at RT for 30 min, and then 0.59 mg (0.00053 mmol) of Intermediate Q10 dissolved in 50 μl of DMSO was added. After a further 20 h of stirring at RT, the reaction was diluted to a total volume of 2.5 ml with PBS buffer. This solution was then applied to a PD 10 column (Sephadex® G-25, GE Healthcare) which had been equilibrated with PBS buffer (pH 7.2) and was eluted with PBS buffer (pH 7.2). This was followed by concentration by ultracentrifugation and redilution with PBS buffer (pH 7.2).

| Example | Target | Antibody TPP- | Procedure | C [mg/ml] | DAR |
|---|---|---|---|---|---|
| 10a-981 | EGFR | 981 | A | 1.9 | 3.2 |
| 10c-9476 | CD123 | 9476 | A | 1.83 | 2.7 |
| 10c-9476 hD | CD123 | 9476 | C | 1.97 | 4.8 |
| 10e-1015 | HER2 | 1015 | A | 1.83 | 3.4 |
| 10k-7007 | TWEAKR | 7007 | A | 1.9 | 4.7 |
| 10x-9574 | CXCR5 | 9574 | A | 1.41 | 3.8 |
| 10x-9574 hD | CXCR5 | 9574 | C | 0.97 | 6.3 |

Examples 11

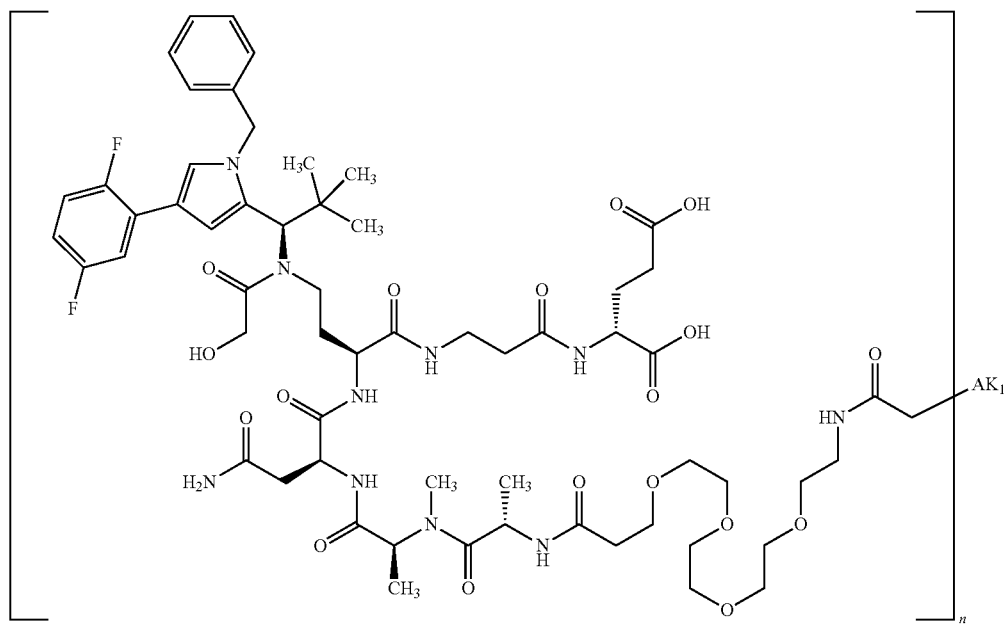

Exemplary Procedure A:

Under argon, a solution of 0.029 mg of TCEP in 0.05 ml of PBS buffer was added to 5 mg of the antibody in question in 0.4 ml of PBS buffer (pH 7.2) (c=12.5 mg/ml). The mixture was stirred at RT for 30 min, and then 0.32 mg (0.00023 mmol) of Intermediate Q11 dissolved in 50 µl of DMSO was added. After a further 20 h of stirring at RT, the reaction was diluted to a total volume of 2.5 ml with PBS buffer. This solution was then applied to a PD 10 column (Sephadex® G-25, GE Healthcare) which had been equilibrated with PBS buffer (pH 7.2) and was eluted with PBS buffer (pH 7.2). This was followed by concentration by ultracentrifugation and redilution with PBS buffer (pH 7.2).

| Example | Target | Antibody TPP- | Procedure | C [mg/ml] | DAR |
|---|---|---|---|---|---|
| 11a-981 | EGFR | 981 | A | 1.88 | 1.9 |
| 11c-9476 | CD123 | 9476 | A | 1.89 | 1.6 |
| 11e-1015 | HER2 | 1015 | A | 1.69 | 2.3 |
| 11k-7007 | TWEAKR | 7007 | A | 1.17 | 1.9 |

For comparative purposes, the following ADCs were prepared:

Reference Example R1

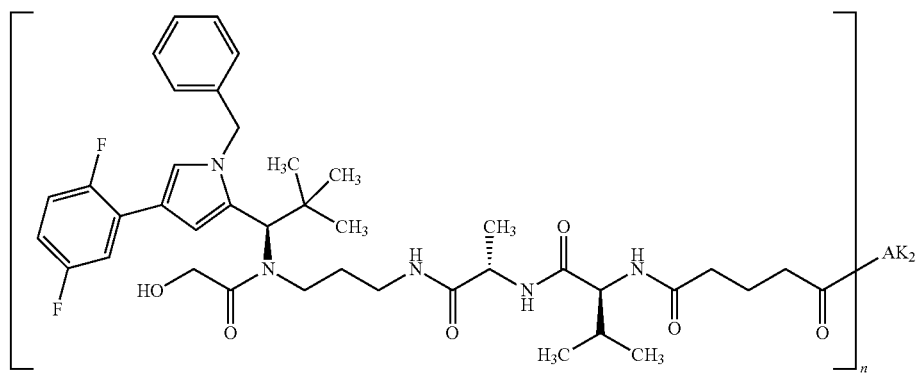

Such ADCs were disclosed in WO2015/096982 and in WO2016/096610 with various antibodies including, for example, cetuximab and trastuzumab. For comparative purposes, the precursor Intermediate F194 disclosed therein was furthermore also reacted with TPP-6013 (anti-CD123 AK). The following ADCs were used for comparative purposes:

| Example | Target | Antibody TPP- | C [mg/ml] | DAR |
|---|---|---|---|---|
| R1a | EGFR | 981 | 1.67 | 1.9 |
| R1c | CD123 | 6013 | 0.42 | 2.9 |
| R1e | HER2 | 1015 | 1.39 | 2.4 |
| R1x | CXCR5 | 9574 | 1.28 | 2.2 |

Reference Example R2

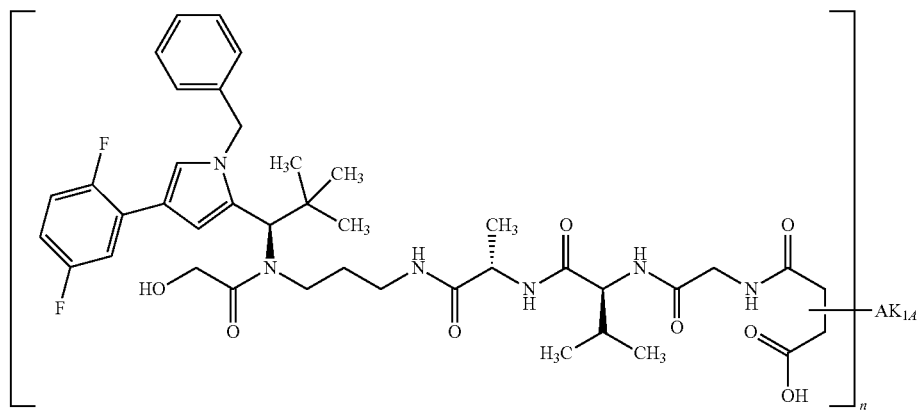

Such ADCs were disclosed in WO2016/096610 with an aglycosylated anti-TWEAKR antibody. For comparative purposes, the precursor Intermediate F291 disclosed therein was furthermore also reacted with TPP-9574 (anti-CXCR5 AK), TPP-981 (anti-EGFR) and TPP-1015 (anti-HER2 AK). The following ADCs were used for comparative purposes:

| Example | Target | Antibody TPP- | C [mg/ml] | DAR |
|---|---|---|---|---|
| R2a | EGFR | 981 | 1.46 | 3.4 |
| R2e | HER2 | 1015 | 1.42 | 3.5 |
| R2x | CXCR5 | 9574 | 1.41 | 3.6 |

For the Reference Examples R1, WO2015/096982 describes the metabolite Example 98 derived therefrom. For the Reference Examples R2, WO2016/096610 describes the identical metabolite Example M9, which is listed here as Reference Example R3M.

Reference Example R3M

N-(3-Aminopropyl)-N-{(1R)-1-[1-benzyl-4-(2,5-difluorophenyl)-1H-pyrrol-2-yl]-2,2-dimethylpropyl}-2-hydroxyacetamide

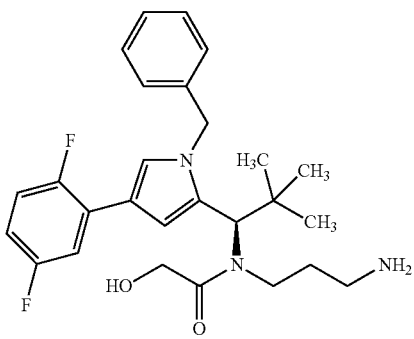 [SMILES: CC(C)(C)[C@H](c1cc(-c2cc(F)ccc2F)cn1Cc1ccccc1)N(CCCN)C(=O)CO]

The preparation was described in WO2015/096982 as Example 98.

The biological data for these reference compounds disclosed in said applications or obtained for the novel reference compounds are described in Chapter C.

C: Assessment of Biological Efficacy

The biological activity of the compounds according to the invention can be shown in the assays described below:

a. C-1a Determination of the Cytotoxic Effect of the ADCs

The analysis of the cytotoxic effect of the ADCs was carried out with various cell lines:

NCI-H292: human mucoepidermoid lung carcinoma cells, ATCC-CRL-1848, standard medium: RPMI 1640 (Biochrom; #FG1215, stab. glutamine)+10% FCS (Sigma; #F2442), TWEAKR-positive; EGFR-positive.

BxPC3: human pancreas carcinoma cells, ATCC-CRL-1687, standard medium: RPMI 1640 (Biochrom; #FG1215, stab. glutamine)+10% FCS (Sigma; #F2442), TWEAKR-positive.

LoVo: human colorectal cancer cells, ATCC No. CCL-229, cultivation for MTT assay: standard medium: Kaighn's+L-glutamine (Invitrogen 21127)+10% heat inactivated FCS (from Gibco, No. 10500-064). Cultivation for CTG assay: RPMI 1640 (Biochrom; #FG1215, stab. glutamine)+10% FCS (Sigma #F2442). TWEAKR-positive.

KPL4: human breast cancer cell line, Bayer Pharma AG (identity checked and confirmed on 19 Jul. 2012 at DSMZ), standard medium: RPMI 1640 (from Gibco; #21875-059, stab. L-glutamine)+10% heat inactivated FCS (Gibco, No. 10500-064); HER2-positive.

SK-HEP-1: human liver cell cancer line, ATCC No. HTB-52, standard medium: MEM with Earle's salts+Glutamax I (Invitrogen 41090)+10% heat inactivated FCS (from Gibco, No. 10500-064); EGFR-positive, TWEAKR-positive MOLM-13: human acute monocytic leukaemia cells (AML-M5a), DSMZ, No. ACC 554, standard medium: RPMI 1640 (from Gibco; #21875-059, stab. L-glutamine)+20% heat inactivated FCS (Gibco, No. 10500-064); CD123-positive.

MV-4-11: human biphenotypic B myelomonocytic leukaemia cells obtained from peripheral blood, ATCC-CRL-9591, standard medium: IMDM (ATCC: 30-2005), +10% heat inactivated FCS (Gibco, No. 10500-064); CD123-positive.

NB4: human acute promyelocytic leukaemia cells obtained from bone marrow, DSMZ, No. ACC 207, standard medium: RPMI 1640+GlutaMAX I (Invitrogen 61870)+10% heat inactivated FCS (Gibco, No. 10500-064)+2.5 g of glucose (20% glucose solution, Gibco, No. 19002)+10 mM Hepes (Invitrogen 15630)+1 mM sodium pyruvate (Invitrogen 11360); CD123-negative Rec-1: human mantle cell lymphoma cells (B cell non-Hodgkin's lymphoma) ATCC CRL-3004, standard medium: RPMI 1640+GlutaMAX I (Invitrogen 61870)+10% heat inactivated FCS (Gibco, No. 10500-064)+10 mM) CXCR5-positive U251: human glioblastoma cells, standard medium: RPMI 1640 (Biochrom; #FG1215, stab. glutamine)+10% FCS (Biochrom; #S$_{0415}$), B7H3-positive.

HBL-1: human B cell lymphoma cells (diffuse large B-cell lymphoma) ATT CRL-RRID (Resource Identification Initiative): CVCL 4213, first described in Abe et al. Cancer 61:483-490(1988), obtained from Prof. Lenz, Universitst Munster; standard medium: RPMI 1640 (Biochrom; #FG1215, stab. glutamine)+10% FCS (Biochrom; #S0415), cultivation analogous to Rec-1 cells; CXCR5 positive The cells were cultivated by the standard method as stated by the American Tissue Culture Collection (ATCC) or the Leibniz-Institut DSMZ-Deutsche Sammlung von Mikroorganismen und Zellkulturen GmbH (DSMZ) for the cell lines in question.

CTG Assay

The cells were cultivated by the standard method, with the growth media specified under C-1. The test was carried out by detaching the cells with a solution of trypsin (0.05%) and EDTA (0.02%) in PBS (Biochrom AG #L2143), pelleting, resuspending in culture medium, counting and sowing into a 96-well culture plate with white bottom (Costar #3610) (at 75 µl/well, the following cell numbers per well are: NCI-H292: 2500 cells/well, BxPC3 2500 cells/well, LoVo 3000 cells/well) and incubating in an incubator at 37° C. and 5% carbon dioxide. The suspension cells were counted and sown in a 96-well culture plate with white bottom (Costar #3610) (at 75 µl/well, the following cell numbers per well: Rec-1: 3000 cells/well, HBL-1: 6000 cells/well). After 24 h, the antibody drug conjugates were added in 25 µl of culture medium (concentrated four-fold) to the cells to give final antibody drug conjugate concentrations of $3 \times 10^{-7}$ M to $3 \times 10^{-11}$ M on the cells (triplicates). The cells were then incubated in an incubator at 37° C. and 5% carbon dioxide.

On a parallel plate, the cell activity at the start of the drug treatment (day 0) was determined using the Cell Titer Glow (CTG) luminescent cell viability assay (Promega #G7573 and #G7571). To this end, per cell batch 100 µl of the substrate were added, the plates were then covered with aluminium foil, shaken on the plate shaker at 180 rpm for 2 minutes, allowed to stand on the laboratory bench for 8 minutes and then measured using a luminometer (Victor X2, Perkin Elmer). The substrate detects the ATP content in the living cells generating a luminescence signal whose intensity is directly proportional to the viability of the cells.

After 72 h of incubation with the antibody drug conjugates, the viability of these cells was then also determined using the Cell Titer Glow luminescent cell viability assay as described above. From the data measured, the $IC_{50}$ of the growth inhibition was calculated in comparison to day 0 using the DRC (Dose Response Curve) analysis spreadsheets and a 4-parameter fit. The DRC analysis spreadsheet is a biobook spreadsheet developed by Bayer Pharma AG and Bayer Business Services on the IDBS E-WorkBook Suite platform (IDBS: ID Business Solutions Ltd., Guildford, UK).

MTT Assay

The cells were cultivated by the standard method, with the growth media specified under C-1. The test was carried out by detaching the cells with a solution of Accutase in PBS (from Biochrom AG #L2143), pelletizing, resuspending in culture medium, counting and sowing into a 96-well culture plate with white bottom (from Costar #3610) (NCI H292: 2500 cells/well; SK-HEP-1: 1000 cells/well; KPL-4: 1200 cells/well; in total volume 100 µl). The cells were then incubated in an incubator at 37° C. and 5% carbon dioxide. After 48 h, the medium was replaced. The antibody drug conjugates in 10 µl of culture medium in concentrations from $10^{-5}$M to $10^{-13}$M were then pipetted to the cells (in triplicate), and the assay was then incubated in an incubator at 37° C. and 5% carbon dioxide. The suspension cells were counted and sown into a 96-well culture plate with white bottom (from Costar #3610) (#3610) (MOLM-13: 2000 cells/well; NB4: 7000 cells/well; MV-4-11: 5000 cells/well in a total volume of 100 µl). After 6 hours of incubation at 37° C. and 5% carbon dioxide, the medium was changed and the antibody-drug conjugates or metabolites were added by pipette in 10 µl of culture medium in concentrations of $10^{-5}$M to $10^{-13}$M to the cells (triplicates) in 90 µl. The batch was incubated in an incubator at 37° C. and 5% carbon dioxide. After 96 h, the cell proliferation was detected using the MTT assay (ATCC, Manassas, Va., USA, catalogue No. 30-1010K). To this end, the MTT reagent was incubated with the cells for 4 h, followed by lysis of the cells overnight by addition of the detergent. The dye formed was detected at 570 nm (Infinite M1000 pro, Tecan). The measured data were used to calculate the $IC_{50}$ of the growth inhibition using the DRC (dose response curve). The proliferation of cells which were not treated with test substance but were otherwise identically treated was defined as the 100% figure.

Tables 1a and 1b below set out the $IC_{50}$ values for representative working examples from these assays:

TABLE 1a

| Example | MOLM 13 $IC_{50}$ [M] MTT | MV-4-11 $IC_{50}$ [M] MTT | NCI-H292 $IC_{50}$ [M] MTT/CTG | LoVo $IC_{50}$ [M] CTG | SKHep-1 $IC_{50}$ [M] MTT | BxPC3 $IC_{50}$ [M] CTG | KPL-4 $IC_{50}$ [M] [MTT] |
|---|---|---|---|---|---|---|---|
| 1a-981 | | | 2.65E-11 | | 6.70E-08 | | |
| 1c-6013 | 3.15E-10 | 2.29E-08 | | | | | |
| 1c-9476 | 2.28E-09 | 3.19E-09 | | | | | |
| 1e-1015 | | | | | | | 1.51E-09 |
| 1k-7006 | | | 1.12E-10 | 5.37E-11 | 3.62E-11 | 1.04E-10 | |
| 1k-7007 | | | 6.56E-11 | 6.70E-11 | 8.42E-11 | 9.61E-11 | |
| 2a-981 | | | 5.50E-12 | | 1.79E-10 | | |
| 2c-6013 | 1.78E-11 | 4.77E-10 | | | | | |
| 2c-8987 | 4.59E-10 | 1.26E-10 | | | | | |
| 2c-8988 | 8.91E-11 | 4.39E-09 | | | | | |
| 2c-9476B | 9.15E-10 | 5.08E-10 | | | | | |
| 2c-9476C | 1.3E-08 | 2.01E-09 | | | | | |
| 2c-9476D | 1.10E-09 | 6,80E-11 | | | | | |
| 2e-1015 | | | | | | | 1.43E-10 |
| 2k-7006 | | | 5.86E-11 | 1.50E-11 | 2.04E-11 | 9.92E-11 | |
| 2k-7007 | | | 8.82E-11 | 1.50E-11 | | 7.54E-11 | |
| 3a-981 | | | 7.73E-13 | | 1.11E-10 | | |
| 3c-9476 | 2.00E-10 | 1.05E-11 | | | | | |
| 3e-1015 | | | | | | | 3.64E-11 |
| 3k-7007 | | | 5.49E-11 | 1.50E-11 | | 9.80E-11 | |
| 4a-981 | | | 8.40E-10 | | 1.57E-10 | | |
| 4c-9476 | 8.40E-10 | 1.57E-10 | | | | | |
| 4k-7007 | | | 7.74E-10 | 1.50E-11 | | 1.18E-10 | |
| 5c-9476 | 1.08E-09 | 4.40E-11 | | | | | |
| 5e-1015 | | | | | | | 4.50E-10 |
| 5k-7007 | | | 1.12E-10 | 1.50E-11 | | 3.03E-10 | |
| 5x-9574 | | | | | | | |
| 6a-981 | | | 1.68E-12 | | 5.00E-07 | | |
| 6c-9476 | 4.46E-10 | 1.24E-10 | | | | | |
| 6e-1015 | | | | | | | 5.54E-10 |
| 6k-7007 | | | 6.94E-11 | 4.93E-11 | | 1.89E-10 | |
| 7a-981 | | | 2.34E-10 | | | | |
| 7c-9476 | 1.09E-09 | 6.4E-10 | | | | | |
| 7e-1015 | | | | | | | 4.51E-10 |
| 7k-7007 | | | 1,03E-10 | 1.43E-09 | | 4.39E-10 | |
| 8a-981 | | | 9,87E-12 | | 3.96E-08 | | |
| 8c-9476 | 3,36E-10 | 3.46E-11 | | | | | |
| 8e-1015 | | | | | | | 4.30E-10 |

TABLE 1a-continued

| Example | MOLM 13 IC$_{50}$ [M] MTT | MV-4-11 IC$_{50}$ [M] MTT | NCI-H292 IC$_{50}$ [M] MTT/CTG | LoVo IC$_{50}$ [M] CTG | SKHep-1 IC$_{50}$ [M] MTT | BxPC3 IC$_{50}$ [M] CTG | KPL-4 IC$_{50}$ [M] [MTT] |
|---|---|---|---|---|---|---|---|
| 8k-7007 | | | 1.84E−10 | 3.66E−11 | | 4.17E−10 | |
| 9a-981 | | | 1.00E−11 | | 4.29E−08 | | |
| 9c-9476 | 5.00E−07 | 1.44E−07 | | | | | |
| 9e-1015 | | | | | | | 1.39E−10 |
| 9k-7007 | | | 1.45E−10 | 3.17E−11 | | 2.69E−10 | |
| 10a-981 | | | 1.00E−12 | | 5.00E−07 | | |
| 10c-9476 | 1,41E−09 | 8,42E−10 | | | | | |
| 10c-9476 hD | 1.79E−10 | 5.45E−11 | | | | | |
| 10e-1015 | | | | | | | 3.78E−11 |
| 10k-7007 | | | 9.60E−11 | 1.50E−11 | | 1.29E−10 | |
| 11a-981 | | | 1.98E−12 | | 2.59E−08 | | |
| 11c-9475 | 9.61E−08 | 6.90E−08 | | | | | |
| 11e-1015 | | | | | | | 2.37E−10 |
| 11k-7007 | | | 1.74E−10 | | | 1.62E−10 | |

TABLE 1b

| Example | Rec-1 IC$_{50}$ [M] CTG | U251 IC$_{50}$ [M] CTG | HBL1 IC$_{50}$ [M] CTG |
|---|---|---|---|
| 1h-8382 | | 9.98E−10 | |
| 1x-9574 | 1.50E−11 | | 7.69E−9 |
| 2x-9574 | 1.5E−11 | | 2.76E−10 |
| 2x-9580 | 7.7E−11 | | |
| 3x-9574 | 1.50E−11 | | |
| 4x-9574 | 1.50E−11 | | 6.17E−11 |
| 5x-9574 | 1.50E−11 | | |
| 10x-9574 | 1.50E−11 | | 2.76E−9 |
| 10x-9574 hD | 1.50E−11 | | 4.64E−11 |

Table 1c below lists the IC$_{50}$ values for the reference examples from these assays.

TABLE 1c

| Example | MOLM 13 IC$_{50}$ [M] MTT | Rec-1 IC$_{50}$ [M] CTG | NCI-H292 IC$_{50}$ [M] MTT | SKHep-1 IC$_{50}$ [M] MTT | KPL-4 IC$_{50}$ [M] [MTT] |
|---|---|---|---|---|---|
| R1a | | | 6.14E−11 | 1.85E−10 | |
| R1c | 1.24E−07 | | | | |
| R1e | | | | | 1.55E−08 |
| R1x | | 3.00E−07 | | | |
| R2a | | | 2.10E−10 | 6.02E−08 | |
| R2e | | | | | 4.39E−08 |
| R2x | | 3.00E−07 | | | |

The activity data reported relate to the working examples described in the present experimental section, with the drug/mAB ratios indicated. The values may possibly deviate for different drug/mAB ratios. The IC50 values are means of several independent experiments or individual values. The action of the antibody drug conjugates was selective for the respective isotype control comprising the respective linker and toxophore. For the ADCs directed against CD123, the target specificity was additionally demonstrated by testing with a CD123-negative cell.

In general, the ADCs according to the invention exhibit significantly improved cytotoxic potency compared to the corresponding reference examples.

C-1b Determination of the Inhibition of the Kinesin Spindle Protein KSP/Eg5 by Selected Examples The motor domain of the human kinesin spindle protein KSP/Eg5 (tebu-bio/Cytoskeleton Inc, No. 027EG01-XL) was incubated in a concentration of 10 nM with microtubuli (bovine or porcine, tebu-bio/Cytoskeleton Inc) stabilized with 50 µg/ml taxol (Sigma No. T7191-5MG) for 5 min at RT in 15 mM PIPES, pH 6.8 (5 mM MgCl$_2$ and 10 mM DTT, Sigma). The freshly prepared mixture was aliquoted into a 384 MTP (from Corning). The inhibitors to be examined at concentrations of $1.0 \times 10^{-6}$ M to $1.0 \times 10^{-13}$ M and ATP (final concentration 500 µM, Sigma) were then added. Incubation was at RT for 2 h. ATPase activity was detected by detecting the inorganic phosphate formed using malachite green (Biomol). After addition of the reagent, the assay was incubated at RT for 50 min prior to detection of the absorption at a wavelength of 620 nm. The positive controls used were monastrol (Sigma, M8515-1 mg) and ispinesib (AdooQ Bioscience A10486). The individual data of the dose-activity curve are eight-fold determinations. The IC$_{50}$ values are means of two independent experiments. The 100% control was the sample which had not been treated with inhibitors.

Table 2 below lists the IC$_{50}$ values of representative working examples from the assay described and summarizes the corresponding cytotoxicity data (MTT assay):

TABLE 2

| Examples | KSP assay IC$_{50}$ [M] | NCI-H292 IC$_{50}$ [M] MTT | SK-Hep-1 IC$_{50}$ [M] MTT | KPL4 IC$_{50}$ [M] MTT | MOLM-13 IC$_{50}$ [M] MTT |
|---|---|---|---|---|---|
| M1 | 1.59E−09 | 1.74E−07 | 1.96E−08 | 1.73E−07 | |
| R3M | 1.09E−09 | 2.70E−10 | 7.62E−09 | 2.57E−10 | 6.69E−11 |

The activity data reported relate to the working examples described in the present experimental section.

C-1c Enzymatic Assays a: Cathepsin B Assay

For every cathepsin B-cleavable prodrug to be examined, a mixture was made up in a micro reaction vessel (0.5 ml, from Eppendorf). The enzyme used here was obtained from human liver tissue. 2 µg of cathepsin B (Sigma C8571 25 µg) were initially charged and made up to a total volume of 200 µl with 50 mM Na phosphate buffer, pH6.0, 2 mM DTT. Then 50 µl of the substrate solution to be examined were pipetted in. The mixture was incubated in a thermoblock (from Thermo Fisher Scientific) at 40° C. under constant agitation at 300 rpm. The enzymatic reaction was controlled kinetically. For this purpose, a 10 µl sample was taken at different times. The sample taken was admixed immediately with 20 µl of ice-cold methanol in order to stop the enzymatic reaction and then frozen at −20° C. The times selected for sampling were after 10 min, 2 h, 4 h and 24 h. The samples were examined by RP-HPLC analysis (reverse phase HPLC, Agilent Technologies 1200 Series). The determination of the toxophore released enabled the determination of the half-life $t_{1/2}$ of the enzymatic reaction.

b: Legumain Assay

The legumain assay was conducted with recombinant human enzyme. The rhlegumain enzyme solution (catalogue

2199-CY, R&D Systems) was diluted in 50 mM Na acetate buffer/100 mM NaCl, pH 4.0 to the desired concentration and preincubated at 37° C. for 2 h. rhLegumain was then adjusted to a final concentration of 1 ng/μl in 50 mM MES buffer, 250 mM NaCl, pH 5.0. For every legumain-cleavable prodrug to be examined, a mixture was made up in a micro reaction vessel (0.5 ml, from Eppendorf). For this purpose, the substrate solution was adjusted to the desired concentration (double concentration) with 50 mM MES buffer, 250 mM NaCl, pH 5.0. For the kinetic measurement of the enzymatic reaction, 250 μl of the legumain solution were first initially charged and the enzyme reaction was started by adding 250 μl of the substrate solution (final concentration: single concentration; 3 μM). At various points in time, 50 μl samples were taken. Immediately, 100 μl of ice-cold methanol were added to this sample in order to stop the enzymatic reaction, and the sample was then frozen at −20° C. The times selected for sampling were after 0.5 h, 1 h, 3 h and 24 h. The samples were then analysed by means of RP-HPLC analysis and by LC-MS analysis. The determination of the toxophore released enabled the determination of the half-life $t_{1/2}$ of the enzymatic reaction.

As representative examples to show the legumain-mediated cleavage, the substrates produced in the legumain assay were the model compounds A and B.

Reference Example Model Compound A

N-(Pyridin-4-ylacetyl)-L-alanyl-L-alanyl-$N^1$-[(2S)-4-[{(1R)-1-[1-benzyl-4-(2,5-difluorophenyl)-1H-pyrrol-2-yl]-2,2-dimethylpropyl}(glycoloyl)amino]-1-(methylamino)-1-oxobutan-2-yl]-L-aspartamide

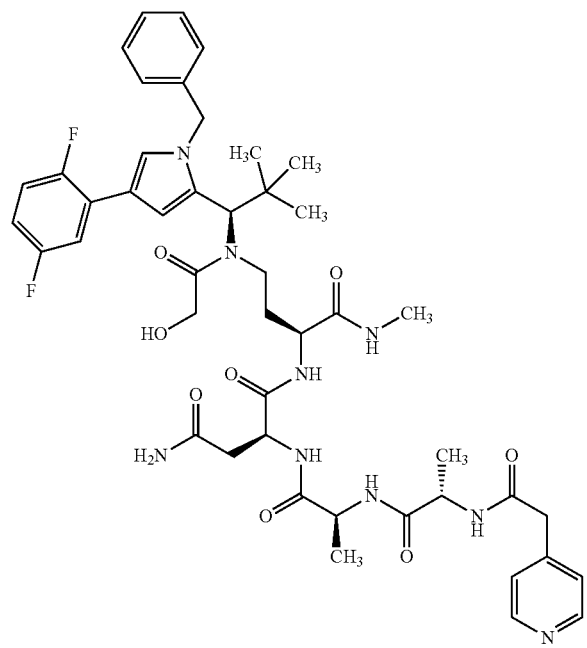 [SMILES: CNC(=O)[C@H](CCN(C(=O)CO)[C@@H](c1cc(-c2cc(F)ccc2F)cn1Cc1ccccc1)C(C)(C)C)NC(=O)[C@H](CC(N)=O)NC(=O)[C@H](C)NC(=O)[C@H](C)NC(=O)Cc1ccncc1]

First of all, trifluoroacetic acid (2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide was prepared as described in WO 2015096982 A1. Subsequently, this intermediate was used to prepare the title compound by coupling to Intermediate L103 in DMF in the presence of HATU and of N,N-diisopropylethylamine.

LC-MS (Method 1): $R_t$=0.86 min; MS (ESIpos): m/z=902 [M+H]$^+$.

Reference Example Model Compound B

N-(Pyridin-4-ylacetyl)-L-alanyl-N-methyl-L-alanyl-$N^1$-[(2S)-4-[{(1R)-1-[1-benzyl-4-(2,5-difluorophenyl)-1H-pyrrol-2-yl]-2,2-dimethylpropyl}(glycoloyl)amino]-1-(methylamino)-1-oxobutan-2-yl]-L-aspartamide

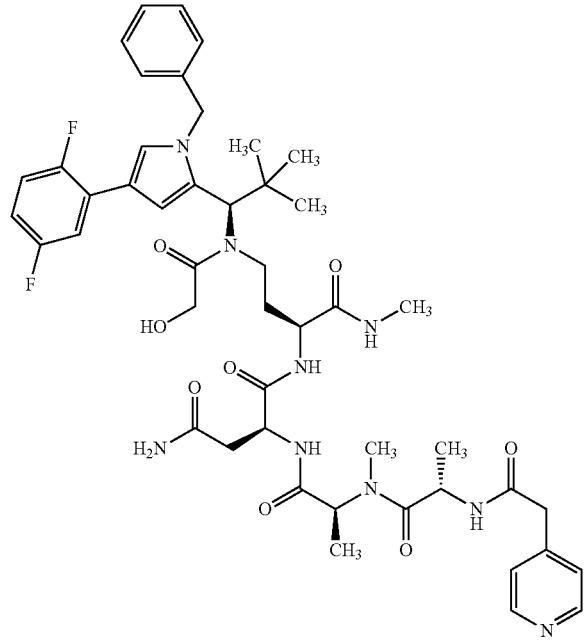 [SMILES: CNC(=O)[C@H](CCN(C(=O)CO)[C@@H](c1cc(-c2cc(F)ccc2F)cn1Cc1ccccc1)C(C)(C)C)NC(=O)[C@H](CC(N)=O)NC(=O)[C@H](C)N(C)C(=O)[C@H](C)NC(=O)Cc1ccncc1]

First of all, trifluoroacetic acid (2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide was prepared as described in WO 2015096982 A1. Subsequently, this intermediate was used to prepare the title compound by coupling to Intermediate L118 in DMF in the presence of HATU and of N,N-diisopropylethylamine.

LC-MS (Method 1): $R_t$=0.83 min; MS (ESIpos): m/z=916 [M+H]$^+$.

Model compound A was cleaved under the conditions described above for legumain to the target compound with a half-life of 0.4 h.

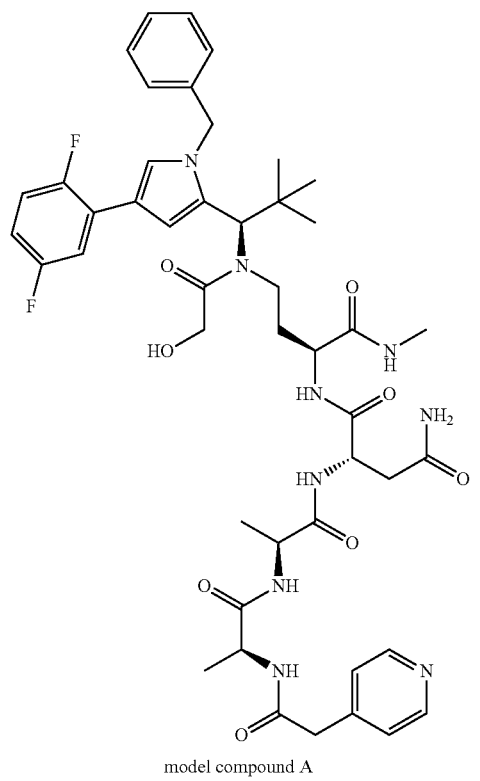

model compound A

→ legumain →

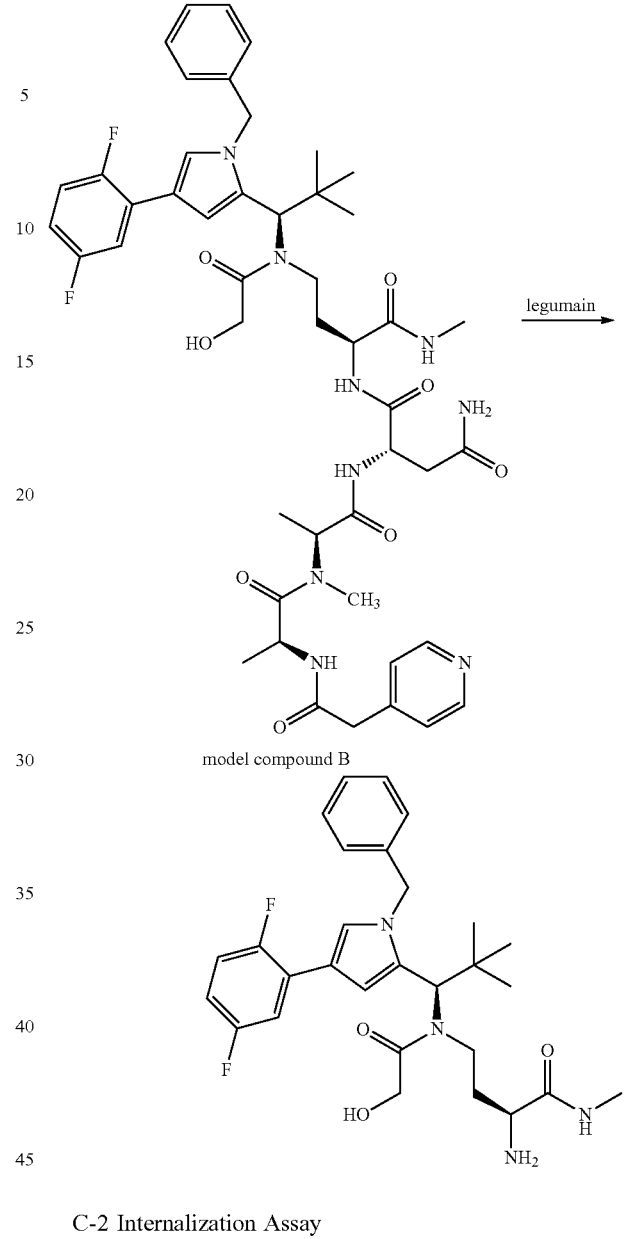

model compound B

→ legumain →

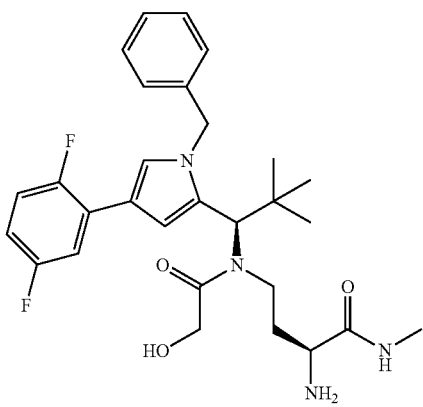

Model compound B was cleaved under the conditions described above for legumain to the target compound with a half-life of 0.5 h.

C-2 Internalization Assay

Internalization is a key process which enables specific and efficient provision of the cytotoxic payload in antigen-expressing cancer cells via antibody drug conjugates (ADC). This process is monitored via fluorescent labelling of specific antibodies and an isotype control antibody. First, the fluorescent dye was conjugated to lysines of the antibody. Conjugation was carried out using a two-fold to 10-fold molar excess of CypHer 5E mono NHS ester (Batch 357392, GE Healthcare) at pH 8.3. After the coupling, the reaction mixture was purified by gel chromatography (Zeba Spin Desalting Columns, 40K, Thermo Scientific, No. 87768; elution buffer: DULBECCO'S PBS, Sigma-Aldrich, No. D8537), to eliminate excess dye and to adjust the pH. The protein solution was concentrated using VIVASPIN 500 columns (Sartorius stedim biotec). The dye load of the antibody was determined by means of spectrophotometry analysis (from NanoDrop) and subsequent calculation $(D/P = A_{dye} \, \varepsilon_{protein}:(A_{280} - 0.16 A_{dye}) \varepsilon_{dye})$.

The dye load of the antibodies examined here and the isotype control were of a comparable order of magnitude. In cell binding assays, it was confirmed that the coupling did not lead to any change in the affinity of the antibodies.

The labelled antibodies were used for the internalization assay. Prior to the start of the treatment, cells ($2\times10^4$/well) were sown in 100 µl medium in a 96-well MTP (fat, black, clear bottom No 4308776, from Applied Biosystems). After 18 h of incubation at 37° C./5% $CO_2$, the medium was replaced and labelled antibodies were added in different concentrations (10, 5, 2.5, 1, 0.1 µg/ml). The same treatment protocol was applied to the labelled isotype control (negative control). The chosen incubation times were 0 h, 0.25 h, 0.5 h, 1 h, 1.5 h, 2 h, 3 h, 6 h and 24 h. The fluorescence measurement was carried out using the InCellAnalyzer 1000 (from GE Healthcare). This was followed by kinetic evaluation via measurement of the parameters granule counts/cell and total granule intensity/cell.

Following binding to the receptor, antibodies were examined for their internalization capacity. For this purpose, cells with different receptor expression levels were chosen. A target-mediated specific internalization was observed with the antibodies, whereas the isotype control showed no internalization.

C-2b Internalization Assay with Suspended Cells

Coupling of the fluorescent dye was carried out as described under C2. The antigen to be examined is expressed by haematopoietic suspension cells; consequently, the internalization was examined in an FACS-based internalization assay.

Cells having different target expression levels were examined—The cells ($5\times10^4$/well) were sown in a 96-MTP (Greiner bio-one, CELLSTAR, 650 180, U-bottom) in a total volume of 100 µl. After addition of the target-specific antibody in a final concentration of 10 µg/ml, the batches were incubated at 37° C. for different periods of time (1 h, 2 h, 6 h, in triplicate). The isotype control was treated under identical conditions. A parallel batch was treated and incubated constantly at 4° C. (negative control). FACS analysis was carried out using the Guava flow cytometer (Millipore). Kinetic evaluation was carried out by measuring the fluorescence intensity, and evaluation took place using the guavaSoft 2.6 software (Millipore). For the targets and target-specific antibodies described here, a significant and specific internalization was detected in various cells; the isotype controls showed no internalization.

C-2c Co-Localization Assays of the Anti-CD123 Antibodies

Owing to the linker, the active metabolite of the antibody-drug conjugate is generated by lysosomal degradation. Accordingly, intracellular trafficking after internalization has taken place is of essential importance. Studies about the co-localization of the antibody using labels specific for the lysosomal organelle (e.g. surface molecules or small GTPases) allow the selection of antibodies having the desired profile. To this end, target-positive cells ($5\times10^4$/well) in a total volume of 100 µl were sown into a 96-MTP (Greiner bio-one, CELLSTAR, 650 180, U-bottom). Following addition of the CypHer5E-labelled anti-target antibody (final concentration 20 µg/ml), the batches (duplicates per point in time) were incubated at 37° C. for 30 min, 2 h and 6 h in an incubator (5% $CO_2$). 30 min prior to the end of the chosen incubation time, the lysosome-specific label was added to the batches to be examined. The lysosomes were stained with CytoPainter LysoGreen indicator reagent (final concentration 1:2000; abcam, ab176826). After incubation, 200 µl of ice-cold FACS buffer (DULBECCO'S PBS, Sigma-Aldrich, No. D8537+3% FBS heat inactivated FBS, Gibco, No. 10500-064) were added and the cell suspension was centrifuged at 400×g and 4° C. for 5 min. The cell pellet was resuspended in 300 µl ice-cold FACS buffer and centrifuged again (4 min, 400×g at 4° C.). After centrifugation, the supernatant was discarded and the cell pellet was taken up in 30 µl of ice-cold FACS buffer. The samples were then immediately subjected to FACS/image analysis (FlowSight amnis, Millipore). Co-localization was evaluated using a special software (co-localization software IDEAS Application v6.1). Table 3 summarizes the results from this assay in an exemplary manner for anti-CD123 antibodies.

TABLE 3

| Example | Co-localization [%] |
|---|---|
| TPP-9476 | 29 |
| TPP-8987 | 28 |
| TPP-8988 | 41 |
| TPP-6013 | 43 |
| 7G3 | 10 |
| Isotype control | 0.2 |

The humanized antibodies TPP-9476 and TPP-8987 exhibit a markedly improved profile compared to the parental murine antibody.

C-3 In Vitro Tests for Determining Cell Permeability

The cell permeability of a substance can be investigated by means of in vitro testing in a flux assay using Caco-2 cells [M. D. Troutman and D. R. Thakker, Pharm. Res. 20 (8), 1210-1224 (2003)]. For this purpose, the cells were cultured for 15-16 days on 24-well filter plates. For the determination of permeation, the respective test substance was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Böblingen, Germany) using reverse phase columns. The HPLC system was coupled via a Turbo Ion Spray Interface to a Triple Quadropole mass spectrometer API 4000 (AB SCIEX Deutschland GmbH, Darmstadt, Germany). The permeability was evaluated on the basis of a Papp value, which was calculated using the formula published by Schwab et al. [D. Schwab et al., J. Med. Chem. 46, 1716-1725 (2003)]. A substance was classified as actively transported when the ratio of $P_{app}$ (B-A) to $P_{app}$ (A-B) (efflux ratio) was >2 or <0.5.

Of critical importance for toxophores which are released intracellularly is the permeability from B to A [$P_{app}$ (B-A)] and the ratio of $P_{app}$ (B-A) to Papp (A-B) (efflux ratio): The lower this permeability, the slower the active and passive transport processes of the substance through the monolayer of Caco-2 cells, so that the substance, following intracellular release, remains in the cell for longer. As a consequence of the metabolite remaining in the cell for longer, the probability of interaction with the biochemical target (here: kinesin spindle protein KSP/Eg5) is increased, resulting in an improved cytotoxic action.

Table 4 below sets out permeability data for representative working examples from this assay:

TABLE 4

| Working Example | $P_{app}$ (B-A) [nm/s] | Efflux ratio |
|---|---|---|
| M1 | 2.7 | 1.6 |
| R3M | 213 | 16 |

The metabolite M1, which can be formed from the binder-drug conjugates according to the invention, exhibits both reduced transport from the cell and a reduced efflux ratio compared with the reference metabolite R3M, which can be formed from the binder-drug conjugates of Reference Examples 2.

C-4 In Vitro Tests for Determining the Substrate Properties for P-Glycoprotein (P-Gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., J. Clin. Invest. 96, 1698-1705 (1995)]. For this purpose, the LLC-PK1 cells or L-MDR1 cells were cultured on 96-well filter plates for 3-4 days. For determination of the permeation, the respective test substance, alone or in the presence of an inhibitor (such as ivermectin or verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to an API 3000 triple quadropole mass spectrometer (Applied Biosystems Applera, Darmstadt, Germany). The permeability was evaluated on the basis of a $P_{app}$ value, which was calculated using the formula published by Schwab et al. [D. Schwab et al., J. Med. Chem. 46, 1716-1725 (2003)]. A substance was classified as P-gp substrate when the efflux ratio of $P_{app}$ (B-A) to $P_{app}$ (A-B) was >2.

As further criteria for the evaluation of the P-gp substrate properties, the efflux ratios in L-MDR1 and LLC-PK1 cells or the efflux ratio in the presence or absence of an inhibitor may be compared. If these values differ by a factor of more than 2, the substance in question is a P-gp substrate.

C-5 Pharmacokinetics

After i.v. administration of 5 mg/kg of Example 2c-9476 (DAR 6.3) and Example 2c-9476 (DAR 3.4) in male Wistar rats, the plasma concentrations of the ADCs were measured by ELISA and the pharmacokinetic parameters such as clearance (CL), area under the curve (AUC) and half-life ($t_{1/2}$) were calculated.

Table 5 summarizes the pharmacokinetic parameters of Example 2c-9476 with DAR 6.3 and DAR 3.4.

TABLE 5

| Example | | 2c-9476C | 2c-9476D |
|---|---|---|---|
| DAR | | 3.4 | 6.3 |
| Species | | Rat | Rat |
| Strain | | Wistar | Wistar |
| Sex | | male | male |
| Administration | | iv bolus | iv bolus |
| Dose admin | [mg/kg] | 5.0 | 5.0 |
| $AUC_{normal}$ | [kg * h/l] | 4897 | 4069 |
| AUC | [mg *h/l] | 24484 | 20343 |
| $Cl_{matrix}$ | [ml/h/kg] | 0.20 | 0.25 |
| Vss | [l/kg] | 0.063 | 0.069 |
| MRT | [h] | 306 | 281 |
| $t_{1/2}$ | [h] | 229 | 219 |

In this exploratory PK study on rats, for both examples a typical IgG profile was observed following i.v. administration. No significant differences were observed between Example 2c-9476 with DAR 6.3 and Example 2c-9476 with DAR 3.4.

Analysis for Quantification of the ADCs Used

The antibody part of the ADCs was determined using a ligand binding assay (ELISA) as total IgG concentration in plasma samples and tumour lysates. Here, the sandwich ELISA format was used. This ELISA had been qualified and validated for the determination in plasma and tumour samples. The ELISA plates were coated with anti-human goat IgG Fc antibodies. After incubation with the sample, the plates were washed and incubated with a detector conjugate of simian anti-human IgG(H+L) antibody and horseradish peroxidase (HRP). After a further washing step, the HRP substrate was added to OPD and the colour development was monitored via absorption at 490 nm. Standard samples having a known IgG concentration were fitted using a 4-parameter equation. Within the lower (LLOQ) and upper (ULOQ) quantification limits, the unknown concentrations were determined by interpolation.

C5a: Identification of the ADC Metabolites after Internalization In Vitro

Description of the Method:

Internalization studies with immunoconjugates are carried out to analyse metabolites formed intracellularly. To this end, human lung tumour cells NCI H292 ($3 \times 10^5$/well) are sown in 6-well plates and incubated overnight (37° C., 5% $CO_2$). The cells are treated with 10 µg/ml (66 nM) of the ADC to be examined. Internalization was carried out at 37° C. and 5% $CO_2$. Cell samples are taken for further analysis at various times (0, 4, 24, 48, 72 h). First of all, the supernatants (about 5 ml) are harvested and, after centrifugation (2 min, RT, 1000 rpm Heraeus Variofuge 3.0R), stored at −80° C. The cells are washed with PBS and detached with Accutase, and the cell number is determined. After another washing, a defined number of cells ($2 \times 10^5$) is treated with 100 ml of lysis buffer (Mammalian Cell Lysis Kit (Sigma MCL1) and incubated with continuous shaking (Thermomixer, 15 min, 4° C., 650 rpm) in Protein LoBind tubes (Eppendorf Cat. No. 0030 108.116). After the incubation, the lysate is centrifuged (10 min, 4° C., 12000 g, eppendorf 5415R) and the supernatant is harvested. The supernatant obtained is stored at −80° C. All samples are then analysed as follows.

For workup of 50 µl of culture supernatant/cell lysate, 150 µl of precipitation reagent (methanol) are added and the mixture is shaken for 10 seconds. The precipitation reagent contains an internal standard (ISTD) in a suitable concentration (generally in the range of 20-100 µg/l). After centrifugation at 1881 g for 10 minutes, the supernatant is transferred into an autosampler vial, made up with 300 µl of a buffer matched to the eluent and shaken again and centrifuged at 1881 g for 10 min.

The cell lysate and supernatant samples are finally analysed using the HPLC-coupled AP16500 triple-quadrupole mass spectrometer from AB SCIEX Deutschland GmbH.

For calibration, blank lysate or blank supernatant is admixed with appropriate concentrations (0.1-1000 µg/l). The detection limit (LLOQ) is about 0.2 µg/l.

Quality controls for testing validity contain 4 and 40 µg/l.

C5b: Identification of the ADC Metabolites In Vivo

After i.v. administration of 3-30 mg/kg of different ADCs, the plasma and tumour concentrations of the ADCs and any metabolites occurring can be measured, and the pharmacokinetic parameters such as clearance (CL), area under the curve (AUC) and half-times ($t_{1/2}$) can be calculated.

Analysis for Quantification of the Potential Metabolites

The analysis of the compounds in the plasma, tumour, liver and kidney follows after precipitation of the proteins with generally methanol by high-pressure liquid chromatography (HPLC) coupled to a triple-quadrupole mass spectrometer (MS).

For workup of 50 µl of plasma, 150 µl of precipitation reagent (generally methanol) are added and the mixture is shaken for 10 sec. The precipitation reagent contains an internal standard (ISTD) in a suitable concentration (generally in the range of 20-100 µg/l). After centrifugation at 1881 g for 10 minutes, the supernatant is transferred into an autosampler vial, made up with 300 µl of a buffer matched to the eluent and shaken again.

In the workup of tumour or organ material, the particular material is admixed with 3-20 times the amount of extraction buffer. The extraction buffer contains 50 ml of Tissue Protein Extraction Reagent (Pierce, Rockford, Ill.), two pellets of Complete-Protease-Inhibitor-Cocktail (Roche Diagnostics GmbH, Mannheim, Germany) and phenylmethylsulfonyl fluoride (Sigma, St. Louis, Mo.) in a final concentration of 1 mM. According to the tissue type (hard: tumour; soft: liver, kidney), the lysis and homogenization programme of the Prescellys 24 lysis and homogenization system (Bertin Technologies) is selected. The homogenized samples are left to stand at 4° C. overnight. 50 µl of the homogenizate are transferred into an autosampler vial and made up with 150 µl of methanol including ISTD, agitated for 10 sec and then left to stand for 5 min. After adding 300 µl of ammonium acetate buffer (pH 6.8) and agitating briefly, the sample is centrifuged at 1881 g for 10 minutes.

For calibration, plasma for plasma samples and corresponding blank matrix for tissue samples is admixed with concentrations of 0.6-1000 µg/l. According to the sample type or tissue type, the detection limit (LOQ) is between 1 and 20 µg/l.

The plasma and matrix samples are finally analysed using the HPLC-coupled AP14500 triple-quadrupole mass spectrometer from AB SCIEX Deutschland GmbH.

Quality controls for testing validity contain 4, 40 and 400 µg/l.

Table 6 shows metabolite concentrations in the MOLM-13 xenograft mouse model measured in -tumour, -liver, -kidney and plasma 24 h after administration of 5 mg/kg of the ADC from Example 2c-9476 (n=3). The metabolite measured was: metabolite M1. n.c.=not calculated; LOQ: limit of quantification

TABLE 6

|  |  | Metabolite M1 MW (µg/l) | Metabolite M1 SD (µg/l) | LOQ (µg/l) |
| --- | --- | --- | --- | --- |
| Tumour | Example 2c-9476B | 59.5 | 0.3 | 2.0-20.0 |
| Liver | Example 2c-9476B | <LOQ | n.c. | 2.5 |
| Kidney | Example 2c-9476B | 10.9 | 6.5 | 5.0 |
| Plasma | Example 2c-9476B | <LOQ | n.c. | 1.0 |

Administration of the ADC Example 2c-9476 according to the invention having a legumain-cleavable linker lead to a markedly selective enrichment of the active compound at the target tissue (tumour) compared to other, healthy organs/tissues.

C-6 Activity Test In Vivo

The activity of the conjugates according to the invention was tested in vivo, for example, using xenograft models. The person skilled in the art is familiar with methods in the prior art which allow the activity of the compounds according to the invention to be tested (see, for example, WO 2005/081711; Polson et al., Cancer Res. 2009 Mar. 15; 69(6): 2358-64). To this end, a tumour cell line expressing the target molecule of the binder was inoculated into rodents (for example mice). A conjugate according to the invention, an isotype antibody control conjugate, a control antibody or isotonic saline was then administered to the inoculated animals. The administration took place once or more than once. Following an incubation time of several days, the size of the tumour was determined by comparing conjugate-treated animals and the control group. The conjugate-treated animals displayed a smaller tumour size.

C-6a. Growth Inhibition/Regression of Experimental Tumours in the Mouse

Human tumour cells which express the antigen for the antibody-drug conjugate are inoculated subcutaneously into the flank of immunosuppressed mice, for example NMRi nude or SCID mice. 1-10 million cells are detached from the cell culture, centrifuged and resuspended in medium or medium/matrigel. The cell suspension is injected under the skin of the mouse.

Within a few days, a tumour grows. Treatment is commenced after the tumour is established, at a tumour size of approximately 40 mm$^2$. To examine the effect on larger tumours, treatment may be initiated only at a tumour size of 50-100 mm$^2$.

Treatment with APDCs and ADCs is carried out via the intravenous (i.v.) route into the tail vein of the mouse. The ADC is administered in a volume of 5 ml/kg.

The treatment protocol depends on the pharmacokinetics of the antibody. With the conjugates according to the invention, treatment is effected once per week for 2 or 3 weeks as the standard. For a quick assessment, a protocol with a single treatment may also be suitable. However, the treatment may also be continued, or a second cycle of three treatment days may follow at a later time.

As standard, 8 animals are used per treatment group. In addition to the groups to which the active substances are administered, one group is treated as control group only with the buffer, according to the same protocol.

During the experiment, the tumour area is measured regularly in two dimensions (length/width) using a caliper. The tumour area is determined as length×width. The ratio of the mean tumour area of the treatment group to that of the control group is stated as T/C area.

When, after the end of the treatment, all groups of the experiment are terminated at the same time, the tumours can be removed and weighed. The ratio of the mean tumour weights of the treatment group to that of the control group is stated as T/C weight.

C-6b. Efficacy of the ADCs According to the Invention in Various Tumour Models

The tumour cells (e.g. NCI-H292, REC-1, MOLM-13 and MV-4-11 are inoculated subcutaneously into the flank of female NMRI-nude mice (Janvier). At a tumour size of ~40 mm$^2$, intravenous treatment is effected with the antibody-drug conjugate. After the treatment, monitoring of the tumour growth continues if appropriate.

The treatment with the ADCs according to the invention leads to a distinct and in some cases long-lasting inhibition of tumour growth compared to the control group and the conjugated isotype control antibody. Table 7 shows the T/C values determined for tumour area on the respective day of the end of the experiment, calculated from the start of treatment.

TABLE 7

| Example | Antigen | Tumour model | Dose | Dose scheme | T/C area |
|---|---|---|---|---|---|
| 2k-7007 | TWEAKR | NCI-H292 (human lung carcinoma) | 5 mg/kg | Q7dx3 | 0.09 (day 25) |
| 2x-9574 | CXCR5 | REC-1 (human mantle cell lymphoma) | 10 mg/kg | Q7dx3 | 0.20 (day 24) |
| 2c-9476D | CD123 | MOLM-13 (human acute myeloid leukaemia) | 5 mg/kg | Q7dx2 | 0.15 (day 17) |
| 2c-9476D | CD123 | MV-4-11 (human acute myeloid leukaemia) | 5 mg/kg | Q7dx2 | 0.16 (day 18) |

The invention claimed is:
1. An antibody-drug conjugate of formula (I):

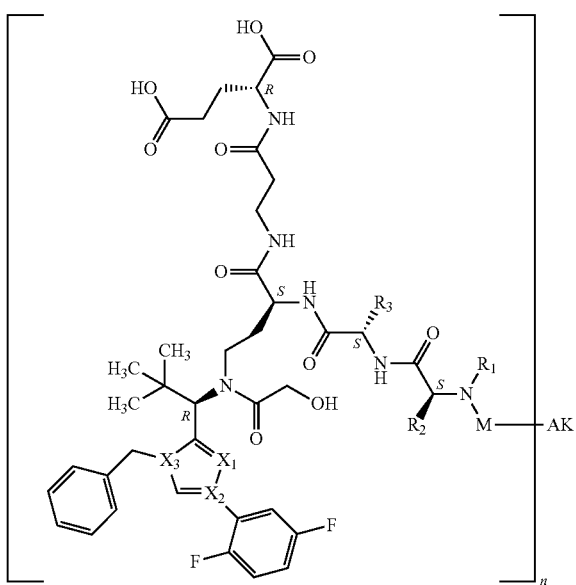

formula (I)

or a pharmaceutically acceptable salt thereof,
wherein:
AK is an antibody or an antigen-binding antibody fragment thereof;
n is a number from 1 to 50;
$X_1$ is N,
$X_2$ is N and
$X_3$ is C;
or
$X_1$ is N,
$X_2$ is C and
$X_3$ is N;
or
$X_1$ is CH or CF,
$X_2$ is C and
$X_3$ is N;
or
$X_1$ is NH,
$X_2$ is C and
$X_3$ is C;
or
$X_1$ is CH,
$X_2$ is N and
$X_3$ is C;
$R^1$ is methyl;
$R^2$ is methyl, ethyl, —CH$_2$—CH(CH$_3$)$_2$, —CH$_2$—C(=O)OH or isopropyl;
$R^3$ is methyl, ethyl, —CH$_2$—CH(CH$_3$)$_2$ or —CH$_2$—C(=O)—NH$_2$; and
M is the group
—C(=O)—CH(CH$_3$)—NH—C(=O)—CH$_2$—NH—C(=O)—CH$_2$—CH(##)-COOH,
—C(=O)—CH(CH$_3$)—NH—C(=O)—CH$_2$—NH—C(=O)—CH(##)—CH$_2$—COOH,
—C(=O)—CH(CH$_3$)—NH—C(=O)—CH$_2$—W,
—C(=O)—CH$_2$—NH—C(=O)—CH$_2$—CH(##)-COOH,
—C(=O)—CH$_2$—NH—C(=O)—CH(##)—CH$_2$—COOH,
—C(=O)—CH$_2$—W,
—C(=O)—CH(CH$_3$)—NH—C(=O)—(CH$_2$)$_{2-8}$—C(=O)-###,
—C(=O)—(CH$_2$)$_3$—C(=O)-###,
—C(=O)—CH(CH$_3$)—NH—C(=O)—(CH$_2$)$_5$—W,
—C(=O)—CH(CH$_3$)—NH—C(=O)—(CH$_2$)-##, or
—C(=O)—CH(CH$_3$)—NH—C(=O)—(CH$_2$—CH$_2$—O)$_{1-8}$—(CH$_2$)$_2$—NH—C(=O)—CH$_2$-##;
wherein:
\# represents the bond to —NR$^1$—,
W is the group:

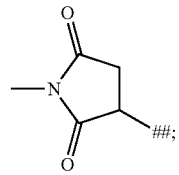

\#\# represents the bond to a sulfur atom of a cysteine side-chain of the antibody or antigen-binding antibody fragment thereof; and
\#\#\# represents the bond to a nitrogen atom of a lysine side-chain of the antibody or antigen-binding antibody fragment thereof,
wherein the antibody or antigen-binding antibody fragment binds to CD123.

2. The antibody-drug conjugate of claim 1, or a pharmaceutically acceptable salt thereof,
wherein:
$X_1$ is CH,
$X_2$ is C,
$X_3$ is N;
$R^1$ is methyl;
$R^2$ is methyl, —CH$_2$—CH(CH$_3$)$_2$, —CH$_2$—C(=O)OH or isopropyl;
$R^3$ is methyl, —CH$_2$—CH(CH$_3$)$_2$ or —CH$_2$—C(=O)—NH$_2$; and
M is the group:
—C(=O)—CH(CH$_3$)—NH—C(=O)—CH$_2$—NH—C(=O)—CH$_2$—CH(##)-COOH,
—C(=O)—CH(CH$_3$)—NH—C(=O)—CH$_2$—NH—C(=O)—CH(##)—CH$_2$—COOH,
—C(=O)—CH(CH$_3$)—NH—C(=O)—CH$_2$—W,
—C(=O)—CH$_2$—NH—C(=O)—CH$_2$—CH(##)-COOH,
—C(=O)—CH$_2$—NH—C(=O)—CH(##)—CH$_2$—COOH,
—C(=O)—CH$_2$—W,
—C(=O)—CH(CH$_3$)—NH—C(=O)—(CH$_2$)$_3$—C(=O)-###,
—C(=O)—(CH$_2$)$_3$—C(=O)-###,
—C(=O)—CH(CH$_3$)—NH—C(=O)—(CH$_2$)$_5$—W,
—C(=O)—CH(CH$_3$)—NH—C(=O)—(CH$_2$)-##, or
—C(=O)—CH(CH$_3$)—NH—C(=O)—(CH$_2$—CH$_2$—O)$_4$—(CH$_2$)$_2$—NH—C(=O)—CH$_2$-##.

3. The antibody-drug conjugate of claim 1, or a pharmaceutically acceptable salt thereof, wherein:
$R^2$ is methyl;
$R^3$ is methyl, —CH$_2$—CH(CH$_3$)$_2$, or —CH$_2$—C(=O)—NH$_2$;

M is the group
—C(=O)—CH(CH₃)—NH—C(=O)—CH₂—NH—C(=O)—CH₂—CH(##)-COOH,
—C(=O)—CH(CH₃)—NH—C(=O)—CH₂—NH—C(=O)—CH(##)—CH₂—COOH,
—C(=O)—CH(CH₃)—NH—C(=O)—(CH₂)₃—C(=O)-###;
—C(=O)—CH(CH₃)—NH—C(=O)—(CH₂)₅—W,
—C(=O)—CH(CH₃)—NH—C(=O)—(CH₂)-##, or
—C(=O)—CH(CH₃)—NH—C(=O)—(CH₂—CH₂—O)₄—(CH₂)₂—NH—C(=O)—CH₂-##.

4. The antibody-drug conjugate of claim 1, or a pharmaceutically acceptable salt thereof, wherein:
R² is methyl;
R³ is —CH₂—C(=O)—NH₂;
M is the group:
—C(=O)—CH(CH₃)—NH—C(=O)—(CH₂)₃—C(=O)-###; or
—C(=O)—CH(CH₃)—NH—C(=O)—(CH₂)₅—W.

5. The antibody-drug conjugate of claim 1, or a pharmaceutically acceptable salt thereof, wherein:
n is a number from 1 to 20;
R² is methyl;
R³ is —CH₂—C(=O)—NH₂;
M is the group
—C(=O)—CH(CH₃)—NH—C(=O)—(CH₂)₃—C(=O)-###.

6. The antibody-drug conjugate of claim 1, or a pharmaceutically acceptable salt thereof, wherein the antibody-drug conjugate has a structure selected from the group consisting of

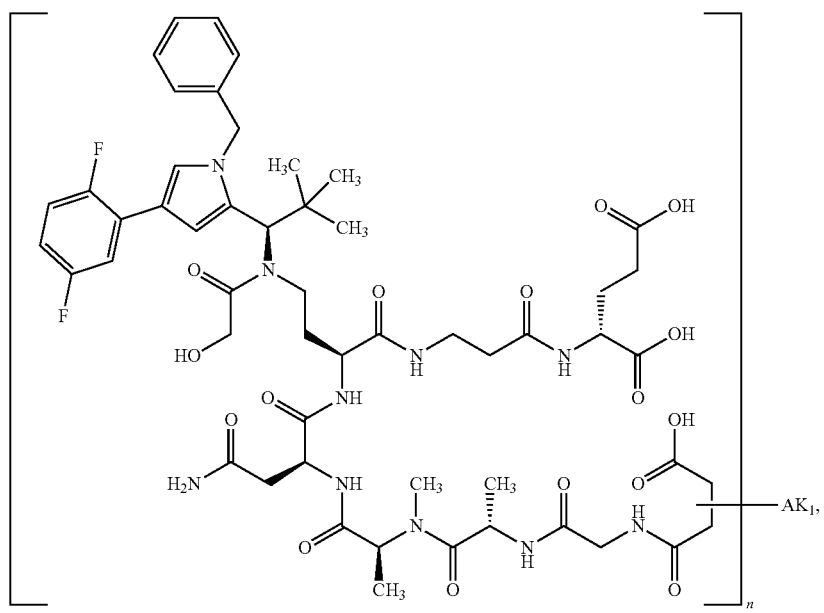

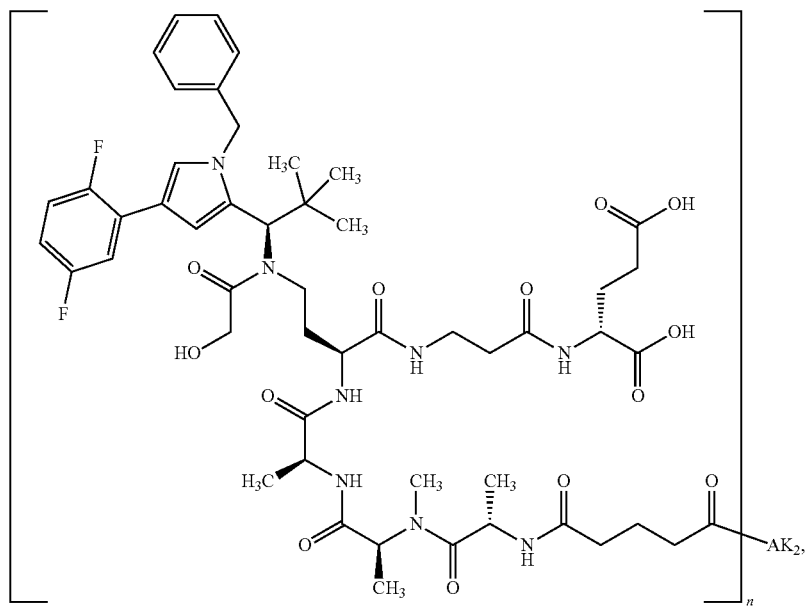

-continued
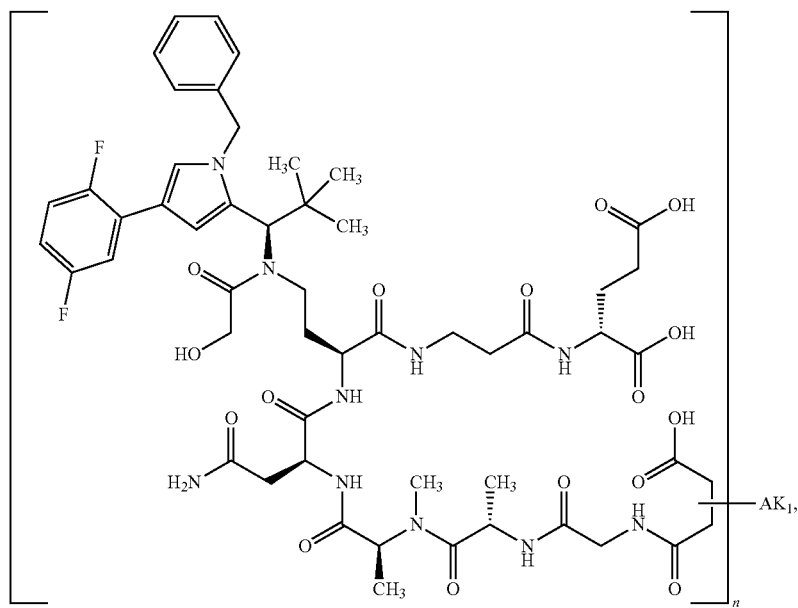
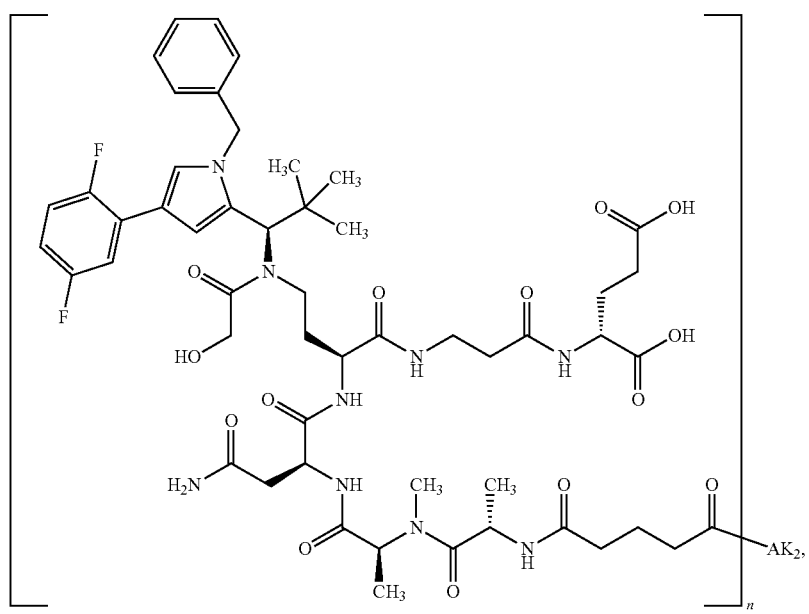

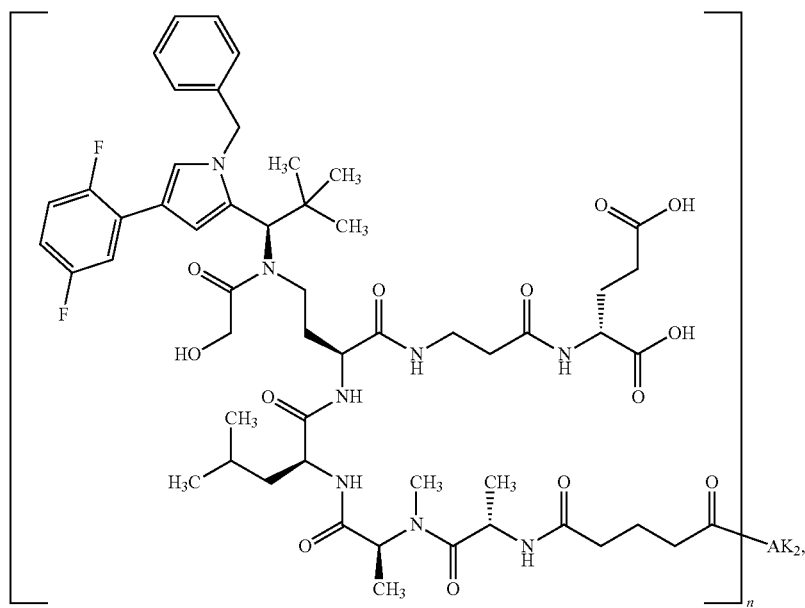
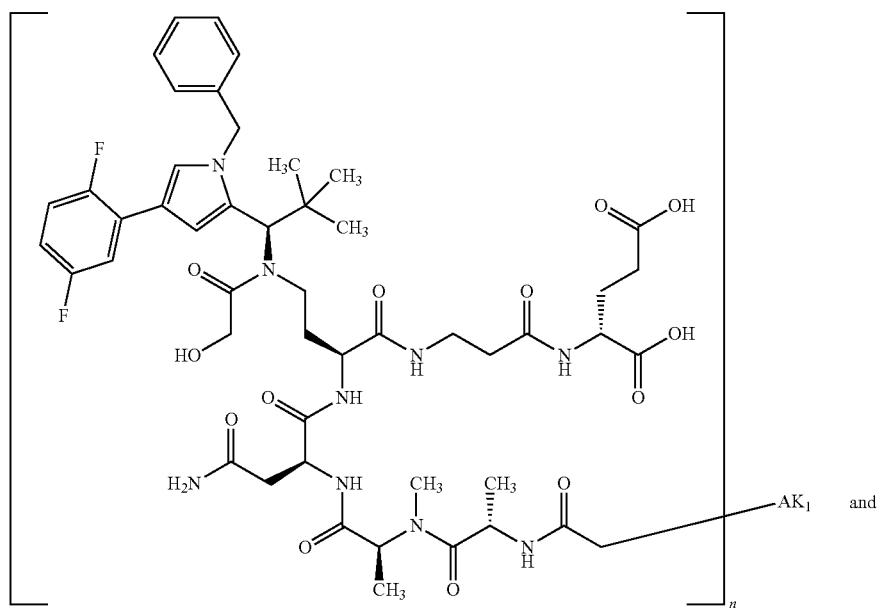

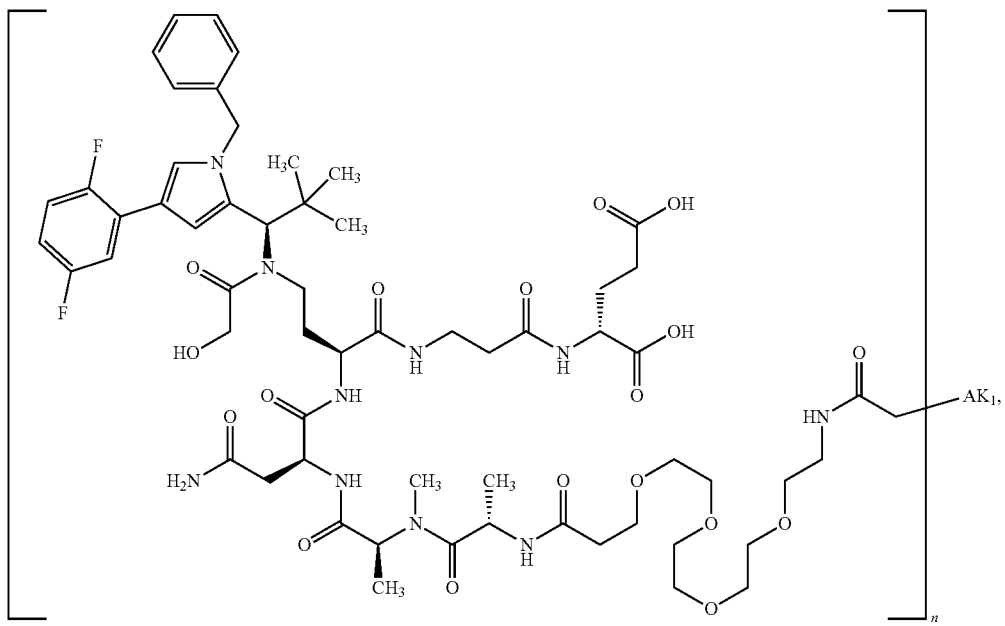

wherein
AK1 is the antibody or antigen-binding fragment thereof, which is attached via a sulfur atom of a cysteine side-chain,
AK2 is the antibody or antigen-binding fragment thereof, which is attached via a nitrogen atom of a lysine side-chain, and
n is a number from 1 to 50.

7. The antibody-drug conjugate of claim 6, or a pharmaceutically acceptable salt thereof, wherein n is a number from 1 to 20.

8. The antibody-drug conjugate of claim 7, a pharmaceutically acceptable salt thereof, wherein n is a number from 1 to 8.

9. The antibody-drug conjugate of claim 8, or a pharmaceutically acceptable salt thereof, wherein n is a number from 4 to 8.

10. The antibody-drug conjugate of claim 1, or a pharmaceutically acceptable salt thereof, wherein the antibody or the antigen-binding antibody fragment thereof, after binding to CD123, is internalized by the target cell through the binding.

11. A pharmaceutical composition comprising at least one antibody-drug conjugate of claim 1, or a pharmaceutically acceptable salt thereof, in combination with an inert, non-toxic, pharmaceutically suitable auxiliary.

12. The antibody-drug conjugate of claim 1, wherein the antibody or antigen-binding antibody fragment comprises a variable heavy chain comprising the variable CDR1 sequence of the heavy chain, as shown in SEQ ID NO: 82, the variable CDR2 sequence of the heavy chain, as shown in SEQ ID NO: 83, and the variable CDR3 sequence of the heavy chain, as shown in SEQ ID NO: 84; and a variable light chain comprising the variable CDR1 sequence of the light chain, as shown in SEQ ID NO: 86, the variable CDR2 sequence of the light chain, as shown in SEQ ID NO: 87, and the variable CDR3 sequence of the light chain, as shown in SEQ ID NO: 88.

13. The antibody-drug conjugate of claim 12, wherein the variable heavy chain comprises SEQ ID NO: 81 and the variable light chain comprises SEQ ID NO: 85.

14. The antibody-drug conjugate of claim 12, wherein the antibody or antigen-binding fragment comprises a heavy chain comprising SEQ ID NO: 89 and a light chain comprising SEQ ID NO: 90.

15. The antibody-drug conjugate of claim 6, or a pharmaceutically acceptable salt thereof, wherein the antibody-drug conjugate has the structure:

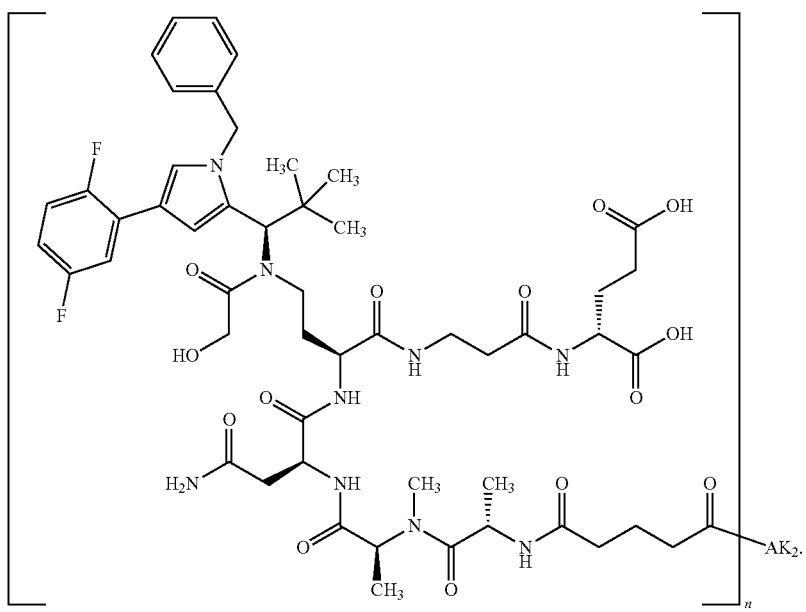

16. The antibody-drug conjugate of claim 15, wherein the antibody or antigen-binding antibody fragment comprises a variable heavy chain comprising the variable CDR1 sequence of the heavy chain, as shown in SEQ ID NO: 82, the variable CDR2 sequence of the heavy chain, as shown in SEQ ID NO: 83, and the variable CDR3 sequence of the heavy chain, as shown in SEQ ID NO: 84; and a variable light chain comprising the variable CDR1 sequence of the light chain, as shown in SEQ ID NO: 86, the variable CDR2 sequence of the light chain, as shown in SEQ ID NO: 87, and the variable CDR3 sequence of the light chain, as shown in SEQ ID NO: 88.

17. The antibody-drug conjugate of claim 16, wherein the variable heavy chain comprises SEQ ID NO: 81 and the variable light chain comprises SEQ ID NO: 85.

18. The antibody-drug conjugate of claim 16, wherein the antibody or antigen-binding fragment comprises a heavy chain comprising SEQ ID NO: 89 and a light chain comprising SEQ ID NO: 90.

19. The antibody-drug conjugate of claim 6, or a pharmaceutically acceptable salt thereof, wherein the antibody-drug conjugate has the structure:

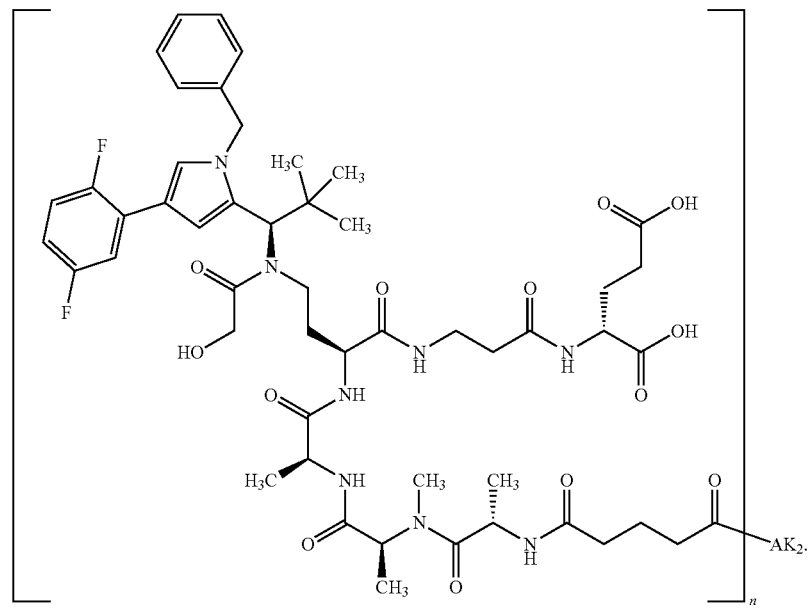

20. The antibody-drug conjugate of claim 19, wherein the antibody or antigen-binding antibody fragment comprises a variable heavy chain comprising the variable CDR1 sequence of the heavy chain, as shown in SEQ ID NO: 82, the variable CDR2 sequence of the heavy chain, as shown in SEQ ID NO: 83, and the variable CDR3 sequence of the heavy chain, as shown in SEQ ID NO: 84; and a variable light chain comprising the variable CDR1 sequence of the light chain, as shown in SEQ ID NO: 86, the variable CDR2 sequence of the light chain, as shown in SEQ ID NO: 87, and the variable CDR3 sequence of the light chain, as shown in SEQ ID NO: 88.

21. The antibody-drug conjugate of claim 20, wherein the variable heavy chain comprises SEQ ID NO: 81 and the variable light chain comprises SEQ ID NO: 85.

22. The antibody-drug conjugate of claim 20, wherein the antibody or antigen-binding fragment comprises a heavy chain comprising SEQ ID NO: 89 and a light chain comprising SEQ ID NO: 90.

23. The antibody-drug conjugate of claim 6, or a pharmaceutically acceptable salt thereof, wherein the antibody-drug conjugate has the structure:

24. The antibody-drug conjugate of claim 23, wherein the antibody or antigen-binding antibody fragment comprises a variable heavy chain comprising the variable CDR1 sequence of the heavy chain, as shown in SEQ ID NO: 82, the variable CDR2 sequence of the heavy chain, as shown in SEQ ID NO: 83, and the variable CDR3 sequence of the heavy chain, as shown in SEQ ID NO: 84; and a variable light chain comprising the variable CDR1 sequence of the light chain, as shown in SEQ ID NO: 86, the variable CDR2 sequence of the light chain, as shown in SEQ ID NO: 87, and the variable CDR3 sequence of the light chain, as shown in SEQ ID NO: 88.

25. The antibody-drug conjugate of claim 24, wherein the variable heavy chain comprises SEQ ID NO: 81 and the variable light chain comprises SEQ ID NO: 85.

26. The antibody-drug conjugate of claim 24, wherein the antibody or antigen-binding fragment comprises a heavy chain comprising SEQ ID NO: 89 and a light chain comprising SEQ ID NO: 90.

27. The antibody-drug conjugate of claim 6, or a pharmaceutically acceptable salt thereof, wherein the antibody-drug conjugate has the structure:

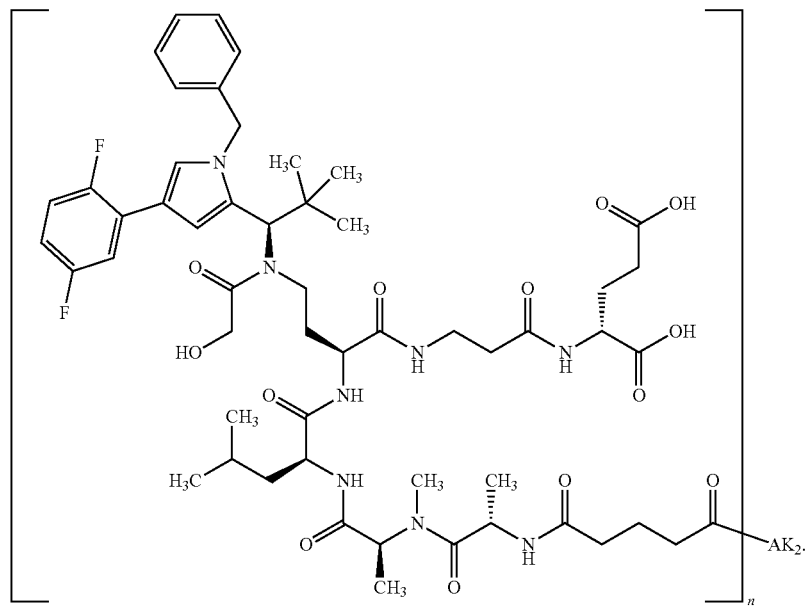

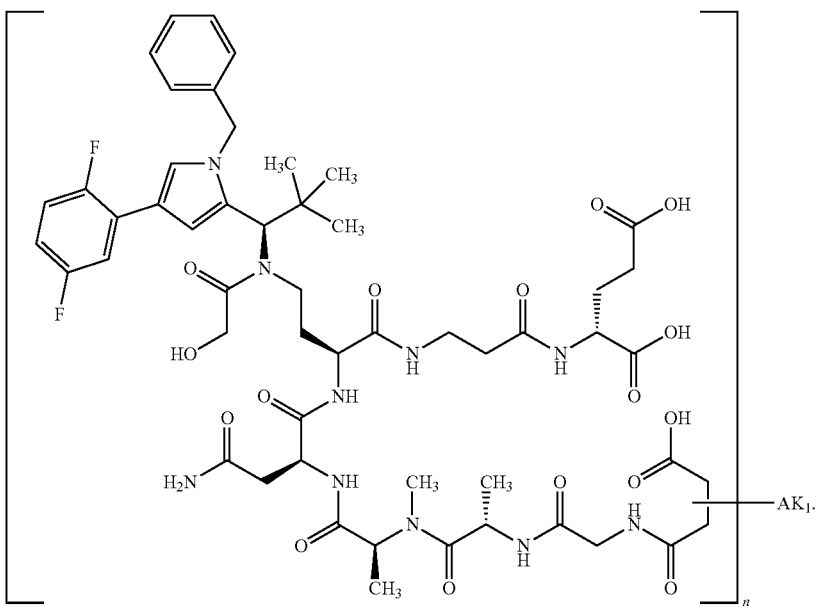

28. The antibody-drug conjugate of claim 27, wherein the antibody or antigen-binding antibody fragment comprises a variable heavy chain comprising the variable CDR1 sequence of the heavy chain, as shown in SEQ ID NO: 82, the variable CDR2 sequence of the heavy chain, as shown in SEQ ID NO: 83, and the variable CDR3 sequence of the heavy chain, as shown in SEQ ID NO: 84; and a variable light chain comprising the variable CDR1 sequence of the light chain, as shown in SEQ ID NO: 86, the variable CDR2 sequence of the light chain, as shown in SEQ ID NO: 87, and the variable CDR3 sequence of the light chain, as shown in SEQ ID NO: 88.

29. The antibody-drug conjugate of claim 28, wherein the variable heavy chain comprises SEQ ID NO: 81 and the variable light chain comprises SEQ ID NO: 85.

30. The antibody-drug conjugate of claim 28, wherein the antibody or antigen-binding fragment comprises a heavy chain comprising SEQ ID NO: 89 and a light chain comprising SEQ ID NO: 90.

31. The antibody-drug conjugate of claim 6, or a pharmaceutically acceptable salt thereof, wherein the antibody-drug conjugate has the structure:

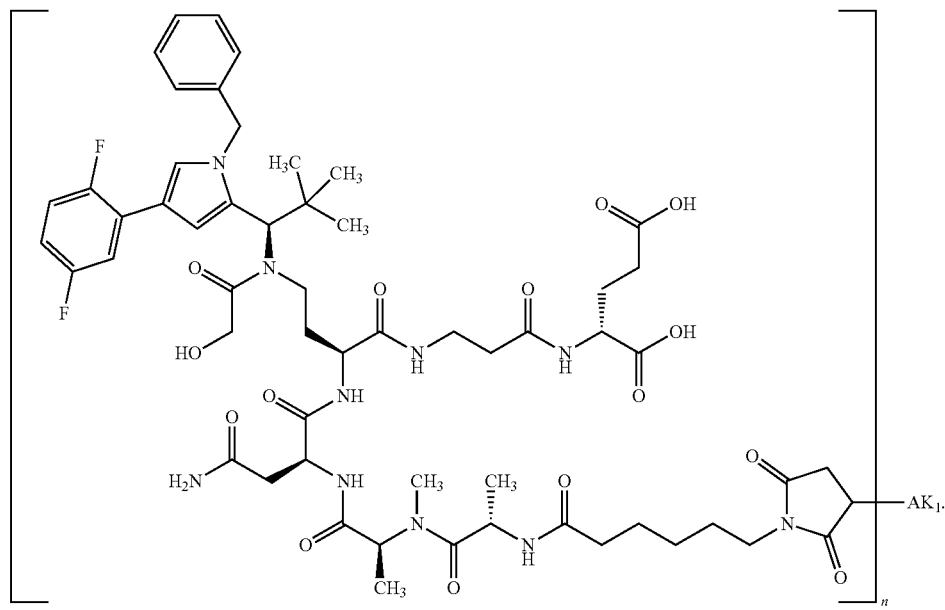

32. The antibody-drug conjugate of claim 31, wherein the antibody or antigen-binding antibody fragment comprises a variable heavy chain comprising the variable CDR1 sequence of the heavy chain, as shown in SEQ ID NO: 82, the variable CDR2 sequence of the heavy chain, as shown in SEQ ID NO: 83, and the variable CDR3 sequence of the heavy chain, as shown in SEQ ID NO: 84; and a variable light chain comprising the variable CDR1 sequence of the light chain, as shown in SEQ ID NO: 86, the variable CDR2 sequence of the light chain, as shown in SEQ ID NO: 87, and the variable CDR3 sequence of the light chain, as shown in SEQ ID NO: 88.

33. The antibody-drug conjugate of claim 32, wherein the variable heavy chain comprises SEQ ID NO: 81 and the variable light chain comprises SEQ ID NO: 85.

34. The antibody-drug conjugate of claim 32, wherein the antibody or antigen-binding fragment comprises a heavy chain comprising SEQ ID NO: 89 and a light chain comprising SEQ ID NO: 90.

35. The antibody-drug conjugate of claim 6, or a pharmaceutically acceptable salt thereof, wherein the antibody-drug conjugate has the structure:

36. The antibody-drug conjugate of claim 35, wherein the antibody or antigen-binding antibody fragment comprises a variable heavy chain comprising the variable CDR1 sequence of the heavy chain, as shown in SEQ ID NO: 82, the variable CDR2 sequence of the heavy chain, as shown in SEQ ID NO: 83, and the variable CDR3 sequence of the heavy chain, as shown in SEQ ID NO: 84; and a variable light chain comprising the variable CDR1 sequence of the light chain, as shown in SEQ ID NO: 86, the variable CDR2 sequence of the light chain, as shown in SEQ ID NO: 87, and the variable CDR3 sequence of the light chain, as shown in SEQ ID NO: 88.

37. The antibody-drug conjugate of claim 36, wherein the variable heavy chain comprises SEQ ID NO: 81 and the variable light chain comprises SEQ ID NO: 85.

38. The antibody-drug conjugate of claim 36, wherein the antibody or antigen-binding fragment comprises a heavy chain comprising SEQ ID NO: 89 and a light chain comprising SEQ ID NO: 90.

39. The antibody-drug conjugate of claim 6, or a pharmaceutically acceptable salt thereof, wherein the antibody-drug conjugate has the structure:

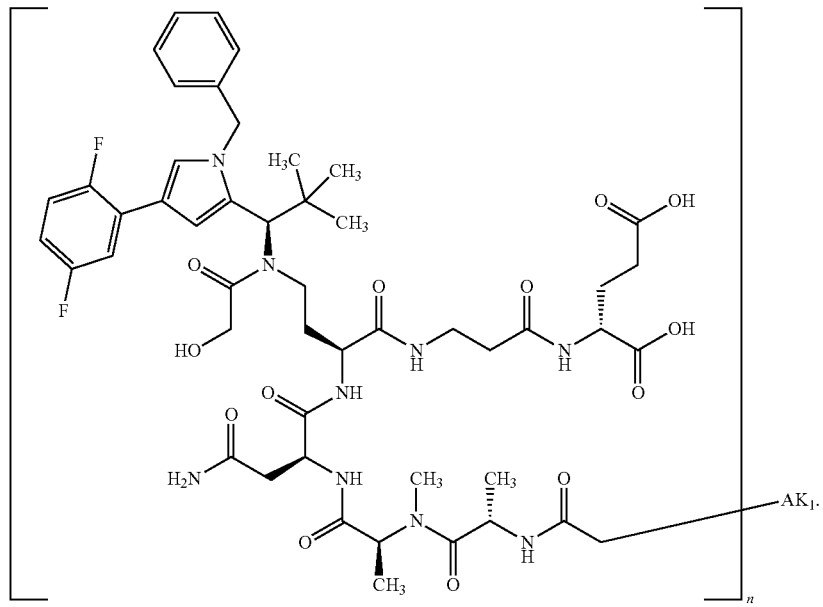

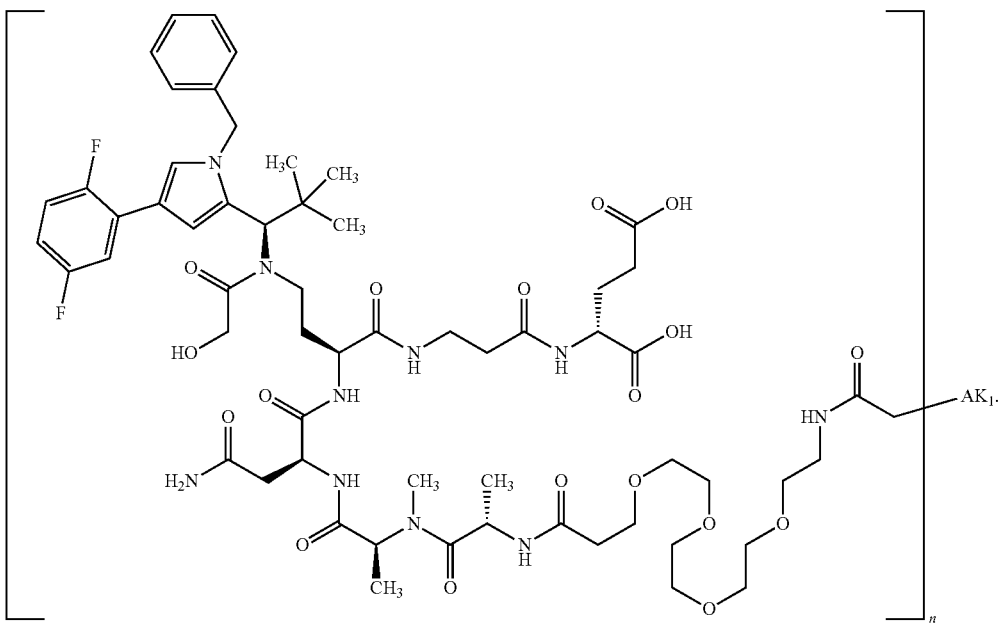

40. The antibody-drug conjugate of claim 39, wherein the antibody or antigen-binding antibody fragment comprises a variable heavy chain comprising the variable CDR1 sequence of the heavy chain, as shown in SEQ ID NO: 82, the variable CDR2 sequence of the heavy chain, as shown in SEQ ID NO: 83, and the variable CDR3 sequence of the heavy chain, as shown in SEQ ID NO: 84; and a variable light chain comprising the variable CDR1 sequence of the light chain, as shown in SEQ ID NO: 86, the variable CDR2 sequence of the light chain, as shown in SEQ ID NO: 87, and the variable CDR3 sequence of the light chain, as shown in SEQ ID NO: 88.

41. The antibody-drug conjugate of claim 40, wherein the variable heavy chain comprises SEQ ID NO: 81 and the variable light chain comprises SEQ ID NO: 85.

42. The antibody-drug conjugate of claim 40, wherein the antibody or antigen-binding fragment comprises a heavy chain comprising SEQ ID NO: 89 and a light chain comprising SEQ ID NO: 90.

43. A method for treatment of a disease associated with CD123 expression, comprising administering to a subject in need thereof an effective amount of the antibody-drug conjugate of claim 16.

44. A method for treatment of a disease associated with CD123 expression, comprising administering to a subject in need thereof an effective amount of the antibody-drug conjugate of claim 20.

45. A method for treatment of a disease associated with CD123 expression, comprising administering to a subject in need thereof an effective amount of the antibody-drug conjugate of claim 24.

46. A method for treatment of a disease associated with CD123 expression, comprising administering to a subject in need thereof an effective amount of the antibody-drug conjugate of claim 28.

47. A method for treatment of a disease associated with CD123 expression, comprising administering to a subject in need thereof an effective amount of the antibody-drug conjugate of claim 32.

48. A method for treatment of a disease associated with CD123 expression, comprising administering to a subject in need thereof an effective amount of the antibody-drug conjugate of claim 36.

49. A method for treatment of a disease associated with CD123 expression, comprising administering to a subject in need thereof an effective amount of the antibody-drug conjugate of claim 40.

50. A method for treatment of a disease associated with CD123 expression, comprising administering to a subject in need thereof an effective amount of the antibody-drug conjugate of claim 1.

* * * * *